(12) United States Patent
Winfield et al.

(10) Patent No.: US 6,873,914 B2
(45) Date of Patent: Mar. 29, 2005

(54) METHODS AND SYSTEMS FOR ANALYZING COMPLEX BIOLOGICAL SYSTEMS

(75) Inventors: Stephanie Winfield, Raleigh, NC (US); Norman Glassbrook, Chapel Hill, NC (US); Yasmin Ranasinghe, Southington, CT (US); David Broadwell, Garner, NC (US); Ioana Popa-Burke, Durham, NC (US); Gordon James Nye, Morrisville, NC (US); Christopher Beecher, Chapel Hill, NC (US)

(73) Assignee: Icoria, Inc., Research Triangle Park, NC (US)

( * ) Notice: Subject to any disclaimer, the term of this patent is extended or adjusted under 35 U.S.C. 154(b) by 17 days.

(21) Appl. No.: 10/300,360

(22) Filed: Nov. 20, 2002

(65) Prior Publication Data

US 2004/0019435 A1 Jan. 29, 2004

Related U.S. Application Data

(60) Provisional application No. 60/414,488, filed on Sep. 27, 2002, provisional application No. 60/408,721, filed on Sep. 6, 2002, provisional application No. 60/407,840, filed on Sep. 3, 2002, provisional application No. 60/404,233, filed on Aug. 16, 2002, provisional application No. 60/384,445, filed on May 30, 2002, provisional application No. 60/379,562, filed on May 10, 2002, provisional application No. 60/374,229, filed on Apr. 19, 2002, provisional application No. 60/372,679, filed on Apr. 15, 2002, provisional application No. 60/368,776, filed on Mar. 29, 2002, provisional application No. 60/363,685, filed on Mar. 12, 2002, provisional application No. 60/356,994, filed on Feb. 14, 2002, provisional application No. 60/344,953, filed on Dec. 21, 2001, and provisional application No. 60/331,948, filed on Nov. 21, 2001.

(51) Int. Cl.[7] ............................................. G01N 33/48
(52) U.S. Cl. ........................................ 702/19; 707/102
(58) Field of Search ............................. 702/19, 32, 90, 702/182, 183, 104; 700/26–30, 266; 707/100–102, 103 R, 103 Y, 103 Z

(56) References Cited

U.S. PATENT DOCUMENTS 5,777,888 A 7/1998 Rine et al.

(Continued)

FOREIGN PATENT DOCUMENTS

WO 96/03981 2/1996

(Continued)

OTHER PUBLICATIONS

Khodadoust M & Klein T., "Redifining priorities in gene-based drug discovery", 19 Nature Biotech: 707 (2001).

(Continued)

Primary Examiner—Marc S. Hoff
Assistant Examiner—Edward Raymond
(74) Attorney, Agent, or Firm—Deborah H. Spencer; Timothy G. Hofmeyer; Laura L. Kiefer

(57) ABSTRACT

The present invention provides methods and systems for organizing complex and disparate data. More specifically, the present invention provides methods and systems for organizing complex and disparate data into coherent data sets. Coherent data sets resulting from the methods and systems of the present invention serve as models for biological systems. Methods and systems for integrating data and creating coherent data sets are useful for numerous biological applications, such as, for example, determining gene function, identifying and validating drug and pesticide targets, identifying and validating drug and pesticide candidate compounds, profiling drug and pesticide compounds, producing a compilation of health or wellness profiles, determining compound site(s) of action, identifying unknown samples, and numerous other applications in the agricultural, pharmaceutical, forensic, and biotechnology industries.

2 Claims, 37 Drawing Sheets

U.S. PATENT DOCUMENTS

| | | | |
|---|---|---|---|
| 5,965,352 A | | 10/1999 | Stoughton et al. |
| 5,978,804 A | * | 11/1999 | Dietzman ................. 707/10 |
| 6,087,090 A | | 7/2000 | Mascarenhas |
| 6,113,763 A | * | 9/2000 | Henry et al. ............... 204/451 |
| 6,132,969 A | | 10/2000 | Stoughton et al. |
| 6,146,830 A | | 11/2000 | Friend et al. |
| 6,197,517 B1 | | 3/2001 | Roberts |
| 6,200,803 B1 | | 3/2001 | Roberts |
| 6,203,987 B1 | | 3/2001 | Friend et al. |
| 6,218,122 B1 | | 4/2001 | Friend et al. |
| 6,221,597 B1 | | 4/2001 | Roberts |
| 6,222,093 B1 | | 4/2001 | Marton et al. |
| 6,278,794 B1 | * | 8/2001 | Parekh et al. .............. 382/129 |
| 6,312,893 B1 | * | 11/2001 | Van Ness et al. .............. 435/6 |
| 6,334,099 B1 | | 12/2001 | Grace et al. |
| 6,416,643 B1 | | 7/2002 | Henry et al. |
| 6,558,955 B1 | | 5/2003 | Kristal et al. |
| 6,594,588 B1 | * | 7/2003 | Peden et al. .................. 702/32 |
| 6,680,203 B2 | * | 1/2004 | Dasseux et al. ............. 436/86 |
| 6,681,198 B2 | * | 1/2004 | Buote et al. ................ 702/185 |
| 2002/0009740 A1 | | 1/2002 | Kaddurah-Daouk et al. |
| 2002/0095260 A1 | | 7/2002 | Huyn et al. |
| 2002/0145425 A1 | | 10/2002 | Ebbels et al. |
| 2003/0023386 A1 | | 1/2003 | Aranibar et al. |
| 2003/0130798 A1 | | 7/2003 | Hood et al. |
| 2003/0229451 A1 | | 12/2003 | Hamilton et al. |
| 2004/0002842 A1 | | 1/2004 | Woessner et al. |
| 2004/0018500 A1 | | 1/2004 | Glassbrook et al. |
| 2004/0018501 A1 | | 1/2004 | Allen et al. |
| 2004/0019429 A1 | | 1/2004 | Coffin et al. |
| 2004/0019430 A1 | | 1/2004 | Hurban et al. |
| 2004/0023295 A1 | | 2/2004 | Hamilton et al. |
| 2004/0024293 A1 | | 2/2004 | Lawrence et al. |
| 2004/0024543 A1 | | 2/2004 | Zhang et al. |

FOREIGN PATENT DOCUMENTS

| | | |
|---|---|---|
| WO | 00/51054 | 8/2000 |
| WO | 00/65366 | 11/2000 |
| WO | 00/65472 | 11/2000 |
| WO | 01/57518 | 8/2001 |
| WO | 02/10456 | 2/2002 |
| WO | 02/057989 | 7/2002 |
| WO | 02/085195 | 10/2002 |
| WO | 02/086478 | 10/2002 |
| WO | 02/086500 | 10/2002 |
| WO | 02/086501 | 10/2002 |
| WO | 02/086502 | 10/2002 |

OTHER PUBLICATIONS

Wilson et al., "Assessing Annotation Transfer for Genomics: Quantifying the Relations between Protein Sequence, Structure and Function through Traditional and Probabilistic Scores", 297 J.mol. Biol.: 233–249 (2000).

McGovern, P.G. et al., "Recent Trends in Acute Coronary Heart Disease: Mortality, Morbidity, Medical Care, and Risk Factors", 334(14) New England J. Med.: 884–890 (1996).

Wilson, P.W.F. et al., "Prediction of Coronary Heart Disease Using Risk Factor Categories", '97 Circulation: 1837–1847 (1998).

Detsky, A.S. et al., "Predicting Cardiac Complications in Patients Undergoing Non–cardiac Surgery", i J. Gen. Int. Med.: 211–219 (1986).

Gail, M.H. et al., "Weighing the Risks and Benefits of Tamoxifen Treatment for Preventing Breast Cancer", 91(21) J. Nat'l Cancer Inst.: 1829–1846 (1999).

Manning, A.P. et al., "Towards Positive diagnosis of the Irritable bowel", 2 Brit. Med. J.: 653–654 (1978).

Sachidanadam, R. et al., "A Map of Human Genome Sequence variation containing 1.42 Million Single Nucleotide Polymorphisms", 409 Nature: 928–933(2001).

Ward, E. & Benasconi, P., "Target–based discovery of crop protection chemicals", 17 Nature Biotech: 618–19 (1999).

Davies, J.L. et al, "A genome–wide search for human type 1 diabetes susceptibility genes", 371 Nature: 130–136 (1994).

Hashimoto, L.et al., "Genetic mapping of a susceptibility locus for insulin–dependent diabetes mellitus on chromosome 11q", 371 Nature: 161–164 (1994).

Cho, H. et al., "Insulin Resistance and a Diabetes Mellitus–like Syndrome in Mice Lacking the Protein Kinase Akt2 (PKBβ)", 292 Science: 1728–1731 (2001).

Boyes, D. et al.,"Growth Stage–Based Phenotypic Analysis of Arabidopsis: A model for High Throughput Functional Genomics in Plants", 13 Plant Cell: 1499–1510 (2001).

Winkelmann, B.R."Genomics and large scale phenotypic databases", 2(1) Pharmacogenomics: 3–5(2001).

Owen, K. & Hattersley, A.T. "Maturity–onset diabetes of the young: from clinical description to molecular genetic characterization", 15(3) Best Pract. Res. Clin. Endocrinol. Metab.: 309–323 (2001).

Labow, B.I. et al., "Mechanisms Governing the Expression of the Enzymes of Glutamine Metabolims–Glutaminase and Glutamine Synthetase$^{1,2}$", 131 J. Nutrition: 2467S–2474S (2001).

Treasure, R.A.R. et al., "Misdiagnosis of diabetic Ketoacidosis as hyperventilation syndrome", 294 Br. Med. J. (clin. res.ed.): 630 (1987).

Laloux, S. et al., "Maladie coeliaque de L'adulte et diabète de type 1:Une Association génétique Sévère et parfois méconnue" 13 Diabètes & Métabolisme : 520–528 (1987).

Roessner, U. et al., "Metabolic Profiling Allows Comprehensive Phenotyping of Genetically or Environmentally Modified Plant Systems", 13 Plant Cell: 11–29 (2001).

Glassbrook, N. et al., "Metabolic profiling on the right path", 18 Nature Biotec: 1142–1143 (2000).

Selkov, E. & Gaasterland, T., "Reconstruction of Metabolic Networks Using Incomplete Information" 3 Proc. Intl. Conf. Intell.Syst. Mol. Biol.: 127–135 (1995).

Selkov, E. et al., "Functional analysis of gapped microbial genomes: Amino acid metabolism of *Thiobacillus ferrooxidans*", 97(7) Proc. Nat'l Acad. Sci. U.S.A.: 3509–3514 (2000).

Covert, M.W. et al., "Metabolic modeling of microbial strains in silico", 26(3) TRENDS in Biochem Sci.: 179–186 (2001).

Devine et al., "An Introduction to Herbicide Action", Physiology of Herbicide Action (1993).

Daum, G. et al., "Biochemistry, Cell Biology and Molecular Biology of Lipids of *Saccharmyces Cerevisiae*", 14 Yeast: 1471–1510 (1998).

Lamb, D.C. et al., "Purification, Reconstitution, and Inhibition of Cytochrome P–450 Sterol$\Delta^{22}$ Desaturase from the Pathogenic Fungus *Candida glabrata*", 43 (7) Antimicrob. Agents andChemother.:1725–1728 (1999).

Oakley, K.L. et al., "In Vitro Activity of SCH—56592 and Comparison with Activities of Amphotericin B and Itraconazole against *Aspergillus SPP.*", 41(5) Antimicrob. Agents Chemother.: 1124–1126 (1997).

De Backer, M.D. et al., "Genomic Profiling of the Response of *Candida albicans* to Itraconazole Treatment Using a DNA Microarray", 45(6) Antimicrob. Agents and Chemother: 1660–1670 (2001).

Jia, M.H. et al., "Global expression profiling of yeast treated with an inhibitor of amino acid biosynthesis, sufometuron methyl", 3 Physiol. Genomics: 83–92 (2000).

Fiehn, O, "Metabolomics–the link between genotypes and phenotypes", 48 Plant Mol. Biol.: 155–171 (2002).

Kuile, B.H. Ter & Westerhoff, H.V., "Transciptome meets metabolome: hierarchical and metabolic regulation of the glycolytic pathway", 500 FEBS Lett.: 169–171(2001).

Halket, J.M. et al., "Deconvolution Gas Chromatography/Mass Spectrometry to Urinary Organic Acids–Potential for Pattern Recognition and Automated Identification of Metabolic Disorders", 13 Rapid Commun Mass. Spectrom.: 279–284 (1999).

Adams, M.A. et al., "Simultaneos Determination by Capillary Gas Chromatography of Organic Acids, Sugars, and Sugar Alcohols in Plant Tissue Extracts as their Trimethylsilyl Derivatives", 266 Anal Biochem.: 77–84 (1999).

Ito, H. et al., "Tranformation of Intact Yeast Cells Treated with Alkall Cations", 153(1) Journal.of Bactriol.: 163–168 (1983).

Nicholson, J. K. et al., "Metabonomics: A platform for Studying drug toxicity and Gene Function", 1 Nature Reviews Drug Discovery: 153–161 (2002).

Nicholson, J. K. et al., "Metabonomics: understanding the metabolic responses of living systems to pathophysiological stimuli via multivariate statistical analysis of biological NMR Spectroscopic data", 29 (11) Xenobiotica: 1181–1189 (1999).

Nicholls, A.W. et al., "Metabonomic investigations into hydrazine toxicity in the rat: induction of 2–aminoadipic acid", 14 Chem. Res. Tox.: 975–987 (2001).

Espina, J.R. et al., "Detection of in vivo biomarkers of phospholipidosis using NMR–based metabonomic approaches", 39 Magn. Reson. Chem.: 559–565 (2001).

Holmes, E. et al., "Chemometric models for toxicity classification based on NMR spectra of biofluids", 13 Chem. Res. Tox.: 471–478 (2000).

Holmes, E. et al., "The Identification of novel Biomarkers of renal toxicity using automatic data reduction techniques and PCA of proton NMR spectra of Urine", 44 Chemomet. &Intel. Lab. Systems: 245–255 (1998).

Holmes, E. et al., "Development of a model for classification of toxin–induced lesions using 1HNMR Spectroscopy of urine combined with pattern recognition", 11 NMR in Biomed.: 235–244 (1998).

Lindon, J.C. et al., "Pattern recognition methods and applicatins in biomedical magnetic resonance", 39 Prog.NMR Spectrosc.:1–40 (2001).

Lindon, J.C. et al., "Metabonomics: metabolic processess studied by NMR Spectroscopy of biofluids", 12 Concepts in Magnetic Resonance: 289–320 (2000).

Sommerville, C. et al., "Plant Functional Genomics", 285 Science: 380–383; (Jul. 16, 1999).

Thiellement, H. et al., "Proteomics or Genetic and Physiological Studies in Plants", 20 Electrophoresis: 2013–2026 (1999).

Martzen, M.R. et al., "A Biochemical Genomics Approach for Identifying Genes by the Activity of Their Products"; 286 Science: 1153–1155 (Nov. 5, 1999).

Brenner, S.E., "Errors in Genome Annotation", 15 (4) TIG: 132–133 (1999).

Roessner, U. et al. "Simultaneous Analysis of Metabollites in Potato Tuber by Gas Chromatogrphy– Mass Spectrometry"; 23(1) The Plant Journal: 131–142 (2000).

Raamsdonk, L.M. et al., "A Functional Genomics Strategy that uses Metabolome Data to Reveal the Phenotype of Silent Mutation", 19 Nature Biotechnology: 45–50 (2001).

Huges, T.R. et al., "Functional Discovery Via a Compendium of Expression Profiles", 102 Cell: 109–126 (Jul. 7, 2000).

Ross, D. T. et al., "Systematic Variation in Gene Expression Patterns in Hman Cancer Cell lines"; 24 Nature Genetics: 227–235 (2000).

Fiehn, O., "Combining Genomics, Metabolome Analysis, and Biochemical modelling to Understand Metabolic Networks"; 2 Comparative and Functional Genomics: 155–168 (2001).

Aranibar, N. et al., "Automated Mode–of–Action Detection by Metabolic Profiling"; 286 Biochemical and Biophysical Research Communication: 150–155 (2001).

Fiehn, O. et al., Metabolite Profiling for Plant Functional Genomics; 18 Nature Biotechnology: 1157–1161 (2000).

Glassbrook, N. et al., "A Systematic Approach to Biochemical Profiling"; 4 Current Openion in Plant Biology: 186–190 (2001).

Ideker, T. et al., " Integrated Genomics and Proteomic Analyses of a Systematically Perturbed Metabolic Network", 292 Science: 929–934 (May 4, 2001).

Scherf, U., et al., "A gene expression database for the Molecular Pharmacology of Cancer", 24 Nature Genetics: 236–244 (Mar. 2000).

Hodgson, J., "Rapidly resolving the pharmacokinetic and toxicological properties of drug candidates remains a key challenge for drug developers", 19 Nature Biotechnology: 722–726 (Aug. 2001).

Myers, S. et al., "Drug Discovery—an operating model for a new era", 19 Nature Biotechnology: 727–730 (Aug. 2001).

Huang, S., "The practical problems of post–genomics biology", 18 Nature Biotechnology: 471–472 (May 2000).

Trethewey, R.N. et al."Metabolomic profiling: a resetta stone for genomics?" Current openion in Plant Biology; Mar. 1999 edition; Current Biology Publications, London.

Walkins, S.M. "Comprehensive Lipid Analysis: A powerful Metanomic Tool for Predictive and Diagnostic Medicine", 2 IMAJ: 722–724 (Sep. 2000).

Aharoni, A. et al., "Nontargeted Metabolome Analysis by Use of Fourier Transform Ion Cyclotron Mass Spectrometry", 6(3) OMICS: A Journal of Integrative Biology: 217–234 (2002).

Trethewey, R.N. " Gene discovery via metabolic profiling", 12 Current Opinion in Biotechnology: 135–138; (2001).

Brindle, J.T. et al "Rapid and noninvasive diagnosis of the presence and severity of coronary heart disease using $^1$H–NMR– based metabonomics", 8(12) Nature Medicine: 1439–1444; (Dec. 2002).

Keun, H.C. Analytical Reproducibility in $^1$H NMR–Based Metabolomic Urinalysis, 15 Chem. Res. Toxicol.: 1380–1386; (2002).

Baker, P.G. et al " Recent developments in biological sequence databases", 9 Current Openion in Biotechnology: 54–58 (1998).

* cited by examiner

Integrated Data

METHODS AND SYSTEMS FOR ANALYZING COMPLEX BIOLOGICAL SYSTEMS

RELATED APPLICATIONS

This application claims the benefit of U.S. Provisional Application No. 60/414,488, filed Sep. 27, 2002; U.S. Provisional Application No. 60/408,721, filed Sep. 6, 2002; U.S. Provisional Application No. 60/407,840, filed Sep. 3, 2002; U.S. Provisional Application No. 60/404,233, filed Aug. 16, 2002; U.S. Provisional Application No. 60/384,445, filed May 30, 2002; U.S. Provisional Application No. 60/379,562, filed May 10, 2002; U.S. Provisional Application No. 60/374,229, filed Apr. 19, 2002; U.S. Provisional Application No. 60/372,679, filed Apr. 15, 2002; U.S. Provisional Application No. 60/368,776, filed Mar. 29, 2002; U.S. Provisional Application No. 60/363,685, filed Mar. 12, 2002; U.S. Provisional Application No. 60/356,994, filed Feb. 14, 2002; U.S. Provisional Application No. 60/344,953, filed Dec. 21, 2001; and U.S. Provisional Application No. 60/331,948, filed Nov. 21, 2001. All of the foregoing patent applications are incorporated in their entirety by reference.

The present application is related to U.S. application Ser. No. 10/300,262, filed Nov. 20, 2002, titled "Methods and Systems for Analyzing Complex Biological Systems"; U.S. application Ser. No. 10/300,204, filed Nov. 20, 2002, titled "Methods and Systems for Analyzing Complex Biological Systems"; U.S. application Ser. No. 10/300,291, filed Nov. 20, 2002, titled "Methods and Systems for Analyzing Complex Biological Systems"; U.S. application Ser. No. 10/300,599, filed Nov. 20, 2002, titled "Methods and Systems for Analyzing Complex Biological Systems"; U.S. application Ser. No. 10/300,166, filed Nov. 20, 2002, titled "Methods and Systems for Analyzing Complex Biological Systems"; U.S. application Ser. No. 10/300,551, filed Nov. 20, 2002, titled "Methods and Systems for Analyzing Complex Biological Systems"; U.S. application Ser. No. 10/300, 598, filed Nov. 20, 2002, titled "Methods and Systems for Analyzing Complex Biological Systems"; U.S. application Ser. No. 10/300,184, filed Nov. 20, 2002, titled "Methods and Systems for Analyzing Complex Biological Systems"; and U.S. application Ser. No. 10/300,543, filed Nov. 20, 2002, titled "Methods and Systems for Analyzing Complex Biological Systems".

FIELD OF THE INVENTION

The present invention provides a method for organizing complex and disparate biological data into a single, logical data set. Specifically, the method of the present invention pertains to the creation of a common data currency for integrating and analyzing large quantities of heterogeneous data. The invention is useful in multiple applications, including applications in the agricultural, pharmaceutical, forensic, and nutriceutical industries.

BACKGROUND OF THE INVENTION

The application of genomics to life science industries promises to change the way pharmaceutical, agricultural, and biotechnology companies operate, saving significant amounts of time and money in the development of new and efficacious products. The original core concept of genomics research was that obtainment of a genomic sequence of an organism would lead directly to identification of every gene in the organism and an unambiguous determination of the function of each identified gene. Assumptions serving as a foundation for the conceptualized promise of genomic research are reliant upon two basic tenets. First, a basic paradigm of molecular biology is that each gene encodes one protein having one function. Second, it is assumed that by performing homology-based sequence comparisons, scientists can identify the function of most genes based on the sequence information available from public databases. Unfortunately, both of these assumptions have faults and as a result, the genomics era has yet to provide an accelerated route from gene discovery to blockbuster product. An additional complicating factor in the study of biological systems is that protein function is often defined in the context of a given situation, i.e. through interactions with other proteins and within specific cellular and subcellular compartments.

The assumption of a linear relationship between gene and function is now being recognized as overly simplistic, at best. A "cause-and-effect" relationship between a single gene, its product, and a phenotype (or disease state) is the exception, not the rule. Some highly successful biopharmaceutical products, including insulin and erythropoietin, operate through their ability to modulate such linear relationships. However, problems such as ligand redundancies and cell-type specificities obfuscate the development of a pharmaceutical or agricultural product. To further complicate matters, many systems operate through nonlinear dose dependencies. In other words, at one concentration a compound may have one effect (such as an anti-inflammatory effect), while at a different concentration in the same cell type the compound may have an opposite effect (such as a pro-inflammatory effect). Issues of ligand redundancy, cell-type specificity, and nonlinear dose dependency are difficult to reconcile in a product development environment, even in cases where gene function is known or predictable. To further complicate matters, many diseases are polygenic, so not only do multiple gene products require identification, but alternate treatment compounds are likely required to address the role each gene product plays in a disease process. M. Khodadoust & T. Klein, 19 NATURE BIOTECH. 707 (2001).

For years it was assumed that gene function was determinable by obtaining a gene sequence and performing a homology-based comparison. The central dogma is that similar sequence equals similar structure that equals similar function. Gene annotations found in public databases are far from infallible and overreliance on them may misdirect research efforts. In many cases, only a very small percentage of any given genome is actually experimentally annotated. Homology sequence comparisons and blanket application of the central dogma supply the remaining annotation. While amino acid identity greater than 40 percent of two complete protein sequences infers structural similarity, it does not necessarily infer functional similarity. Additional sequence conservation in an active site region is required for accurate prediction of function. Wilson et al., 297 J. MOL. BIOL. 233–249 (2000). Proteins are typically organized into families based on the similarity of three-dimensional structures. In some cases, members of the same protein family may have no detectable sequence similarity, illustrating that structural similarities do not necessarily impute sequence similarities, and vice versa. Current annotation available from public sources is largely incomplete, and as a result, sequence comparison is not a viable approach to determining the relative roles of genes sequenced in genomics projects.

To meet the challenge of understanding complex biological systems, scientists require the ability to analyze complex data sets. As noted above, the sequencing of entire genomes has not led to an industry pipeline bulging with new life sciences products, nor has it led to an understanding of the function of all the sequenced genes. Currently, less than 5 percent of genes with annotation available from a public database are sufficiently well annotated for the information to be used directly in the development of products. As a result, a number of research technologies, such as gene expression profiling, metabolite analysis, phenotypic profiling, proteomics, 3-D protein structural analysis, protein expression, identification of biochemical pathways or networks, genotyping (including polymorphisms) and scientific literature tools are under development to help identify gene function. Each technology has its strengths and weaknesses and no single existing technology is sufficient to identify the function of all genes.

Since no single technology is the answer to gene function identification, the challenge is to combine data from different technology types in resultant data sets that are meaningful. Unfortunately, combining data from various sources is wrought with substantial technical problems in data organization and data analysis. Research technology systems organize data in different ways. Different research technologies use different analysis tools, which ask conceptually different questions. Analysis tools used in association with different technologies can provide dissimilar and even contradictory conclusions with respect to gene function and other data end points. It seems likely that for the majority of genes, the identification of function will only become possible if data from a variety of sources and technologies are organized as a single, logical data set. That is, the potential of multi-technology genomic research has not yet been realized because there is no common currency for integration and analysis of large quantities of heterogeneous data. Thus, there exists a need for the development of a meaningful way to produce and analyze multi-technology-derived data to provide scientists with yet untapped knowledge to aid in the development of new and efficacious agricultural, pharmaceutical, forensic, and nutriceutical products.

SUMMARY OF THE INVENTION

The present invention provides methods and systems for organizing complex and disparate data into coherent data sets. Coherent data sets serve as models for biological systems under examination. Methods and systems for integrating data and creating coherent data sets are useful for numerous biological applications, such as, for example, determining gene function, identifying and validating drug and pesticide targets, identifying and validating drug and pesticide candidate compounds, profiling of drug and pesticide compounds, producing a compilation of health or wellness profiles, determining compound site(s) of action, identifying unknown samples, and numerous other applications in the agricultural, pharmaceutical, forensic, and biotechnology industries.

The invention provides methods and systems for creating coherent data sets for modeling biological systems, wherein the methods include entering a unique identifier of a biological sample into a computer tracking system, and storing data in the computer tracking system, wherein the data are linked to the unique identifier. All linked data are converted to a numeric format, and the numeric data are converted to a common unit system, wherein the common unit system data are a coherent data set and can serve as a model for a biological system. The methods and systems of the invention are not limited in terms of the order in which the data are linked to the identifier or converted to numeric and common unit system format. For example, in an alternative embodiment of the invention, numeric format data or common unit system data are collected; the data are linked to a unique identifier; and the data are stored in the computer tracking system.

In one embodiment, the invention provides a method and a system for creating coherent data sets for modeling biological systems, wherein the method includes entering a unique identifier of a biological sample into a computer tracking system, and storing in the computer tracking system disparate data, wherein the disparate data comprise at least two types of data, and the disparate data are linked to the unique identifier. The linked disparate data are converted to a numeric format, and the numeric data are converted to a common unit system, wherein the common unit system data are a coherent data set and can serve as a model for a biological system.

In another embodiment, the invention provides a method and a system for creating coherent data sets for modeling biological systems, wherein the method includes entering a unique identifier of a biological sample into a computer tracking system, and storing in the computer tracking system disparate data, wherein the disparate data comprise at least three types of data, and the disparate data are linked to the unique identifier. The linked disparate data are converted to a numeric format, and the numeric data are converted to a common unit system, wherein the common unit system data are a coherent data set and can serve as a model for a biological system.

In yet another embodiment, the invention provides a method and a system for establishing a signature profile indicative of the physiological status of an individual, wherein the method includes entering a unique identifier of at least one biological sample into a computer tracking system and storing in the computer tracking system data, wherein the data are linked to the unique identifier. The linked data are converted to a numeric format, and the numeric data are converted to a common unit system, wherein the common unit system data are a coherent data set. The most informative of the common unit system data are determined, wherein the most informative data are a signature profile indicative of physiological status.

In still another embodiment, the invention provides a method and a system for examining chemical components in biological samples, comprising entering a unique identifier of at least one biological sample into a computer tracking system and simultaneously collecting data from the sample, for a plurality of peaks, each peak comprising at least one chemical component, wherein the data comprise data from at least two processes. The data from the sample are stored in the computer tracking system, wherein the data are linked to the unique identifier, and the chemical components are characterized and/or identified.

In another embodiment, the invention provides a method and a system for examining chemical components in biological samples, comprising entering a unique identifier of at least one biological sample into a computer tracking system and simultaneously collecting data from the sample, for a plurality of peaks, each peak comprising at least one chemical component, wherein the data comprise data from at least three processes. The data from the sample are stored in the computer tracking system, wherein the data are linked to the unique identifier, and the chemical components are characterized and/or identified.

In yet another embodiment, the invention provides a method and a system for examining metabolites in biological samples, comprising entering a unique identifier of at least one biological sample into a computer tracking system and simultaneously collecting data from the sample, for a plurality of peaks, each peak comprising at least one chemical component. The data from the sample are stored in the computer tracking system, wherein the data are linked to the unique identifier, and the chemical components are characterized and/or identified. The characterized and/or identified chemical components are linked to metabolites in biochemical pathways.

In still another embodiment, the invention provides a method and a system for establishing a signature profile indicative of the physiological status of an individual, comprising entering a unique identifier of at least one biological sample into a computer tracking system, and collecting and storing in the computer tracking system metabolite data, wherein the data are linked to the unique identifier. The linked data are compared to a reference, and the most informative of the compared data are determined, wherein the most informative data are a signature profile indicative of physiological status.

BRIEF DESCRIPTION OF THE FIGURES

FIG. 8A) Gene expression data (y-axis) and metabolite data (x-axis). FIG. 8B) Phenotypic data (y-axis) and gene expression data (x-axis). C) Phenotypic data (y-axis) and metabolite data (x-axis). None of the pair wise analyses resulted in accurate grouping of the herbicides by site/mode of action.

FIG. 11A) Mouse heart tissue. FIG. 11B) Mouse kidney tissue.

FIG. 12A) Phenotype representative of negative control plants. FIG. 12B) Phenotype representative of Amitrole treated plants. FIG. 12C) Phenotype representative of Glufosinate treated plants. FIG. 12D) Phenotype representative of Glyphosate; Imazapyr; Imazethapyr; and Chlorosulfuron treated plants. FIG. 12E) Phenotype representative of 2,4-D; Dicamba; and Benazolin treated plants. FIG. 12F) Phenotype representative of Acifluorfen and Bifenox treated plants. FIG. 12G) Phenotype representative of Atrazine; Metribuzin; Diuron; Bentazon; Paraquat; Diquat and Metolachlor treated plants.

FIG. 13A) Gene expression profile data collected at early time point. FIG. 13B) Gene expression profile data collected at middle time point. FIG. 13C) Gene expression profile data collected at late time point. FIG. 13D) Biochemical profile data collected at early time point. FIG. 13E) Biochemical profile data collected at middle time point. FIG. 13F) Biochemical profile data collected at late time point. The biochemical and gene expression profile data were clustered using SAS PROC CLUSTER and SAS PROC TREE was used to produce the dendrograms. The nine herbicide groups according to site of action are represented as follows: O=Glyphosate; □=Gulfosinate; ▲=Acifluorfen and Bifenox; ▼=Imazapyr, Imazethapyr, and Clorosulfuron; ●=Atrazine, Metribuzin, Diuron, and Bentazon; ◇=Paraquat and Diquat; ■=2,4-D; Dicamba and Benazolin; ♥=Amitrole; and ◆=Metolachlor.

FIG. 15A) Negative control treated with THFA alone. FIG. 15B) Treated with Unknown 1 in THFA. FIG. 15C) Treated with Unknown 2 in THFA. FIG. 15D) Treated with Unknown 3 in THFA. FIG. 15E) Treated with Unknown 4 in THFA. FIG. 15F) Treated with Unknown 5 in THFA. FIG. G) Negative control treated with Tween 80 alone. FIG. 15H) Treated with Unknown 1 in Tween 80. FIG. 15I) Treated with Unknown 2 in Tween 80. FIG. 15J) Treated with Unknown 3 in Tween 80. FIG. 15K) Treated with Unknown 4 in Tween 80. FIG. 15L) Treated with Unknown 5 in Tween 80.

FIG. 18A) Amphoteracin B; FIG. 18B) Fluconazole; FIG. 18C) Ketoconazole; and FIG. 18D) Posaconazole.

FIG. 21A) Amphoteracin B; FIG. 21B) Fluconazole; FIG. 21C) Ketoconazole; and FIG. 21D) Posaconazole.

DETAILED DESCRIPTION

Figure 1:
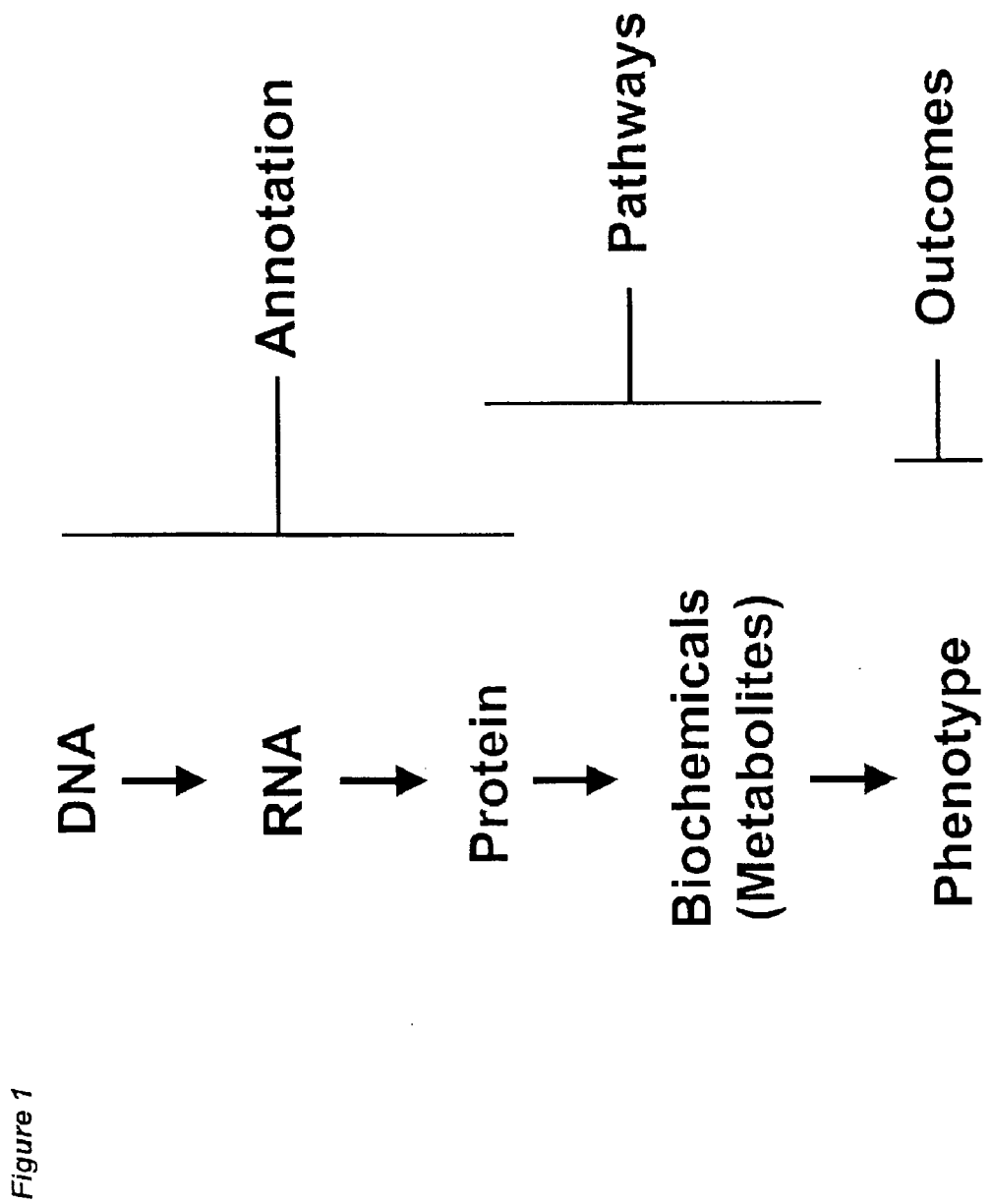
FIG. 1 depicts various indicators that can be examined to determine the biological status of an individual.

For clarity and consistency, the following definitions will be used throughout this patent document. To the extent that the following definitions conflict with other definitions for the defined terms, the following definitions shall control.

"Agriculture" or "agricultural," as used in this document, refers to the science, art, or practice of cultivating the soil, producing crops, and raising livestock and in varying degrees the preparation and marketing of the resulting products. Thus, development of agricultural products includes development of pesticides against organisms harmful to crops and/or livestock, as well as development of products to enhance the health and market value of livestock and crops, such as improved agronomic traits in crop plants.

Identifying a "baseline" value is an essential element to biological experimentation and provides, but is not limited to, a mechanism for distinguishing experimental error from biological variation. A baseline is used in the invention to standardize data to a common or commonly relevant unit of measure. The term "baseline" is herein used to refer to and interchangeably with "reference" and "control." Baseline populations consist, for example, of data from organisms of a particular group, such as healthy or normal organisms, or organisms diagnosed as having a particular disease state, pathophysiological condition, or other physiological state of interest. An example of the use of a baseline is the expression of data measurements as standard deviations from the corresponding baseline mean.

"Biochemical pathway" is a term commonly used to define a series of biochemical reactions that are linked one to another, i.e., the product of one reaction is a substrate for the subsequent reaction. Biochemical pathway is not limited to linearity with respect to biochemical reactions of biological organisms. Rather, biochemical pathway is understood to include individual pathways that function as networks of interrelated biochemical reactions.

The phrase "chemical components" refers to small molecules, including endogenous metabolites, and any derivative or degradation product thereof.

As used herein, a "coherent data set" is a data set comprised of disparate data that is: integrated; expressed in a numeric format; converted to a common unit system; and optionally, dimensionally reduced. Certain types of data are generally expressed in numeric format while other types of data require conversion to numeric format. Those data in numeric format are converted to a common unit system relative to a baseline value. The term "baseline" is herein used to refer to and used interchangeably with "control" and "reference." Certain data, for example, phenotypic data are not generally expressed in numeric format. Such non-numeric data, for example, leaf necrosis and cellular dysplasia are converted to a numeric scale relative to a baseline value. As the number of data points associated with different types of measurements can differ by orders of magnitude, the data are balanced as necessary, so that direct comparisons are meaningful. The dimensionality of the data is reduced, for example, in cases where there are many measurements obtained for a first type of data and fewer measurements for a second type of data. Dimensionality reduction is viewed as "balancing" individual data types to form a coherent data set, and may be accomplished, for example, by applying principle components analysis. The coherent data sets of the present invention serve as models for biological systems.

Coherent data sets comprised of cumulatively greater quantitative and qualitative indicators of biological status result in increasingly comprehensive data sets capable of reaching increasingly accurate biological predictions and conclusions. One characteristic of a coherent data set is that it is dynamic, so that previously non-incorporated data can be added as it is obtained or becomes available. The process for incorporating new data is iterative; the steps listed above are repeated with the inclusion of the new data. One purpose for creating a coherent data set is to obtain new information otherwise not available prior to data combination and analysis as a set.

"Integrated data" are data linked to, or associated with, a unique identifier of a biological sample from which the data were obtained.

For the purpose of this invention, "metabolites" refers to the native small molecules (e.g. non-polymeric compounds) involved in metabolic reactions required for the maintenance, growth, and function of a cell. Enzymes, other proteins, and most peptides are generally not small molecules and thus excluded. Many proteins participate in biochemical reactions with small molecules (e.g. isoprenylation, glycosylation, and the like). The construction and degradation of polypeptides results in either the consumption or generation of small molecules and, thus, the small molecules rather than the proteins are metabolites. Genetic material (all forms of DNA and RNA) is also excluded as a metabolite based on size and function. The construction and degradation of polynucleotides results in either the consumption or generation of small molecules and, thus, the small molecules rather than the polynucleotides are metabolites. Structural molecules (e.g. glycosaminoglycans and other polymeric units) similarly may be constructed of and/or degraded to small molecules, but do not otherwise participate in metabolic reactions. Thus, structural molecules are excluded as metabolites. Polymeric compounds such as glycogen are important participants in metabolic reactions, but are not chemically defineable and are a source of metabolites (i.e. an input/output to metabolism). Thus, polymeric compounds are excluded as metabolites. Metabolites of xenobiotics are neither native, required for maintenance or growth, nor required for normal function of a cell, and thus are not metabolites. However, it is useful to monitor xenobiotics when observing the effects of a drug therapy program, or in experimentally determining the effects of a compound on an individual. Essential or nutritionally required compounds are not synthesized de novo, (i.e. not native), but are required for the maintenance, growth, or normal function of a cell. Therefore, essential or nutritionally required compounds are metabolites.

"Morphology" refers to the form and structure of an organism or any of its parts. Morphology is one way of referring to a phenotype.

"Peak" refers to the readout from any type of spectral analysis or metabolite analysis instrumentation, as is standard in the art, and can represent one or more chemical components. The instrumentation can include, but is not limited to, liquid chromatography (LC), high-pressure liquid chromatography (HPLC), mass spectrometry (MS), hyphenated detection systems such as MS-MS or MS-MS-MS, gas chromatography (GC), liquid chromatography/mass spectroscopy (LC-MS), gas chromatography/mass spectroscopy (GC-MS), Fourier transform-ion cyclotron resonance-mass spectrometry (FT-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS), and matrix-assisted laser desorption/ionization time-of-flight mass spectrometry (MALDI-TOF MS). It is understood that the phrase "mass spectrometry" is used interchangeably with "mass spectroscopy" in this application.

"Phenotype" refers to the observable physical, morphological, and/or biochemical/metabolic characteristics of an organism, as determined by genetic and/or environmental factors.

"Types of data," as used herein, refers to data derived from different biological indicators. For example, types of data include, but are not limited to, data from DNA, data from RNA, data from proteins, data from metabolites, and data from phenotypic characteristics. Types of data are obtained by any process or technique known in the art; the process or technique used is immaterial to the creation of the coherent data set. However, the process or technique from which the data emanates may affect how the data are integrated. "Disparate data" are comprised of different types of data.

The present invention provides methods for organizing complex and disparate data into logical coherent data sets. Such coherent data sets serve as models for biological systems under examination. The present invention provides methods for integration and analysis of large quantities of heterogeneous data. The invention is useful in numerous applications in the agricultural, pharmaceutical, forensic, nutriceutical and biotechnology industries. Integration of data and formation of coherent data sets can be employed in a variety of settings, such as determining gene function; identifying drug, pesticide, and nutriceutical targets; identifying drug, nutriceutical, and pesticide compound candidates; profiling drug, nutriceutical, and pesticide compound candidates; producing a compilation of health or wellness profiles for prognostic and diagnostic use; determining compound site(s) of action; and identifying unknown samples, such as in a forensic setting.

Technologies abound which generate data useful in determining gene function. Gene expression analysis, phenotypic analysis, metabolite analysis, proteomics, 3-D protein structural analysis, and protein expression all provide valuable data in a quest for gene function determination. Scientific tools, techniques, and technologies, in combination with nucleotide sequence data, single nucleotide polymorphism (SNP) data, scientific literature, clinical chemistry data, and biochemical pathway data, can provide tremendous insight into the workings of complex biological systems when the data are combined to form coherent data sets.

The invention provides a method for standardizing and combining disparate data for modeling biological systems.

Methods of the present invention include entering a unique identifier of a sample into a computer tracking system, and storing in the computer tracking system data, wherein the data are linked to the unique identifier. All linked data are converted to a numeric format, and the numeric data are converted to a common unit system, wherein the common unit system data is a coherent data set and serves as a model for a biological system. Another embodiment of the invention comprises entering a unique identifier of a sample into a computer tracking system, and collecting and storing in the computer tracking system data, wherein the data are linked to the unique identifier. All linked data are converted to a numeric format, and the numeric data are converted to a common unit system. The methods of the invention are not limited in terms of the order in which the data are linked to the identifier or converted to numeric and common unit system format. For example, in one embodiment of the invention, numeric format data or common unit system data are collected; the data are linked to a unique identifier; and the data are stored in the computer tracking system.

In one embodiment of the present invention the data are RNA data (gene expression analysis), phenotypic data, and metabolite data (biochemical profiling analysis), but one skilled in the art will understand that data from any technology or process may be utilized in the methods of the invention. Further, it is understood by one skilled in the art that data from any biological organism (alive or dead) or part thereof may be incorporated into a coherent data set. Suitable biological organisms include, but are not limited to, plants, such as *Arabidopsis* (*Arabidopsis thaliana*) and rice, fungal organisms including *Magnaporthe grisea, Saccharomyces cerevisiae,* and *Candida albicans,* and mammals, including rodents, rabbits, canines, felines, bovines, equines, porcines, and human and non-human primates.

Suitable sample parts of biological organisms include, but are not limited to, human and animal tissues such as heart muscle, liver, kidney, pancreas, spleen, lung, brain, intestine, stomach, skin, skeletal muscle, uterine muscle, ovary, testicle, prostate, and bone; human and animal fluids such as blood, plasma, serum, urine, mucus, semen, sweat, tears, amniotic fluid, milk; freshly harvested cells such as hepatocytes or spleen cells; immortal cell lines such as the human hepatocyte cell line HepG2 or the mouse fibroblast line L929; human and animal cells grown in culture as three-dimensional culture spheres (e.g. liver spheroids); and plant tissues such as cotyledons, leaves, seeds, open flowers, pistils, senescent flowers, sepals, siliques, and stamens.

Gene expression analysis (GEA) refers to a simultaneous analysis of the expression levels of multiple genes. Traditionally, the expression of individual genes was analyzed by a technique called Northern-blot analysis. In a Northern-blot, RNA is separated on a gel, transferred to a membrane, and a specific gene is identified via hybridization to a radioactive complementary probe, usually made from DNA. A technological improvement in the area of GEA has been the development of small 1–2 cm chips used to concurrently determine expression levels of multiple genes from mulitple to samples. In a gene chip format, probes for the genes of interest are ordered as an array on a glass slide. After hybridization to appropriate samples, gene expression changes are often visualized with colors overlaid on an image of the chip. The color indicates the gene expression level and the location indicates the specific gene being monitored. Other technologies can be used to obtain the same type of gene information, including high-density array spotting on glass or membranes and quantitative PCR.

Phenotype refers to the observable physical or biochemical/metabolic characteristics of an organism, as determined by genetic and environmental factors. For example, in an *Arabidopsis thaliana* plant model system, a phenotype can be described by using distinctly defined attributes such as, but not limited to, number of: abnormal seeds, cotyledons, normal seeds, open flowers, pistils per flower, senescent flowers, sepals per flower, siliques, and stamens. Many times, perturbation of a biological system is indicated by a phenotypic trait. In humans, a perturbed biological system may result in symptoms disease such as chest pain, signs such as elevated blood pressure, or observable physical traits such as those exhibited by individuals afflicted with Trisomy 21. A normal phenotype is useful as a reference, or baseline value, against which a physiological status can be measured.

Medical history, examination, and testing techniques are well known to medical practitioners and data derived from the same can be used in practicing the methods and systems of the present invention. For example, in cases where a practitioner is examining a patient to determine the likelihood, existence, or extent of coronary heart disease (CHD), phenotypic traits observed or identified in a clinical setting include, but are not limited to, risk factors such as blood pressure, cigarette smoking, total cholesterol (TC), low density lipoprotein cholesterol (LDL-C), high density lipoprotein cholesterol (HDL-C), and diabetes. P. G. McGovern et al., 334 NEW ENG. J. MED. 884–890 (1996). Additonal phenotypic characteristics such as weight, family history of CHD, hormone replacement therapy, and left ventricular hypertrophy are also useful in determining CHD risk. It is common in the medical arts to scale or score a patient's condition based on a set of phenotypic signs and symptoms. For example, predictive models have been described based on blood pressure, cholesterol, and LDL-C categories as identified by the National Cholesterol Education Program and the Joint National Committee on Detection, Evaluation, and Treatment of High Blood Pressure. P. W. F. Wilson et al., 97 CIRCULATION 1837–1847 (1998) (incorporated herein by reference). Furthermore, predictive outcome models have also been described for patients undergoing coronary artery bypass grafting surgery and percutaneous transluminal coronary angioplasty.

Medical scoring of phenotypic triats are applicable to the assessment of patient well-being pre- and post-therapeutic intervention. For example, Short-Form 36 (SF-36) is gaining acceptance as a generic health outcome assessment form. The SF-36 validates health outcomes with 8 indices of health and well-being including general health (GH), physical function (PF), role function due to physical limitations (RP), role function due to emotional limitations (RE), social function (SF), mental health (MH), bodily pain (BP), vitality and energy (VE). Each health object is scored on a 0 to 100 basis with higher scores representing better function or less pain. Other scoring or ranking schemas for identifying and quantifying physiologic and pathophysiologic (phenotypic) states (traits) include, not are not limited, the following: ATP III Metabolic Syndrome Criteria; Criteria for One Year Mortality Prognosis in Alcoholic Liver Disease; APACHE II Scoring System and Mortality Estimates (Acute Physiology and Chronic Health disease Classification System II); APACHE II Scoring System by Diagnosis; Apgar Score; Arrhythmogenic Right Ventricular Dysplasia Diagnostic Criteria; Arterial Blood Gas Interpretation; Autoimmune Hepatitis Diagnostic Criteria; Cardiac Risk Index in Non-cardiac Surgery (L. Goldman et al., 297 NEW ENG. J. MED. 20 (1977)); Cardiac Risk Index in Noncardiac Surgery (A. S. Detsky et al., 1 J. GEN. INT. MED. 211–219 (1986)); Child Turcotte Pugh Grading of Liver Disease Severity; Chronic Fatigue Syndrome Diagnostic Criteria; Community Acquired Pneumonia Severity Scale; DVT Probability Score System; Ehlers-Danlos Syndrome IV (Vascular Type) Diagnostic Criteria; Epworth Sleepiness Scale (ESS); Framingham Coronary Risk Prediction (P. W. F. Wilson et al., 97 CIRCULATION 1837–1847 (1998)); Gail Model for 5 Year Risk of Breast Cancer (M. H. Gail et al., 91 J. NAT'L CANCER INST. 1829–1846 (1999); Geriatric Depression Scale; Glasgow Coma Scale; Gurd's Diagnostic Criteria for Fat Embolism Syndrome; Hepatitis Discriminant Function for Prednisolone Treatment in Severe Alcoholic Hepatitis; Irritable Bowel Syndrome Diagnostic Criteria (A. P. Manning et al., 2 BRIT. MED. J. 653–654 (1978)); Jones Criteria for Diagnosis of Rheumatic Fever; Kawasaki Disease Diagnostic Criteria; M. I. Criteria for Likelihood in Chest Pain with LBBB; Mini-Mental Status Examination; Multiple Myeloma Diagnostic Criteria; Myelodysplastic Syndrome International Prognostic Scoring System; Nonbiliary Cirrhosis Prognostic Criteria for One Year Survival; Obesity Management Guidelines (National Institutes of Health/NHLBI); Perioperative Cardiac Evaluation (NHLBI); Polycythemia Vera Diagnostic Criteria; Prostatism Symptom Score; Ranson Criteria for Acute Pancreatitis; Renal Artery Stenosis Prediction Rule; Rheumatoid Arthritis Criteria (American Rheumatism Association); Romhilt-Estes Criteria for Left Ventricular Hypertrophy; Smoking Cessation and Intervention (NHLBI); Sore Throat (Pharyngitis) Evaluation and Treatment Criteria; Suggested Management of Patients with Raised Lipid Levels (NHLBI); Systemic Lupus Erythematosis American Rheumatism Association 11 Criteria; Thyroid Disease Screening for Females More Than 50 Years Old (NHLBI); and Vector and Scalar Electrocardiography.

Still other phenotypic traits could be observed or identified by x-ray; electrocardiogaphy; blood pressure (BP) examination; pulse; weight and height; ideal body weight or BMI; retinal examination; thyroid examination; carotid bruits; neck vein examination; congestive heart failure (CHF) signs; palpable intercostal pulses; cardiovascular examination traits including, but not limited to, S4 gallop, tachycardia, bradycardia, heart sounds, aortic insufficiency, murmur, and echocardiography; abdominal examination; genitourinary examination; peripheral vascular disease examination; neurologic examination; and skin examination. In addition to standard x-ray technologies, numerous imaging techniques are also useful in observing and identifying phenotypic traits including, but not limited to, ultrasound, magnetic resonance imaging (MRI) positron emission tomography (PET), single photon emission computed tomography (SPECT), x-ray tranmission x-ray computed tomography (X-ray CT), ultrasound electrical impedance tomography (EIT), electrical source imaging (ESI), magnetic source imaging, (MSI) laser optical imaging.

Global assays (or global analyses) are performed as a means of making gross comparisons in materials for substances including, but not limited to, total protein, carbohydrate, and fat content.

Metabolite analysis refers to an analysis of organic, inorganic, and/or bio-molecules (hereinafter collectively referred to as "small molecules") of a cell, cell organelle, tissue and/or organism. It is understood that a small molecule is also referred to as a metabolite. Techniques and methods of the present invention employed to separate and identify small molecules, or metabolites, include but are not limited to: liquid chromatography (LC), high-pressure liquid chromatography (HPLC), mass spectroscopy (MS), gas chromatography (GC), liquid chromatography/mass spectroscopy (LC-MS), gas chromatography/mass spectroscopy (GC-MS), nuclear magnetic resonance (NMR), magnetic resonance imaging (MRI), Fourier Transform InfraRed (FT-IR), and inductively coupled plasma mass spectrometry (ICP-MS). It is further understood that mass spectrometry techniques include, but are not limited to, the use of magnetic-sector and double focusing instruments, transmission quadrapole instruments, quadrupole ion-trap instruments, time-of-flight instruments (TOF), Fourier transform ion cyclotron resonance instruments (FT-MS), and matrix-assisted laser desorption/ionization time-of-flight mass spectrometry (MALDI-TOF MS).

Metabolite analysis allows the relative amounts of metabolites to be determined in an effort to deduce a biochemical picture of physiology and/or pathophysiology. In one embodiment of the present invention, individual metabolites present in cells are identified and a relative response measured, establishing the presence, relative quantities, patterns, and/or modifications of the metabolites. In a related embodiment of the invention, the metabolites are linked to enzymatic reactions and metabolic pathways. In another embodiment, rather than identifying metabolites, the spectral properties of chemical components in a biological sample are characterized and the presense or absense of the chemical components noted. In a further embodiment of the invention, a metabolic profile is obtained by analyzing a biological sample for its metabolite composition under particular environmental conditions.

In one embodiment of the invention, a method is provided for examining metabolites in a biological sample, comprising entering a unique identifier of at least one biological sample into a computer tracking system; simultaneously collecting data from the sample, for a plurality of peaks, each peak comprising at least one chemical component; storing in the computer tracking system the chemical component data, wherein the data are linked to the unique identifier; characterizing and/or identifying the chemical components; and linking the characterized and/or identified chemical components to metabolites in biochemical pathways.

In the methods of the invention, data is collected for a plurality of peaks, each peak comprising at least one chemical component. In the methods of the invention the plurality of peaks comprises at least 25, 30, 40, 50, 60, 75, 85, 100, 125, 150, 175, 200, 225, 250, 275, 300, 350, 400, 450, 500, 550, 600, 650, 700, 750, 800, 850, 900, 950, 1000, 1050, 1100, 1150, 1200, 1250, 1300, 1350, or 1400 or more peaks.

In another method of the invention, a method is provided for examining metabolites in a biological sample. The method comprises entering a unique identifier of at least one biological sample into a computer tracking system; simultaneously collecting data for a plurality of peaks, each peak comprising at least one chemical component, from the sample, wherein the data comprise data from at least two processes; storing in the computer tracking system the data, wherein the data are linked to the unique identifier; adding the linked data to a database wherein the database comprises linkages between chemical components, biochemical pathways, and phenotype; identifying the chemical components; and querying the database for correlations between the chemical components, the biochemical pathways, and the phenotype.

In an alternate embodiment of the invention, GEA profiling, phenotypic analysis, and metabolite analysis are combined into one data set. Inclusion of GEA data allows the level of transcription of numerous genes to be monitored, while the inclusion of phenotypic analysis allows observable traits to be correlated with their molecular and cellular causes. Inclusion of metabolite analysis data allows correlation of small molecule profile data with the gene expression patterns and phenotypic characteristic data. Inclusion of biologically disparate data in a coherent data set allows creation of a model that accurately represents a biological system.

The methods and systems of the present invention include, as another type of technology data source, SNP-derived data. SNPs, or single nucleotide polymorphisms, are alterations in DNA sequences that involve only a single DNA base pair and may be shared by multiple individuals. Many SNPs do not produce observable physical changes in individuals with affected DNA. However, even SNPs that do not themselves alter protein expression or play a role in a pathenogenesis may be proximal to deleterious mutations on a chromosome. It is thought that 85 percent of exons in the human genome are within 5 kb (kilobases) of the nearest SNP. Because of this proximity, SNPs may be shared among groups of people with harmful, but unknown, mutations and the SNP may serve as a marker for the mutation. Such markers help reveal the mutations and accelerate efforts to find novel targets for diagnostic and therapeutic intervention, and may help in personalizing drug regimens by allowing a signature profile representative of a patient's tolerance to be interpreted prior to beginning a treatment. R. Sachidanandam, et al., 409 NATURE 928 (2001). Inclusion of SNP data in the formation of coherent data sets, along with other data types, has the potential to significantly improve identification of new signature profiles for disease staging and personalizing drug regimens. SNPs may also play a significant role in the investigation of haplotypes, a combination of many neighboring SNPs on a single chromosome. Haplotyping may yield more information about the genotype-phenotype relationship than individual SNPs.

Still another type of technology useful in the methods and systems of the present invention is proteomics. Proteins play an important role as structural and functional components of cells and body fluids of living organisms. Proteomics involves the identification of proteins in cells or tissues and their role in physiological function, enabling identification, as well as quantification, of tens of thousands of proteins present in biological samples. Since the total number of proteins expressed in an organism is encoded in its genome, one aim of proteomics is to correlate gene sequences to proteins, and hence to elucidate the function of various genes. The production or suppression of proteins in tissues or cells in response to external stimuli provides an important insight into gene regulation. Proteomic studies can be designed to shed light on the mechanism(s) by which a drug or pesticide acts, as well as provide information regarding various side effects that may be associated with its administration. Relative comparison of protein profiles from normal and diseased tissue may represent proteins that are potential targets for pharmaceutical or agricultural discovery. An understanding of mechanisms occurring at the molecular level is important to designing effective drug therapies, or in determining the function of genes with agricultural importance. In one embodiment of the present invention, proteomics-derived data are contained in a coherent data set to provide an improved understanding of the relationship between genes, proteins, and function.

In one embodiment, the methods and systems of the current invention provide ways of combining biologically disparate data for the creation of coherent data sets that serve as models of biological systems. Biologically disparate data are data derived from different indicators of the biological status of an organism or individual. These indicators include DNA, RNA, proteins, metabolites, and phenotypes, as shown in FIG. 1. The resolution power of coherent data sets promises to be enormous, as not only can different types of data from a single organism be combined and directly compared for improved representation of an entire biological system or organism, but data from completely different organisms can be analyzed together in a coherent data set for similarities and differences. This may be prove to be very valuable in the pharmaceutical arena, for instance, where the effect of a drug compound on both the pathogen and the host can be analyzed and compared (see Specific Examples 5 and 7, infra).

In the methods and systems of the present invention, data are acquired in a manner that facilitates the formation of coherent data sets as models of biological systems that are applicable to many different areas of the life sciences industry. Identification of novel targets for drug, pesticide, and nutriceutical applications is of primary importance. In the pharmaceutical arena alone, it is estimated that existing drugs interact with fewer than 500 biological targets out of an estimated 10,000 potential ones. Based on this estimation, a significant majority of potential drug targets remain undiscovered. In the field of agricultural crop protection, only 20 distinct sites of action for herbicidal compounds have been discovered and reported in the past 60 years, even though estimates of potential herbicide targets exceed this number by two orders of magnitude.

A key component of applying genomics tools to target discovery is the collection of functional information on how genes and gene products impact cells, tissues, organs and their associated healthy and diseased states. While biologically disparate data are being collected and analyzed categorically to address target discovery, the present invention provides a method for combining the disparate data into biologically meaningful groupings to create a data set that describes a condition in greater detail than that achievable through a collective analysis of its individual components.

Figure 2:
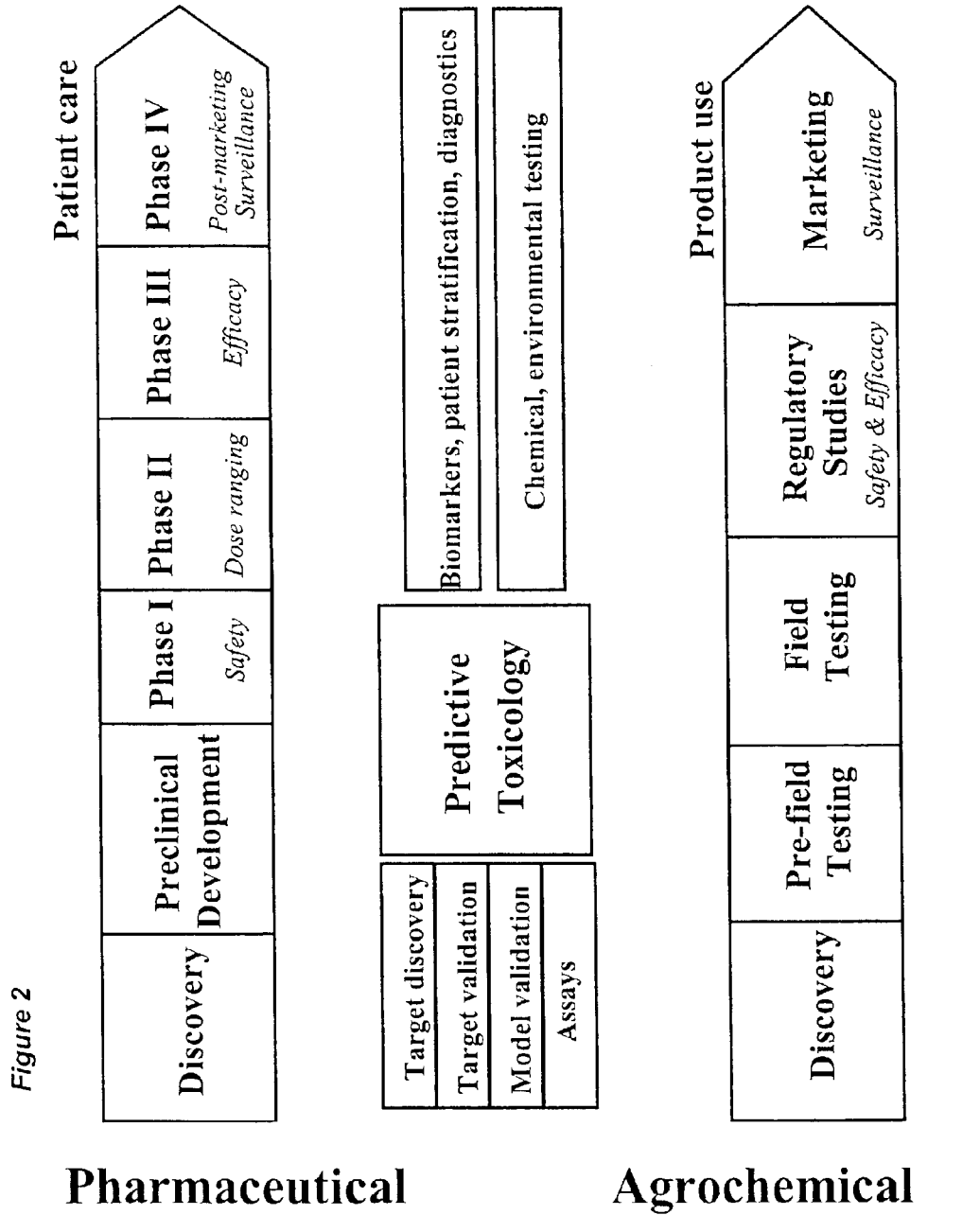
FIG. 2 is a representation of the parallel nature of the pharmaceutical and agrochemical product discovery and development processes.

After new targets for drug, pesticide, and nutriceutical applications are identified, there remains a long and difficult process for the development of an effective product aimed at the identified target, as shown in FIG. 2. Using the pharmaceutical field as an example, an average of 10,000 lead compounds must be tested in pre-clinical development for every one drug that is ultimately marketed. The methods of the present invention maximize efficiency in bringing targets to product development. In one embodiment of the invention, coherent data sets are created from disparate data. By using data derived from multiple biological indicators of physiological status, compelling targets can be more thoroughly validated and optimized for greatest effectiveness.

Another area of primary importance in the life sciences industry is the identification of novel lead compounds for use in drug, pesticide, and nutriceutical applications. The methods and systems of the present invention allow biological samples to be screened using multiple technologies, providing for the simultaneous examination of disparate indicators of biological status, so that the effect of a particular chemical compound on a sample can be understood more thoroughly than was historically possible. Creation of coherent data sets allows subtle and complex effects to be observed so that target and lead compound identification, validation and selection are more efficient. The optimization of lead compounds is more efficient as well, as it is possible to optimize the application of the selected leads, and screen-out selected leads based on parameters such as toxicity. The methods and systems of the present invention allow for the development of highly efficacious products while spending as little time and money as possible at a discovery stage.

Discovering and developing new pharmaceutical drugs has become increasingly expensive and challenging. According to the Tufts Center for the Study of Drug Development, the cost of developing a single new drug and bringing it to market (including failures) now exceeds $800 million in the United States. The length of time from the discovery of a candidate to its approval by the FDA has increased from eight years in the 1960s to more than 14 years at the time of this filing. Adverse toxic side effects from drugs result in more than two million hospitalizations each year and more than 100,000 deaths. The methods of the present invention lower the cost of drug discovery, decrease the time to market for new drugs, lower the incidence of adverse toxic side effects, and complement other genomics tools to help researchers better understand the link between cellular or biochemical function, pharmaceutical compounds, toxicity, and disease response. The present invention is also applicable to the discovery and development of new pesticides and nutriceutical products, by lowering the cost of discovery, decreasing the time to market, and lowering the incidence of adverse side effects.

In one embodiment of the present invention, promising pharmaceutical or pesticidal compounds that have failed to reach commercial production due to toxic effects are studied using coherent data sets to determine precisely the origin of the toxicity. Armed with information from a coherent data set, it is possible to rescue a failed drug or herbicide compound, or to use coherent data set-derived information to select a similar candidate more likely to succeed as a marketable product. The large sums of money invested in the development of failed compounds are not lost and can still result in an effective and marketable product.

The methods and systems of the present invention are useful for compiling health or wellness profiles for organisms and for providing profiles representative of particular diseases or other specific physiological states. Profiles generated by methods of the present invention are composed of data from a single indicator of physiological status, or from any combination of such indicators. Data obtained from an individual are compared to a baseline, or reference population, to determine physiologic status. It is understood that a baseline, a control, a reference, and a standard are used as equivalent terms in referring to the present invention. Baseline populations, for example, consist of data from individuals of a particular group, such as healthy or normal individuals, or individuals diagnosed as having a particular disease state or other physiological state of interest. This feature allows scientists to choose the types of data most informative for a particular condition and representative of an individual's state of wellness, referred to herein as a signature profile.

In one embodiment of the invention, a method is provided for establishing a signature profile indicative of the physiological status of an individual. The method comprises entering a unique identifier of at least one biological sample into a computer tracking system; storing in the computer tracking system data from the sample, wherein the data are linked to the unique identifier. The linked data are compared to a reference and the most informative of the compared data are determined, wherein the most informative data are a signature profile indicative of physiological status.

In another embodiment of the invention, a method is provided for establishing a signature profile indicative of the physiological status of an individual. The method comprises entering a unique identifier of at least one biological sample into a computer tracking system; storing in the computer tracking system metabolite data from the sample, wherein the data are linked to the unique identifier. The linked data are compared to a reference and the most informative of the compared data are determined, wherein the most informative data are a signature profile indicative of physiological status.

In an alternative embodiment of the invention, signature profiles indicative of physiological status are established by integration of disparate data and formation of coherent data sets according to the methods and systems of the present invention. The method comprises entering a unique identifier of at least one biological sample into a computer tracking system; storing in the computer tracking system disparate data linked to the unique identifier; converting the linked disparate data to a numeric format; and converting the numeric format data to a common unit system. The method further comprises determining the most informative of the common unit system data, wherein the most informative data are a signature profile indicative of physiological status. The disparate data of the invention include, but are not limited to, RNA data (for example, gene expression data), phenotypic data (visible or diagnostic trait), metabolite data, protein data (such as a 2D gel), or DNA data (such as SNP information).

Another embodiment of the invention provides a method for establishing a signature profile indicative of the physiological status of an individual comprising entering a unique identifier of at least one biological sample into a computer tracking system; storing data comprising metabolite data in the computer tracking system, wherein the data are linked to the unique identifier; converting the linked data to a numeric format; and converting the numeric format data to a common unit system. The method further comprises determining the most informative of the common unit system data, wherein the most informative data are a signature profile indicative of physiological status. In a related embodiment of the invention, the data comprise metabolite data and at least one other type of data. In another related embodiment of the invention, the data comprise metabolite data and at least two other types of data.

In further embodiments of the invention, a signature profile consists of one type of data, such as RNA data (for example, gene expression data), phenotypic data (visible or diagnostic trait), metabolite data, protein data (such as a 2D gel), or DNA data (such as SNP information). In another embodiment of the invention, a signature profile consists of two types of data, such as RNA data and phenotypic data, or RNA data and metabolite data, or any paired combination of the above. In another embodiment of the invention, a signature profile consists of three types of data, such as RNA data, metabolite data, and phenotypic data, or any three-way combination of the above. In another embodiment, a signature profile consists of four types of data, such as RNA data, metabolite data, DNA data and phenotypic data, or any four-way combination of the above. In another embodiment, a signature profile consists of five types of data, such as RNA data, metabolite data, DNA data, protein data and phenotypic data, or any five-way combination of the above. In yet another embodiment, a signature profile consists of a plurality of types of data.

The most informative data is the data most informative for the physiological state of interest. The most informative data is, for example, but not limited to, data exhibiting the most statistically significant change as compared to a baseline, or is data exhibiting the most unusual or unique characteristics, or the characteristics which are most predictive of, or most often correlate with, the physiological state of interest. The most informative data may, for example, be a group of relatively small changes in physiological state, rather than one large change. A powerful feature of the signature profiles of the invention is that there is no upper limit on the number or types of data that can be incorporated into the profiles, thus allowing vastly more complex, and more representative, signature profiles to be generated than has been previously possible. Another feature of the signature profiles of the invention is that, because the methods of the invention may be applied iteratively, a signature profile for a particular use, such as diagnosis of a disease state, or identification of exposure to a toxin, can continue to be refined and improved as more data is collected. The addition of more data does not necessarily lead to an enormously complex signature profile, with many data measurements. Rather, in one embodiment, it leads to reduction of the data and identification of the most valid indicators of a particular perturbation.

Various embodiments of the invention provide methods and systems for the development of, for example, signature profiles for diagnosing physiological states, including disease stages, and for providing a prognosis of a disease state, thereby determining which therapeutic program to apply. A physiological state of an individual is then monitored to determine whether the therapeutic program as applied is providing a return to a desired state. If not, or if undesirable side effects are observed, the therapeutic program is adjusted to improve its efficacy. The individual is monitored throughout the treatment/disease process, so that the therapeutic program is a dynamic, iterative process that is constantly adjusted or fine-tuned to suit the individual's needs. Further embodiments of the invention provide methods and systems for the development of signature profiles useful as indicators of exposure to particular chemical or environmental toxins.

Figure 3:
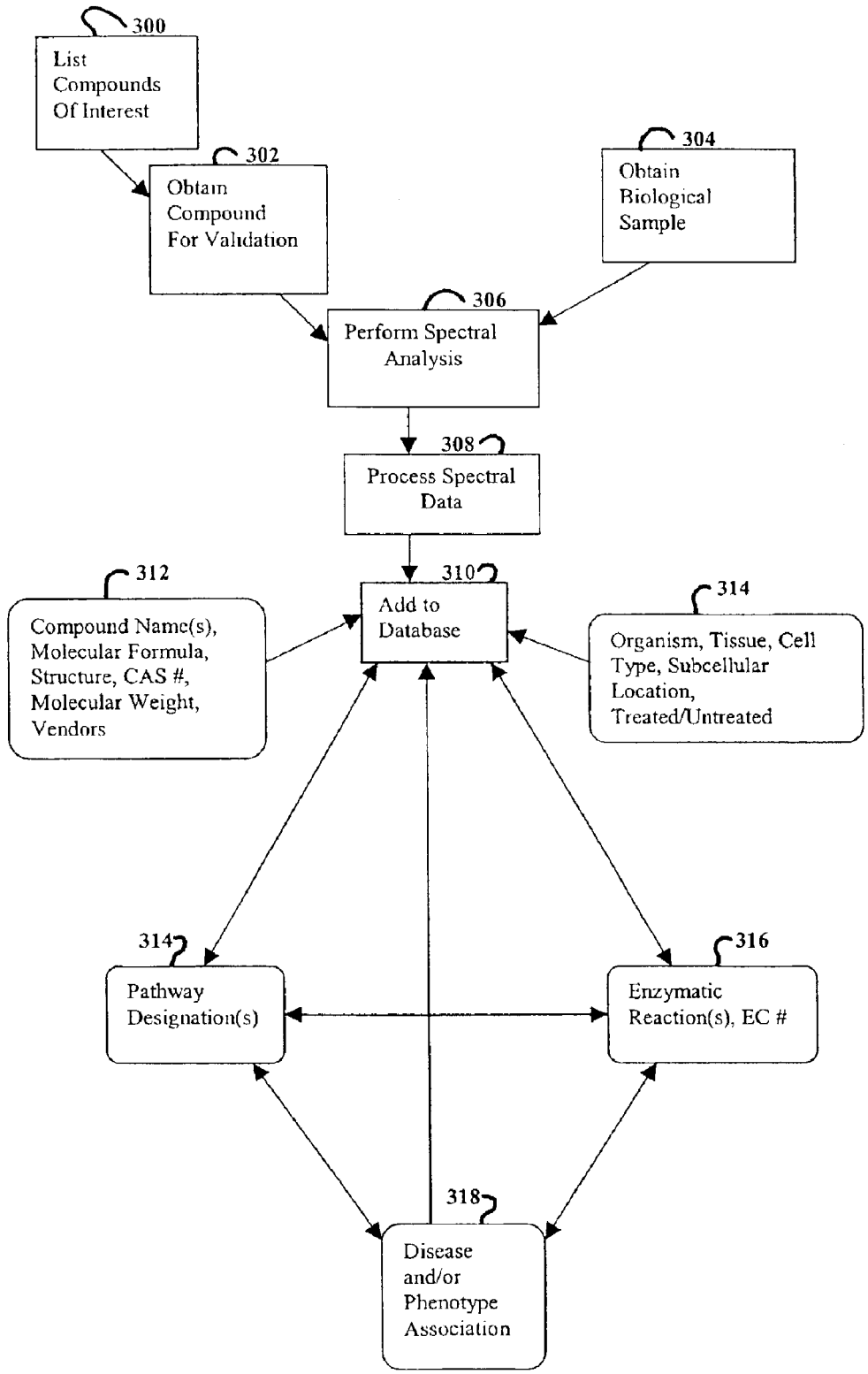
FIG. 3 is a diagram representing the construction of an endogenous metabolite database.

A database of endogenous metabolites for analysis of biological samples is useful in determining an individual's physiological state. The present invention provides methods and systems for creating a database of endogenous metabolites that provides information pertinent to biochemical pathway designation and disease or phenotype association for compounds of interest, and provides data useful in a coherent data set. As illustrated in FIG. 3, a nominated compound is examined by one or more metabolite analysis method(s), also called spectral analysis methods, such as liquid chromatography (LC), high-pressure liquid chromatography (HPLC), mass spectroscopy (MS), hyphenated detection methods such as MS-MS or MS-MS-MS, gas chromatography (GC), liquid chromatography/mass spectroscopy (LC-MS), gas chromatography/mass spectroscopy (GC-MS), Fourier transform-ion cyclotron resonance-mass spectrometer (FT-MS), nuclear magnetic resonance (NMR), magnetic resonance imaging (MRI), Fourier Transform InfraRed (FT-IR), inductively coupled plasma mass spectrometry (ICP-MS), and the like. Resulting data are processed, characteristics of the compound are noted (for example, retention time, intensity, and mass), and information is stored in the database. In addition to spectral characteristics, the database of endogenous metabolites can contain any information or data pertaining to the compound. This information can include, but is not limited to and need not include, compound nomenclature and synonyms, chemical structure, molecular formula, molecular weight, Enzyme Commission number (EC #), Chemical Abstracts Service number (CAS #), vendor information, biological sample types in which the compound is found, enzymatic reactions and/or biochemical pathways in which the compound is involved, and disease states or phenotypic characteristics with which the compound is associated. It is important to note that only one piece of information is required for a compound to be eligible for entry into the database of endogenous metabolites, so that, for example, as soon as a spectral peak is consistently observed or a compound is identified, it is added to the database. The database of endogenous metabolites is updated, and information continually added as it becomes available, so that linkage of compounds to gene function, biochemical pathways, and physiological states becomes more complete over time. It is understood to a person skilled in the art that any information from the database of endogenous metabolites which is to be included directly in a coherent data set must first be converted to a numeric format.

A database of endogenous metabolites is useful in linking data contained in coherent data sets to enzymatic reactions and biochemical pathways, and ultimately linking to associated diseases and/or phenotypes. It is generally accepted that metabolic responses of living organisms are altered by genetic makeup (or change), disease state, chemical (including therapeutic) treatment/insult, or environmental insult. An insult, as used herein, refers to an injury to an organism or one of its parts, or something that causes or has a potential for causing such injury. Air pollution, for example, is accepted to be one type of environmental insult. Other types of chemical and environmental insults to humans and animals include, but are not limited to, exposure to pesticides, exposure to industrial wastes, diet and changes therein, and weather changes. It is understood that although some types of chemical treatment are intended to, and do, have positive effects in the treatment of disease, the same chemical treatment may have detrimental effects as well. Other types of chemical and environmental insults to plants include, but are not limited to, exposure to pesticides, exposure to industrial wastes, exposure to temperature changes, exposure to low light conditions, exposure to changes in the amounts of nitrogen and phosphorous available in the soil, exposure to drought, exposure to salinity changes in the soil, and exposure to too much moisture. Thus, the methods and systems of the invention are useful for understanding the relationship between biochemical response and disease and/or phenotype association. As illustrated in FIG. 3, once any of the three information fields of enzymatic reaction, biochemical pathway, or disease or phenotype association is known, it is possible to link to the other information fields, thus maximizing the efficiency with which new correlations are made with research data. The database of endogenous metabolites is a dynamic information source, meaning that more information is entered into it as data becomes available, making pathway correlations and linkages more complete.

While not typically associated with gene function, forensic sciences are important as a research field, especially in the area of suspect identification through analysis of biological evidence collected from a crime scene. The methods and systems of the present invention are useful in generating a wealth of information from a small sample size, which is typical of crime scene evidence, and allows meaningful analysis of the information through the formation of coherent data sets, leading to more accurate interpretation of the data. This is useful not only in linking suspects to crime scenes, but also, for example, in the identification of unknown deceased individuals, determination of toxicology involved in death, and determination of the specifics of drug or alcohol abuse when it is an element of a crime. Forensic pathological and toxicological results are complex and often difficult to interpret. The present invention improves the acquisition of useful data from crime scene evidence and the subsequent analysis of the data, making interpretation of results and presentation in legal proceedings more efficient.

The present invention introduces coherent data sets as a way to manage biologically relevant data by making them analytically comparable, including disparate data from different indicators of the biological status of an individual or organism. Prerequisites for creating a coherent data set are integrated data and a baseline value for each type of data used to measure various biological indicators. In biological experimentation, measured values reflect the sum of several types of variation. A baseline, or reference, is needed so that biological variation can be distinguished from variation due to experimental error. In the methods and systems of the invention, data are converted to a common unit system relative to a control (the baseline). A control, or reference, can be as typically thought of in a scientific experiment, wherein a rigorously controlled standard is included in an experiment. It can also be simply a measure of a sample or group of samples of interest, such as a group of samples from humans who are defined as healthy or having a particular disease state. The nature of the reference depends on the type of information sought and what is most pertinent to that. It is accepted that a person skilled in the art can determine an appropriate baseline or reference.

Coherent data sets can be vastly more informative and biologically meaningful than data collected and analyzed from individual data streams. The present invention provides tools to integrate data and to create coherent data sets that encompass data from multiple indicators of biological status. The invention also comprises tools for analysis of coherent data sets to facilitate the identification of product leads, determination of gene function; identification of product candidates; production of a compilation of health or wellness profiles for prognostic and diagnostic use; determination of compound site(s) of action; and identification of unknown samples, such as in a forensic setting.

The methods and systems of the present invention are applicable to any organism or cell culture system and are flexible enough to accommodate data from any combination of biological indicators. Tools of the present invention are provided in such a way that data from additional technologies or sources can be added as each is developed and adopted in a scientific community, or excluded as desired. It is understood that disparate data are derived from different indicators of a biological status of an individual or organism. For example, different physiological indicators include DNA, RNA, proteins, metabolites, and phenotypes, and are measured using a variety of different technological approaches such as, but not limited to, DNA sequencing, gene expression analysis, 2D gels, mass spectrometry, NMR, and direct measurement of various phenotypic traits. Newly developed technologies are likely to improve identification of gene function and product leads in a high throughput environment and data from emerging technologies can be readily incorporated into coherent data sets. The methods of the invention are suitable for a broad range of applications in industry, government, and academia. With the present invention, the standard for the generation of coherent data sets produces a system for high throughput, automated data analysis to identify gene function and leads for product development. The invention further provides methods for creating, managing, processing, and using coherent data sets specifically for the purpose of predicting gene function and compound site of action, the results of which can lead directly to product development.

Figure 4:
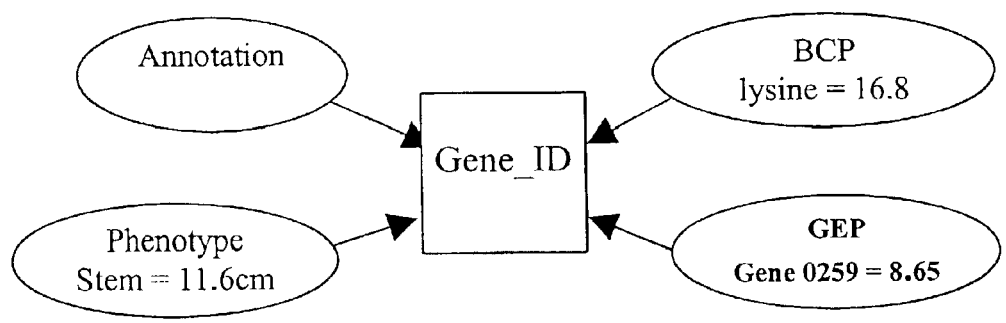
FIG. 4 is a schematic diagram illustrating an example of integrated data. In the example, gene expression was experimentally altered for a particular gene identified as Gene_ID. The unique gene identifier, Gene_ID, is linked in a computer tracking system to the gene annotation, the relative amount of gene substrates/products, the relative amount of gene transcript, and the phenotype of the organism in which the gene was altered.

Current capabilities to generate integrated data are not sufficient and are oftentimes highly inefficient, resulting in a loss of data. FIG. 4 illustrates how the concept of coherent data sets shifts the focus from relatively simple gene identification schemes in integrated data to a "rich annotation" that includes analysis from coherent data sets in addition to traditional annotation. It is helpful to employ biological resources to validate functional predictions. As validated predictions are added to the annotation database, the database becomes increasingly more valuable.

The present invention provides methods and systems that can greatly improve the reliability and efficiency of gene function determination and lead discovery, including enabling technologies such as generic methods and tools to integrate data and to generate coherent data sets. Modular tools can be utilized to efficiently analyze coherent data sets, but are not necessarily required to generate coherent data sets. The present invention also provides methods and tools that enable the efficient integration of data, and the creation and testing of coherent data sets to predict gene function independently of organism or cell culture system. The development of the methods of the present invention is an interdisciplinary project at the interface of biology, bioinformatics, and software engineering.

In one embodiment, the present invention uses real-time data streams from biological experiments from multiple research technologies. The development of analytical tools for biological research often occurs without sufficient input from biologists. Coherent data sets depend upon biologists to validate predictions made with the tools described herein. This biology-dependent approach to the development of analytical tools helps to strengthen and build the concept of coherence and prediction of gene function.

Integrated data are a prerequisite to the development of coherent data sets. With data streams from a variety of technologies increasing at an unprecedented rate, the problem of data overload is addressed by a richer annotation database that includes a wide range of information, including experimental results and inferential conclusions. The annotation database is the "data to knowledge" link, a key to gene function discovery. Data generating technologies currently in use include, but are not limited to, sequencing and annotation, metabolite analysis, gene expression analysis, and phenotypic analysis (morphometrics). Suitable biological systems include, but are not limited to, plants, such as *Arabidopsis* (*Arabidopsis thaliana*) and rice, fungal organisms including *Magnaporthe grisea, Saccharomyces cerevisiae*, and *Candida albicans*, and mammals, including rodents, rabbits, canines, felines, bovines, equines, porcines, and human and non-human primates. However, it should be remembered that the methods and systems of the present invention are applicable to any biological system. Informatics technologies can include bioinformatics, laboratory information management systems (LIMS), software engineering, and information technologies.

Figure 5:
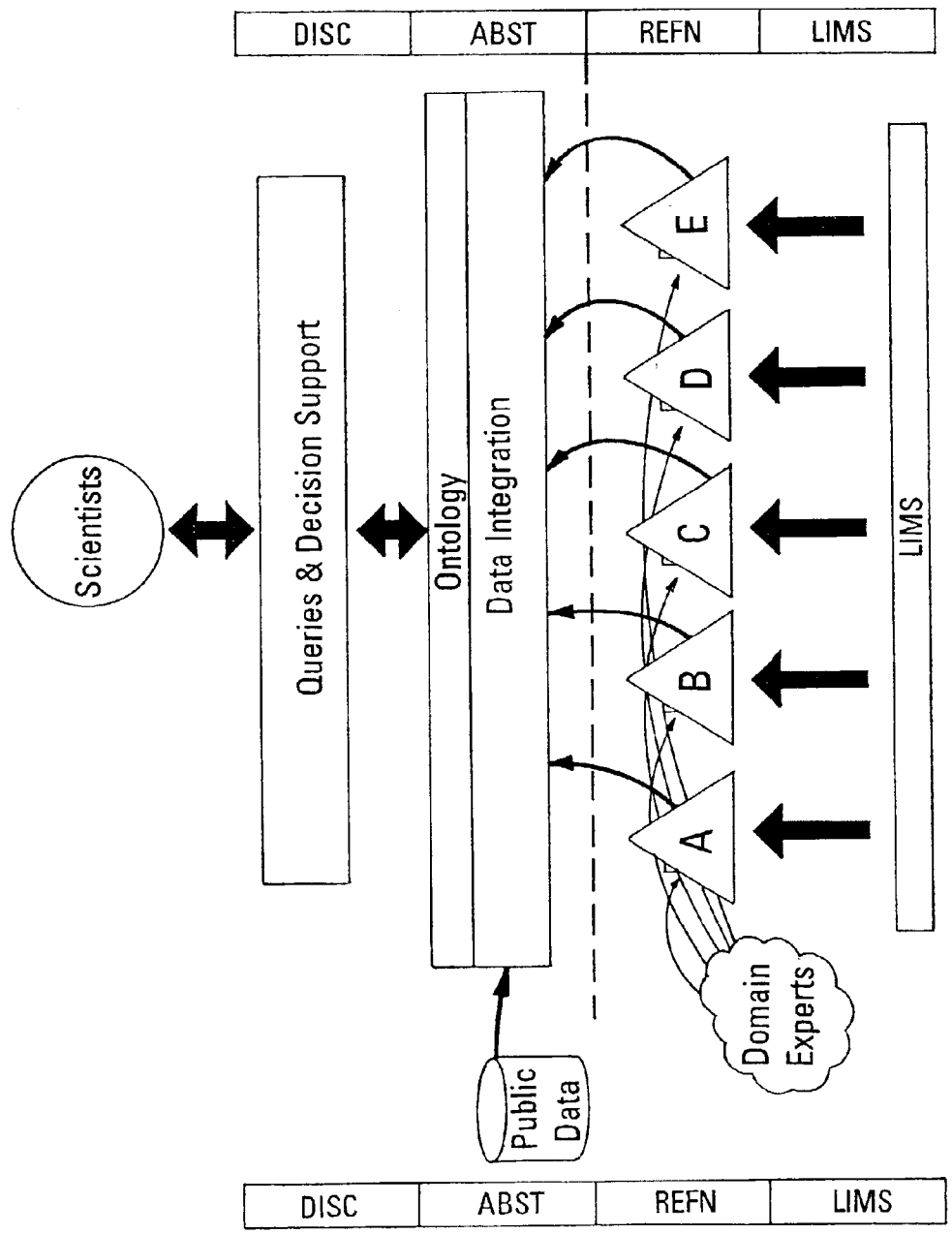
FIG. 5 is a schematic diagram illustrating FUNCTION-FINDER technology, comprising four interrelated components: databases, data processing, data analysis tools, and user interfaces.

The organization of FUNCTIONFINDER technology is shown in FIG. 5. FUNCTIONFINDER technology (Paradigm Genetics, Inc., Research Triangle Park, N.C.) comprises four interrelated components: databases, data processing, data analysis tools, and user interfaces. Data are extracted from a Refinery layer (REFN) and integrated in the Abstraction (ABST) layer. Public databases and other sources of relevant data are integrated in the Abstraction layer with proprietary data generated "in-house." Integrated data are used to generate coherent data that is stored in a relational database and subsequently extracted into coherent data sets for efficient access by Discovery layer (DISC) tools.

Data are generated from a plurality of instruments and stored in a variety of media, such as proprietary databases, LIMS, flat files, Excel spreadsheets, and other electronic storage methods well known in the art, and then loaded into an integrated database. For example, a refinery database can contain data related to soil samples, such as experimental plants grown in a flat (container) of soil. Soil sample data are stored in LIMS, and a computer program copies information from LIMS into the refinery. Gene mutation data related to the experimental plants is stored in a separate proprietary database. To populate the refinery, a computer program copies information from the proprietary database to the refinery database. To ensure accurate and efficient integration, integrity checking and enforcement steps occur as the data are loaded to the refinery. Integrity checking and enforcement further ensures that the data in the database are fully integrated, properly identified, and linked to all associated data. Data in the refinery belong to, or are uniquely associated with, a measurement set, a collection of measurements related to an experiment. One aspect of enforcing integrity is to ensure that each data point belongs to, or is associated with, a measurement set. The integrated database stores data in a tree-like structure, so that a measurement can be linked to other measurements further up the tree, and measurements further down the tree can be linked to the integrated database. Integrity checking further ensures that all upward links are present and valid when a data point is stored.

In one embodiment, the efficiency of data integration is improved using, for example, DiscoveryCenter software (Lion bioscience, Inc., Cambridge, Mass.), including components for data integration at the refinery and abstraction layers, as well as components for presentation and analysis at the discovery layer. DiscoveryCenter includes DataMarts (mini data warehouses) for sequence, expression, and genotyping data and IBM's DiscoveryLink (IBM Corp., Armonk, N.Y.) technology for federated data management. DiscoveryCenter uses DataMarts and DiscoveryLink technologies to concertedly address a wide range of data integration needs in life sciences research. FUNCTIONFINDER and DiscoveryCenter contribute components to support a comprehensive, integrated environment for gene functional analysis. One embodiment of the invention involves having a first research group or company generating complex integrated data sets emanating from several technologies, including sequence and annotation, metabolite analysis, gene expression analysis, and phenotypic analysis, with a second research group developing data integration technologies spanning biological and chemical information to generate flexible, integrated systems for gene function analysis.

An alternate embodiment of the invention supports, for example, two parallel approaches for identification of leads for pharmaceutical or pesticide product development: 1) testing compound site of action, and 2) conducting genomic research (functional gene knock-outs). In a gene knock-out experiment, the goal is to identify the function of a gene that has been disrupted. In a site of action (SOA) experiment, a goal is to predict a site or process in a cell that is affected by treatment with a specific compound. In either case, the approach is to perturb a biological system and then characterize the effect(s) of that perturbation as completely and comprehensively as possible. The present invention provides coherent data sets derived from multiple technologies/sources to further provide different views of the depth and complexity which characterize the status of a normal versus perturbed biological system. Although the gene knock-out approach leads directly to the identification of gene function, SOA experiments also contribute to an understanding of a biological system by providing information that can lead, indirectly, to identification of gene function. Accordingly, coherent data sets derived from SOA and genomic technologies may provide synergisms to gene function and site of action research.

The present invention provides methods and systems for the integration of data from disparate sources. Broad initiatives like the Human Genome Project generate data in quantities previously unavailable to the scientific community. Technology continues to advance the study of biological and other systems to an extent that the technical capacity to generate, capture, and store data is outpacing the ability to analyze data to a results-oriented endpoint. In recent years a number of new technologies have become available for generating data in life sciences research. Advances in technology include, but are not limited to, high-throughput sequencing for expressed and genomic DNA, the identification and sequencing of SNPs (single nucleotide polymorphisms), microarray experiments for measuring gene expression, various technologies for measuring protein-protein interactions and protein expression, combinatorial chemistry, and high-throughput screening. The aforementioned advances in technology, combined with more traditional technologies such as phenotypic measurements and metabolite analysis, provide a broad range of technologies for generating data. While advances in technology continue to provide the scientist with ever increasing data generation capacity, technology developers rarely consider the challenges of integrating certain technology types with existing technology types to facilitate integrated analysis of the information available from the combined data streams. The present invention provides methods and systems for producing integrated systems as the first step in creating and analyzing coherent data sets.

In order to support the creation and analysis of coherent data sets, proper technical infrastructure must be available. Appropriate computer hardware is supplied, for example, by the Sun Microsystems' E420 workgroup server (Sun Microsystems, Inc., Santa Clara, Calif.). Appropriate operating systems include, but are not limited to, Solaris (Sun Microsystems, Inc., Santa Clara, Calif.), Windows (Microsoft Corp., Redmond, Wash.), or Linux (Red Hat, Inc., Raleigh, N.C.). Appropriate software applications include, but are not limited to, relational databases such as Oracle 9.0.1 (9i) (Oracle Corp., Redwood Shores, Calif.), DB2 Universal Database V8.1 (IBM Corp., Armonk, N.Y.), or SQL Server 2000 (Microsoft Corp., Redmond, Wash.), and software for statistical analyses, such as packages available from SAS (SAS Institute, Inc., Cary, N.C.) or SPSS, Inc. (SPSS, Inc., Chicago, Ill.). In one embodiment, the server is the E420 workgroup server (Sun Microsystems, Inc., Santa Clara, Calif.), the operating system is Solaris (Sun Microsystems, Inc., Santa Clara, Calif.), and the software is Oracle 9.0.1 (9i) (Oracle Corp., Redwood Shores, Calif.), and statistical software is from SAS (SAS Institute, Inc., Cary, N.C.).

Each research technology presents unique integration challenges. Some research technologies produce data that reside in-house within a research organization, while some research technologies produce data that are located externally on the Internet. Data may be stored in flat-files on a local file system, in relational databases, in object databases, or on web servers. Since there are very few accepted standards in the bioinformatics industry, file formats, database schemas, and software interfaces are highly varied and difficult to reconcile. Vocabulary and nomenclature are not exceptions to the lack of standards. It is not uncommon, for example, for a single gene to have multiple names in multiple contexts with no simple mechanism for mapping them together or distinguishing one from another.

It is useful in data integration to employ relational and object-oriented database design, data warehousing, federated database systems, normalized and de-normalized schema design, pre-processing, and other techniques to produce high-performance, highly extensible, data integration systems. One approach to addressing data integration is developing powerful and flexible software and database components to integrate and manage data generated from multiple sources. For example, a flexible combination of data warehousing and federated database systems is used to balance performance with flexibility in a rapidly changing environment.

Those skilled in the art can participate in the development and adoption of ontologies for life science research and help standardize the current widely disparate vocabularies. A standard vocabulary is very helpful, not only for integrating external sources of gene function data that can be used as part of an analysis, but also for representing the results of efforts to identify gene function. The nomenclature and ontology portion of the database of endogenous metabolites (FIG. 3) utilizes standardization efforts as applicable. Using the present invention, one skilled in the art can investigate and develop representations for modeling functional information that facilitates queries and inferences regarding gene function. Current laboratory information management systems (LIMS) can be expanded into all technologies so that data pertaining to a unique identifier is reliably tracked. Defining components in LIMS as the samples are processed vastly improves the efficiency by which data are integrated in comparison to component definition subsequent to data generation and storage.

The methods and systems of the present invention provide effective ways to manage large amounts of information as is required to create coherent data sets. In one embodiment of the present invention, a method for creating coherent data sets comprises an integrated data set containing disparate data, such as sequence data, gene expression data, metabolite data, and phenotype information.

A first step in processing disparate data is to create an inventory of types of information requiring integration. In addition to sequence data, gene expression data, metabolite data, and phenotype information, additional types of information include, but are not limited to, 3-D protein structural analysis, protein expression, biochemical pathways, genotypes (including polymorphisms), SNPs (including haplotypes), and scientific literature. The identification step involves working with scientists to determine the types of data that contribute to the knowledge of gene function. A second step in processing disparate data is identifying the specific sources of each type of information and the specific integration challenges for each. For example, one may determine that the GenBank database (National Center for Biotechnology Information, Bethesda, Md.), the SWISS-PROT database (European Bioinformatics Institute, Cambridge, UK), and an organization's in-house sequence repository are the key sources of sequence annotation data. By implementing an embodiment of the present invention, one skilled in the art can then determine the location of the information and the technology necessary to access it. For example, GenBank and SWISS-PROT are available on the Internet and accessed through a World Wide Web connection, while an in-house sequence repository is usually located in-house, such as an in-house repository stored in a relational database on a central server. As such, in an alternate embodiment of the present invention, a set of components are utilized for downloading, processing, and storing GenBank and SWISS-PROT sequence data and annotations associated therewith. Specific data sources required to complete the process and locations of the same are determined by interviewing scientists and bioinformaticians, with ongoing efforts to remain current with the state-of-the-art.

Data integration systems of the present invention are designed to handle the types and sources of data that are identified in the first two steps as described above. For example, data warehousing, federated database management, text indexing, precomputation, and several innovative technologies are combined to form a robust, flexible, and powerful data integration system, comprising a third step of the present invention in processing a broad range of data from a plurality of sources. The third step utilizes an iterative design and review process whereby software engineers and scientists collaborate on the design of the system.

A fourth step in processing disparate data is the construction of a data integration system based on designs produced in the previous above-described steps. Construction involves implementing software and databases to fulfill specific requirements, typically specifications from software engineers, with support from project management and testing resources, as well as consultation from domain experts.

A fifth step in processing a broad range of data from a plurality of sources is the integration and representation of gene function data. The expressive power of vocabularies and ontologies currently in use within the scientific community are evaluated to describe gene function. Ontological terms are applied to the results of biological studies, such as site-of-action (SOA) studies, to determine whether the terms are expressive and exacting enough to describe the gene function data that is inferred from coherent data sets. An initial ontological assessment provides a starting point for a process of refining and standardizing a vocabulary of gene function that proceeds in iterative cycles throughout the duration of a project. At each iterative stage of refinement, the vocabulary is applied to integrate external sources of gene function data and gene functions identified by ongoing analysis of coherent data sets. The kinds of statements used to characterize gene function are based on the analysis of coherent data sets. Development of data representations for gene functions are used to query and apply the information produced.

The requirements for the LIMS employed with the integration of data for the present invention are carefully identified and implemented. LIMS are employed in most research organizations and are generally well-known in the art to facilitate data capture and storage, typically allowing the automation of many routine data management and processing tasks. Unfortunately, each research technology and data type usually has its own specific LIMS, and LIMS from different technologies do not communicate well with one another. Tools for integrating multiple technology-specific LIMS into a common framework include key components of the data integration system of the present invention. A suite of tools is developed by those skilled in the art for managing data coming from each type of LIMS, and modules are developed for moving data between the suite of tools. Data vehicle modules can validate data on both the sending and receiving sides, following common LIMS rules for sample handling throughout. Alerting mechanisms are provided to bring errors to a user's attention and to protect data integrity.

Once the data integration system is in place, the efficiency of the integrated data is measured. Two primary metrics are used to measure the efficiency of the data integration systems: 1) time savings provided to downstream users of the system by having integrated data versus working with the data in an unintegrated manner; and 2) the time required to integrate additional data sources into the system. Measuring the time savings from having integrated data requires a comparison between a user performing an operation in the integrated system versus performing the same operation on data that has not been integrated. In the unintegrated case, the user must look up all of the relevant information in each of the data sources individually, then integrate the information by manually entering it into a report or an analysis tool. If the number of data sources or the size of the data set is large, manual entry can be extremely time-consuming. Integration systems sold by a vendor, such as Lion bioscience, can reduce the effort required to pull together large amounts of disparate data by as much as several orders of magnitude. In some extreme cases, weeks of work in an unintegrated system can be reduced to mere minutes of work in an integrated system.

Manual integration of data from different technologies requires a great deal of manual integration effort, in the order of hundreds of hours for a relatively small experiment, and up to thousands of hours for a larger data set. Time required to integrate data is reduced dramatically by developing tools and data structures to efficiently integrate multiple data sources in a repeatable fashion. The time and effort required to integrate a new data source into the system is impacted by data source size, complexity, and similarity to previously integrated data sources. Larger data sets require more engineering effort to design a scalable solution, tune performance, and to implement backup and recovery strategies than do small data sets. More complex data structures (such as sequence annotation) require a great deal more design work to integrate than do simple data structures or data structures which are fairly easy to reduce to a simple format (such as gene expression data). Finally, it is usually much more straightforward to integrate a new data source that is very similar in structure to a data source that has already been integrated, e.g., integrating sequence records from the EMBL database (European Molecular Biology Laboratory, Cambridge, UK) after GenBank sequence records have been integrated.

One aspect of the data integration system of the present invention is to enable integration of previously non-integrated data sources. The present invention provides a system that is fully scalable (i.e., handles a range of data sizes), handles complex data structures, and facilitates integration of a new data sources similar to subsisting integrated data sources. User time required to integrate each new data source in operator-hours, taking the size, complexity, and similarity of the data source to subsisting integrated sources into account, is then measured. Thus, the overall time required to integrate previously non-integrated data sources decreases over time in the integration system of the present invention.

Once the data are integrated, the creation of coherent data sets occurs. A coherent data set is an integrated data set that is transformed through a series of protocols and statistical analytical methods to create a comprehensive data set. Consequently, data from multiple indicators of biological status are compared to one another and analyzed using the same tools or suite of tools. A coherent data set (or group of coherent data sets) creates a biologically relevant, virtual map of cellular processes. Coherent data sets are vastly more informative than integrated data from individual data streams for identifying gene function and other leads for product development.

In one embodiment of the invention, a biological system is perturbed and the effects of that perturbation are characterized as completely as possible. To quantify the changes due to the perturbation, all measurements are compared to corresponding data from experimental controls (the baseline or reference). In any biological experiment, measurements reflect the sum of several types of variation. Variation may be due to natural biological variation, experimental process variation, and variation that is a result of the perturbation of the system that is the focus of the experiment. A baseline is a profile of measurements associated with a control. Use of the baseline is necessary to account for variation due to an intentional perturbation of the system and its precise inflection or deflection from the control.

To establish a baseline, sufficient control experiments are carried out to provide an understanding of the biological and experimental variation inherent in the technology. Establishing a baseline, that is, collecting data from control experiments that correspond to all types of measurements taken, makes it possible to transform all kinds of data formats to a common presentation. At a basic level, a coherent data set consists of a set of measurements that have all been standardized to a common (or commonly relevant) baseline. For example, all measurements could be expressed as a number of standard deviations above or below the mean of a baseline control. Establishing a baseline for each type of measurement makes it possible to weight each measurement with an appropriate level of sensitivity. That is, if the control shows very little variation for a particular type of measurement, then a relatively small difference in that measurement type can be significant. If the control varies widely for a particular type of measurement, then only relatively large differences in that measurement type may be significant.

The prerequisites for creating a coherent data set are integrated data and a baseline, or standard for each measurement type. In a research technology wherein data are collected for long periods of time (i.e. years), each set of baseline data potentially may possess different distributional parameters. That is, due to inevitable changes in any number of factors, growth environment, laboratory practices, raw materials, etc., a plant grown during one period may not be directly comparable to a plant grown a year prior to that period or, alternatively, a plant grown a year following that period. Therefore, strict guidelines are implemented to provide quality control within baseline measurements and to maintain the integrity of the baseline.

Methods and systems of the present invention were used to create a coherent data set with a relatively small but reasonably complex integrated data set from a herbicide SOA experiment in which 18 compounds were examined. After validating coherence for the SOA data set, it was expanded and coherence was reestablished, and a larger and more complex integrated data set describing 65 mutants (functional gene knock-out data) in *Arabidopsis* was added to the SOA. After establishing coherence for the expanded data set, the process was scaled and applied to even larger data sets that describe 600 or more *Arabidopsis* mutants. The process for developing coherence for each integrated data sets is largely iterative, so that with each new project, the creation of coherent data sets becomes increasingly straightforward.

An Integrated Data Set

Initially, integrated data from a small, well-defined compound (herbicide) site of action (SOA) experiment in *Arabidopsis* was used, as mentioned above. The integrated data comes from three data streams: gene expression analysis (GEA), phenotypic analysis, and metabolite analysis. Several of the tasks relating to the creation and testing of a coherent data set are repeated using larger and more complex data sets as more data and information become available. The creation and testing cycle is an iterative process.

Following the establishment of a baseline, methods are developed and automated to monitor changes in the baseline. Monitoring methods are similar to some types of automated quality controls that detect changes in the location or variation of a response. One skilled in the art can begin monitoring changes in the baseline by adapting quality control methods and exploring their suitability. Ideally, baseline-monitoring methods are largely data-driven. Alternatively, one can explore the use of methods based on external data (e.g. data from a temperature monitor, or from a LIMS system) that may indicate or identify baseline shift. In addition, one can utilize an algorithm for estimating the size of "windows" of data that share a common and stable baseline. Such an algorithm is useful in planning budgets for laboratory procedures.

Standard quality control measures in combination with a variety of decision rules are evaluated, process error rates are compared, and minimum sets of decision rules are developed. A number of commonly used rule sets are used. However, the false-positive and false-negative error rates of all rules sets work against each other. That is, if the rule set is larger than necessary, then (even if every rule is sound if used independently) the result can be an inflated false-positive error rate. Thus, the optimization of the rule set is performed by statisticians who can develop custom rule sets as needed.

Historical, known changes in a research technology are used to test the rule sets and to assess the process error rates. During development, many documented systematic changes are typically made to a research technology. A number of changes can affect the output of research technologies. This information can be used to test rule sets and assess their process error rates. For example, by developing a hybrid system that considers quality control-like decisions, but also uses external information about the laboratory procedures to make decisions, a system can determine whether it performs its function more robustly. A purely data-based decision system can be improved by utilizing information about changes in suppliers, materials, laboratory procedures, or the like. Development and testing of data-based methods for estimating "window size" for a stable baseline is also a useful approach.

Each quality control step is computationally intense. To address problems efficiently, the prototype data set is kept small, and the dependent variables screened to locate a small set that is known to be sensitive to changes in the experimental environment. Once a promising strategy is developed, it is tested and validated for the next, larger set of dependent variables.

Processing Integrated SOA Data: Toward Coherence

Each data measurement collected is standardized to a control or reference. If no matched control exists, then a similar control is substituted, the experiment repeated, or the data excluded. Data can be selected for comparability to compound concentration and response times according to baseline experiments. Using this data set, automated methods for standardizing data are developed. In one embodiment, algorithms are explored for transforming data to approximate normality and/or common variance before standardizing. In another embodiment, distribution-free methods for expressing measurements on a common scale are also explored. Such distribution-free methods are widely applicable because they do not depend on normality, constant variance, or other assumptions that may or may not hold true for a given set of data derived under process conditions that are monitored and evaluated against established process error models.

Standard algorithms are developed for transforming data to normality with constant variance. In one theory, any distribution can be transformed to a normal, or Gaussian, distribution. In practice, and for a given set of data, finding the right transformation can be challenging. Computer algorithms exist for suggesting an appropriate transformation. Algorithms also exist for suggesting a variance-stabilizing transformation. Sometimes these two transformations are the same (or similar), while in other instances a transformation that solves one problem makes the other worse. On the other hand, one of a small number of transformations often helps greatly, even though it may not be the "analytically correct" choice. Such transformations are assessed for how effective, and efficient in computer processing time, they are for managing process variation and how they affect the informative value derived from the inherent biological variation in the system.

Distribution-free methods are assessed for expressing data on a common scale. Distribution-free methods based on ranks, medians, or interquartile ranges are commonly used, and are often found to be nearly as powerful as standard methods applicable to a wider variety of data types. The two-sample location and dispersion tests suggest methods for adjusting data sets to a common location and/or spread. In addition, the usual standardization techniques are adaptable to more robust statistics (such as the median and interquartile range) in a statistically sound manner. Small integrated data sets are readily developed through the use of these methods. The integrated data set is screened and a few variables are chosen that are clearly non-normal and have non-constant variances. By focusing on a small set of "least favorable" variables, the quickest and most robust results are achieved. Methods developed in this way that show promise are tested and verified on a larger variable set.

Data that are not normally distributed can be transformed to a normal or Gaussian distribution. For example, GEA and metabolite analysis data are not normally distributed, but appear much more so after being converted to a logarithmic scale. The conversion step is important in that many statistical analyses behave more reliably on normally distributed data. A caveat to conversion is that some data sets may not be readily transformed to a normal distribution. In such cases, "robust" analysis methods are used that do not rely on an assumption of normality, and may work reasonably well even if the data set is not normally distributed. Key characteristics of a coherent data set are whether the data can be transformed to normality and whether assumptions of normality will be necessary.

Values are assigned to all potentially valuable data measurements. Metabolite analysis and GEA technologies have upper and lower limits of detection. If a data point falls outside of the limit, then no value is assigned. To avoid the loss of data and to create a more representative data set, values are assigned in cases where a data point falls outside of a predetermined limit. Compounds with known sites of action assist in clarifying if the assignments are not appropriate and modifications are made accordingly.

Selection of significant data depends on the amount of variability in the baseline control. In the herbicide SOA experiments, data that did not differ significantly from the standard by at least two standard deviations (corresponding to a 95 percent probability based on a normal distribution) is excluded. The determination of what data is considered to be significant can be changed and tested empirically for any given data set.

To establish coherent data, a degree of confidence is required with respect to data from all technologies contributing to an appropriate extent. Quantitative discrepancies of data from each technology are weighted to ensure adequately reflective analyses. In a human genomics study, GEA can provide data for all (estimated) 35,000 genes, and state-of-the-art technology in metabolite analysis could provide data for up to 500 or more metabolites. The significant quantitative differences in the amount of data generated from different technologies is accounted for to ensure that possible qualitative variations do not adversely affect coherence.

Data are assayed for coherence. The data are analyzed using a variety of multivariate analyses, applied appropriately by one skilled in the art. For example, the compounds are clustered based on the phenotypic data, and then are reviewed to determine whether they exhibit similar profiles when viewed in light of multicomponent metabolite analysis data and/or gene expression data.

Figure 6:
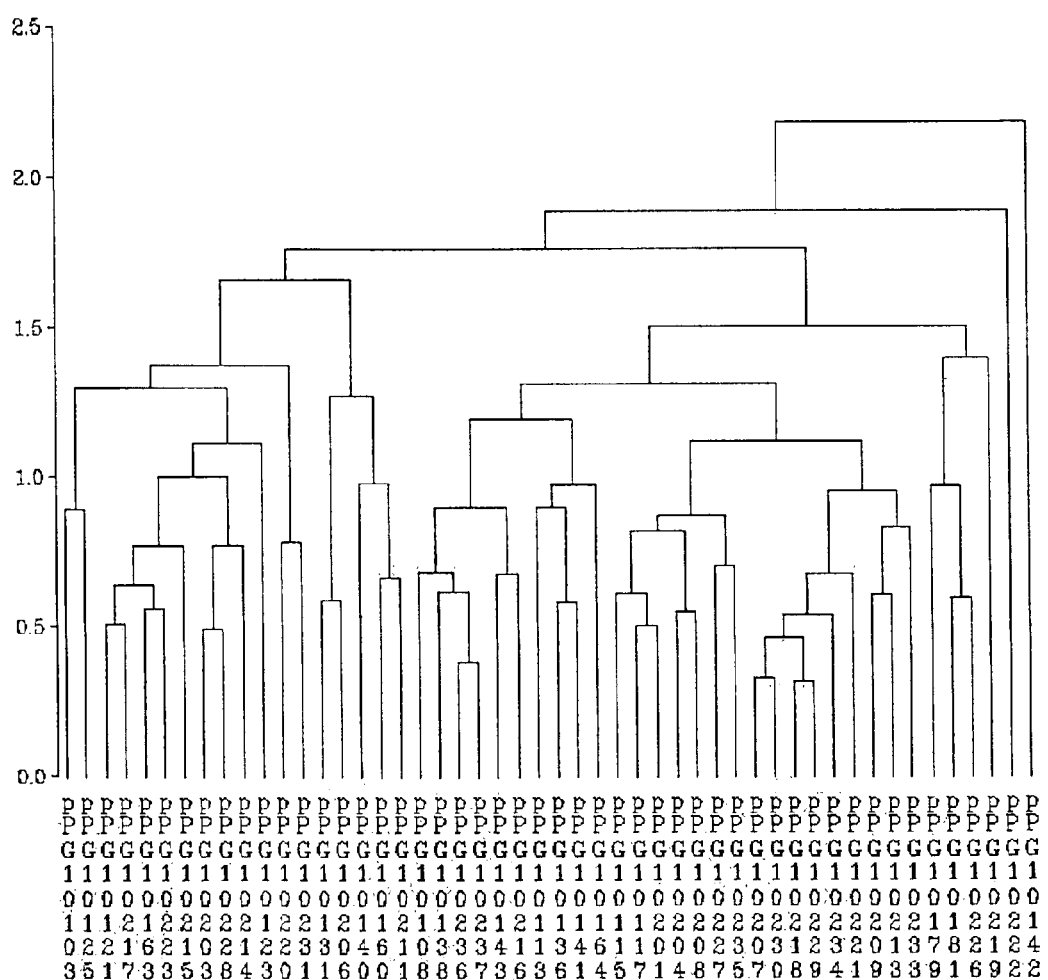
FIG. 6 is a graphical depiction of the results of a cluster analysis performed on phenotypic data corresponding to plants in which the expression of a particular gene was knocked out using antisense technology. The x-axis of the graph represents the particular gene identifier and the y-axis is the maximum distance between clusters.

Several statistical methods are used to test a coherent data set. For example, cluster analysis is performed and hypotheses formulated based on the results of the clustering. A well-designed cluster analysis can provide information leading to the identification of gene function, as genes that cluster together in this type of analysis may infer similar function. FIG. 6 illustrates an example of cluster analysis performed on phenotypic data. Additional analyses can be carried out to determine whether the hypotheses are valid. In one embodiment, a statistician visually evaluates cluster analyses and evaluates whether a coherent data set yields an expected result. If the result is inconsistent with that which is expected, each of the process steps is reevaluated.

If the results of the various analyses are consistent with expectations, a score is derived based on how close to ideal (normally distributed with constant variance) the data set is. This is taken under consideration together with a score that reflects the size and complexity of the data set. These scores make it possible to follow the progress of coherent data set development.

Once a coherent data set is established and validated, more information can be added and the set re-validated in an iterative process. For example, in the herbicide SOA experiment, the baseline was expanded by adding 100 additional compounds with known sites of action. The data was expanded by adding similar data from a different organism, for example a microbe. Data corresponding to the effect of the above-referenced 18 compounds on one or more microbes was provided as a useful data set for creating and testing coherence.

In one embodiment of the invention, a second integrated data set is used to create a coherent data set describing, for example, 65 *Arabidopsis* mutants with functional gene knock-outs. The data are from three data streams/biological indicators: gene sequencing and annotation, metabolite analysis, and phenotypic analysis. The larger data set is processed through one embodiment of the methods of the invention, that is, the data are standardized, transformed to a Gaussian distribution, numerical values are assigned, significant data are selected, and the data are weighted, or balanced. As with the smaller herbicide SOA data set, the data from the 65 mutants are then assayed for coherence by applying multivariate analyses and predictions, additional analyses are performed, hypotheses are validated, and coherence score and metrics are calculated.

Methods of the invention are scalable for creating and testing coherent data sets. Scaling includes repeating all of the methods of the invention described above for a larger integrated data set. For example, an integrated data set with 600 gene knock-out mutants is suitable as a large data set. In a particular embodiment, the data are from three different technologies: sequencing and annotation, metabolite analysis, and phenotypic analysis. In addition, other data sets and improved methods for integrating data are available to use in combination with the 600 gene knock-out mutants, creating an even larger data set. Preferably, most of the work to create coherent data sets is automated to produce a first-pass coherent data set that is reviewed through a user interface by a statistician who can input refinements to the process.

The methods of the present invention further provide steps that include multiple computational and analysis steps for producing a coherent data set. A number of analysis tools are developed or adapted for use in specific research technologies, including a standard suite of sequence analysis and comparison tools, such as, but not limited to, BLAST, Smith-Waterman, and Hidden Markov Model (HMM) searches. In addition, a standard suite of sequence analysis and comparison tools will likely include an open reading frame (ORF) prediction program called ESTscan. For metabolite analysis, there is Target DB (Thermo Electron Corp., Waltham, Mass.), a chromatographic database and analysis tool, that houses data on metabolite levels in plant tissues, performs automated quality control on the data, and aids in identifying unknown compounds. Additional analysis tools can be written using SAS (Statistical Analysis Software, SAS Institute, Cary, N.C.) to perform additional and more sophisticated analyses (such as discriminant analyses) and 2-D and 3-D visualization of metabolite analysis data.

There are also a number of SAS modules that operate on phenotypic data. These modules perform automated quality control and provide visualization for numeric and descriptive phenomic measurements. In addition, a number of SAS modules are developed that perform a variety of multivariate analyses and present tools for data visualization. These modules include a principle components and factor analysis module; a phenomic clustering module; and a discriminant analysis module, for applications, for example, to a plant phenotyping process. Other tools and databases are available for sequence, genetic, and gene expression information. Expertise is useful for integrating public domain and commercial analytic and visualization tools with open, extensible integration systems.

In theory, analysis of a coherent data set should provide new information not available by separate analysis of the individual data streams that contributed to the coherent data set. However, in creating a coherent data set, a multidimensional space is defined that is not optimal for analysis. One of the most daunting problems that must be considered when designing the analyses is the multidimensionality of a coherent data set. That is, as the number of dimensions (data streams) increases, the data that populates that "data-space" becomes increasingly sparse. This situation makes it difficult to draw relevant conclusions from cluster or other types of analyses. There are two simple approaches to solving this problem: increase the amount of data collected to populate the space, or find ways to reduce the dimensionality of the data to obtain relevant results from analyses. In practice, increasing the amount of data in many cases is often not economically viable, so an alternate preferred approach in many cases may be to reduce the dimensionality without losing information.

In one embodiment of the present invention, the dimensionality is reduced by selecting certain data sets for "pretreatment," for example, by calculating the correlation between complex profiles and then using the correlative data rather than individual profiles in further analyses. Technology specific analysis tools for are commercially available, but considerable effort is required to manipulate the output from any one tool and use it as the input to an unrelated tool without corrupting the data. For example, even when both tools are written in SAS, different software modules often require that data be in very different formats. Furthermore, users trained to operate the analysis tools are typically limited to bioinformaticists and biostatisticians, and domain scientists rarely have access to the modules or the appropriate training. Finally, very little is known about the most effective ways to present and display highly multivariate results.

Gene function technology tools used in the methods of the present invention are preferably designed as modules. A research scientist can request an analysis without having to specify the format of the input data. Preferably, the tools are visual, and whenever possible, analysis results are presented in graphical forms that are easy for non-statisticians to understand. Also, it is preferred that the tools are interactive. If a scientist indentifies an interesting set of data points, he/she can query the data set for more information on the points of interest, and define a permanent "research set" for the queried data points, providing an opportunity return to the research set for further analysis in another session.

Similarly, but on a larger scale, the definition of a useful pipeline of analyses can be archived for future re-use and analysis. With the availability of flexible analysis tools, a scientist can visualize and analyze coherent data sets and form hypotheses directed to gene function. The process of developing coherent data sets by employing the methods of the present invention facilitates gene function hypothesis formation by making data available in standard formats. In addition, data architects can determine standard storage architectures for input and output data, so that output from one tool can easily be used as input to another. A software engineering team can work with domain scientists and statisticians to develop user interfaces. The most challenging data display can yield a huge amount of information to an educated user. In such situations, one can address and interpret information using visualized multivariate data, as developed by domain scientists, statisticians, and engineers with expertise in visualization and computer-human interaction. Data analysis and management developmental processes can involve trial-and-error approaches as different visualization methods are examined and modified, prior to the derivation and adoption of solutions that are statistically sound and intuitively appealing.

To fully understand and utilize coherent data sets, tools and methods for predicting gene function (or compound site of action) are required. Such tools and methods entail reiterative development tasks that are developed using validated coherent data sets. Data in coherent data sets tend to be highly multidimensional. For example, even the smallest data set described herein represents 18 herbicide treatments for which samples are collected at three time points. For each sample, responses are measured for approximately 6000 genes, approximately 250 compounds, and about a dozen morphometric, or phenotypic, traits. Data dimensionality is reduced to determine an optimal degree of reduction. Dimension reduction is done via data pre-clustering, correlation analysis, principle components analysis, or regression analysis. Aggressive dimension reduction leads to a much smaller and more tractable data set, but there is a caveat that biologically relevant detail could be lost. Thus, some experimentation is useful to determine which data can be reduced without a loss in statistically verified quality.

Figure 7:
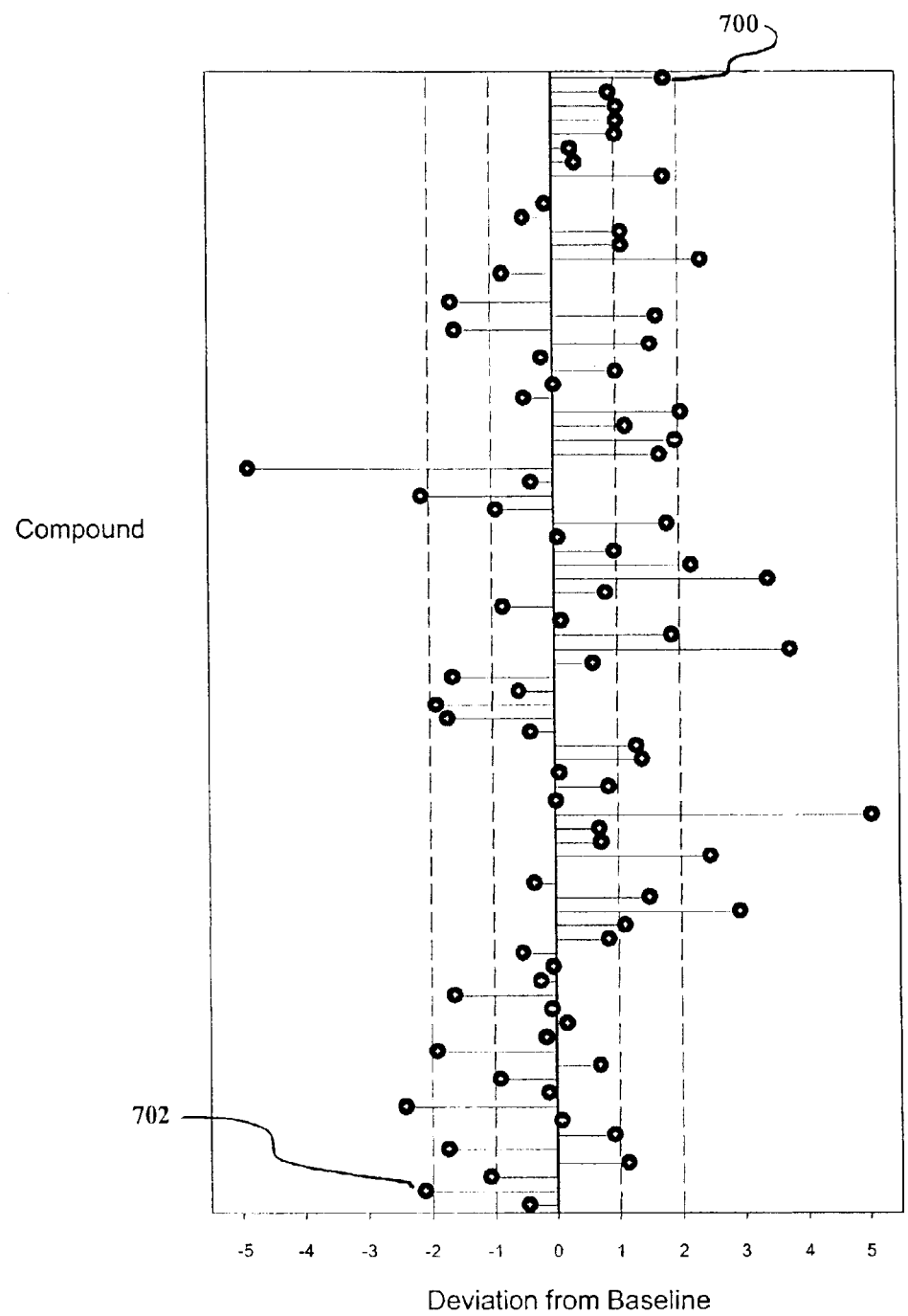
FIG. 7 is a graphical depiction illustrating the relative response of a multitude of compounds in a biological sample data relative to a baseline. Each compound is represented on the y-axis and is plotted as number of standard deviations from the baseline on the x-axis. For example, compound 700, sinapinic acid, is present in the sample at a response that is slightly less than 2 standard deviations above that of the baseline. Compound 702, hydroxyphenol pyruvic acid, is present at a response that is slightly more than 2 standard deviations below that of the baseline.
Figure 8A:
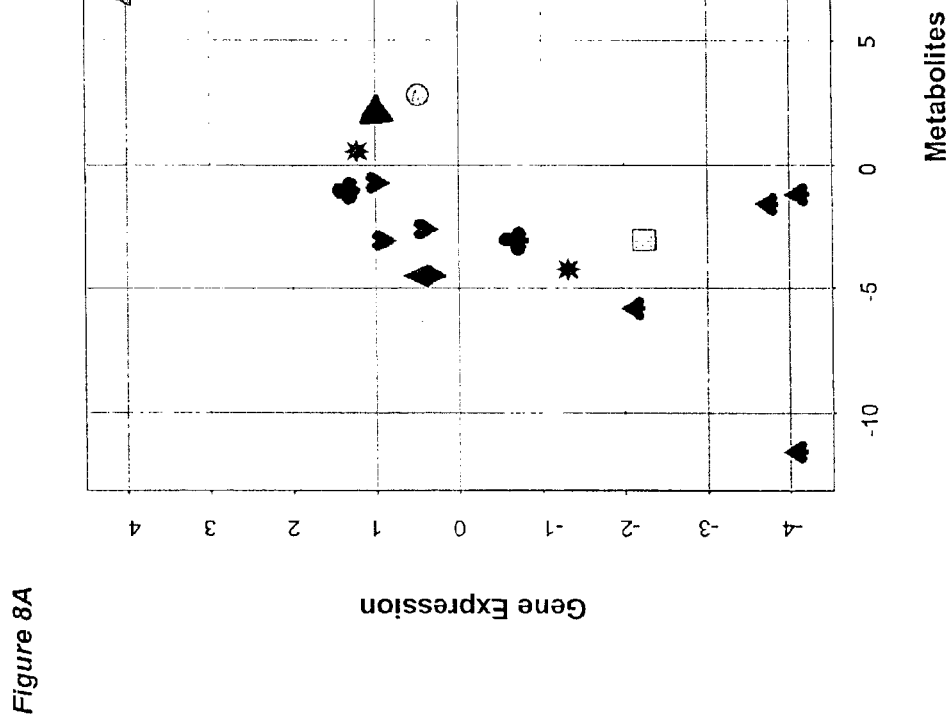
FIGS. 8A–8C are a visualization of principal components analysis of phenotypic, gene expression, and metabolite data collected for *Arabidopsis* plants treated with the eighteen different herbicides in Table 3. The data were normalized to a baseline prior to the analysis. Each of the nine herbicide site of action groups are represented by a separate symbol.
Figure 8B:
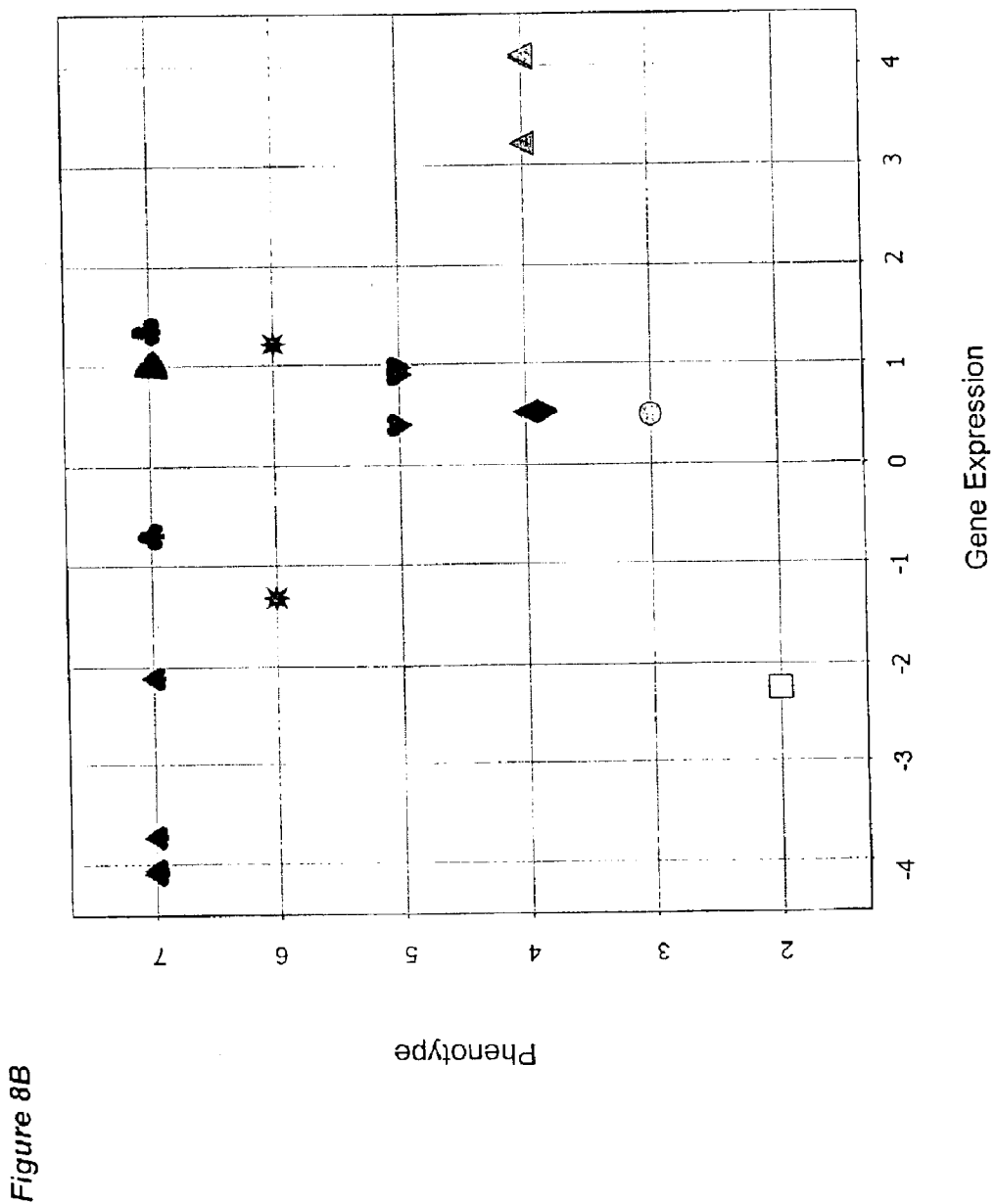
Figure 8C:
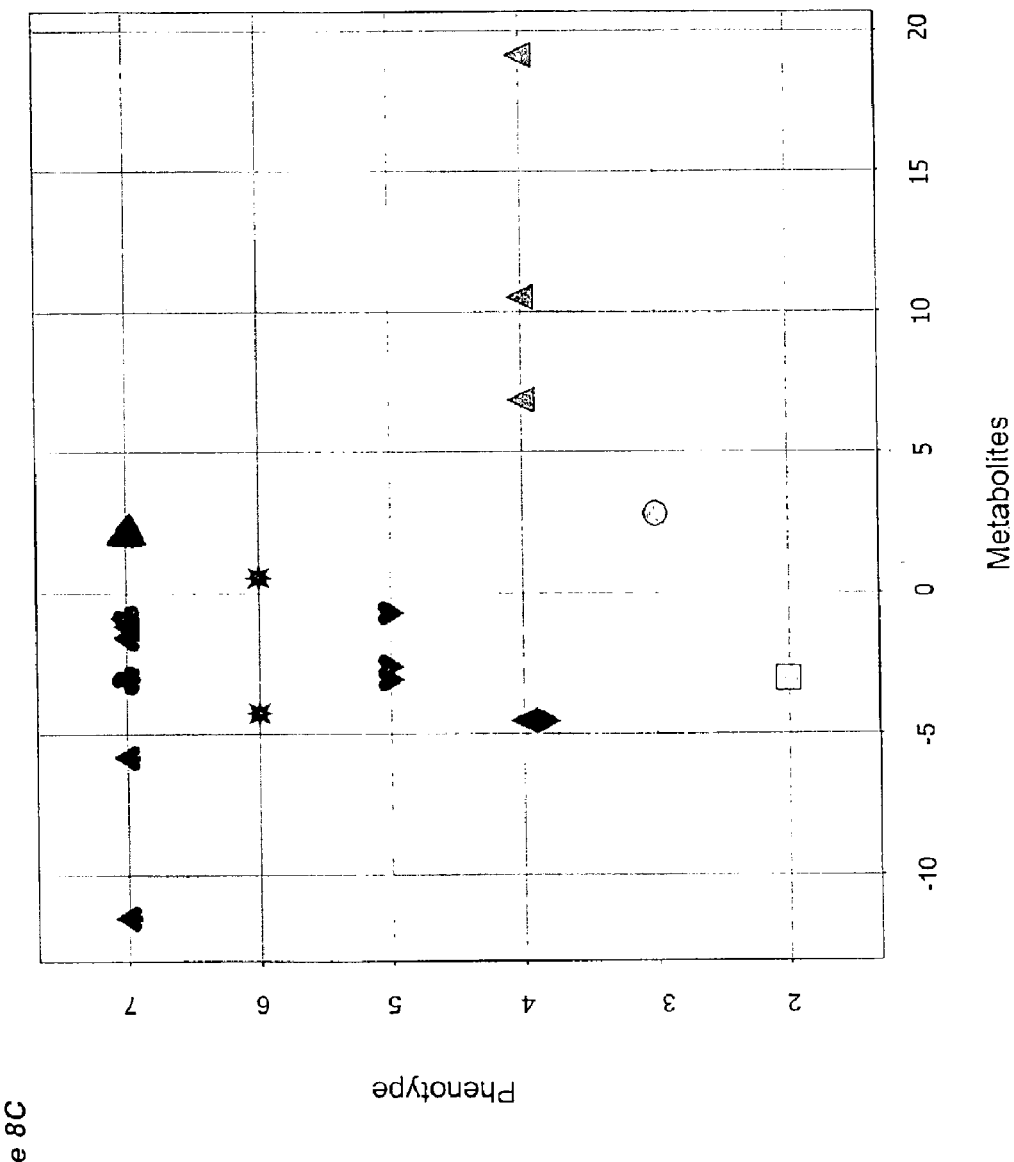
Figure 9A:
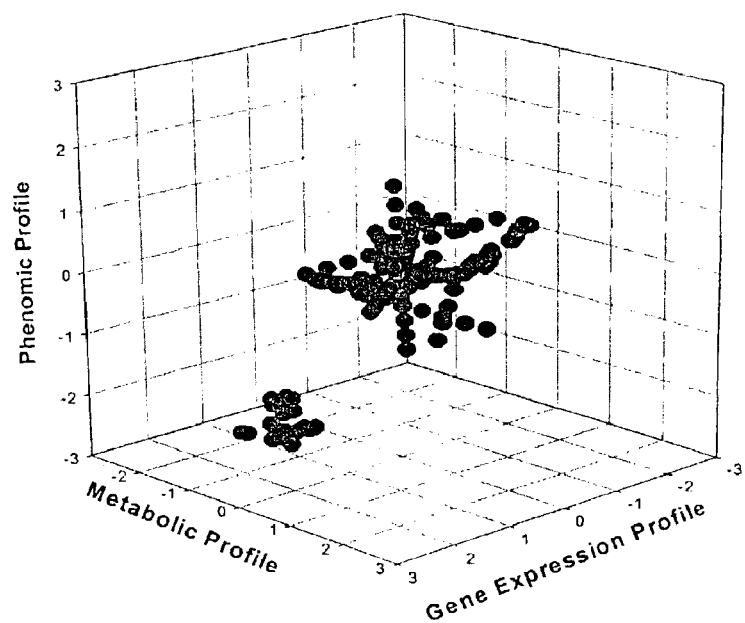
FIGS. 9A–9B are two different views of a 3-dimensional graphical depiction of 3 types of hypothetical data. The figure was generated to demonstrate that interpretation of data may change depending on the particular view. For example, at an axis rotation of 50° horizontal and 20° vertical (FIG. 9A) two separate clusters are observable, while at an axis rotation of 95° horizontal and 15° vertical (FIG. 9B) three separate clusters are visible.
Figure 9B:
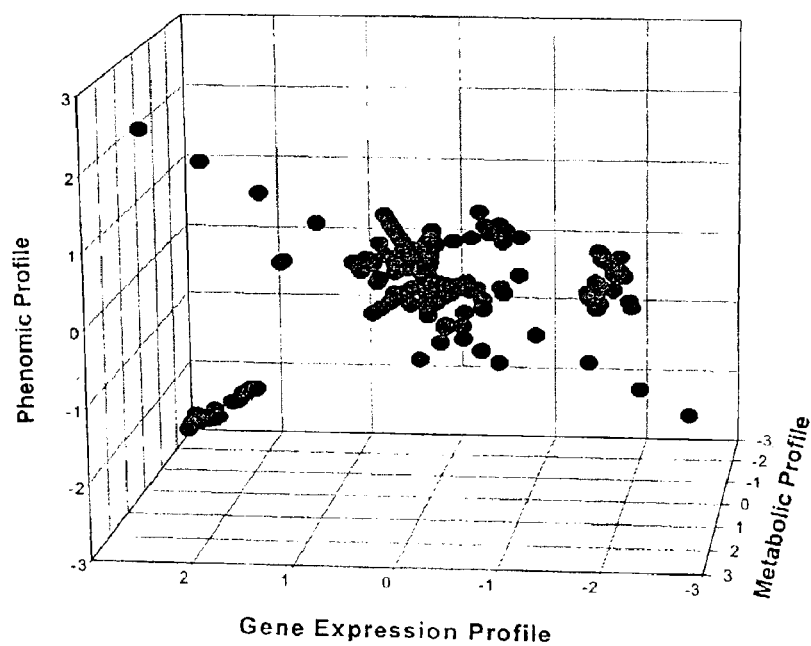

Following a reduction in data dimensionality, patterns and similarities are identified. A number of multivariate analysis tools are employed, such as, but not limited to, factor analysis, principle components analysis, cluster analysis, and discriminant analysis to identify patterns or similarities among the compounds (herbicides, for example) or genes (knock-outs, for example). Research scientists evaluate specific combinations of data and tools that are most informative with respect to identification of gene function. Different views of multidimensional data enable the research scientist to develop insights and formulate hypotheses directed to the relatedness of data. FIG. 7 shows an example of a tool that allows quick visualization of normalized data with respect to the baseline. FIG. 8 is an example of visualization of a two-dimensional comparison of data from two different technologies. FIG. 9 shows different perspectives of data made by using a three-dimensional visualization tool and illustrates the value of looking at complex data in a three-dimensional format. FIG. 9 parts A and B illustrate two different three-dimensional views of the same data set. Note that while in FIG. 9A, the data appear to fall into two discrete groups, but if the figure is turned in three-dimensional space and viewed from a different side (FIG. 9B), the data no longer appear to be in only two groups. FIG. 9 is illustrative of the fact that data from complex systems and/or complex data sets can become overly simplified and thus, misleading, when viewed in only two dimensions. FIGS. 7 through 9 provide examples of how complex data are visualized. In the embodiment illustrated in FIGS. 7–9, the data sets shown are from gene expression analysis, phenotypic analysis, and metabolite analysis. However, data could be from any combination of technologies or data types.

Figure 10:
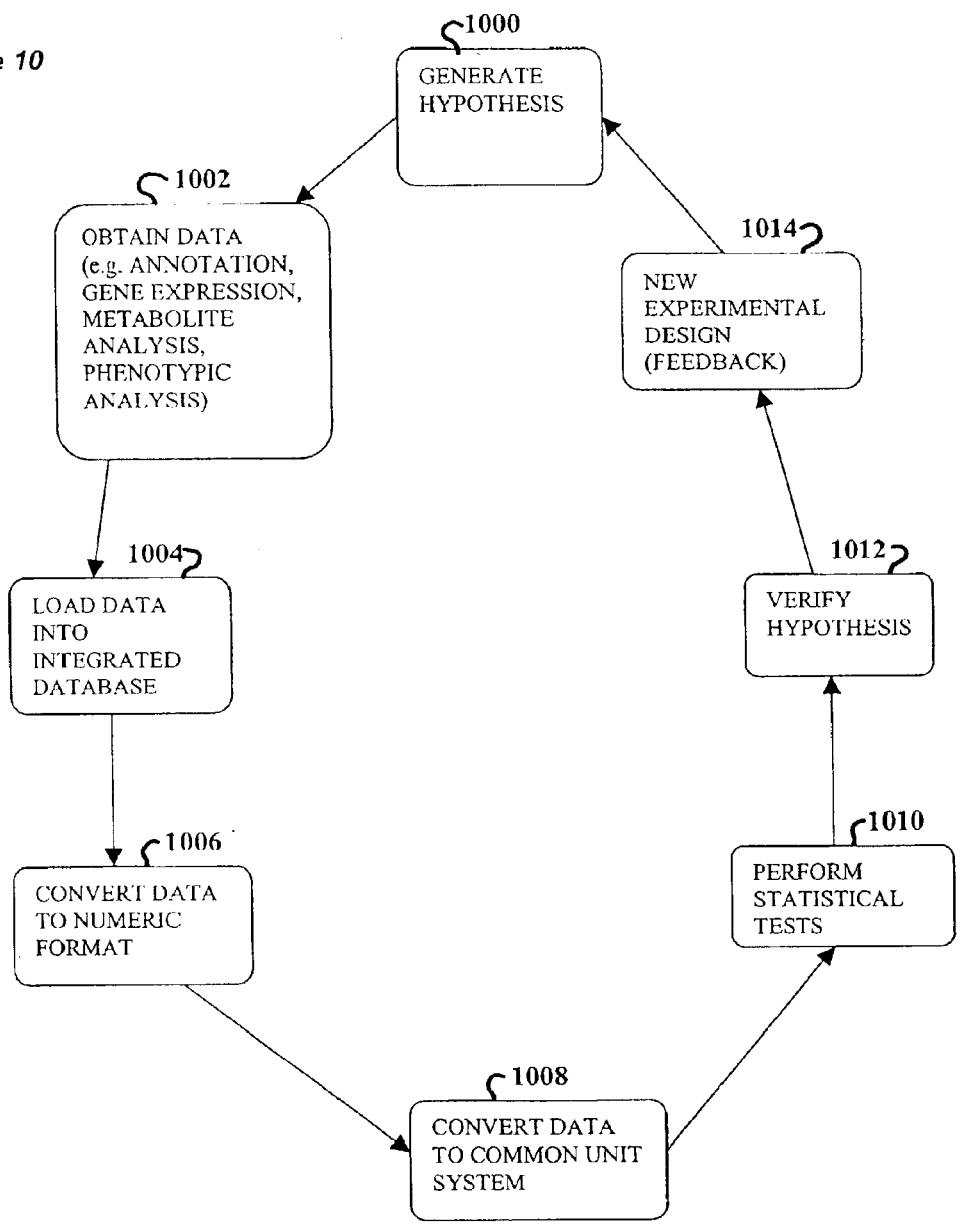
FIG. 10 is a diagram illustrating one example of the creation and use of a coherent data set, in which hypotheses are formed and tested by laboratory experiments.

The use of the present invention in analyzing complex data sets allows the formation of decision trees leading to hypotheses of gene function or site of action. Based on identified patterns, decision trees are derived to predict gene function or compound site of action. FIG. 10 illustrates one embodiment of the present invention demonstrating the creation and use of a coherent data set, in which hypotheses are formed and tested by laboratory experiments. In the case of the herbicide site of action (SOA) data set (Specific Example 2, infra), experimental results from compounds (herbicides) with known sites of action are used to test and refine the multivariate models. Using models that classify known herbicides with a high degree of accuracy, predictions are made with respect to herbicides having unknown sites of action. Predictions are validated in the laboratory, and the results (both positive and negative) are used to further refine predictive models. Similarly, for the gene knock-out experiments, data for genes of known function are used to generate predictive models. As part of the iterative process, if predictions for compounds with known site of action, or genes with known function are unreliable, then each step of the methodology from which the prediction is formed is reviewed and re-evaluated.

Criteria are established for selecting high-confidence predictions, and for calculating the extent to which high confidence predictions are produced as a percentage of a data set. Validated predictions formed by the methods of the present invention undergo further validation in a laboratory. Although time consuming, the results of laboratory validation studies enable the calculation of predictive success rate, further enabling monitoring of improvement in the quality of analytical tools.

In one embodiment of the present invention, a high-throughput system is used for applying methods of the invention to an analysis of complex disparate data. A high-throughput system for identifying gene function preferably utilizes automation of tools and methods for building predictive models. Automating and generalizing predictive modeling is possible following verification that the logic and analysis tools used to generate predictions are performing accurately. Developing and automating the tools is a reiterative process. Guidelines are developed for choosing analysis tools for different scenarios and for diagnosing potential problems. In addition, semi-automated gene function analysis tools provide higher degrees of access to complex data than that currently available in the art.

All predictions based on a coherent data set model are tested in a laboratory. From the herbicide SOA data set, unknown compounds with high-confidence predictions of site of action are subsequently validated. With the addition of data sets which characterize gene knock-out mutants, predictions of gene function are made. The particular approaches used to test predictions of site of action or gene function are identified and implemented with the assistance from domain experts.

Creation of an Integrated Data Set

In one embodiment of the present invention, three integrated data sets were generated, each with increasing size and complexity. The first and simplest integrated data set was generated from a site of action (SOA) experiment, (hereinafter SOA1) that evaluated the effects of 18 compounds (herbicides) on *Arabidopsis*. The site of action is known for some of the 18 compounds. For two of the compounds, the mode of action at the site of action is also known. SOA experiments are commonly performed, since identification of the site of action is often sufficient knowledge for product development, even if the mode of action has not been determined. Of the 18 commercially available herbicides used in SOA1, herbicides had nine known sites of action and one unknown site of action. In some cases, different chemical classes of herbicides affecting a common site of action were used. For each herbicide, a series of dose response curves were generated and a time course for symptom development was established. Plant tissue was sampled at 3 stages (early, middle and late) in symptom development. Sufficient mock-treated control plants were used at each sample stage to establish a baseline for each technology type. Data for the SOA1 experiment were collected from three different technologies: gene expression analysis, metabolite analysis, and phenotypic analysis, which provided a total of approximately 50,000 data points.

A larger integrated data set was generated for data corresponding to 65 *Arabidopsis* mutants that were functional gene knock-outs (hereinafter GKO1). Data for the GKO1 experiment came from three different technology types: sequencing and annotation, metabolite analysis, and phenotypic analysis. The GKO1 data set contained approximately 300,000 data points. Challenges were encountered in integrating the GKO1 data set. The data was stored in a variety of formats from several different technologies and utilized domain-expert screening for quality control. Data architects, working in conjunction with biostatisticians and laboratory scientists within each technology, designed an integrated database schema capable of handling data from the different technologies. The schema was normalized so that all information related to a particular mutant could be easily retrieved. Faced with highly heterogeneous sets of input data, bioinformaticists wrote custom conversion programs to populate the database. Software engineers worked with laboratory scientists and biostatisticians to build an interactive quality control module that allowed domain scientists to query the database for a mutant, to view graphs of pertinent characteristics, and to remove low quality data. In addition, some parts of the quality control effort were fully automated. These modules enabled unusually rapid and complete quality screening of a very large set of data.

The challenges of integrating the collection of GKO1 data were overcome by a team with knowledge in database architecture, design, and implementation; data processing and conversion; statistics and data visualization; and software engineering and human-computer interaction. A view of an integrated data set for a single gene (or compound) is shown in FIG. 4. Referring now to FIG. 4, a Gene ID (a unique identifier) is linked to data from sequence and annotation (annotation; DNA indicator), metabolite or biochemical analysis (BCP; metabolite indicator), gene expression analysis (GDP; RNA indicator), and phenotypic analysis (phenotype indicator).

The largest integrated data set generated (hereinafter GKO2), corresponds to 600 *Arabidopsis* mutants that are functional gene knock-outs. Data for the GKO2 experiment were obtained from three different technology types: sequencing and annotation, metabolite analysis, and phenotypic analysis. The GKO2 data set contained approximately 3.5 million data points. Implementing batch processing when possible improved the process and efficiency of integrating the GKO2 data.

The FUNCTIONFINDER system is used in the acquisition and storage of data. The organization of FUNCTIONFINDER is shown in FIG. 5. FUNCTIONFINDER comprises four interrelated components: databases, data processing, data analysis tools, and user interfaces. Data are extracted from the Refinery layer (REFN) and integrated in the Abstraction layer (ABST). Public databases and other sources of data are integrated in the Abstraction layer with any proprietary data or data generated "in-house." Integrated data are used to generate coherent data which is stored in a relational database and subsequently extracted into coherent data sets for efficient access by Discovery layer (DISC) tools.

Data are produced on a variety of instruments, and initial storage is in a variety of media, such as proprietary databases, LIMS, flat files, Excel spreadsheets, and the like. In the methods of the present invention, all generated data are loaded into an integrated database. A Refinery database can contain data related to soil samples, such as experimental plants grown in a flat (container) of soil. Data collected on the soil samples is stored in a Laboratory Information Management System (LIMS). To populate the Refinery, a computer program copies information from LIMS into the Refinery. Data about a mutated gene in the experimental transgenic plants is stored in a separate proprietary database. To further populate the Refinery, another computer program copies information from the proprietary database to the Refinery Database. Integrity checking and enforcement takes place as the data are loaded, ensuring that all data in the database are integrated: i.e., identified and linked to all associated data. Data in the refinery are associated with a measurement set, a collection of measurements all related to one experiment. Enforcing data integrity ensures that each data point is correctly associated to a measurement set. The integrated database stores data in a tree-like structure, so that a measurement can be linked to other measurements further up the tree, and measurements further down the tree can be linked to it. Integrity checking ensures that all upward links are present and valid when a data point is stored.

Sample identification (ID) is a necessity to the methods and systems of the present invention. To obtain truly integrated data, each sample must have a unique identifier that allows it to be linked with all data acquired from each sample. For example, in the herbicide SOA experiment, samples were derived from *Arabidopsis* plant tissue. Each *Arabidopsis* transgenic construct is made of two plasmid parts, a driver and a target, and the construct entry has references to the identity of the driver and target used. When a construct is added to the list, integrity checking ensures that the Target Plasmid ID and Driver Plasmid ID both refer to plasmids that are already in the list. If not, the entry is rejected. The mutant plants are grown in flats. Each flat set that is planted uses experimental (mutant) plants from a single construct. The flat set entry contains a reference to the Construct ID that is planted. When a flat set is added to the list, integrity checking ensures that the Construct ID refers to a construct that is already in the list. If not, the entry is rejected.

When data are acquired, they are fed directly into the Refinery Database. Data in the Refinery Database are subjected to a number of quality checks to insure that the data used in later calculations are accurate and consistent. In the example of the herbicide SOA experiment in *Arabidopsis* plants, the number of rosette leaves is counted and recorded on each even-numbered day from Day 14 (after planting) until the first flower buds are observed on the plant. Throughout this observation period, the number of rosette leaves should be a non-decreasing sequence, such as is characterized in Table 1.

TABLE 1

| Day 14 | Day 16 | Day 18 | Day 20 | Day 22 |
|--------|--------|--------|--------|--------|
| 0 | 2 | 2 | 4 | 6 |

If the number entered on Day 20 were "8," it would indicate that a mistake was made in the data entry or data observation. A data quality check relies on examination of the entire sequence of measurements: a value of 8 rosette leaves on Day 20 may be perfectly reasonable by itself, but is clearly an error in the context of the other measurements.

An example of another type of data that could be used in the creation of integrated data and, ultimately, coherent data sets, is the measurement set collected for flower production in *Arabidopsis*. The day on which flower production started, the day on which flower production stopped, and the day on which seeds are harvested, are all recorded. The day on which flower production stopped must be greater than the day on which it started, and also must be less than the day on which seeds were harvested. If a data point is chronologically outside the pattern, it can be inferred that one of the recorded values is in error, although it cannot always be inferred which recorded value is wrong. Data points that are clearly in error (as in the example for rosette leaves) are flagged as erroneous data points in the Refinery Database so that they will not be used in future calculations and conclusions. Data points that may be error prone (as in the flower production example) are flagged as questionable data points in the Refinery Database. Depending on the application, future calculations may or may not use flagged observations.

Creation of a Coherent Data Set from an Integrated Data Set

Data that passes quality control is transformed into coherent data sets. One goal of a coherent data set is to directly compare data of different types recorded in different measurement scales. When a coherent data set is created, the same analysis methods can be used on any subset of the coherent data set. In one embodiment of the present invention, a coherent data set is created from the *Arabidopsis* herbicide SOA experimental data (SOA1) in the following way:

1. Each data point is expressed as a numeric measurement. In the case of a descriptor (such as "Brown leaf color"), the number or frequency of such observations can be recorded. In other cases, one could record the severity of an observation, such as rating the lesions on a leaf on a scale of 0 (no lesions) to 10 (completely covered with lesions).
2. Each measurement type (e.g. leaf count or stem length) is transformed to a Gaussian distribution.
3. Each data point is standardized to an appropriate control measurement, and expressed as a number of standard deviations above or below control, or baseline, mean.
4. Optionally, the data are further summarized (such as taking a weighted average of several measurements) to reduce the dimensionality of the data set.

The above steps 1–4 are followed for each measurement type in the data set. When the steps are completed, all the measurements have the same distribution, and all are expressed in the same units, for example, standard deviations above or below a control mean.

Deriving Coherent Information from Experimental Data

The maximum rosette radius is recorded for each plant in a phenomics flat. Analysis has shown that maximum rosette radius is not normally distributed, so a square root transformation is used to achieve approximate normality. The average square root rosette radius is then normalized to a comparable control value to obtain a normalized value of −2.84, indicating that the square root rosette radius is 2.84 standard deviations below the control mean. When the same process is performed for a biochemical compound reading, such as lysine, which requires a log-transformation, a normalized value of 3.22 is obtained. In this particular case, rosette radius is significantly smaller, and lysine production significantly larger, when compared to control plants.

Correlation Analysis of Coherent Information and Hypothesis of Gene Function for Glabrous Gene Coherent information is analyzed in a variety of ways. Statistical analyses that are widely used include cluster analysis, discriminant analysis, principle components analysis, correlation analysis, and factor analysis. Broadly, the purpose of statistical analyses is to find patterns of similarity and difference in the coherent data sets. One purpose of the analyses is to gather information about how perturbations (genetic, chemical, etc) of an organism affects the total phenotype (gene expression, biochemical expression, morphometric expression) of the organism. For example, correlation analysis shows that when a particular *Arabidopsis* gene (called "glabrous") is inactivated, the resulting plant will have no trichomes, or plant hairs. The absence of plant hairs indicates that one function of the glabrous gene is involved in trichome production. Further experimentation revealed that glabrous is a transcription factor that acts as a "switch" which turns on or off the gene that is directly responsible for forming the cellular structure of trichomes. Thus, a useful correlation is established between the phenotype (no plant hairs) and the disruption of glabrous, the transcription factor that controls the gene responsible for the formation of trichomes.

Principle Components Analysis of Coherent Information and Hypothesis of Gene Function for Herbicidal Action Principle components analysis of the herbicide SOA data (SOA1) shows that the application of a herbicide that accepts electrons from a photosystem I (PSI) inhibitor is linked to several observable effects: differential regulation of a suite of genes (GEA data), differential expression of a collection of biochemicals (metabolite analysis), and a specific observed phenotype. Data gathered from observable traits enables the hypothesis that particular genes cause particular chemical changes to bring about particular phenotypic behavior. The SOA1 data are discussed in more detail in Specific Example 1, infra.

Verifying Hypothesis of Gene Function and Designing New Experiments: PSI Inhibitor A hypothesis of gene function is limited by the assumptions relied upon in forming the hypothesis. An unverified or untested hypothesis is nothing more than an educated guess about what a gene does. A variety of "wet bench" (laboratory) and bioinformatic experiments can be used to prove or disprove hypotheses. Principle components analysis suggests that a particular herbicide induces reactions similar to those of a PSI inhibitor. A laboratory experiment performed directly on the herbicide in solution demonstrates that the herbicide is not a PSI inhibitor, thereby disproving the initial hypothesis of herbicide function. FIG. 10 illustrates one embodiment of the methods of the present invention as applied to, for example, the experimental data from SOA1 (Specific Example 2, infra).

Verifying Hypothesis of Gene Function and Designing New Experiments: Transcription Factor When the original connection between the glabrous gene and trichome production was observed, a number of hypotheses were suggested. One hypothesis was that glabrous might be directly responsible for trichome production. A second hypothesis was that glabrous might be a transcription factor for another gene that is directly responsible for trichome production. A third hypothesis was that glabrous and the directly responsible gene might both be regulated by a third gene. Bioinformatic analysis shows that glabrous has a structure similar to other transcription factors and wet bench experiments show that regulating glabrous affects another gene but not vice versa. Finally, it can be demonstrated that glabrous binds to a specific protein. A review of the evidence resulted in a conclusion that glabrous is a transcription factor for the gene that causes trichome production.

Integrating Profiling Technologies for Defining Herbicidal Site of Action

Herbicide development has traditionally involved multiple rounds of spray trials to identify and refine lead compounds accompanied by lengthy biochemical experiments in a search for the site of action. The convergence of multiple technologies has positioned the agrochemical discovery and development process for potentially dramatic change. One change is the transition from whole organism testing to the use of mechanistic in vitro assays for primary screening. Transitioning to in vitro assays has been driven, in part, by the emergence of combinatorial chemistry, a methodology capable of generating vast chemical libraries containing small quantities of each chemical. In vitro assays are more amenable to high or ultra high throughput screening and miniaturization than whole organism testing and the latter has been relegated to later stages of the herbicide development process. Whole organism testing as an initial screen is also less desirable in light of the waning number of new targets found by this approach despite screening with increasing numbers of compounds. Interestingly, whole organism testing has lead to the discovery of only 20 distinct sites of action for all herbicides in the past 60 years, while estimates of potential herbicide targets exceed this number by two orders of magnitude. Ward & Bernasconi, 17 NATURE BIOTECH. 618–19 (1999). Thus, despite the fact that all potential targets sites are available when screening with whole organisms, only a fraction of the potential herbicide targets have been identified and exploited.

The advent of complete sequence information for the model plant system *Arabidopsis* has enabled a systematic exploration of gene function that directly complements herbicide discovery via in vitro assays. Efforts to increase and decrease the expression of every gene in *Arabidopsis* by molecular genetic manipulations are underway. Phenotypes of the corresponding mutants are being systematically profiled in both public and private efforts. In this way, all potential herbicide targets can be identified and the most promising chosen for a screening program using in vitro assays.

A number of genomic technologies have been developed to capture the molecular details of genetically altered or treated tissue. Genomic technologies include profiling changes at the transcript, protein, and metabolite levels. Previous investigators have validated the approach of creating a compendium of transcriptional profiles to facilitate the identification of the site of action or site of action of an unknown compound. Profiles of known mutants were compared to profiles of unknown mutants, and where a reasonable similarity occurred, it was determined that the unknowns had a common site of action/mode of action (SOA/MOA). Generation of a database of profiles corresponding to all putative herbicide targets would be an extremely valuable resource for development of new herbicides. Currently there are many herbicides where the site of action and/or the mode of action are not known, but could be rapidly determined using a compendium approach.

Herbicides developed via an in vitro system must be plant-tested and the molecular details of the plant response need to be defined. Herbicides developed against a target in vitro may preferentially inactivate a different site in vivo or may target multiple sites. Insight into these details is essential for responsible product stewardship in an intense regulatory environment. One purpose of the *Arabidopsis* herbicide SOA study was to evaluate phenotypic, transcriptional, and metabolic analysis technologies for building a compendium database to determine herbicide SOA/MOA. A collection of herbicide treated tissue, forming a test set, was used to generate data from three different technology types. Data was evaluated for accuracy in grouping the herbicides into target classes. Determining the site of action of herbicides has traditionally been an involved and lengthy process requiring extensive biochemical studies. Described herein are methods for utilizing phenotypic, transcriptional, and metabolite analysis technologies that accurately grouped a set of 18 herbicides into nine distinct sites of action. It is important to note that using data obtained from only any one or two of the technology types resulted in false groupings. The results suggest that a comprehensive database of integrated, coherent data derived from tissue systematically treated with specific chemical inhibitors enables the prediction of the site of action of virtually any herbicide.

Integrating Profiling Technologies for Defining a Human Disease State

Methods and systems of the present invention provide for the diagnosis and treatment of human diseases, such as diabetes mellitus. Diabetes Mellitus (DM) is a disorder characterized by chronic hyperglycemia, and diabetes symptoms include altered carbohydrate, fat, and protein metabolism. Diabetes is a complex disease of multiple etiology, which complicates treatment, and increases the risk of misdiagnosis. In many cases, a collective view of test results is required for even a non-exacting diagnosis, and the data from no single test is inherently diagnostic, nor are singular test results readily able to posit causality, explain anomalies, or direct further research or testing. Data can be and has been generated through a variety of approaches, but within a technology only gross fluctuations may be evident or capable of correlation and association with DM. An expanded view across integrated data streams can increase the benefits of current test results through furthering interpretive capacity, as well as furthering opportunities to establish correlations by increasing levels of experimental range, resolution, and accuracy. Coherence may, in part, have already been established through the standardization of methods for obtaining data, and analysis may further refine methods for obtaining data. As coherence is more definitively established in the data, diagnostic capacity should increase, and patterns or profiles, limited not only to the gross disease, but also for individual variants within the disease, should begin to emerge.

The present invention provides methods and systems for the use of coherent data sets in studies of DM, and other human and animal diseases. A murine model system contains data streams generated via six different technologies: genotype/sequence data, gene expression data (GEA), metabolite analysis, phenotypic analysis data, SNP data, and proteomics data. Data from each technology type can be collected; subjected to quality control; integrated with data from the other technology types; and analyzed into increasing degrees of coherence.

A hereditary link has already been established for diabetes mellitus, but it is a complex disease with both genetic and environmental components. Davies et al., 371 NATURE 130–136 (1994). Some regions of the genome have been established as indicators of risk of DM, but are not wholly diagnostic. Hashimoto et al., 371 NATURE 161–164 (1994). In many cases, genetic factors are not clearly evidenced for all forms of the disease. To narrow down and understand the genetic alterations relevant to DM, additional specific information is needed with respect to genetic lesions an individual carries, as well as coherent links to more specific information about patient health (gross phenotype), gene expression, protein expression, and metabolite analysis. Coherent links are particularly instructive to establish possible causative factors in cases where a hereditary link is not clear. Although the use of human genotypic data are desirable, a mouse model system provides greater initial comparability through the controlled nature of gene knock-out and knock-in experiments, and provides a foundation upon which to build heterogenous human genetic data. Knock-out murine models have been reported in the literature as a model for the study of DM, specifically with a Akt2 gene knock-out. Cho et al., 202 SCIENCE 1728–1731 (2001).

A controlled genetic system also provides for comparable phenotypic data. Comparable phenotypic data refers primarily to gross phenotypes with potentially diverse individualized measurements, as compared to the molecular phenotypes (often of limited range) and aspects of measurements from other technologies (such as genotype, gene expression analysis, metabolite analysis, SNP analysis, and proteomics). In mice, phenotypic data can extend many levels beyond those available with humans, allowing analysis of organ architecture and age-related profiles. Even with humans, however, the expansion of phenotypic data beyond the limited range currently known to have diagnostic potential could lead to an improved understanding and establishment of relevant correlations when placed within a set of coherent data. Qualitative and quantitative data are used as criteria for diagnosing diabetes, such as, for example, increased thirst, increased urine production, blurred vision, and blood sugar levels, but are not always diagnostic. New phenotypic data could be measured and those already measured could be made more exacting. A similar approach has been reported using a plant model. Boyes et al., 13 PLANT CELL 1499–1510 (2001). Linkage of phenotypic data to coherent data sets could ultimately provide earlier, more exacting and reliable diagnoses of DM. Winkelmann, 2 PHARMACOGENOMICS 11–24 (2001).

Gene expression analysis (GEA) provides a quantitative measure of individual gene expression as reflected in cellular RNA content for various mRNAs and alternative mRNA forms. A number of studies of gene expression have been performed to look at changes associated with DM. For example, GEA data has been used to observe differences in the expression of glutaminase and glutamine synthase and tissue specific glutaminase and glutamine synthase transcripts in DM. Labow et al., 131 J. NUTRITION 2467S–2474S (2001). Independent of other data, such as levels of the metabolite glutamine, or expression of the proteins coded for by the mRNAs, conclusions based upon glutaminase and glutamine synthase data are limited in a way that is overcome by inclusion of the data in a coherent data set. Similarly, a range of gross and molecular phenotypes are traceable to mutation in a single transcription factor, for example MODY, most easily identified by a GEA profile when the data are properly interlinked and available for analysis in a coherent data set. Owen & Hattersley, 15 BEST PRAC. RES. CLIN. ENDOCRINOL. METAB. 309–323 (2001).

Proteomics, in the context of the present invention, is understood as data largely produced through two-dimensional gel electrophoresis to identify the presence and patterns of cellular protein expression and modification. In this respect, it is quite analogous to GEA data. Some forms of DM show specific alterations in protein expression and modification, most obviously in the expression and modification of insulin. Insulin is initially produced as peptide preproinsulin. A portion of the peptide is then cleaved off to produce proinsulin in the lumen of a cell's rough endoplasmic reticulum. Within secretory granules of a pancreatic beta cell, proinsulin is then cleaved to form the final alpha and beta chains of insulin, plus the "connecting" peptide. Misexpression of insulin precursors and the final form of the insulin protein may indicate a critical defect causative of diabetes, and one that might be correlated with, for example, mutations in the gene sequence (genotype data), or altered expression of relevant proteases (GEA data), if combined with the methods and systems of the present invention to create coherent data sets. Likewise, previously unidentified protein alterations might be discovered by correlation with data from other technologies in a coherent data set.

Metabolite analysis is particularly useful in the study of DM, since DM is a metabolic disorder. Individual metabolites present in cells are identified and/or measured, establishing the presence, quantities, patterns, and modifications of small biomolecules, often the substrates and products of enzymatic reactions. Uniting genotype, GEA, proteomics, and metabolite analytical data provides a deep and interconnected window to the molecular/cellular level to correlate with intercellular and gross phenotype data. DM is a metabolic disorder with a failure of cellular uptake of glucose and a consequent altering of protein and fat metabolism, and these changes are detected using metabolite analysis technologies. Increased fat metabolism can lead to ketoacidosis, but as with the other technologies, absent contraindication, metabolite analysis data reflecting ketoacidosis can lead to misdiagnosis, in this case as hyperventilation syndrome. Treasure et al., 294 BR. MED. J. (Clin. Res. Ed.) 630 (1987).

Establishing coherent data sets created from data streams of different research technologies and manipulating and analyzing the data by computer-based methods and systems allows emergence of new connections, correlations, and understanding of gene function, which results in new and improved tools and treatments for managing disease. Ultimately, coherent data sets improve diagnosis and monitoring by providing exacting profiles of genetic, metabolic, and gene and protein expression alterations that correspond to disease states, independent of postulating rules, higher order structures, or causation. In a complex disease like DM, coherent data sets also allow a very exacting reclassification of subtypes of the disease based on the different signature profiles that lead to the disease state. Signature profiles in a computer database of high coherence (comparability) will allow for rapid and clear diagnosis when used to match patient data with signature profiles for disease. Identification of co-heritable diseases that might otherwise be masked, such as coeliac disease with Type 1 diabetes, is greatly simplified through establishing clear signature profiles and profile subtypes. Laloux et al., 13 DIABETES METAB. 520–528 (1987). Disease diagnosis is dynamic, requiring monitoring and re-evaluation. By monitoring a patient from one diagnostic state to another, coherent data sets are produced for the changes that occur as a disease either progresses or improves, permitting enhanced predictive and preventive measures, and increasing the chances of stabilizing a condition.

By postulating causative agents and critical targets from the analysis of specific profiles, treatment is individualized, and specific targets are provided for high throughput efforts of drug discovery. Monitoring changes in a signature profile over a course of treatment will make clear whether a drug is directly affecting the molecular phenotypes/symptoms, permitting drug validation, as well as making clear undesirable secondary effects that will be further monitored in attempts to optimize the drug design and dosage. Methods of the present invention can result in coherent data sets that provide rational, and thus less costly, drug screening, as well as rational and validated design and product improvement.

Correlation of Data with Biochemical Pathway Information

Another aspect of the present invention is to provide comprehensive methods and systems for linking metabolites in cells, biofluids, and tissues, to biochemical reactions, pathways, and pathway networks. It is generally accepted that a metabolic response of living organisms is altered by genetic makeup (or change), disease state, chemical exposure (including therapeutic treatment) or environmental insult. Thus, the methods of the present invention are particularly useful for understanding the relationship between biochemical response and disease or phenotypic association.

The methods and systems of the present invention are useful for linking a particular metabolite or enzyme with all associated biochemical reactions and/or pathways. Existing metabolic databases such as KEGG (Kyoto Encyclopedia of Genes and Genomes, Institute for Chemical Research, Kyoto University, Japan), BRENDA (Institute of Biochemistry, University of Cologne, Germany), and EMP (Enzymes and Metabolic Pathways, EMP, Inc., New York, N.Y.) are large, but error prone. Furthermore, above databases do not represent the complex network of metabolism in a manner that allows for retrieval of an accurate, comprehensive list of the metabolic linkages. For example, BRENDA contains information on genes with associated reactions, but fails to provide linkages to the corresponding biochemical pathways. While KEGG provides pathway information, the pathways are stored as unordered collections of catalyzed reactions. In addition to the lack of order in the pathways, KEGG consists of a generic listing of multiple species, rendering accurate retrieval of human metabolic data impossible. In contrast, the current invention provides methods and systems for obtaining the linkage of any metabolite or enzyme, in a particular cell, biofluid, or tissue, with all associated biochemical reactions and/or pathways, and/or disease, and/or phenotype associations.

In one embodiment of the present invention, methods and systems are provided for linking a complete spectrum of metabolites in a cell, biofluid, or tissue, from an organism to biochemical reactions and pathways, and correlating the biochemical reactions and/or pathways to a phenotype of the organism. In this manner the methods of the invention are useful for correlating a biochemical profile with a disease state. The methods and systems of the invention provide for linking a complete spectrum of metabolites in a cell, biofluid, or tissue, from a diseased or treated organism to biochemical reactions and pathways, and correlating the biochemical reactions and/or pathways to a site of action of a disease or therapeutic modality. In this manner the methods and systems of the invention are used for discovering or validating that a therapeutic affects a target biochemical reaction and/or pathway. The methods and systems of the present invention are also useful for monitoring the disease stage of an organism, diagnosing an organism with a particular disease, and monitoring the efficacy of a therapeutic on an organism, such as the yeast azole drug experiment discussed in Specific Example 5, infra.

In other aspects, the present invention provides methods and systems for computing all possible biochemical pathways that link a first metabolite to a second metabolite; compiling all possible compounds that result from the biosynthesis or degradation of a particular metabolite; identifying all possible biochemical reactions and/or pathways in which a particular enzyme is involved; and identifying all possible biochemical reactions and/or pathways in which a particular metabolite is involved.

The methods and systems of the present invention encompass the development and use of a database of endogenous metabolites, inclusive of the metabolites found in different organisms and the biochemical reactions in which those metabolites are involved. The database of endogenous metabolites is useful in correlating disease states, phenotypes, and metabolites. Data from the database of endogenous metabolites can be incorporated into coherent data sets, ultimately allowing linkage of any coherent data set data, such as gene expression data, to disease states and phenotypes. Included in the methods and systems of the present invention are comprehensive and quantitative analyses of low molecular weight biochemicals revealing a metabolome. The metabolome is best described by analogy to the genome, i.e. where the human genome is the set of all genes in a human, the human metabolome is the set of all endogenous metabolites in a human. The science of genomics is based upon a genome and the science of metabolomics is based upon a metabolome. To continue the genome/metabolome analogy, any published human genomic sequence is a statistical approximation, as it is derived from a limited number of individuals, and any individual necessarily has a unique genome. Similarly, the human metabolome is a statistical approximation of the total human metabolic potential. Furthermore, just as the human genome is differentiable from other genomes, for instance, the *Xenopus* or *Caenothus* genomes, the human metabolome that defines the human biochemical potential is differentiable from other metabolomes.

The database of endogenous metabolites is a comprehensive set of all potential metabolites, or chemical components, which can be found in the cells, biofluids, or tissues of any individual under all conditions. It is likely that most individuals vary in their biochemical potential, expressing only incomplete subsets of the metabolome, depending on their genetic makeup, environmental conditions, and state of health. Indeed, many metabolic diseases and even the efficacy of most drugs is variable, due, at least in part, to individual variances in metabolism and the resulting biochemistry.

Figure 11A:
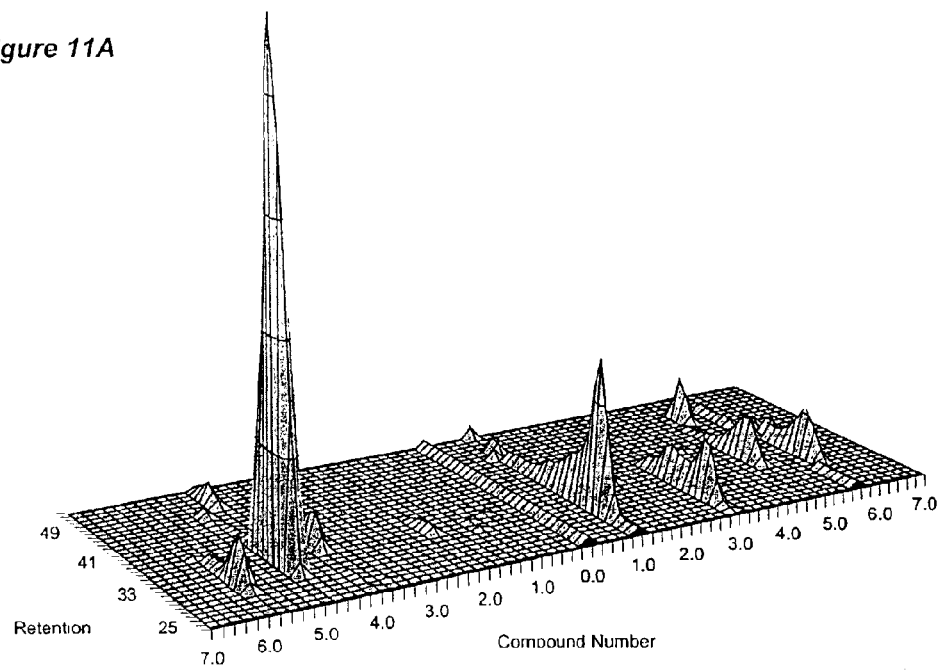
FIGS. 11A–11B are a three dimensional plot of mass spectral electrospray ionization chromatograms (LC-MS-ESI) of mouse tissue samples showing retention time, compound number and relative response. The left side of the plots (left of 0.0) depicts the positive mode chromatograms and the right side depicts the negative mode chromatograms.
Figure 11B:
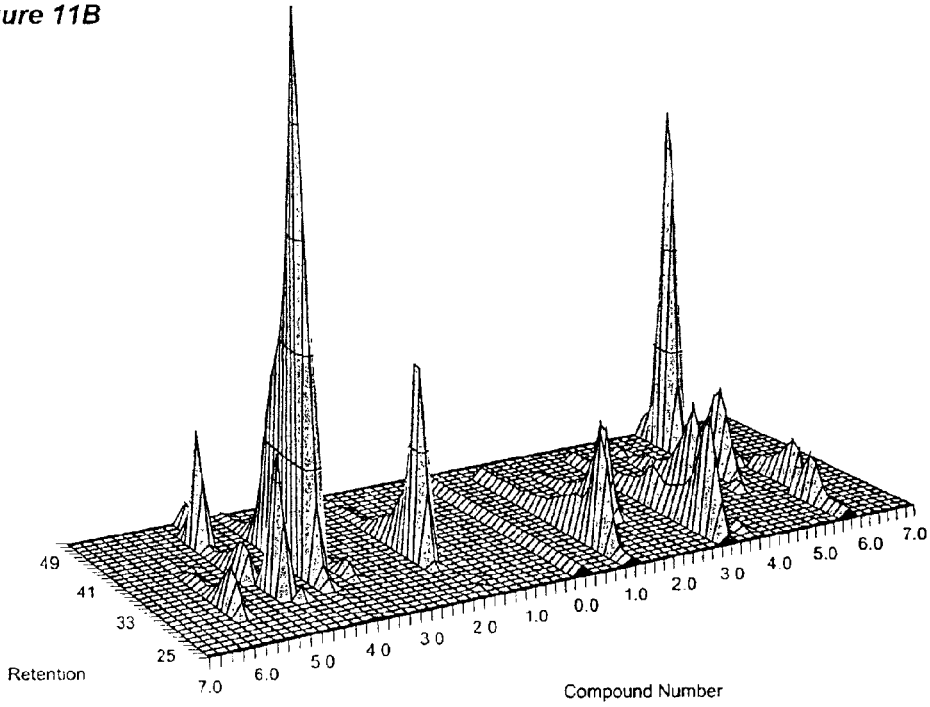
Figure 12A:
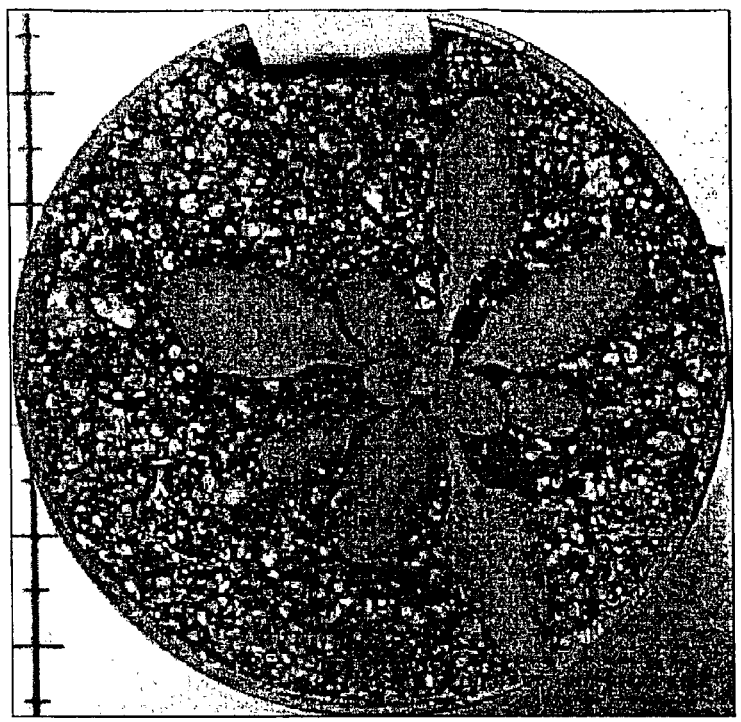
FIGS. 12A–12G are images depicting the phenotypes of three-week-old *Arabidopsis* plants treated with a herbicide representative of each of the six symptom classes listed in Table 3. Herbicides were applied in either 15% DMSO or 20% tetrahydrofurfural alcohol. The negative control contained a corresponding solution lacking herbicide. Plants treated with the herbicides displayed six separate phenotypes depicted in panels B–G.
Figure 12B:
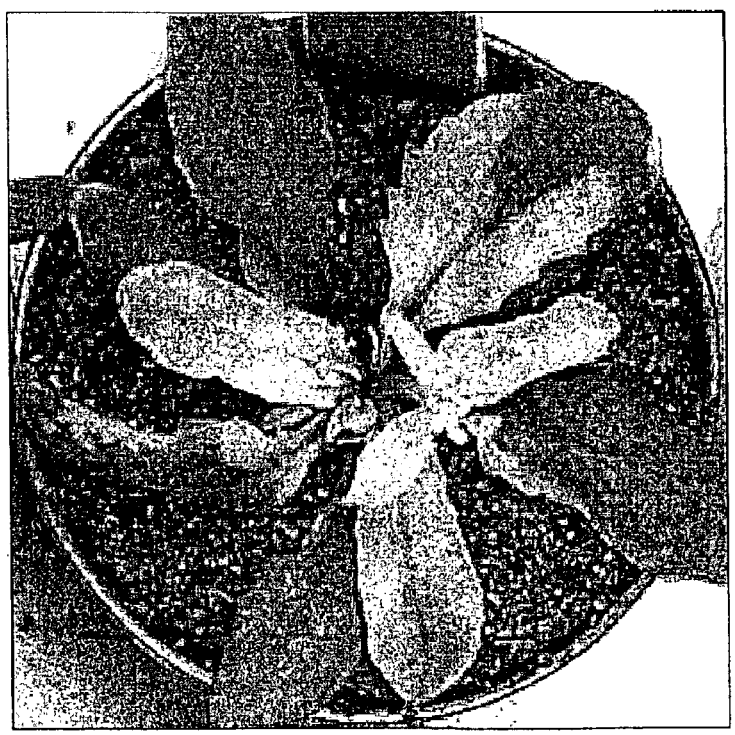
Figure 12C:
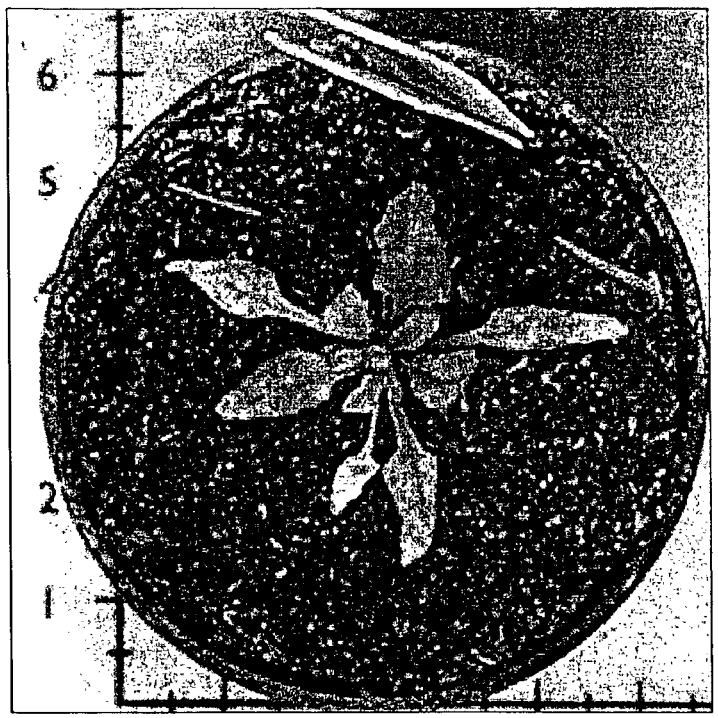
Figure 12D:
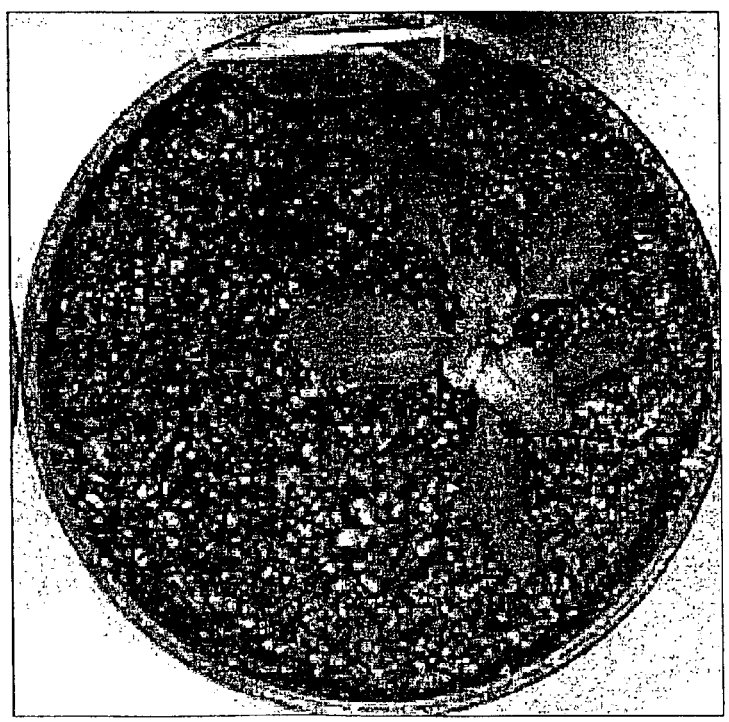
Figure 12E:
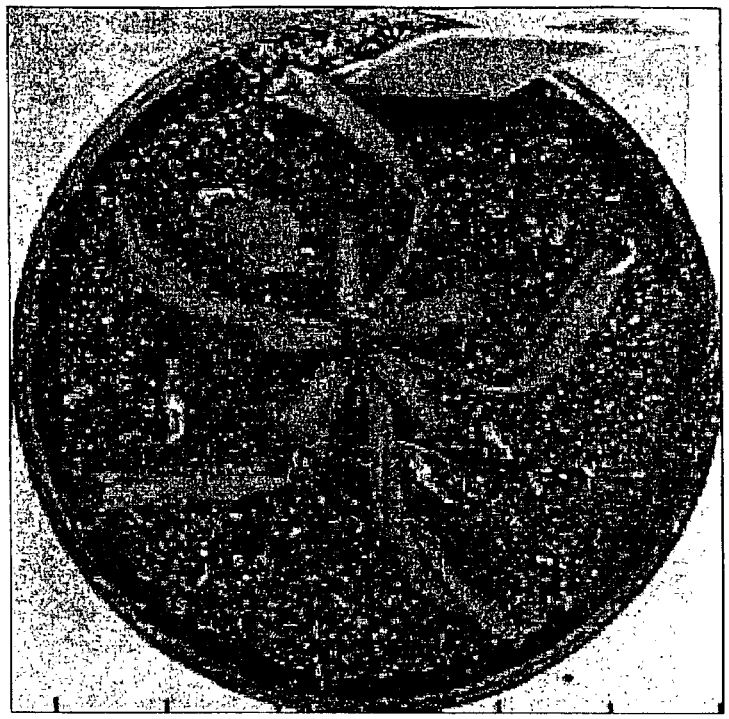
Figure 12F:
Figure 12G:
Figure 13A:
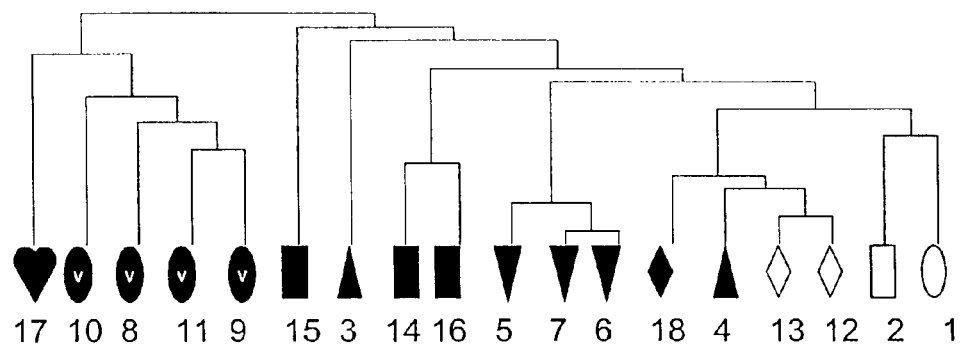
FIGS. 13A–13F are graphical representations of the results of cluster analysis of gene expression and biochemical profile data collected for *Arabidopsis* plants treated with the 18 herbicides listed in Table 3. Gene expression and biochemical profiles were derived by calculating the average response for the control treatments and standardizing the average test responses to the respective control averages in units of standard deviations.
Figure 13B:
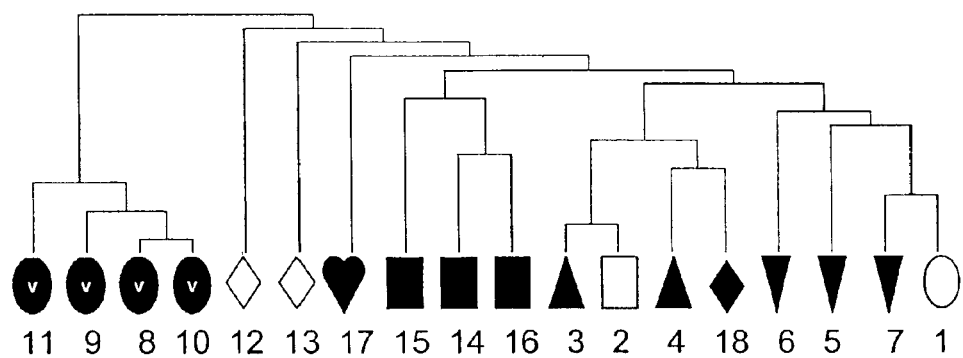
Figure 13C:
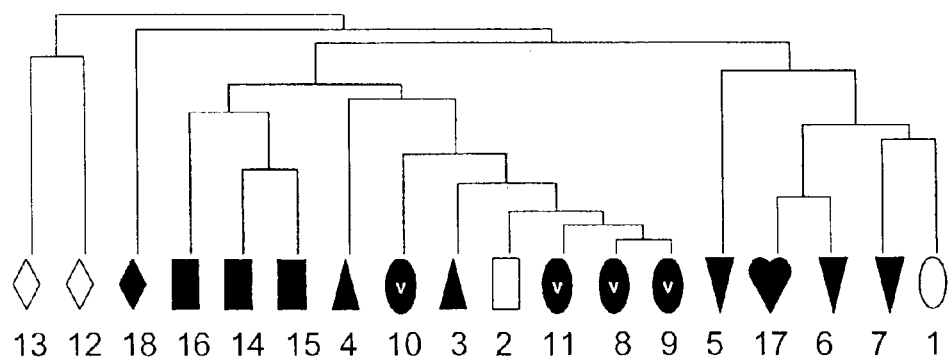
Figure 13D:
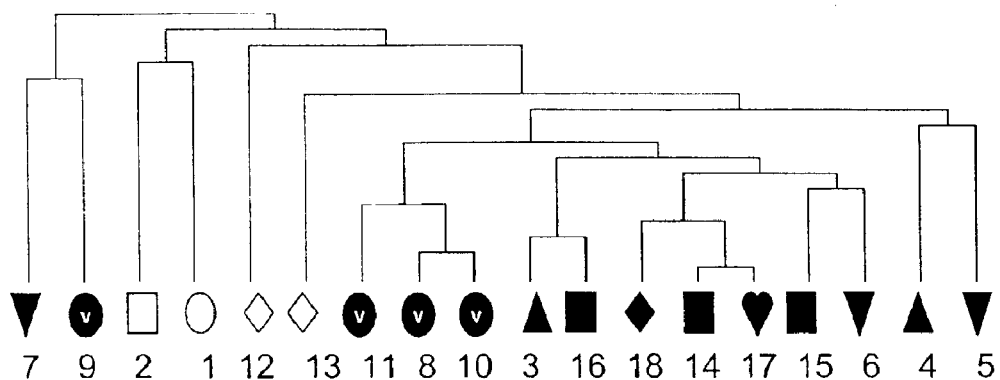
Figure 13E:
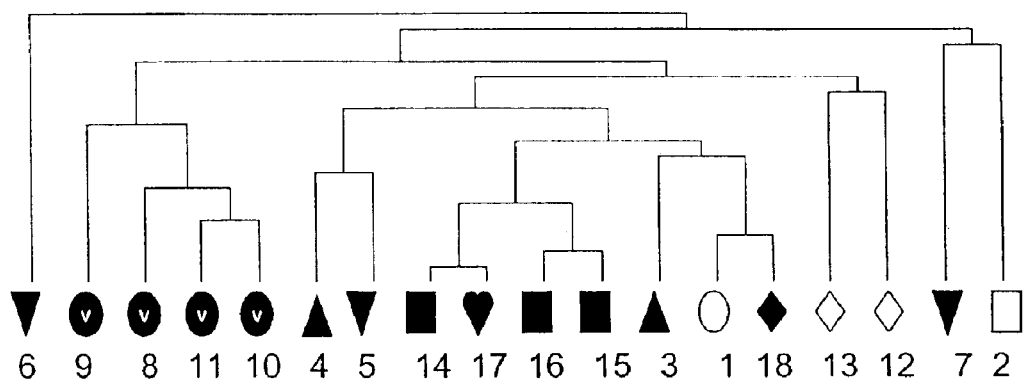
Figure 13F:
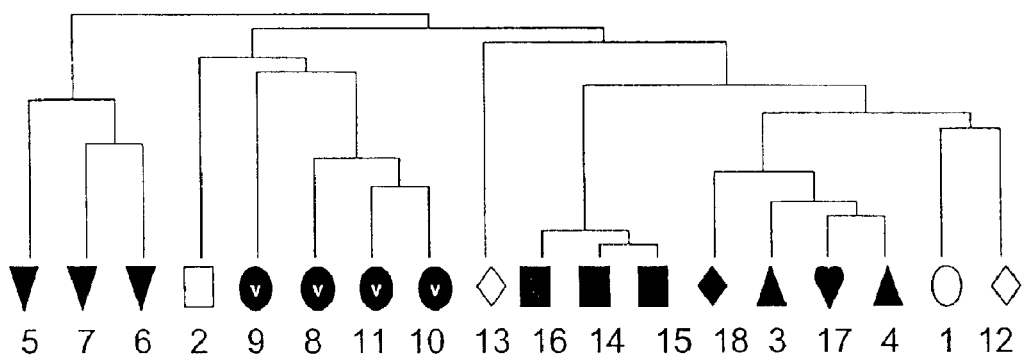

The metabolome of an organism is the total set of all endogenous metabolites found in the organism. The metabolite, or biochemical, profile of a biological sample is a list of any endogenous metabolites detected in the sample, together with a measure of how far each metabolite varies from its baseline value. Experiments show that the biochemical profile of a mouse heart (FIG. 11A) is different from the biochemical profile of a mouse kidney (FIG. 11B). By monitoring biochemical or endogenous metabolite profiles, one can diagnose disease, identify the stage of the disease, offer a prognosis, and suggest a treatment. Further, a treated individual can be monitored throughout the course of a disease, tracking the stages of the disease as treatment is applied to ensure that the treatment received remains efficacious. Treatment can be adjusted according to results obtained from metabolite analysis.

Metabolite analysis is particularly applicable to problems in which physiology is altered, e.g. through stress, disease, chemical, or other insult. Roessner et al., 13 PLANT CELL 11–29 (2001); Glassbrook et al., 18 NATURE BIOTECH. 1142–1143 (2000). Similar to transcriptomics and proteomics, the application of metabolomics is a global view of an organism, i.e. attempting to understand the current physiological status of a sample or organism in light of its full physiologic potential. Metabolomics information can be combined with data from other biological indicators in a coherent data set.

Unlike transcriptional or proteomic analysis, biochemical analysis directly reflects physiological status. Whereas the nature and relationship of almost all metabolomic entities (i.e. biochemicals) have been thoroughly established through decades of biochemical investigations, the vast majority of genes, transcripts, and/or proteins are only partially characterized; the functional significance thereof is often largely hypothetical, if understood at all. The application of metabolomics characterizes the physiological state of a sample by determining the actual or relative concentration of the entire set of small molecules that constitute metabolism. The establishment of a database of endogenous metabolites will enhance the application of metabolomics.

For the purpose of this invention, the database of endogenous metabolites consists of the native small molecules (e.g. non-polymeric compounds) involved in metabolic reactions required for the maintenance, growth, and function of a cell. The following implications flow from this definition:

1. Enzymes, other proteins, and most peptides are generally not small molecules and thus excluded. Many proteins participate in biochemical reactions with small molecules (e.g. isoprenylation, glycosylation, and the like). The construction and degradation of polypeptides results in either the consumption or generation of small molecules and, thus, the small molecules rather than the proteins make up the metabolome.
2. Genetic material (all forms of DNA and RNA) is also excluded from the metabolome based on size and function. The construction and degradation of polynucleotides results in either the consumption or generation of small molecules and, thus, the small molecules rather than the polynucleotides are part of the metabolome.
3. Structural molecules (e.g. glycosaminoglycans and other polymeric units) similarly may be constructed of and/or degraded to small molecules, but do not otherwise participate in metabolic reactions. Thus, structural molecules are excluded from the metabolome.
4. Polymeric compounds such as glycogen are important participants in metabolic reactions, but are not chemically defineable and, but are source of metabolites (i.e. an input/output to metabolism). Thus, polymeric compounds are excluded from the metabolome.
5. Metabolites of xenobiotics are neither native, required for the maintenance or growth, nor required for the normal function of a cell, and thus are not part of the metabolome. However, it is useful to monitor xenobiotics when observing the effects of a drug therapy program, or in experimentally determining the effects of a compound on an individual.
6. Essential or nutritionally required compounds are not synthesized de novo, (i.e. not native), but are required for the maintenance, growth, or normal function of a cell. Therefore, essential or nutritionally required compounds are part of the metabolome.

The foregoing definition of the database of endogenous metabolites emphasizes the focus of one embodiment of the present invention with respect to metabolism and physiology. As a matter of historical precedence, the term "metabolite" is often interpreted to consist of only the subset of metabolites that are part of degradation pathways. However, in the instant case, the terms "biochemical" and "metabolite" are viewed as congruent terms and used interchangeably. Similar congruence is intended for the terms "biochemical profiling," "metabolite profiling," and "metabolic profiling." The foregoing definition is not meant to be limiting in the sense of metabolites only as part of degradation pathways, but rather the intention of the term "metabolite" is the broadest possible definition of a biochemical involved in metabolism inclusive of catabolism.

The present invention encompasses methods and systems for establishing a database of endogenous metabolites. Construction of metabolic networks in microbes has been accomplished previously. Selkov, 3 PROC. INT. CONF. INTELL. SYST. MOL. BIOL. 127–135 (1995). In the present invention, and as shown in FIG. 3, the database of endogenous metabolites is constructed using a combination of mining existing databases and literature sources for known metabolites having associated reactions and/or pathways and characterizing and/or identifying metabolites present in experimentally derived chromatograms. The present invention provides methods and systems for creating a database of endogenous metabolites that provides information about biochemical pathway designation and disease and/or phenotype association for compounds of interest, and provides data useful in the formation of coherent data sets. Selkov et al., 28 PROC. NAT'L. ACAD. Sci. U.S.A. 3509–3514 (2000); Covert et al., 26 TRENDS BIOCHEM. SCI. 179–186 (2001). When required, biochemical standards are obtained so that the database of endogenous metabolites is based on empirical data. In this manner, an accurate and comprehensive representation of biochemical potential is obtained.

For example, to generate and build a database of endogenous metabolites, a genome of an organism of interest is mined for all genes annotated as enzymes. The organisms of interest include animalia, plantae, protista, monera, and fungi. More specifically, the organisms of interest include, but are not limited to, human and non-human primates, canines, felines, equines, bovines, porcines, rabbits, rodents, *Magnaporthe, Candida, Mycosphaerella, Botrytis, Saccharomyces, Aspergillus, Puccinia, Erysiphe, Ustilago, Fursarium, Phytophthor, Penicillium, Arabidopsis,* corn, wheat, barley, rye, legumes, mint, tobacco, tomatoes, rice, spinach, and peas. A preliminary list of enzymes is qualified to ascertain that the enzymes are all generally accepted in the art as being involved in the metabolism of the organism of interest. The qualified enzymes are used to generate a preliminary list of associated reactions by reference to existing metabolic databases. Biochemical and metabolic linkage information is entered into a database, and additional reactions in which the preliminary metabolites are known to participate are characterized and/or identified. The sequence of the enzymes involved in the newly identified reactions is obtained from the genome of the organism of interest. The foregoing steps are reiterated until as much metabolic information as possible is uncovered and retained. At the point of sufficient understanding of the framework of the metabolism of an organism of interest, whole pathways are deduced from the existing collection of metabolic reactions. The enzymes involved in the newly implicated pathways become a source of additional information, and the steps are repeated as described.

To obtain a comprehensive metabolite database, additional methods are used to complete pathways and identify peripheral pathways. One such method is curating biochemicals and associated reactions/pathways based on available literature. Another method is characterizing and/or identifying biochemicals in experimentally derived chromatographs. A benefit of the reaction-based approach of the current invention is that all of the metabolites in the metabolome are associated with one or more enzymes, and fit into known biosynthetic relationships. Previously proposed approaches based completely on chemistry suffer from the drawback of being limited to lists of disjointed compounds.

One aspect of the present invention is to provide a database of endogenous metabolites suitable for use with human conditions. Preliminary estimates of the total number of compounds in a human are varied. The standard wallchart of metabolism, which includes reactions not present in humans, lists only about 800 compounds in core primary metabolism. Most biochemical textbooks extend this list to no more than 1200 to 1500 compounds, again drawing from all life forms. Extensive querying of publicly available databases for human metabolites enables extension of the list to approximately 2000 compounds. Even assuming the final number of compounds in the human metabolome to be between 3000 and 4000, the size of the metabolome is workable and forms a firm foundation for scientific discovery.

The methods and systems used in the present invention to characterize and/or identify biochemicals are based on spectroscopic, or spectral analysis, procedures. Spectroscopic methods have been utilized for decades for the detection of biochemicals. Conventionally, biochemicals were separated based on chemical properties. The types of biochemicals under investigation dictate the detection methods employed (e.g., electrochemical, ultraviolet (UV), nuclear magnetic resonance (NMR), mass spectrometry (MS)). With decades of improvements in instrument hardware and computer systems, greater sensitivity and resolution have been achieved for simultaneous detection of a broad range of biochemicals.

The methods and systems of the present invention encompass, for example, use of Nuclear Magnetic Resonance (NMR) spectroscopy and Mass Spectrometry (MS), two of the most commonly used techniques for the detection of biochemicals. NMR spectroscopy has been applied to develop unique patterns for chemical-induced toxicity, and for determining biomarkers associated with specific disease states. Most of these studies have focussed on analysis of metabolites in biofluids. With high field strength magnets (500 MHz and up), NMR data can be acquired on a broad range of metabolites without the requirement of chromatographic separation. In cases of spectral overlap, multidimensional NMR methods can be used to resolve metabolite profiles. Hyphenated NMR methods (such as liquid chromatography-NMR) have also been used when metabolite separation is necessary. NMR methods are also used for detection of metabolites directly in tissue (using magic angle spinning techniques), and tissue metabolites are measured via NMR following extraction methods that are typically employed with such technologies and are known by those skilled in the art.

The following techniques are also used in the present invention for the characterization and/or identification of biochemicals. Mass Spectrometry (MS) is the most common technique employed for metabolomic studies, and has an advantage over other technologies (NMR) in providing greater sensitivity and resolution. As with NMR, hyphenated techniques are often employed in the MS analysis, including front-end gas chromatography (GC) or liquid chromatography (LC) methods. A variety of MS techniques must be employed to characterize and/or identify and cover the wide-range of chemical classes that occur in biofluids, tissues, and cells. Aspects of MS techniques may include, but are not limited to, time-of-flight, Fourier transform, ion traps, and quadrapoles, using a variety of ionization methods (e.g., electronic spray ionization, chemical ionization, and the like). With a specific combination of MS detector type and ionization method, a highly sensitive and resolved technology method is obtained allowing for simultaneous measurement of the comprehensive set of biochemicals comprising the metabolome. Hyphenated detection systems, such as MS-MS, also result in increased resolution of chemical components.

In the case of the current invention, as for all technologies that result in the measurement of a broad range of components, a major challenge is in data extraction and correlation with biological significance. To effectively manage and utilize the vast amount of data generated to create the human metabolome, informatics software and tools for representing and analyzing data are developed. Complex computational methods are essential for organizing data, analyzing large-scale data sets, generating new hypotheses, and deriving useful information from collected data. These techniques have been successfully demonstrated in the area of gene expression and are applied to metabolomics data with few modifications. To date, most published data analysis methods are based on clustering, principle component analysis, partial least square, and analysis of variance. However, caution is taken to meet the statistical requirements for such tests and to avoid misinterpretations. Bioinformatics tools are available for manipulating complex data sets, however, more advanced tools specifically designed for metabolomics data are provided in the current invention to link specific metabolites with cells and tissues within an organism.

SPECIFIC EXAMPLE 1

Preparation of a Database of Endogenous Metabolites for *Arabidopsis Thaliana*

To generate a database of metabolites, a list of potentially detectable plant compounds for each analysis methodology was created using the known function and metabolic pathways of the plant tissue to be studied. In addition, spectral peaks routinely observed in the plant samples were catalogued in the database. In some cases, data corresponding to the spectral peaks without a confirmed identity indicated additional compounds of interest for validation. The process for generating the database of endogenous metabolites was as follows: nominate compounds of interest, obtain the compounds (if possible), prepare and perform metabolite analysis of the compounds and the plant samples, process the spectral data, and add the spectral data and other compound/sample information to the database of endogenous metabolites (FIG. 3).

In order that the spectral data collected for the compounds in the database of endogenous metabolites accurately reflect the data for the plant samples in the study, the compounds were prepared for metabolite analysis in a manner identical to that for the plant samples in which the compound was expected to be present. The analyses performed were one or more of: LC-MS, GC-MS, ICP-MS, and global assays (e.g. total protein, total carbohydrate, and total fat).

The spectral data entered into the database of endogenous metabolites includes intensity, retention time, mass, and the like. A link was established in the database between the compounds and associated Peak_IDs for the various analysis technologies (LC-MS, GC-MS, ICP-MS, and global assays). In addition, information related to the stability of each compound generated according to the extraction and analysis processes described herein was entered into the database. When available, basic information about the compounds was entered into the database of endogenous metabolites such as name(s), molecular formula, structure, CAS #, vendors (if commercially available), molecular weight, and the like. Compounds in the database of endogenous metabolites were further described according to one or more of organism, tissue, cell type, treatment, disease state, phenotype, pathway(s), enzymatic reaction(s), and associated enzyme EC #.

Plant Tissue Sample Preparation Procedures

Minimal sample preparation was performed on plant tissues for metabolite analysis. *Arabidopsis* tissue (leaves, siliques, seeds) was harvested directly into tared and bar-coded tubes (96-well format) in liquid nitrogen using an automated weighing station (Mettler-Toledo Bohdan, Inc., Vernon Hills, Ill.). Samples were lyophilized without being allowed to thaw, mechanically ground to powder, and stored at low humidity ($\leq 10\%$) until undergoing analysis. In the case of silique samples, polytetrafluorethylene (PTFE) was added at a ratio of 1:3 (sample:PTFE) to facilitate the grinding and dispensing steps. Similarly, polytetrafluorethylene (PTFE) was added at a ratio of 1:5 (sample:PTFE) to facilitate the grinding and dispensing steps for seed samples.

For GC-MS, LC-MS, and ICP-MS analysis, the ground plant tissue was dispensed into 96-well plates using a powder dispensing robot which aspirates and dispenses a fixed powder volume of sample (Zinsser Analytic GmbH, Frankfurt, Germany). Sample location in the plate was tracked by linking sample ID with plate ID in LIMS. The weight of the dispensed samples was re-measured and the actual sample mass values were uploaded to the laboratory information management system (LIMS).

LC-MS Procedures

Approximately 10 mg of dried ground plant tissue were extracted in 0.5 mL 10% aqueous methanol containing labeled internal standards. Tissue was disrupted by a 30 second pulse of high level sonic energy (lithotripsy) at a maximum temperature of 30° C. The extract was centrifuged at 4000 rpm for 2 minutes. The supernatant, diluted with an equal volumn of 50% aqueous acetonitrile (V/V) was chromatographed on C18 HPLC in an acetonitrile/water gradient containing 5 mM ammonium acetate. Samples were passed through a splitter and the split flow was infused to turbo-ionspray ionization sources of two Mariner LC TOF mass spectrometers (PerSeptive Biosystems Inc., Framingham, Mass.). The ionization sources were optimized to generate and monitor positive and negative ions, respectively. The Total Ion Chromatogram (TIC) was analyzed for compounds with masses ranging from 80 to 900 Daltons (Da). The individual ion traces were used for both calibration and quantification. Relative amounts of the compounds were determined using the intensity and peak areas of individual ion traces. Isotopically labeled internal standards were used for peak area ratios, response factor determination, and normalization of data throughout the experiments.

GC-MS Procedures

Approximately 10 mg of dried ground plant tissue samples in 96-well plates were extracted and derivatized in-situ. The procedure yielded trimethylsilyl (TMS) derivatives for a variety of compounds including organic acids, fatty acids, amino acids, sugars, alcohols, and sterols. The procedure involved a two-step derivatization using MSTFA (methyl trimethylsilyl trifluoroacetamide) in acetonitrile, acidified with trifluoroacetic acid, followed by derivatization with a strongly basic silylating agent such as TMSDMA (trimethylsilyldimethylamine). TMS derivatives were analyzed by gas chromatography with time-of-flight mass spectrometry (GC/TOF-MS). Separations were conducted using a 50% phenyl–50% methyl stationary phase, helium carrier gas, and a programmed oven temperature that ramped from a starting temperature of 50° C. to a final temperature of over 300° C. Compounds detected by GC-MS with an electron impact (EI) ion source were cataloged based on Kovats retention indices and mass-to-charge ratio (m/z) of the ions characteristic of each peak. Isotopically labeled internal standards were measured and system suitability checks were performed both prior to and throughout sample analyses, assuring that instrument response remained within statistically derived limits of the initial calibration responses.

ICP-MS Procedures

Approximately 10 mg of plant tissue samples were digested with 1 ml of aqua regia by overnight digestion at 60° C. Samples were passed through 45 μm glass fiber filters, diluted as needed and analyzed on a Micromass Platform ICP-MS (Waters Corp., Beverly, Mass.) with a LEAP CTC PAL autosampler (LEAP Technologies, Inc., Carrboro, N.C.). System suitability checks were performed both prior to and during sample analyses.

Characterization and/or Identification of Compounds Present in Plant Tissue

Control plant tissue samples were analyzed repeatedly by each spectral methodology as described above to determine statistically significant baselines. The resulting data was processed for characterization of all possible peaks and the resulting data entered into the database of endogenous metabolites. In most cases the raw data was processed using a deconvolution algorithm and the peaks present were characterized with retention times/indices and relative mass intensities. The spectral data characteristics corresponding to the peak list was compared to that for the existing metabolite database and the peaks corresponding to known compounds were identified. For the peaks routinely found in the plant samples, but not corresponding to an identified compound, the compound formulas representing the spectral data characteristics with the highest probability were entered into the database of endogenous metabolites. The compounds indicated as corresponding to the characterized but unidentified peaks were linked to metabolic reaction(s)/pathway(s) and the identities of the compounds associated with the pathways of greatest interest were validated (see FIG. 3). A LECO Pegasus II GC/TOF-MS (LECO Corp., St. Joseph, Mich.) and a ThermoFinnigan ion trap GC-MS (Polaris Q) (Thermo Finnigan Corp., San Jose, Calif.) were used in conjunction with additional detector systems, such as an atomic emissions detector (AED) and an infrared (IR) detector for validation of compound identity. A list of compounds present in the database of endogenous metabolites is set forth in Table 2.

SPECIFIC EXAMPLE 2

Creation of a Coherent Data Set for Grouping Herbicides by Site of Action

Described herein is an approach that integrates and standardizes three types of data: gene expression, metabolite (or biochemical) data, and phenotypic (or morphologic) data, to capture a larger share of cellular information than that which is otherwise available from collective results of the three data types. The resulting coherent data was applied to the grouping of herbicides by SOA in *Arabidopsis*. Phenotypic, gene expression, and metabolite analysis was performed on *Arabidopsis* tissues treated with 18 herbicides having nine different sites of action (Table 3). Data types were standardized to allow for simultaneous testing of all the data types or any combination of data types. Data were tested for the ability to accurately indicate the grouping of the herbicides by common SOA. The results indicate that no individual or pair-wise combination of the data types yielded the predictive power achieved by combining all three data types into a coherent data set.

TABLE 2

List of Compounds in Metabolite Database

| | | |
|---|---|---|
| 2,4,6TRIS(TRIFLUOROMETHYL)1,3,5-TRIAZ | CHOLESTANE | CAMPESTEROL |
| 2,6-DIBUTYL-4-METHYLPYRIDINE | CHOLESTENONE | CHOLESTADIENE |
| 2-ISOPROPYLMALIC ACID | CHOLESTEROL | HYDROXYBENZOIC ACID |
| 2-KETOBUTYRIC ACID | CHOLIC ACID | HYPOXANTHINE |
| 2-KETOGLUTARIC | CHROMIUM | INDIUM |
| 2-PHENYL GLYCINE | CINNAMIC ACID | INDOLYLACETONITRILE |
| 3,4-DIOH PHENYLALANINE | CIS + TRANS EPOXY SUCCINIC ACID | INOSITOL |
| 3-NITRO-1,2,4-TRIAZOLE | CIS-EPOXY SUCCINIC ACID | IODINE |
| 4-AMINOBENZOIC ACID | CITRACONIC ACID | IRON |
| 4-AMINOBUTYRIC ACID | CITRIC ACID | ISOCITRIC ACID |
| 4-FLUORO-L-PHENYLALANINE | CITRIC ACIDTRIMETHYL ESTER | ISOLEUCINE |
| 4-OH PHENYL PYRUVIC | CITRULLINE | ITACONIC ACID |
| 41K | COBALT | JASMONIC ACID |
| 43CA | CONIFERYL ALCOHOL | KOJIC ACID |
| 5-FLUOROINDOLE-2-CARBOXYLIC ACID | COPPER | L-ASPARTIC ACID |
| 6-BENZYLAMINOPUR. RIBO | CORTISONE | L-PROLINE |
| 7-METHOXY COUMARIN CARBOXYLIC ACID | CYSTATHIONINE | L-RIBULOSE HYDRATE |
| ACETYL GIBBERELLIC ACID | CYSTEINE | LANOSTEROL |
| ACIFLUORFEN | CYTOSINE | LAURIC ACID |
| ACTINONIN | DECANOIC ACID | LEAD |
| ADENINE | DIAMINOPIMELIC ACID | LEUCINE |
| ADENOSINE | DICYSTEINE | LEUCINE/ISOLEUCINE |
| ADENOSINE 5'DI PO4 | DIHYDROCHOLESTEROL | LITHIUM |
| ALANINE | DIHYDROXYACETONE PO4 | LUPEOL |

TABLE 2-continued

List of Compounds in Metabolite Database

| | | |
|---|---|---|
| ALLANTOIC ACID | DIMETHYL KETAL | LUTEOLIN |
| ALLANTOIN | DIOSGENIN | LYSINE |
| ALLUMINUM | DIPICOLINIC ACID | MAGNESIUM |
| AMINOADIPIC ACID | DOCOSANOIC ACID | MALIC ACID |
| ANTHRANILIC ACID | EICOSANOIC ACID | MANGANESE |
| ANTHRONE | ERGOCALCIFEROL | MERCURY |
| ANTIMONY | ERGOSTEROL | METHIONINE |
| ARGININE | ESTRONE | METHYL STEARATE |
| ARSENIC | FARNESOL | METRIBUZIN |
| ASCORBIC ACID | FLUORESCAMINE | MEVALONIC LACTONE |
| ASPARAGINE | FLUORESCEIN | MOLYBDENUM |
| ASPARTIC ACID | FOLIC ACID | MYRCENE |
| BARIUM | FRUCTOSE | N-C10 |
| BENZOIC ACID | FUMARIC ACID | N-C12 |
| BERYLLIUM | GALLIC ACID | N-C14 |
| BETAINE | GIBBERELLIC ACID | N-C16 |
| BIOTIN | GLUCOSE | N-C18 |
| BISMUTH | GLUTAMIC ACID | N-C20 |
| BIURET | GLUTAMINE | N-C22 |
| BORON | GLUTATHIONE | N-C24 |
| BRASSICASTEROL | GLYCINE | N-C26 |
| CADMIUM | HISTIDINE | N-C28 |
| CAFFEINE | HOMOCYSTEINE | |
| CALCIUM | HOMOGENTISIC ACID | |
| N-C31 | HOMOSERINE | |
| N-C32 | STRONTIUM | |
| HYDROCORTISONE | N-C34 | |
| N-C36 | SUCROSE | |
| N-C38 | SULFOLANE | |
| N-C40 | SYNEPHRINE | |
| NAPTHOL | TAURINE | |
| NEROL | TETRADECANOIC ACID | |
| NIACINAMIDE | THREONINE | |
| NICKEL | THYMINE | |
| NICOTINIC ACID | TIN | |
| NOPALINE | TMS-PHOSPHATE | |
| OCTADECADIENOIC ACID | TRYPTOPHAN | |
| OCTADECANOIC ACID | TYROSINE | |
| OCTADECATRIENIOC ACID | UNKNOWN | |
| ORNITHINE | URACIL | |
| OROTIC ACID | URANIUM | |
| OXALIC ACID DIMETHYL ESTER | URIC ACID | |
| OXALOACETIC ACID | UROCANIC ACID | |
| PALMITIC ACID | URSOLIC ACID | |
| PANTOTHENIC ACID | VALINE | |
| PHENYL PYRUVIC ACID | VANADIUM | |
| PHENYLALANINE | ZEATIN | |
| PHOSPHATE | ZINC | |
| PHOSPHOENOLPYRUVATE | a-TOCOPHEROL | |
| PHOSPHORUS | g-TOCOPHEROL | |
| PINITOL | g-TOCOPHEROL(un) | |
| PIPECOLIC ACID | o-COUMARIC ACID | |
| POTASSIUM | p-COUMARIC ACID | |
| PROGESTERONE | SUCCINIC ACID | |
| PROLINE | STIGMASTEROL METHYL ESTER | |
| PROTEIN | STEARIC ACID | |
| PYRIDOXINE | STIGMASTEROL | |
| PYRUVIC ACID | N-C29 | |
| QUINIC ACID | N-C30 | |
| QUINIC ACID 1,3,4,5R | SQUALENE | |
| RAFFINOSE | SHIKIMIC ACID | |
| RETINOIC ACID | SILVER | |
| RIBOFLAVIN | SINAPINIC ACID | |
| RIBOSE | SITOSTEROL | |
| SALICYLIC ACID | | |
| SELENIUM | | |
| SERINE | | |

TABLE 3

Herbicides Grouped According to Site of Action

| | Chemical | Chemical Family | Site of Action | Suggested MOA | Symptom Class |
|---|---|---|---|---|---|
| 1 | Glyphosate | — | 5-enolpyruvylshikimate-3-phosphate synthase(EPSPS) | reduced photosynthetic intermediates via loss of feedback regulation | 4 |
| 2 | Glufosinate | — | glutamine synthelase | accumulation of ammonia | 3 |
| 3 | Acifluorfen | diphenylether | protoporphyrinogen oxidase (protox) | lipid peroxidation | 6 |
| 4 | Bifenox | diphenylether | | | 6 |
| 5 | Imazapyr | imidazolinone | ALS | depletion of ile, leu, val? | 4 |
| 6 | Imazethapyr | imidazolinone | | | 4 |
| 7 | Chlorosulfuron | sulfonylurea | | | 4 |
| 8 | Atrazine | triazine | Qb binding protein | lipid peroxidation | 7 |
| 9 | Metribuzin | triazine | | | 7 |
| 10 | Diuron | phenylurea | | | 7 |
| 11 | Bentazon | benzothiadiazole | | | 7 |
| 12 | Paraquat | bipyridinium | accepts electrons from photosystem I | lipid peroxidation | 7 |
| 13 | Diquat | bipyridinium | | | 7 |
| 14 | 2,4-D | phenoxy acetic acid | unknown | auxin-like | 5 |
| 15 | Dicamba | benzoic acid | | | 5 |
| 16 | Benazolin | — | | | 5 |
| 17 | Amitrole | — | unknown (carotenoid biosynthesis) | unknown | 2 |
| 18 | Metolachlor | chloroacetamide | unknown (very long chain fatty acids?) | unknown | 7 |

The herbicide SOA study, also referred to as SOA1, was performed according to the procedures described below.

Herbicide Treatment

*Arabidopsis thaliana* plants were grown for 21 days and herbicides were applied by spraying the foliage in a spray hood (Halltech Environmental, Inc, Guelph, Ontario). Herbicide stock solutions were made in dimethylsulfoxide. Working solutions were made by diluting the stock solutions into 15% DMSO or 20% Tetrahydrofurfural alcohol, while the negative control contained a corresponding solution lacking herbicide. The minimum inhibitory concentration (MIC) was defined as the minimum concentration of herbicide that inhibited rosette growth by at least 90% compared to mock treated control plants. The time required for plants to exhibit the full range of symptoms at the minimum inhibitory concentration of herbicide (Tmic) was measured. MIC and Tmic were determined from rosette measurements made every 3 days and daily photographs of plants sprayed with a series of two-fold dilutions. For each herbicide, treated and control plant tissue samples were harvested at 10%, 30%, and 70% of Tmic. A separate flat of plants (approximately 30) was used for each of the herbicide-treated, the mock-treated, and the 10%, 30%, and 70% time points.

Sample Preparation

Plant tissue was harvested directly into bar-coded tubes (96-well format) in liquid nitrogen, lyophilized, ground to powder, and stored according to the procedures described in Specific Example 1. For GC-MS, LC-MS, and ICP-MS analysis, the ground plant tissue was dispensed into 96-well plates as described in Specific Example 1, supra.

GC-MS, LC-MS, and ICP-MS Analysis Procedures

Each of the plant tissue samples was analyzed by GC-MS, LC-MS, and ICP-MS in a 96-well high-throughput format according to the procedures described in Specific Example 1, supra. Sample ID and all associated data were linked through LIMS. The instrumentation used for analysis was validated to ensure the reproducibility and reliability of data collected and processed in the platform.

Error models describing the calibration and validation of the instrumentation were constructed to describe the properties of sample behavior. BEEBE ET AL., CHEMOMETRICS: A PRACTICAL GUIDE 348 (1998). The reliability and sensitivity of the high-throughput analytical techniques (GC-MS, LC-MS, HPLC, ICP) used in the present invention have been previously demonstrated. Fiehn et al., *Metabolite Profiling for Plant Function Genomics,* 18 NATURE BIOTECH. 1157–1161 (2000). The range of detection and the high-throughput nature of the metabolite analysis affected the statistical treatment of the response data. The variance across a 96-well plate was measured to allow for the use of a single replicate injection for each sample. The instrumentation used was qualified for a single replicate injection according to the procedures described as follows. The instrument qualification study was a randomized, parallel assignment of at least three known compounds at three concentrations with a minimum of 12 randomized injections for each compound-concentration combination. A total of 108 injections were used for a complete 96-well study. The variance across a 96-well plate was estimated in this manner. MILLER & MILLER, STATISTICS FOR ANALYTICAL CHEMISTRY 227 (2d. ed., 1988). The minimum number of replicates required to achieve a power of 0.90, at a significance testing level of 0.05, was estimated for a two-tailed analysis of variance test according to Sokal and Rohlf. SOKAL & ROHLF, BIOMETRY: THE PRINCIPLES AND PRACTICE OF STATISTICS IN BIOLOGICAL RESEARCH 887 (3d. ed., 1995).

In the case of LC-MS, a plurality of peaks (up to 300) was detected in both positive and negative mode in the control samples. The ions were likely due to $(M+H)^+$ or $(M+NH4)^+$ for positive mode and $(M-H)^-$ or $(M-OAC)^-$ for negative mode. Exact molecular weights were calculated using previously assigned peaks. Mass spectrum profiles were evaluated for isotopic distribution primarily due to $C_{13}$ contributions, and the most likely elemental composition computed using nitrogen rule, isotopic ratio contributions, and scanning molecular weight libraries. All spectral data were entered into the database of endogenous metabolites as described in Specific Example 1, supra.

GC-MS analysis of plant tissue samples was conducted using a ThermoFinnigan Tempus GC/TOF-MS system (Thermo Finnigan Corp., San Jose, Calif.) including a small bore, capillary column ($\leq 0.18$ mm ID) with a high temperature 50% phenyl stationary phase. Column temperature was programmed to ramp from an initial temperature of 50° C. to over 300° C. Column effluent passed through a heated transfer line into a time of flight mass spectrometer equipped with an electron impact ion source. Calibration of the mass scale on the TOF-MS was performed with perfluorotributylamine (FC-43, PFTBA). Detector linearity was confirmed using a paraffin mix at three different concentrations. Retention times and chain lengths of the various hydrocarbons in the paraffin mix were also used to generate Kovats retention indices.

Compounds detected in the plant tissue samples were cataloged based on Kovats retention indices and mass-to-charge ratio (m/z) of the ions characteristic of each peak. Typically, 50 to 100 major peaks were detected in the total ion chromatograms (TICs) for the plant samples. Over 200 peaks were detected by using deconvolution techniques or by manually selecting unique masses to isolate smaller peaks not readily observed in the TIC. All spectral data were entered into the database of endogenous metabolites as described in Specific Example 1, supra.

Total Protein Assay Procedures

Plant tissue samples prepared as described above were extracted according to manufacturer's instructions (BCA-200 Protein Assay Kit, Pierce Biotechnology, Inc., Rockford, Ill.). Total protein assays were performed in a 96-well format using 10 $\mu$L tissue sample supernatant in accord with manufacturer's instructions.

Gene Expression Analysis Procedures

Arrays of 60 mer oligonucleotide probes were manufactured by using non-contact inkjet microarray printing technology (Agilent Technologies, Palo Alto, Calif.). 6200 *A. thaliana* genes were randomly selected. A number of genes were selected for randomized intra-array replication, and positive and negative control features were added, giving a total of 8400 features on the microarray. RNA was extracted from lyophilized and pulverized tissue using TRIZOL reagent (Invitrogen Corp., Carlsbad, Calif.). Lyophilized tissues were first re-hydrated using RNALATER (Ambion, Inc., Austin, Tex.). The mRNA in the total RNA sample was amplified, fluorescently labeled with either Cy3 (mock-treated) or Cy5 (herbicide treated), and hybridized against microarrays for 17 hours at 60° C. as according with the manufacturer's instructions (Agilent Technologies, Palo Alto, Calif.). Final samples contained 200 ng of each Cy-labeled cRNA. Arrays were washed in 6×SSC, 0.005% TRITON X-102 at 60° C., in the same solution for 10 minutes at room temperature, and in 0.1×SSC, 0.005% TRITON X-102 for five minutes at 4° C. The dried arrays were scanned using an Agilent LP2 Scanner (Agilent Technologies, Palo Alto, Calif.). Images were analyzed using software supplied by the manufacturer (Feature Extraction software, Agilent Technologies, Palo Alto, Calif.) and the resulting data files were evaluated using Rosetta RESOLVER software (Rosetta Inpharmatics, Inc., Kirkland, Wash.).

Experimental Design

Eighteen commercially available herbicides affecting nine distinct sites of action were studied using phenotypic, biochemical, and gene expression analysis (Table 3). Of the nine identified sites of action (SOA), five were represented by at least two herbicides. When available, different chemical classes of herbicides affecting a common site of action were utilized. Tissue was sampled at 10% (early), 30% (middle), and 70% (late) of the time required for the full development of symptoms at the MIC of herbicide. The phenotypic, gene expression, and biochemical responses of herbicide-treated plants were compared to mock-treated controls. Data derived from tissues treated with herbicides having a SOA with at least two representatives formed a training set, while data derived from the four remaining herbicides with distinct sites of action formed a test set. The objective was to find a method for accurately predicting grouping by SOA for both data sets.

Phenotypic Analysis

As shown in FIG. 12, seven distinct morphological phenotypes were observed for the 18 herbicides studied. For the phenotypic analysis, up to twelve traits were measured for each group of herbicide treated plants, and the data were expressed as numeric values standardized to the average response for the mock treated tissues (Table 4). The twelve traits measured were the following leaf characteristics for both new and old leaves: width, chlorosis, anthocyanin accumulation, necrosis, twisting, and curling. While phenotypic analysis indicated the accurate grouping by SOA for a majority of herbicides, in some cases very similar symptoms were observed for herbicides affecting distinct sites of action. For example, leaf bleaching and leaf enlargement were characteristic of the carotenoid inhibitor, amitrole. Chlorosis and leaf curling were characteristic of the glutamine synthethase inhibitor, glufosinate. Necrotic leaf flecks were characteristic of the protoporphyrinogen oxidase (PROTOX) inhibitors, bifenox and acifluorfen. The auxin inhibitors produced thin bent leaves often resembling a pinwheel. However, both the PSII (Photo System II) (diuron, metribuzin, atrazine, and bentazon) and the PSI (Photo System I) (paraquat and diquat) inhibitors caused rapid and widespread leaf necrosis presumably via a convergence in their lipid peroxidation-based mode of action. Similarly, both the acetolactate synthase (ALS) inhibitors (imazethapyr, imazapyr, chlorosulfuron) and the 5-enolpyruvylshikimate-3-phosphate synthase (EPSPS) inhibitor (glyphosate) caused anthocyanin accumulation in the older leaves accompanied by chlorosis of the newly emerging leaves. Phenotypic analysis alone was insufficient to distinguish the herbicides by SOA.

TABLE 4

Eleven Phenotypic Traits Measured for Each Herbicide Treated Group

| | Herbicide | Trait | Dev. |
|---|---|---|---|
| 1 | 2-4-D | leafWidth | −1 |
| 2 | 2-4-D | matureLeafChlorosis | 2 |
| 3 | 2-4-D | newLeafChlorosis | 1 |
| 4 | 2-4-D | matureLeafAnthocyanins | 1 |
| 5 | 2-4-D | newLeafAnthocyanins | 0 |
| 6 | 2-4-D | matureLeafNecrosis | 0 |
| 7 | 2-4-D | newLeafNecrosis | 0 |
| 8 | 2-4-D | leafCurling | 1 |
| 9 | 2-4-D | leafTwisting | 2 |
| 10 | 2-4-D | tMic | 2 |
| 11 | 2-4-D | pointedLeaves | 0 |
| 12 | Acifluor | leafWidth | 0 |
| 13 | Acifluor | matureLeafChlorosis | 0 |
| 14 | Acifluor | newLeafChlorosis | 0 |
| 15 | Acifluor | matureLeafAnthocyanins | 0 |
| 16 | Acifluor | newLeafAnthocyanins | 0 |
| 17 | Acifluor | matureLeafNecrosis | 1 |
| 18 | Acifluor | newLeafNecrosis | 3 |
| 19 | Acifluor | leafCurling | 1 |
| 20 | Acifluor | leafTwisting | 0 |
| 21 | Acifluor | tMic | 1 |
| 22 | Acifluor | pointedLeaves | 0 |
| 23 | Amitrole | leafWidth | 2 |

TABLE 4-continued

Eleven Phenotypic Traits Measured for Each Herbicide Treated Group

| | Herbicide | Trait | Dev. |
|---|---|---|---|
| 24 | Amitrole | matureLeafChlorosis | 3 |
| 25 | Amitrole | newLeafChlorosis | 4 |
| 26 | Amitrole | matureLeafAnthocyanins | 0 |
| 27 | Amitrole | newLeafAnthocyanins | 0 |
| 28 | Amitrole | matureLeafNecrosis | 0 |
| 29 | Amitrole | newLeafNecrosis | 0 |
| 30 | Amitrole | leafCurling | −1 |
| 31 | Amitrole | leafTwisting | 0 |
| 32 | Amitrole | tMic | 2 |
| 33 | Amitrole | pointedLeaves | 0 |
| 34 | Atrazine | leafWidth | −1 |
| 35 | Atrazine | matureLeafChlorosis | 1 |
| 36 | Atrazine | newLeafChlorosis | 1 |
| 37 | Atrazine | matureLeafAnthocyanins | 0 |
| 38 | Atrazine | newLeafAnthocyanins | 0 |
| 39 | Atrazine | matureLeafNecrosis | 4 |
| 40 | Atrazine | newLeafNecrosis | 4 |
| 41 | Atrazine | leafCurling | 1 |
| 42 | Atrazine | leafTwisting | 0 |
| 43 | Atrazine | tMic | 1 |
| 44 | Atrazine | pointedLeaves | 1 |
| 45 | Benazoli | leafWidth | −2 |
| 46 | Benazoli | matureLeafChlorosis | 0 |
| 47 | Benazoli | newLeafChlorosis | 0 |
| 48 | Benazoli | matureLeafAnthocyanins | 0 |
| 49 | Benazoli | newLeafAnthocyanins | 0 |
| 50 | Benazoli | matureLeafNecrosis | 0 |
| 51 | Benazoli | newLeafNecrosis | 0 |
| 52 | Benazoli | leafCurling | 2 |
| 53 | Benazoli | leafTwisting | 2 |
| 54 | Benazoli | tMic | 2 |
| 55 | Benazoli | pointedLeaves | 0 |
| 56 | Bentazon | leafWidth | −2 |
| 57 | Bentazon | matureLeafChlorosis | 2 |
| 58 | Bentazon | newLeafChlorosis | 2 |
| 59 | Bentazon | matureLeafAnthocyanins | 0 |
| 60 | Bentazon | newLeafAnthocyanins | 0 |
| 61 | Bentazon | matureLeafNecrosis | 4 |
| 62 | Bentazon | newLeafNecrosis | 4 |
| 63 | Bentazon | leafCurling | 2 |
| 64 | Bentazon | leafTwisting | 0 |
| 65 | Bentazon | tMic | 1 |
| 66 | Bentazon | pointedLeaves | 1 |
| 67 | Bifenox | leafWidth | 0 |
| 68 | Bifenox | matureLeafChlorosis | 0 |
| 69 | Bifenox | newLeafChlorosis | 0 |
| 70 | Bifenox | matureLeafAnthocyanins | 0 |
| 71 | Bifenox | newLeafAnthocyanins | 0 |
| 72 | Bifenox | matureLeafNecrosis | 1 |
| 73 | Bifenox | newLeafNecrosis | 3 |
| 74 | Bifenox | leafCurling | 1 |
| 75 | Bifenox | leafTwisting | 0 |
| 76 | Bifenox | tMic | 1 |
| 77 | Bifenox | pointedLeaves | 0 |
| 78 | Chlorsul | leafWidth | −1 |
| 79 | Chlorsul | matureLeafChlorosis | 2 |
| 80 | Chlorsul | newLeafChlorosis | 2 |
| 81 | Chlorsul | matureLeafAnthocyanins | 3 |
| 82 | Chlorsul | newLeafAnthocyanins | 0 |
| 83 | Chlorsul | matureLeafNecrosis | 0 |
| 84 | Chlorsul | newLeafNecrosis | 0 |
| 85 | Chlorsul | leafCurling | 1 |
| 86 | Chlorsul | leafTwisting | 1 |
| 87 | Chlorsul | tMic | 2 |
| 88 | Chlorsul | pointedLeaves | 0 |
| 89 | Dicamba | leafWidth | −2 |
| 90 | Dicamba | matureLeafChlorosis | 2 |
| 91 | Dicamba | newLeafChlorosis | 0 |
| 92 | Dicamba | matureLeafAnthocyanins | 0 |
| 93 | Dicamba | newLeafAnthocyanins | 0 |
| 94 | Dicamba | matureLeafNecrosis | 0 |
| 95 | Dicamba | newLeafNecrosis | 0 |
| 96 | Dicamba | leafCurling | 2 |
| 97 | Dicamba | leafTwisting | 2 |
| 98 | Dicamba | tMic | 2 |
| 99 | Dicamba | pointedLeaves | 0 |
| 100 | Diquat | leafWidth | −2 |
| 101 | Diquat | matureLeafChlorosis | 1 |
| 102 | Diquat | newLeafChlorosis | 1 |
| 103 | Diquat | matureLeafAnthocyanins | 0 |
| 104 | Diquat | newLeafAnthocyanins | 0 |
| 105 | Diquat | matureLeafNecrosis | 4 |
| 106 | Diquat | newLeafNecrosis | 4 |
| 107 | Diquat | leafCurling | 2 |
| 108 | Diquat | leafTwisting | 0 |
| 109 | Diquat | tMic | 2 |
| 110 | Diquat | pointed Leaves | 1 |
| 111 | Diuron | leafWidth | −2 |
| 112 | Diuron | matureLeafChlorosis | 2 |
| 113 | Diuron | newLeafChlorosis | 2 |
| 114 | Diuron | matureLeafAnthocyanins | 0 |
| 115 | Diuron | newLeafAnthocyanins | 0 |
| 116 | Diuron | matureLeafNecrosis | 4 |
| 117 | Diuron | newLeafNecrosis | 4 |
| 118 | Diuron | leafcurling | 1 |
| 119 | Diuron | leafTwisting | 0 |
| 120 | Diuron | tMic | 1 |
| 121 | Diuron | pointedLeaves | 1 |
| 122 | Glufosin | leafWidth | −2 |
| 123 | Glufosin | matureLeafChlorosis | 3 |
| 124 | Glufosin | newLeafChlorosis | 3 |
| 125 | Glufosin | matureLeafAnthocyanins | 0 |
| 126 | Glufosin | newLeafAnthocyanins | 0 |
| 127 | Glufosin | matureLeafNecrosis | 0 |
| 128 | Glufosin | newLeafNecrosis | 0 |
| 129 | Glufosin | leafCurling | 2 |
| 130 | Glufosin | leafTwisting | 1 |
| 131 | Glufosin | tMic | 1 |
| 132 | Glufosin | pointedLeaves | 1 |
| 133 | Glyphosa | leafWidth | 0 |
| 134 | Glyphosa | matureLeafChlorosis | 1 |
| 135 | Glyphosa | newLeafChlorosis | 2 |
| 136 | Glyphosa | matureLeafAnthocyanins | 3 |
| 137 | Glyphosa | newLeafAnthocyanins | 1 |
| 138 | Glyphosa | matureLeafNecrosis | 3 |
| 139 | Glyphosa | newLeafNecrosis | 0 |
| 140 | Glyphosa | leafCurling | 0 |
| 141 | Glyphosa | leafTwisting | 0 |
| 142 | Glyphosa | tMic | 2 |
| 143 | Glyphosa | pointedLeaves | 1 |
| 144 | Imazapyr | leafWidth | 0 |
| 145 | Imazapyr | matureLeafChlorosis | 0 |
| 146 | Imazapyr | newLeafChlorosis | 2 |
| 147 | Imazapyr | matureLeafAnthocyanins | 2 |
| 148 | Imazapyr | newLeafAnthocyanins | 0 |
| 149 | Imazapyr | matureLeafNecrosis | 0 |
| 150 | Imazapyr | newLeafNecrosis | 0 |
| 151 | Imazapyr | leafCurling | 0 |
| 152 | Imazapyr | leafTwisting | 0 |
| 153 | Imazapyr | tMic | 2 |
| 154 | Imazapyr | pointedLeaves | 0 |
| 155 | Imazetha | leafWidth | 0 |
| 156 | Imazetha | matureLeafChlorosis | 0 |
| 157 | Imazetha | newLeafChlorosis | 2 |
| 158 | Imazetha | matureLeafAnthocyanins | 3 |
| 159 | Imazetha | newLeafAnthocyanins | 0 |
| 160 | Imazetha | matureLeafNecrosis | 0 |
| 161 | Imazetha | newLeafNecrosis | 0 |
| 162 | Imazetha | leafCurling | 1 |
| 163 | Imazetha | leafTwisting | 1 |
| 164 | Imazetha | tMic | 2 |
| 165 | Imazetha | pointedLeaves | 0 |
| 166 | Metolach | leafWidth | −1 |
| 167 | Metolach | matureLeafChlorosis | 0 |
| 168 | Metolach | newLeafChlorosis | 0 |
| 169 | Metolach | matureLeafAnthocyanins | 0 |
| 170 | Metolach | newLeafAnthocyanins | 0 |
| 171 | Metolach | matureLeafNecrosis | 3 |
| 172 | Metolach | newLeafNecrosis | 3 |
| 173 | Metolach | leafCurling | 2 |

TABLE 4-continued

Eleven Phenotypic Traits Measured for Each Herbicide Treated Group

| | Herbicide | Trait | Dev. |
|---|---|---|---|
| 174 | Metolach | leafTwisting | 1 |
| 175 | Metolach | tMic | 2 |
| 176 | Metolach | pointedLeaves | 1 |
| 177 | Metribuz | leafWidth | −2 |
| 178 | Metribuz | matureLeafChlorosis | 2 |
| 179 | Metribuz | newLeafChlorosis | 2 |
| 180 | Metribuz | matureLeafAnthocyanins | 0 |
| 181 | Metribuz | newLeafAnthocyanins | 0 |
| 182 | Metribuz | matureLeafNecrosis | 4 |
| 183 | Metribuz | newLeafNecrosis | 4 |
| 184 | Metribuz | leafCurling | 1 |
| 185 | Metribuz | leafTwisting | 0 |
| 186 | Metribuz | tMic | 1 |
| 187 | Metribuz | pointedLeaves | 1 |
| 188 | Paraquat | leafWidth | −1 |
| 189 | Paraquat | matureLeafChlorosis | 1 |
| 190 | Paraquat | newLeafChlorosis | 1 |
| 191 | Paraquat | matureLeafAnthocyanins | 0 |
| 192 | Paraquat | newLeafAnthocyanins | 0 |
| 193 | Paraquat | matureLeafNecrosis | 4 |
| 194 | Paraquat | newLeafNecrosis | 4 |
| 195 | Paraquat | leafCurling | 2 |
| 196 | Paraquat | leafTwisting | 0 |
| 197 | Paraquat | tMic | 2 |
| 198 | Paraquat | pointedLeaves | 1 |

Gene Expression Analysis

Gene expression responses were measured for the plant tissues treated with each of the 18 herbicides and the average response calculated for each herbicide. The average response for each herbicide treatment was standardized to the average response for the respective mock treated tissue creating gene expression profiles for each of the 18 herbicide treatments at each of the three time points. The gene expression profiles for the herbicide treated tissues were based on significant changes in gene expression (generally greater than 2-fold) relative to control samples, for a plurality of genes (300 to 1000). The gene expression responses were expressed in units of standard deviations relative to the control mean.

Herbicidal SOA was not readily deduced from examination of gene expression. For example, the SOA for three of the herbicides in the study is ALS, an enzyme used in the synthesis of isoleucine, leucine, and valine from pyruvate. ALS is part of a pathway consisting of eight genes, six of which were included on the array. Of the genes on the array, three were found to be significantly up-regulated in the gene expression profiles of the tissues treated with the ALS-targeting herbicides. Likewise, two herbicides used in the study target PROTOX, an enzyme utilized in heme biosynthesis. In the case of heme biosynthesis, 22 enzymes are known to convert glutamate to heme and chlorophyll. Genes encoding 10 of the 22 enzymes were on the array, and 3 of the 10 genes displayed two to three-fold decreased expression in the profiles of the tissues treated with the PROTOX-targeting herbicides. Thus, it is difficult to deduce SOA from the differential expression of a few genes in a profile containing hundreds, when just a subset of the genes in the target pathway are altered and many genes in other pathways show much greater fluctuations in expression. Experimental error and lack of accurate and comprehensive gene annotation further complicated the analysis.

Although the gene expression analysis failed to conclusively indicate herbicide SOA, the gene expression data were tested for ability to predict the grouping of herbicides by SOA. The data were analyzed for hierarchical clustering according to common changes in gene expression. Clustering was performed with SAS PROC CLUSTER (SAS Institute, Inc., Cary, N.C.), using agglomerative hierarchical clustering with Ward's minimum-variance method on standardized data, to adjust for different ranges of response. SAS PROC TREE (SAS Institute, Inc., Cary, N.C.), was used to produce dendrograms of SOA (see FIG. 13). The data were clustered on the set of genes observed in all herbicide treatment groups, as the clustering algorithm did not allow missing values.

Similar to that observed for the phenotypic profiles, cluster analysis of the gene expression profiles failed to accurately group the herbicides by common SOA (see FIG. 13). In addition, the predicted clustering by gene expression changed with the time of tissue harvesting. Use of the middle time point data resulted in the accurate grouping of 4 of the 5 sites of action (represented by more than one herbicide). Only the grouping of the two PROTOX inhibitors was not indicated with the middle time point data. The late time point data was the least indicative of the SOA. The early and middle time point data resulted in the strongest clustering of the PSII and ALS inhibitors, whereas, the middle and late time point data resulted in the best grouping of the auxin and PROTOX inhibitors.

In some cases the clustering between herbicides with differing sites of action was stronger than for herbicides with the same SOA. For example, diquat is a PSI inhibitor, whereas acifluorfen and bifenox are PROTOX inhibitors, and metolachlor is neither a PSI nor a PROTOX inhibitor (unpublished data). However, the gene expression profile correlation between metolachlor and diquat (r=0.569) and the correlation between metolachlor and bifenox (r=0.499) were both higher than the correlation of bifenox to acifluorfen (r=0.151), which have the same SOA.

In addition, herbicides of different chemical class but with a common site of action were accurately grouped by gene expression analysis in some cases, while herbicides of the same chemical class and common site of action were not. For example, the early and middle time point data indicated the correct grouping of the PSII and the ALS inhibitors represented by different chemical classes of herbicides. The PSII inhibitors consisted of the benzothiadiazole (bentazon), triazines (atrazine and metribuzin), and phenylurea (diuron) and the ALS inhibitors consisted of sulfonylurea (chlorsulfuron) and imidazolinones (imazapyr and imazethapyr). In contrast, clustering was not indicated at any time point for the two PROTOX inhibitors of the same chemical class (diphenylether). The results of the cluster analysis of the gene expression profile data indicate either the need for optimization of time of sampling or the limited utility of a single sampling point in predicting herbicide SOA.

Evidence for similarities in profiles based on mode of action (MOA) rather than SOA is less clear. The PSII, PSI, and PROTOX inhibitors have distinct sites of action but are thought to have a common mode of action (MOA) through the generation of reactive oxygen species that promote lipid peroxidation. DEVINE ET AL., PHYSIOLOGY OF HERBICIDE ACTION (1993). However, when the data for the herbicides were compared, strong clustering was observed at the early time point between the PSI inhibitors, bifenox (one of the PROTOX inhibitors), and metolachlor (unknown MOA), but the PSII inhibitors did not cluster with this group. At the latest time point, some clustering occurred between the PSII and PROTOX inhibitors, but not with the PSI inhibitors. Gene expression analysis alone was insufficient to distinguish the herbicides by SOA or MOA.

Biochemical (Metabolite) Profiling

The same samples subjected to gene expression analysis were also examined using biochemical, or metabolite, analysis. Biochemical responses were measured for the plant tissues treated with each of the 18 herbicides and the average response calculated for each herbicide. The average response for each herbicide treatment was standardized to the average response for the respective mock treated tissue creating biochemical profiles for each of the 18 herbicide treatments at each of the three time points. The biochemical profiles were expressed in units of standard deviations relative to the control mean (data not shown).

In general, the predictive power of the metabolite data displayed many of the limitations observed for the gene expression data. The lack of comprehensive peak identification prevented inference of SOA from the biochemical responses. The metabolite data were tested for ability to predict the grouping of herbicides by SOA. The data were analyzed for hierarchical clustering according to common changes in biochemicals. Clustering was performed with SAS PROC CLUSTER (SAS Institute, Inc., Cary, N.C.), using agglomerative hierarchical clustering with Ward's minimum-variance method on standardized data, to adjust for different ranges of response. SAS PROC TREE (SAS Institute, Inc., Cary, N.C.), was used to produce dendrograms (FIG. 13). The data were clustered on the set of biochemicals observed in all herbicide treatment groups, as the clustering algorithm did not allow missing values.

Similar to that observed for the phenotypic and gene expression data, cluster analysis of the metabolite data failed to accurately predict the grouping of the herbicides by common SOA (FIG. 13). In the case of the biochemical profile data, use of the late time point data for the cluster analysis resulted in the most accurate grouping of the herbicides by SOA and the early time point data were the least indicative of SOA. For the late time point data, three of the five sites of action (represented by more than one herbicide) were accurately grouped. None of the biochemical time point data indicated the grouping of the two PROTOX inhibitors and the late time point biochemical data failed to cluster the two PSI inhibitors. Similar to that observed for the gene expression analysis, the correlation of the biochemical responses of herbicides having different sites of action is often greater than the correlation between the responses of herbicides having the same SOA. Clustering by MOA based on the biochemical responses was less clear than for SOA. The data indicate that biochemical analysis alone is insufficient to distinguish the herbicides by SOA or MOA.

Combination of Profiling Technologies

Neither phenotypic, gene expression, nor metabolite analysis alone is sufficient to infer herbicidal SOA. Using data from any single technology resulted in inaccurate groupings of the herbicides by SOA. As a result, the data from two and three of the technologies were combined and tested to determine whether analysis of the combined data would improve herbicide classification by SOA.

For the three different technologies, the data were first expressed as standardized differences from controls as described above. Each data point represents a distance or degree (in units of standard deviations) a particular observation on a treated sample was from the corresponding observation on a control sample. To reduce the dimensionality of the data and to approximately weight equally the data from the three technologies, principle components analysis was performed separately on the phenotypic, biochemical, and gene expression profiles, using SAS PROC PRINCOMP (SAS Institute, Inc., Cary, N.C.). Gene expression and metabolite data were taken from the early and late time points, respectively. Principle components analysis was applied to balance the data, as gene expression profiling provides an order of magnitude more data points than biochemical profiling. The application ensured that the two platforms were given approximately the same weight in further analysis. The analysis procedure resulted in 45 principle components (17 from gene expression profiling, 17 from biochemical profiling, and 11 from phenotypic profiling). The expression of the phenotypic, gene expression, and biochemical profile data in a common unit system allowed for simultaneous testing of any subset or combination of the data by analysis methods such as cluster analysis, discriminant analysis, or correlation analysis.

To assess the ability to predict the accurate grouping of herbicides according to SOA, pairwise combinations of the principle component data from each technology were tested using correlation analysis (FIG. 8). The results of testing data from pairs of technologies, such as gene expression and biochemical profiles, phenotypic and biochemical profiles, and phenotypic and gene expression profiles, while more accurate than the predictions from any single technology, still failed to indicate the correct grouping of the herbicides by SOA.

Figure 14:
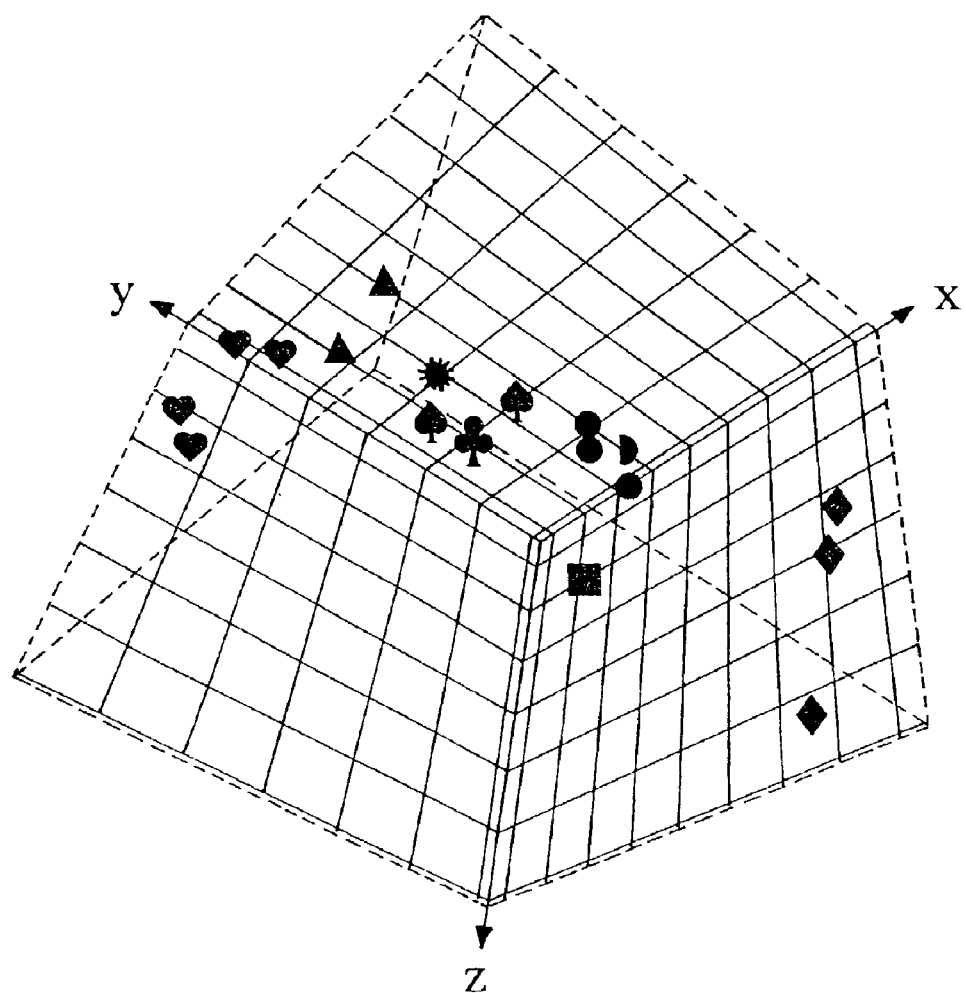
FIG. 14 is a three-dimensional graphical representation of a coherent data set where the first principal component of each of the phenotypic data, the biochemical profile data and the gene expression profile data is represented on the y-axis, z-axis and x-axis, respectively. The plot was made using Spotfire DECISIONSITE. Principle components analysis was performed separately on the phenotypic, biochemical, and gene expression profile data, using SAS PROC PRIN- COMP. The principle components were used to derive a linear discriminant rule using SAS PROC DISCRIM with equal priors. The rule indicated 100% correct classification of the herbicides by SOA. The nine herbicide groups according to site of action are represented as follows: ▶=Glyphosate; ♣=Gulfosinate; ▲=Acifluorfen and Bifenox; ♦=Imazapyr, Imazethapyr, and Clorosulfuron; ♥=Atrazine, Metribuzin, Diuron, and Bentazon; ▶=Paraquat and Diquat; ●=2,4-D; Dicamba and Benazolin; ■=Amitrole; and ✱=Metolachlor.
Figure 15A:
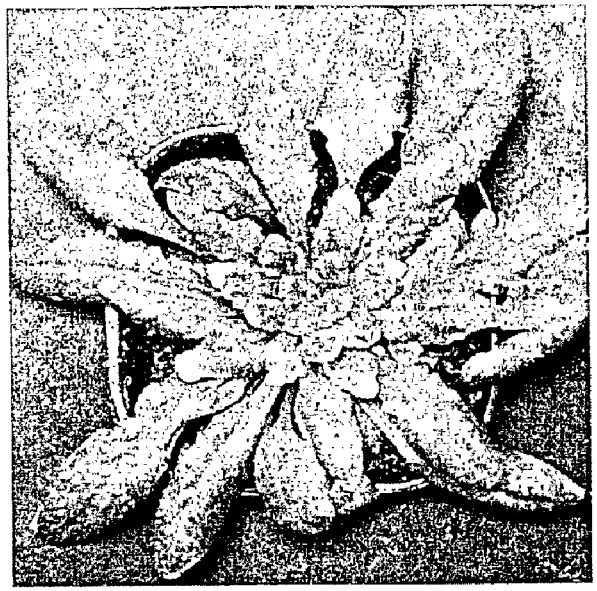
FIGS. 15A–15L display the phenotype of *Arabidopsis* plants treated with five different compounds (Unknown 1 to Unknown 5) suspended in two different spray formulations, THFA and Tween 80. The images were taken five days after treatment.
Figure 15B:
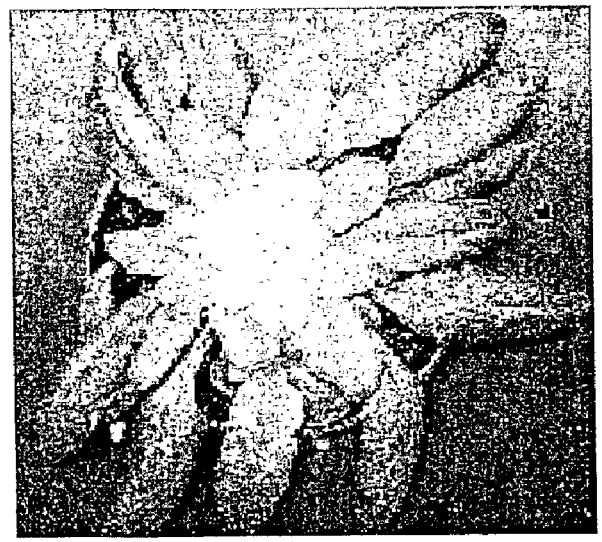
Figure 15C:
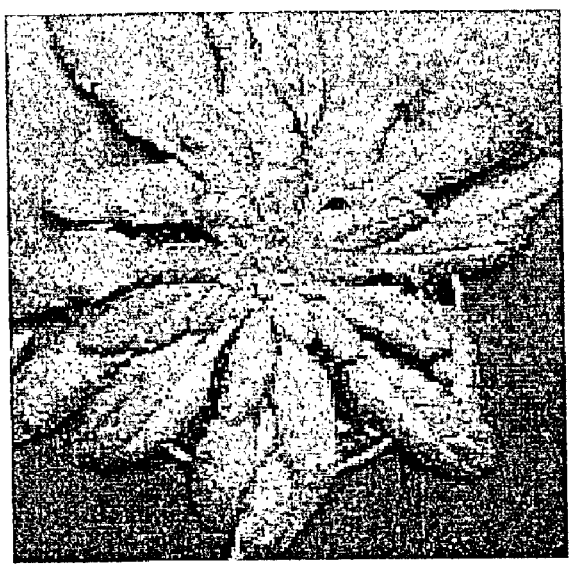
Figure 15D:
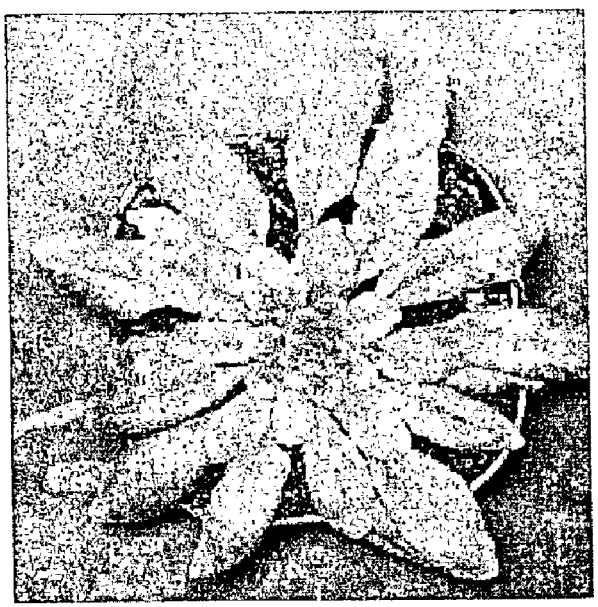
Figure 15E:
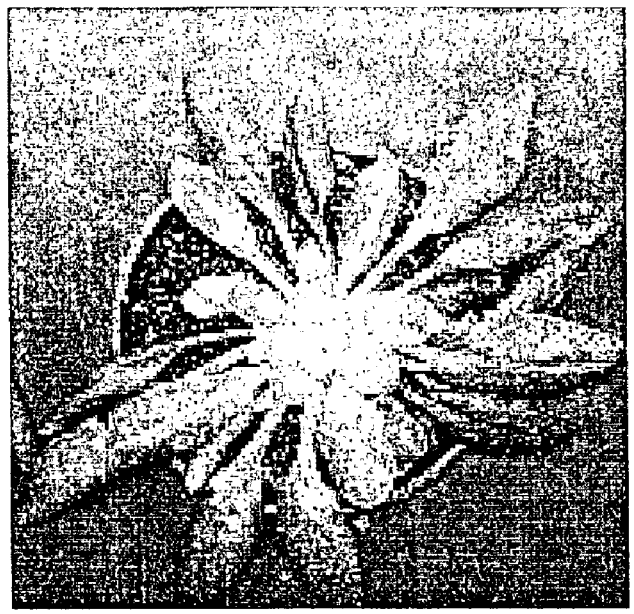
Figure 15F:
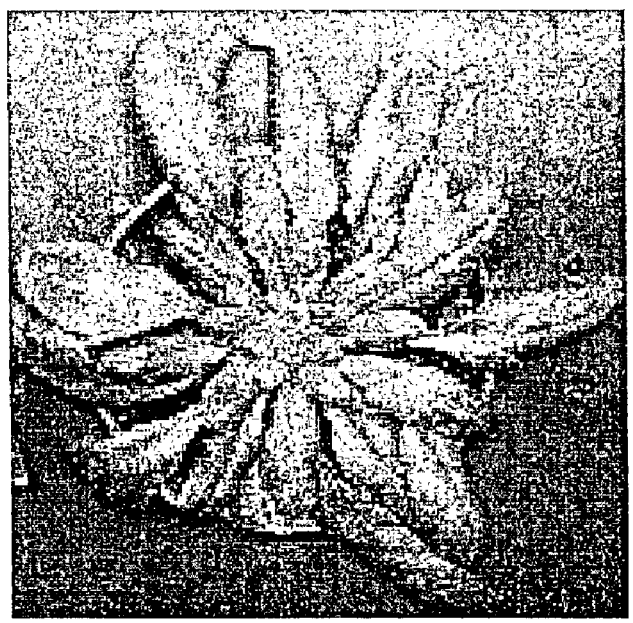
Figure 15G:
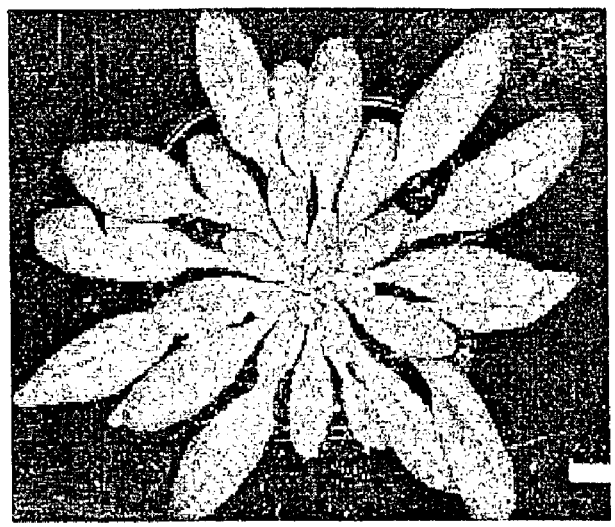
Figure 15H:
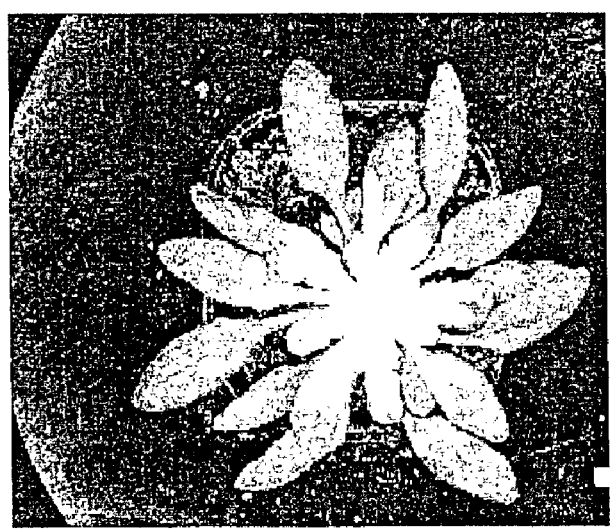
Figure 15I:
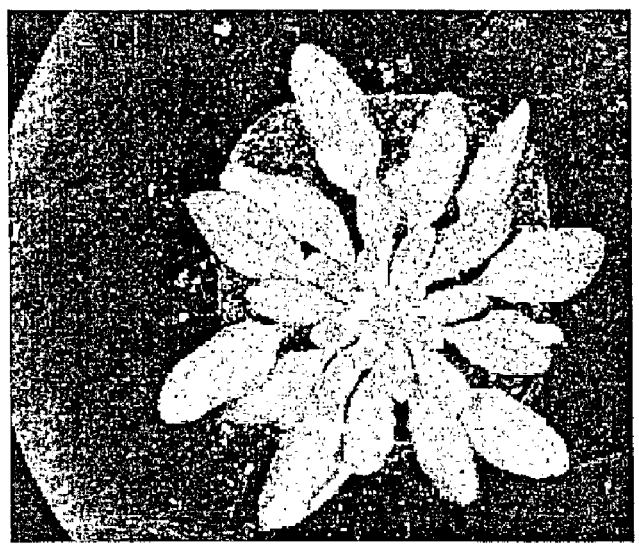
Figure 15J:
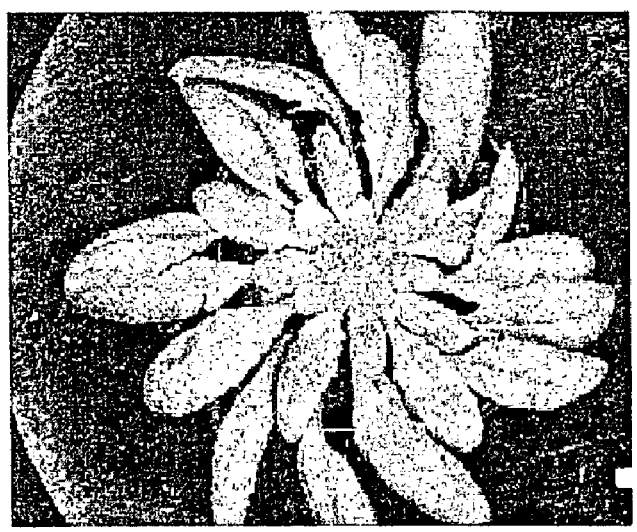
Figure 15K:
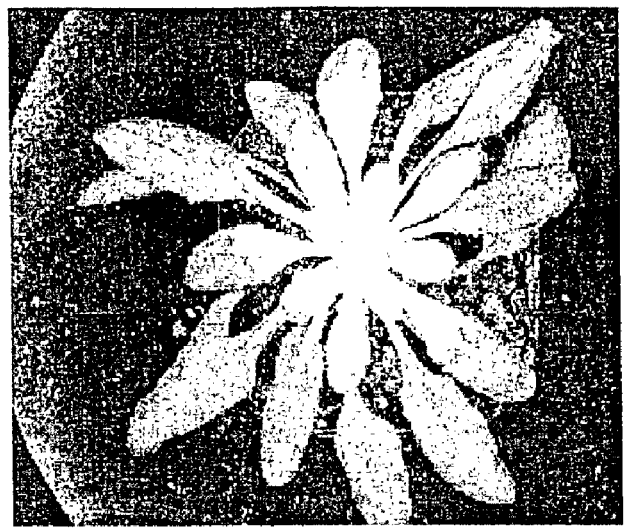
Figure 15L:
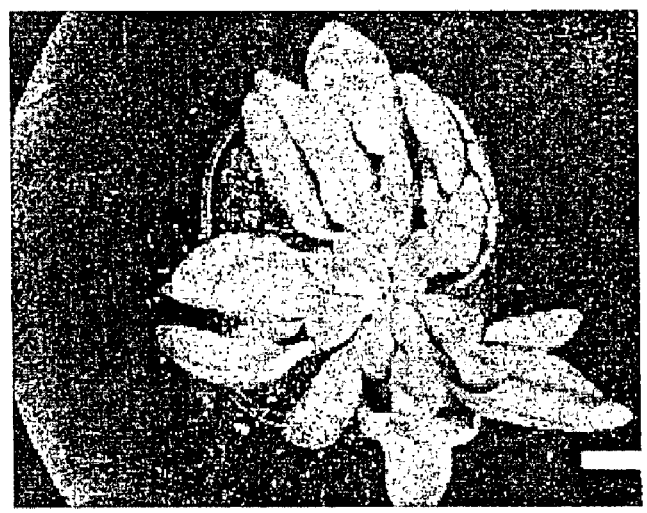

In contrast, 100 percent accuracy in grouping of the herbicides by SOA resulted when the data from all three technologies were combined as a coherent data set (FIG. 14). The data in FIG. 14 were derived using discriminant analysis. The principle components for each technology were used to derive a linear discriminant rule using SAS PROC DISCRIM with equal priors. The four herbicides with either unknown or singular sites of action were used to form a test set, and the data for the other fourteen herbicides formed the training set (Table 3). The discriminant rule was derived on the training set only. Prior to application, the discriminant rule was validated on the test set. The rule correctly indicated that the test herbicides did not belong to any class of herbicide represented in the training set. The rule was cross-validated against the training set as follows: each herbicide was serially removed from the training set, a new rule was derived from the remaining data, and the removed herbicide was classified on the new rule. The cross-validation displayed 100 percent correct classification of the herbicides.

Attempts to discriminate between different sites of action using the principle components from any one platform or any pair of platforms was less than 100 percent successful. For gene expression data alone, the error rates were 100 percent on cross-validation, 0 percent on test data. For metabolite data alone, the error rates were 93 percent on cross-validation, 0 percent on test data. For phenotypic data alone, the error rates were 0 percent on cross-validation, 25 percent on test data. Discriminant analysis on data from pairs of technologies had error rates ranging from 40 to 100 percent on cross-validation, and 0 percent error rate on test data.

This analysis shows that the 45 principle components derived from gene expression, biochemical, and phenotypic profiling are 100 percent accurate in distinguishing between herbicides with different sites of action. To visualize the results, a three-dimensional plot of the first principle components from the three platforms was made using DECISIONSITE software (Spotfire, Inc., Somerville, Mass.) (FIG. 14). FIG. 14 depicts the data in three dimensions where the first principal component of each profiling technology is represented on one axis. The principle components were used to derive a linear discriminant rule using SAS PROC DISCRIM with equal priors. The rule indicated 100% correct classification of the herbicides by SOA. FIG. 14 reveals that each SOA class is part of a discrete group, easily distinguishable from all other classes. (Note: The depiction of the FIG. 14 graph is, by necessity, dimensionally reduced for the purpose of visualization; resolution between herbicide classes is even greater than what is represented in FIG. 14 when all principle components are considered in three dimensions).

The results of the foregoing study show that it is possible to accurately predict the SOA of herbicides using a combination of technologies when the SOA is represented in an existing database. The superior predictive power of combining three disparate data sources relative to the use of one or even two sophisticated and high resolution profiling technologies was demonstrated. It follows that the strategy set forth herein, of standardizing and combining disparate data into coherent data sets for the analysis of biological samples (FIG. 10), will increase the predictive power of the analysis. The strategy is applicable to any experimental system and any data or technology, including alternatives not explored herein, such as protein expression and activity profiling.

SPECIFIC EXAMPLE 3

Herbicide Mode-of-Action Analysis

Herbicides have contributed extensively to increases in crop yield by eliminating or reducing the impact of competitive plant species. Although there are presently numerous registered compounds marketed in thousands of commercial products, there remains a need for new active herbicidal ingredients. Factors that contribute to the need for new active ingredients include the development of herbicide-resistant plant species and stricter regulations for reducing toxicological and environmental effects.

Understanding the mode-of-action and more specifically identifying the site- or pathway-of-action of existing and new herbicidal candidates is extremely valuable. Identification of the target(s) of a herbicidal compound prompts many options that may affect the decision for continued development of that compound. For example, if the target is not novel, continued work on the candidate compound may be stopped. Conversely, additional screening against the target may yield other novel herbicidal chemistries with more desirable traits (e.g. better efficacy, a more favorable environmental fate, and the like). Additionally, selectivity with respect to non-target organisms can be predicted by bioinformatic analysis.

In the instant specific example of the present invention (hereinafter MOA1), phenotypic, metabolite, and gene expression analysis were used to assess the effect of five unknown herbicidal compounds (Unknowns 1–5) on *Arabidopsis thaliana*. Plants were sprayed with recommended concentrations of each unknown compound and tissue samples were collected 20 and 60 minutes after exposure. Treated tissues were processed and subjected to gene expression and metabolite, or biochemical, profiling. In a similar fashion, samples were subjected to biochemical profiling from plants that had been sprayed with 18 commercially known herbicides. A subset of the samples sprayed with the commercially known herbicides were also analyzed by gene expression profiling. A set of plants treated with each compound was subjected to a series of phenotypic assessments five days after treatment. Finally, all unknown and a subset of commercial compounds were also analyzed using a fungal nutritional profiling platform.

The data were analyzed in several ways. First, the profiling results for each compound were examined individually. Next, within each technology or process (gene expression analysis, biochemical analysis, and phenotypic analysis), comparisons were made within the group of unknown compounds and with the group of commercially known compounds. The results from the fungal nutritional profiling were used to guide analysis of the gene expression and metabolite analysis data. The last step of the experiment was to combine the data sets from the three technologies (gene expression analysis, biochemical analysis, and phenotypic analysis) to perform a global analysis of the herbicidal compounds.

Development of Spraying Method and Formulation

Control studies were conducted to improve the efficacy of compound application and minimize compound utilization. First, standard methodologies for application of each herbicidal compound were modified to reduce the amount of compound required per sample. Second, compound formulation was modified to optimize plant response to the test compound while minimizing secondary effects.

Spraying Methods

Plants were grown under short day conditions for 39 days prior to spraying with various herbicides. Under these conditions, the whole rosette for each plant provides approximately 150 mg dry weight material for analysis. Whole rosette leaves from two to four plants were pooled for each sample to reduce the influence of biological variation. Plant samples were flash frozen in liquid nitrogen and stored at −80° C. until further use. Frozen leaf tissue was lyophilized and an aliquot of the lyophilized tissue (~10 to 25 mg) was used to extract total RNA as known in the art (see e.g., SAMBROCK ET AL., MOLECULAR CLONING (1989); AUSUBEL ET AL., (EDS.) CURRENT PROTOCOLS IN MOLECULAR BIOLOGY (1994)) and metabolites as described in Specific Examples 1 and 2, supra.

Each plant was sprayed with herbicide concentrations equivalent to the recommended dosage of application under field conditions. This was achieved by converting kg/ha dosage to mg/ml as follows:

1 flat=32 plants=1352 cm$^2$ 1 hectare (ha)=10,000 m$^2$

Therefore, 1 plant=4.22×10$^{-7}$ ha. 1.0 kg/ha requires 0.42 mg herbicide/plant. Thus, 1.0 kg/ha=0.5 ml per plant at 0.84 mg/ml.

For each compound, six plants were sprayed with 3 ml of solution. Two plants were harvested each at 20 minutes and 1 hour, while the remaining plants were maintained for phenotypic profiling.

Treatment of *Arabidopsis* with Unknown and Commercial Compounds

Five unknown compounds and 18 commercially known herbicides that belong to different chemical families were prepared in a solution containing 0.01% Tween 80 and 3.4% dimethylsulfoxide (DMSO). The 18 commercial herbicides represent 13 different modes-of-action based on the Herbicide Resistance Action Committee (HRAC) classification scheme and 17 different modes-of-action based on the Weed Science Society of America (WSSA) classification scheme (Table 5). Commercial herbicides were included in the study for validation and comparative analysis purposes. The control samples contained Tween 80 and DMSO only. All unknown compounds were sprayed at a concentration equivalent to 1.0 kg/ha. All commercial compounds were sprayed at maximum field dose (MFD) or at 1.0 kg/ha if MFD data was not available (Table 5). For each compound, six plants were sprayed using an artist airbrush at a rate of 0.5 ml/plant. At 1.0 kg/ha, the amount of unknown compound required to spray six plants was 2.54 mg, based upon two timepoints and two plants for assessment of symptomology.

obtained by determining the intensity and peak areas of individual ion traces. Isotopically labeled internal standards were used for peak area ratios, response factor, and normalization of data throughout the experiment.

TABLE 5

List of Commercial Herbicides

| Active Ingredient | Mode of Action | Chemical Family | Conc. (kg/ha) | WSSA Group | HRAC Group |
|---|---|---|---|---|---|
| Chlorsulfuron | Inhibition of acetolactate synthase ALS | Sulfonylureas | 0.02 | 2 | B |
| Imazapyr | Inhibition of acetolactate synthase ALS | Imidazolinones | 1.70 | 2 | B |
| 2,4-D | Action like indole acetic acid (synthetic auxins) | Phenoxy-carboxylic-acids | 1.00 | 4 | O |
| Atrazine | Inhibition of photosynthesis at photosystem II | Triazines | 4.00 | 5 | C1 |
| Bentazon | Inhibition of photosynthesis at photosystem II | Benzothia-diazinone | 2.24 | 6 | C3 |
| Butylate | Inhibition of lipid synthesis - not ACCase inhibition | Thiocarbamates | 4.00 | 8 | N |
| Glyphosate | Inhibition of EPSP Synthase | Glycines | 4.00 | 9 | G |
| Glufosinate | Inhibition of glutamine synthetase | Phosphinic acids | 1.70 | 10 | H |
| Amitrole | Bleaching: Inhibition of carotenoid biosynthesis (unknown target) | Triazoles | 2.00 | 11 | F3 |
| Norflurazon | Bleaching: Inhibition of carotenoid biosynthesis at the phytoene desaturase step (PDS) | Pyridazinone | 4.00 | 12 | F1 |
| Acifluorfen | Inhibition of protoporphyrinogen oxidase (PPO) | Diphenylethers | 0.42 | 14 | E |
| Metolachlor | Inhibition of cell division (Inhibition of VLCFAs) | Chloroacetamides | 4.00 | 15 | K3 |
| Asulam | Inhibition of DHP (dihydropteroate) synthase | Carbamates | 3.00 | 18 | I |
| Naptalam | Inhibition of auxin transport | Phthalamates Semicarbazones | 4.00 | 19 | P |
| Isoxaben | Inhibition of cell wall (cellulose) synthesis | Benzamides | 1.20 | 21 | L |
| Paraquat | Photosystem-1-electron diversion | Bipyridyliums | 0.53 | 22 | D |
| Chloropropham | Inhibition of mitosis/microtubule organisation | Carbamates | 2.00 | 23 | K2 |
| Isoxaflutole | Bleaching: Inhibition of 4-hydroxyphenyl-pyruvate-dioxygenase (4-HPPD) | Isoxazoles | 1.00 | 28 | F2 |

Biochemical Profiling (or Metabolite Profiling): LC-MS Analysis

Lyophilized tissue was disrupted by grinding for 5 minutes at 1800 rpm using a grinder and stored in a controlled environment until further analysis. Approximately 10 mg of dried ground tissue was extracted in 0.5 ml 10% aqueous methanol containing isotopically labeled internal standards. The extract was centrifuged at 4000 rpm for 2 minutes, diluted with an equal volume of 50% aqueous acetonitrile (V/V), and transferred to a temperature-controlled autosampler (4° C.) of a HP1100, HPLC system (Agilent Technologies, Palo Alto, Calif.).

The sample was fractionated on a $C^{18}$ HPLC column in an acetonitrile/water gradient containing 5 mM ammonium acetate. After chromatography, the sample was passed through a splitter and the split flow was infused to the turbo-ionspray ionization sources of two Mariner LC-time of flight mass spectrometers (PerSeptive Biosystems Inc., Framingham, Mass.). The ion sources were optimized to generate and monitor positive and negative ions respectively.

The Total Ion Chromatogram (TIC) of the metabolic profile was analyzed for metabolites with masses ranging from 80 to 900 Daltons (Da). The individual ion traces of the extracted mass chromatogram of the $(M-H)^-$ (negative) and $(M+H)^+$ (positive) ions were used for both calibration and quantification. Relative amounts of the compounds were GC-MS Analysis Approximately 10 mg of dried ground tissue was extracted with 25% v/v N-methyl-N-trimethylsilyl-trifluoroacetamide (MSTFA) and 0.1% v/v trifluoroacetic acid in acetonitrile. Samples were derivatized in 50% N,N-Dimethyltrimethylsilylamine (TMS-DMA), 25% acetonitrile, and 25% 1,2-dimethoxyethane followed by addition of 1,4-Dioxane. Precipitates were removed by centrifugation and the supernatants were used for analysis.

Gas chromatography was performed on a ThermoFinnigan Trace2000 GC (Thermo Finnigan Corp., San Jose, Calif.) equipped with an autosampler and a split/splitless injection port. The gas chromatograph was coupled to a ThermoFinnigan Tempus time-of-flight mass spectrometer (Thermo Finnigan Corp., San Jose, Calif.) fitted with an electron impact (EI) ion source. Chromatographic separations were conducted using a 50% phenyl/50% methyl polysiloxane stationary phase, helium carrier gas, and a programmed oven temperature that ramped from a starting temperature of 50° C. to a final temperature of over 300° C. Analyses were conducted with 1 μL injection volumes in split mode with a split ratio of 50:1. Electron impact mass spectra were acquired at 70 eV, at rate of 10 spectra/second, over the range m/z 41 to 640. Paraffins used as retention standards for calculating retention indices were prepared by diluting a Florida TRPH standard (Restek Corp., Bellefonte, Pa.) to a working concentration of 25 μg/mL each in methyl tert-butyl ether with 0.005% v/v tetramethylene sulfone as an internal standard.

Compounds detected by GC-MS were cataloged based on Kovats retention indices and mass-to-charge ratio (m/z) of the ions characteristic of each peak. The instrument response for each analytical peak was expressed as a relative response of the selected quantitation ion for that peak to the detector response for tetramethylene sulfone at m/z 120.

Peak Characterization and Identification

For both GC-MS and LC-MS analysis, peaks present in Arabidopsis samples were characterized and/or identified: (1) Metabolites known to be of interest were run as standards so that the corresponding metabolites present in the tissue samples could be identified; and (2) Peaks which were observed to appear regularly and repeatedly in Arabidopsis tissue but not corresponding to an identified metabolite were characterized in terms of their spectral properties. These combined methods led to the characterization and/or identification of several hundred peaks in LC-MS and GC-MS together.

Gene Expression Profiling

RNA was extracted from lyophilized and pulverized tissue using TRIZOL reagent (Invitrogen Corp., Carlsbad, Calif.). Lyophilized tissues were first re-hydrated using RNALATER (Ambion, Inc., Austin, Tex.). Arrays of 60 mer oligonucleotide probes were manufactured by Agilent Technologies using non-contact inkjet microarray printing technology (Agilent Technologies, Palo Alto, Calif.). A total of 22,000 A. thaliana genes were spotted onto the array. A number of genes were selected for randomized intra-array replication, and positive and negative control features were added. The mRNA in the total RNA sample was amplified, fluorescently labeled with either Cy3 or Cy5, and hybridized against microarrays as described by the manufacturer (Agilent Technologies, Palo Alto, Calif.). Arrays were scanned using a LP2 Scanner (Agilent Technologies, Palo Alto, Calif.). Images were analyzed using Feature Extraction software (Agilent Technologies, Palo Alto, Calif.). The resulting data files were evaluated using Rosetta RESOLVER software (Rosetta Inpharmatics, Inc., Kirkland, Wash.).

Phenotypic Profiling

Two plants from each treatment were maintained for phenotypic profiling. Images were taken daily for one week and then every other day for the following week. Eleven phenotypic characteristics (data not shown) were assessed at the time point showing maximal symptomology for each herbicide. The phenotypic scores were used for cluster analysis of unknown and commercial herbicides.

Fungal Nutritional Profiling

The inventors have developed a profiling process for chemical mode-of-action analysis utilizing the filamentous fungus, Magnaporthe grisea. Filamentous fungi have the ability to utilize numerous carbon and nitrogen sources and they can utilize many nutrients as supplements for auxotrophic requirements. These attributes are useful for examining the effects of chemicals on the growth of M. grisea under a variety of media conditions. Loss or gain of the ability to utilize a specific nutrient(s) in the presence of a test compound can provide valuable information relating to the pathways that are targeted by that compound. Because plants and filamentous fungi have many metabolic pathways in common, the results obtained from analysis in fungi can sometimes be used to predict the effect of the test compound on a plant.

Typically, candidate chemicals submitted for MOA analysis are not available in large quantities. To minimize the amount of a particular compound required for analysis, a tiered nutritional profiling analysis protocol has been developed in which several nutrients are combined into "pools" for testing. A positive result in one pool triggers deconvolution of that pool into sub-pools or individual nutrients for testing. Using this approach, the total number of growth tests can be reduced approximately five- to ten-fold as compared to testing all nutrients independently.

The initial nutrient pool for the present experiments included amino acids, purines, pyrimidines, and various vitamins and cofactors. The growth conditions were designed to test for both auxotrophy requirements and utilization as nitrogen sources.

M. grisea spores were inoculated into a minimal media with or without nutrient supplementation. Test compounds were added at the minimal inhibitory concentration (MIC) or at a relatively high dose if no growth inhibition was observed in the concentration range tested. Spore suspensions were aliquoted into microtiter plates and incubated for seven days at 25° C. Optical density (OD) measurements at 590 nm were taken daily during the incubation period. Supplemented and minimal media growth were compared to untreated controls for each test compound. A difference between the growth kinetics in control versus treatment indicated that a nutrient utilization pathway was affected. Continued deconvolution of the pools was performed as necessary to identify specific nutrient(s) contributing to the growth response observed.

Phenotypic Profiling

Eleven phenotypic characteristics, identical to the ones listed in Table 6, were assessed for each of the five unknown compounds and the commercial herbicides sprayed with Tween 80. The results for the unknown compounds are shown in Table 6.

TABLE 6

Symptoms scores for the Five Unknown Compounds

| Cmpd | Leaf width | Mature Leaf chlorosis | New Leaf chlorosis | Mature leaf anthocyanins | New leaf anthocyanins | Mature leaf necrosis | New leaf necrosis | Leaf curling | Leaf twisting | Tmic[b] | Pointed Leaves |
|---|---|---|---|---|---|---|---|---|---|---|---|
| Unknown 1 | 0 | 0 | 4 | 0 | 0 | 0 | 0 | 0 | 0 | 2 | 0 |
| Unknown 2 | 0 | 0 | 0 | 0 | 0 | 3 | 0 | 0 | 0 | 2 | 0 |
| Unknown 3 | 0 | 0 | 0 | 0 | 0 | 3 | 2 | 1 | 1 | 1 | 0 |
| Unknown 4 | 0 | 2 | 2 | 0 | 0 | 0 | 0 | 0 | 1 | 2 | 0 |
| Unknown 5 | 0 | 0 | 0 | 0 | 0 | 2 | 0 | 0 | 1 | 2 | 0 |

[b]Tmic - Time to development of symptoms.

Hierarchical cluster analysis of the eleven phenotypic characteristics was used to visualize the relationship of the five unknown compounds to the commercial herbicides using Ward's method in SpotFire DecisionSite 7.0 (Spotfire, Inc., Somerville, Mass.). As expected, inhibitors of photosynthesis machinery and protoporphyrin oxidase clustered together, as did both of the ALS inhibitors. The bleaching herbicides also clustered closely although both glyphosate and glufosinate clustered with amitrole. This observation is consistent with the observation that amitrole exhibited chlorosis and not true bleaching. Unknown 1 clustered with carotenoid biosynthetic inhibitors, which result in a bleaching phenotype. Unknown 4 showed a strong chlorotic phenotype and did not group in the glyphosate/glufosinate/amitrole clade known to induce necrosis. Unknown 2, Unknown 3, and Unknown 5 grouped in a cluster containing commercial compounds that did not show strong phenotypes under our conditions.

Biochemical Profiling

A combined total of 716 peaks from the LC-MS (positive and negative modes) and GS/MS were examined for each treatment and time point. In the 20 minutes and 1 hour time point data, a total of 168 and 176 peaks, respectively, were determined as significantly different from the control ($p<0.11$) in at least one of the treatments. Of these, 69 and 78 peaks, respectively, could be identified as a specific metabolite. The number of metabolites whose abundance was significantly altered in the treated samples relative to the control samples are shown in Table 7.

TABLE 7

Regulated Metabolites Following Herbicide Treatment

| Compound | Number of Metabolites Changed: Total #(unknown #) | | | |
|---|---|---|---|---|
| | 20 min, $p < 0.05$ | 20 min, $p < 0.11$ | 1 hr, $p < 0.05$ | 1 hr, $p < 0.11$ |
| Unknown 1 | 7(5) | 13(8) | 15(12) | 49(29) |
| Unknown 2 | 4(2) | 6(4) | 4(2) | 23(12) |
| Unknown 3 | 4(2) | 9(6) | 4(3) | 10(9) |
| Unknown 4 | 5(2) | 8(3) | 20(10) | 47(24) |
| Unknown 5 | 5(3) | 12(9) | 2(1) | 6(5) |
| 2,4-D | 3(2) | 13(8) | 7(3) | 25(15) |
| Acifluorfen | 17(11) | 32(20) | 19(13) | 31(22) |
| Amitrole | 9(6) | 17(13) | 14(8) | 32(20) |
| Asulam | 9(3) | 14(5) | 10(7) | 18(11) |
| Atrazine | 4(4) | 11(8) | 17(8) | 49(24) |
| Bentazon | 9(3) | 10(6) | 11(9) | 19(14) |
| Butylate | 17(10) | 33(21) | 18(12) | 31(22) |
| Chloropropham | 12(8) | 17(10) | 12(5) | 20(10) |
| Chlorsulfuron | 9(4) | 15(6) | 5(3) | 23(13) |
| Glufosinate | 33(25) | 48(33) | 4(4) | 9(9) |
| Glyphosate | 4(2) | 13(9) | 16(9) | 46(24) |
| Imazapyr | 5(2) | 9(3) | 8(6) | 14(10) |
| Isoxaben | 26(12) | 45(21) | 25(16) | 55(33) |
| Isoxaflutole | 45(29) | 62(39) | 14(13) | 25(21) |
| Metolachlor | 38(25) | 54(34) | 18(11) | 45(22) |
| Naptalam | 28(11) | 39(16) | 13(9) | 46(23) |
| Norfluazon | 38(27) | 55(36) | 6(5) | 12(8) |
| Paraquat | 9(5) | 14(9) | 22(15) | 50(31) |

Since Unknown 4 treatment induced larger perturbations in the metabolite pool size, the data were sorted based on Unknown 4 results. Only two peaks (nLCcmpd2 and nLCcompd229) were uniquely regulated by Unknown 4. In addition, the levels of three other peaks (palmitic acid, nLCcmpd59, and nLCcmpd77) were also observed to change in only one other treatment each (naptalam, paraquat and glyphosate, respectively). Four peaks (pLCcmpd71, pLCcmpd234, omithine, and C18 fatty acids) were determined to be uniquely regulated by Unknown 1. The metabolites regulated in the other three unknown compounds were shared among several other treatments.

Numerous peaks were commonly regulated among a majority of the treatments. For example, sitosterol, octadecadienoic acid, mevalonate lactone, pipecolic acid, ascorbic acid, indoleacetonitrile, and succinate were up-regulated in a variety of treatments. Data derived from plants subjected to various stresses suggested that plants induce changes in many of these metabolites as part of general stress response (unpublished). In addition to known metabolites, the regulation of a number of unidentified peaks was also shared among many treatments. Based on the similarity of the responses to the known metabolites, it is expected that the unidentified peaks may also be stress-related metabolites.

Treatment of plants with several other herbicides resulted in the perturbation of only a few putative stress-related metabolites. For example, neither butylate nor chlorpropham treatment resulted in many changes in these commonly regulated metabolites and neither showed a strong herbicidal phenotype. Only a few, if any, stress-related metabolites were observed with glufosinate, imazapyr, and norflurazon treatments. These observations may be explained by the slow development of symptoms for imazapyr and norflurazon, suggesting that responses to these herbicides may not be apparent in the first hour of post-spraying. Similarly, it has been reported that glufosinate is also slow acting and poorly transported throughout the plant.

Data from the LC-MS and GC-MS platforms were combined for each time point and used for hierarchical cluster analysis. For each treatment, the response of each metabolite was converted to a standardized difference from control on a log scale. A subset of metabolites that showed differential expression ($p<0.10$) in at least one treatment was extracted. The principle components of this subset were calculated and used to cluster the biochemical profiling data.

Clustering of BCP data from both time points yielded different results. However, for both time points the bleaching herbicides, isoxaflutole and norflurazon, as well as glufosinate clustered closely together, while amitrole and glyphosate grouped together with bleaching herbicides, were found in other areas in the dendogram. In addition, the positions of the ALS inhibitors and the photosynthesis inhibitors, which clustered together phenotypically, did not group together at either time point. The relationships of the five unknown compounds to each other and to the commercial herbicides was different for each time point, although Unknown 1 and Unknown 4 remained in close proximity in both cases.

Due to the observation that the commercial herbicides with the same or similar modes-of-action did not cluster well in these experiments, a clear relationship of unknown compounds to the commercial herbicides or to each other cannot be gleaned from the present analyses. Factors that may have contributed to the results include: a) kinetics-of-action unaccounted for in each herbicide; and b) the low number of regulated metabolites in the samples (Table 7). For example, compounds with the same or similar MOAs may have different efficiencies for compound delivery to their target site. Additionally, the efficiency with which the compound inhibits the target may also vary. Thus, it is possible that some of the compounds may show more or less expression of metabolic changes depending on how rapidly they gain entry into the plant tissues and/or target organelles and how well they inhibit the target enzyme(s). Non-target effects within the plant cells may also contribute to variation seen between compounds with common MOAs. The results based purely on biochemical profiling data serve to illustrate the complexity involved when examining a biological system, and point to a need for an ability to collect and store large amounts of data which can be analyzed as one set. The methods of the present invention introduce a solution to the problem of storing and analyzing complex and comprehensive data sets that can serve as models of biological systems.

Gene Expression Analysis

Gene expression analysis was performed on the five unknown compounds and five commercial compounds at the one-hour time point. Two commercial herbicides were selected based on their phenotypic similarities with unknown compounds (isoxaflutole is similar to Unknown 1 and glufosinate is similar to Unknown 4), and three were identified as representative of diverse MOA compounds.

All gene expression experiments were performed with arrays containing 22,000 *Arabidopsis* genes. Each treatment was compared to a control sample and each experiment was repeated with cyamin dye swapping to eliminate dye detection biases. The resulting data was analyzed using Rosetta RESOLVER software (Rosetta Inpharmatics, Inc., Kirkland, Wash.). The total number of genes in each treatment that were down-regulated and up-regulated are shown in Table 8. In addition, the regulated genes for each treatment were compared to a list of "lethal" genes that have previously been identified (unpublished). A "lethal" gene is one without which a plant cannot survive, and so is a likely herbicide target.

The treatments resulting in the fewest gene expression perturbations were the commercial compounds, asulam and naptalam. All other treatments showed comparable levels of regulated genes except Unknown 4. Treatment with Unknown 4 resulted in nearly ten times as many perturbed genes as compared to the other treatments indicating that Unknown 4 acts very rapidly within plant tissues.

TABLE 8

Regulated Genes Following Herbicide Treatment

| Compound | 1 hr, $p < 0.5$ | |
|---|---|---|
| | Down | Up |
| Unknown 1 | 45 | 223 |
| Unknown 2 | 99 | 221 |
| Unknown 3 | 134 | 119 |
| Unknown 4 | 1866 | 1462 |
| Unknown 5 | 144 | 192 |
| Asulam | 7 | 80 |
| Chlorsulfuron | 109 | 97 |
| Glufosinate | 54 | 296 |
| Isoxaflutole | 370 | 143 |
| Naptalam | 47 | 50 |

Figure 16:
FIG. 16 is a graphical representation of the hierarchical clustering of gene expression data from *Arabidopsis* plants treated with five unknown compounds (Unknown 1 to Unknown 5) and five commercially available herbicides. Data were derived from tissue harvested one hour following treatment. The name of the treatment (x-axis) is plotted versus the semi partial r squared value (y-axis).

The relationships among the treatments were examined using hierarchical cluster analysis based on the principal components from each data set (FIG. 16). For cluster analysis, the expression of each gene for each treatment was converted to a logarithmic scale and calculated as a standardized difference from control. A subset of genes that showed differential expression ($p<0.01$) in at least one treatment was extracted. The principle components of this subset of gene expression data were calculated and used to cluster the gene expression data (FIG. 16).

The resulting dendrogram of gene expression data shows characteristics of arbitrary clustering. Only isoxaflutole and chlorsulfuron grouped in an independent lade. The other compounds showed a stairstep pattern in the dendrogram indicating very little overlap between regulated gene sets. Unknown 4 is separated from the remaining compounds as expected based on the relatively large number of regulated genes following this treatment.

Because the clustering results indicate arbitrary clustering, the relationship of the unknown compounds to the commercial herbicides or to each other cannot be gleaned from these analyses. Although the majority of the genome was surveyed in these experiments, and the numbers of regulated genes in the treated samples is relatively high as compared to the number of significantly regulated metabolites, the same caveats relating to sample production for the metabolite analysis apply to this analysis as well, again illustrating the need for a way to combine and analyze all of the data available in one directly comparable data set.

Combined Data Cluster Analysis

In an attempt to identify relationships among the unknown compounds and commercial herbicides, data from all three technologies (gene expression analysis, metabolite analysis, and morphologic/phenotypic analysis) were used in combination for hierarchical cluster analysis. To give equal weighting to each data set, the principal components were used in the cluster analysis. The principal components for the metabolite data and gene expression data were derived as described above. The phenotypic data was coded as deviations from control. That is, the control value of any phenotypic measurement was set to 0, and positive numbers indicate phenotypes greater than control, while negative numbers indicate phenotypes less than control. The principle components of the phenotypic data were calculated for each treatment class.

Figure 17:
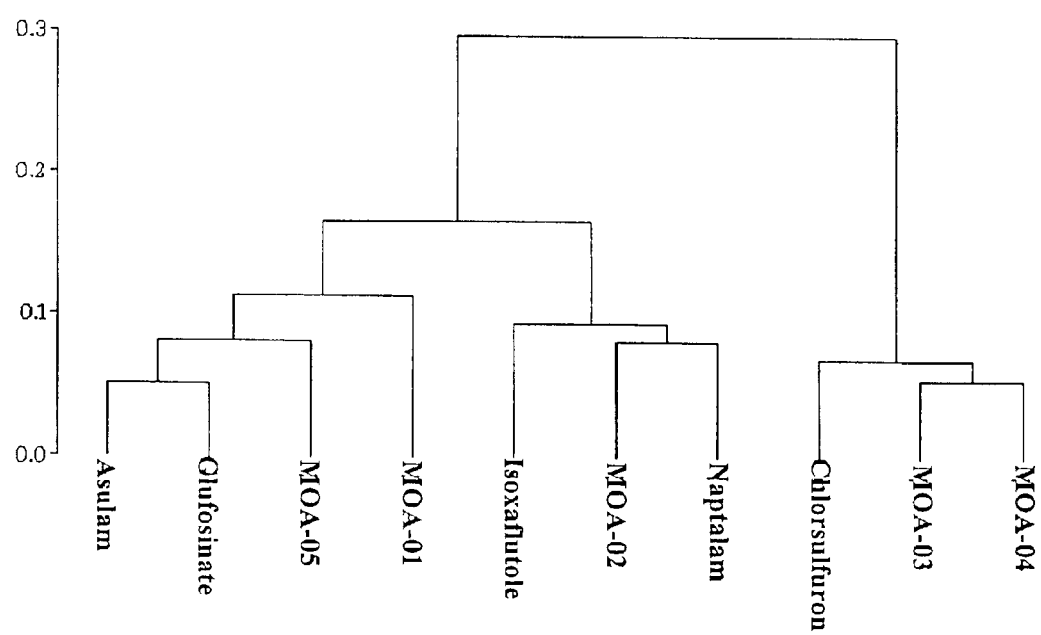
FIG. 17 is a graphical representation of the hierarchical clustering of gene expression data, metabolite data, and phenotypic data from *Arabidopsis* plants treated with five unknown compounds (Unknown 1 to Unknown 5) and five commercially available herbicides. Data were derived from tissue harvested one hour following treatment. The name of the treatment (x-axis) is plotted versus the semi partial r squared value (y-axis).
Figure 18B:
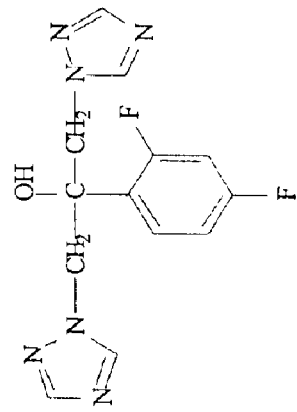
FIGS. 18A–18D are schematic diagrams of the chemical structures of the antifungal drugs as follows.
Figure 18D:
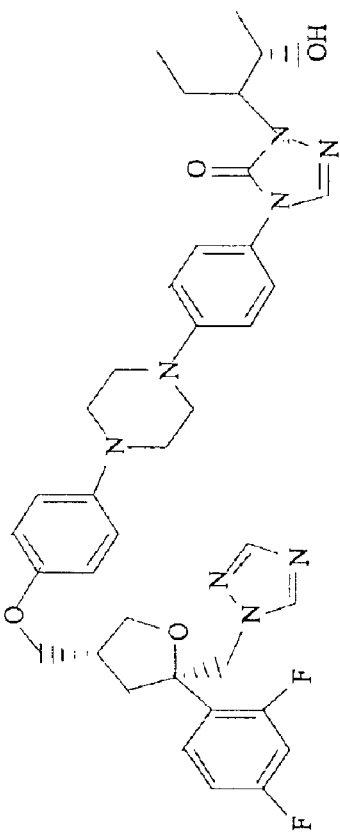
Figure 18A:
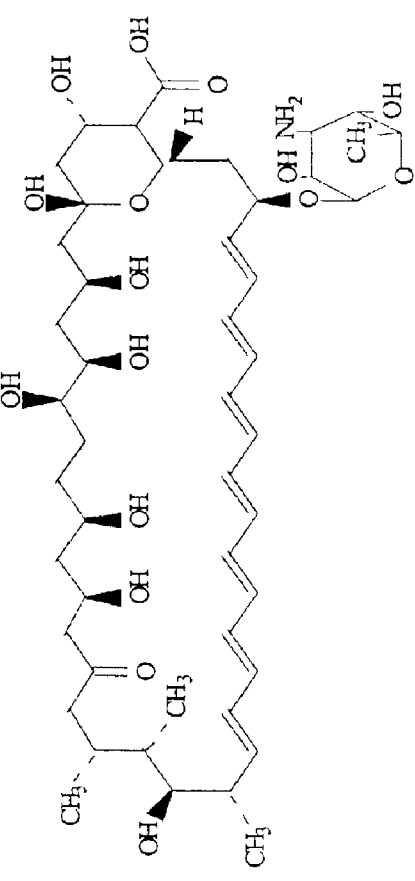
Figure 18C:
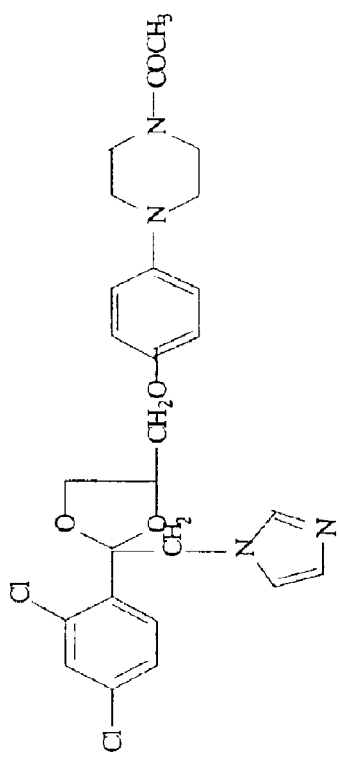

Data from the unknown compounds and the five commercial herbicides for which gene expression analysis, metabolite analysis, and morphologic analysis data was available were used in this analysis. The principle components of the data for these 10 treatments were combined and a cluster analysis was performed on the combined dataset of 30 principle components. The results are shown in FIG. 17.

The combined data cluster analysis produced more definitive results as compared to the gene expression data alone (i.e. not random clusters). However, the data set does not include herbicides with the same MOAs and therefore it is not possible to establish conclusive relationships based on the dendrogram. The inclusion of data from the additional commercial herbicides may help to clarify the relationships between the unknown compounds and the commercial compounds.

Fungal Nutritional Profiling Analysis

Minimally inhibitory concentrations were determined for each unknown compound using a two-fold dilution series in minimal media. In the nutritional experiments, *M. grisea* was only sensitive to Unknown 1 at the highest concentration tested. No other compounds inhibited growth, however Unknown 5 was insoluble at the highest concentrations tested. Table 9 lists the concentrations used for nutritional profiling analysis for each compound. Unknown 4 showed some growth inhibition at 250 mg/ml.

TABLE 9

Test Concentrations for Nutritional Profiling

| Compound I.D. | Inhibitory Concentration | Sub-inhibitory concentration |
|---|---|---|
| Unknown 1 | 500 µg/ml | 6.25 µg/ml |
| Unknown 2 | n/a | 500 µg/ml |
| Unknown 3 | n/a | 500 µg/ml |
| Unknown 4 | n/a | 250 µg/ml |
| Unknown 5 | n/a | 30 µg/ml |

Nutritional Profiling: Tier 1

Tier 1 includes minimal and supplemented media containing all test nutrients. The experiments were performed using the concentrations shown in Table 9. Unknown 1 was tested at both inhibitory and sub-inhibitory concentrations. The concentration of DMSO was normalized for all test compounds and the negative controls. Growth was monitored over seven days. Each treatment was performed in duplicate.

As expected, growth of M. grisea in the presence of Unknown 1 was inhibited in minimal media. No growth was observed in the supplemented media indicating that growth in the presence of Unknown 1 could not be remediated in the presence of any of the nutrients tested. Unknown 2, Unknown 3, and Unknown 5 showed no growth defect in either media, indicating that growth of M. grisea in the presence of these compounds was unaffected by addition of these nutrients. Growth of *M. grisea* in the presence of Unknown 4 was partially inhibited in minimal media and was remediated by the addition of supplements, indicating that one or more nutrients in the supplemented media abrogated the effect of Unknown 4 on growth.

Unknown 1 was also tested at a sub-inhibitory concentration. Only a slight inhibition of growth of *M. grisea* was observed in minimal and supplemented media, again indicating that the mode-of-action of Unknown 1 was unaffected by the addition of these nutrients.

Nutritional Profiling: Tier 2

The supplements tested in Tier 1 were subdivided into four groups, or sub-pools, consisting of amino acids, purines and pyrimidines, vitamins and cofactors subset 1, and vitamins and cofactors subset 2. Growth of *M. grisea* with and without Unknown 4 in each sub-pool, minimal and fully supplemented media was tested.

Growth of *M. grisea* in the presence of Unknown 4 was remediated in fully supplemented media, the amino acid sub-pool, and significantly remediated in the purine/pyrimidine sub-pool. Reduced growth was observed in the other media tested. Restoration of growth in both amino acid and purine/pyrimidine pools indicates that Unknown 4 may act on a central nutrient utilization pathway and not on a specific biosynthetic pathway. To examine this further, the amino acid sub-pool was further subdivided and tested.

Nutritional Profiling: Tier 3

The amino acid sub-pool from Tier 2 was subdivided into five further sub-pools including aromatic, sulfur containing, aliphatic/aliphatic hydroxy, basic−asn/pro, and acidic+gln amino acids. Growth of *M. grisea* with and without Unknown 4 in each sub-pool and minimal media was tested.

Growth of *M. grisea* in the presence of Unknown 4 was remediated in media containing aromatic amino acids, asp/glu/gln, and to a slightly lesser extent, basic+asn/pro amino acids. Growth on aliphatic/aliphatic hydroxy and sulfur amino acids was similar or less than the levels of growth in minimal media in these experiments.

Again, restoration of growth in multiple amino acid pools indicates that Unknown 4 may act on a central nutrient utilization pathway and not on a specific biosynthetic pathway. In addition, in previous experiments, *M. grisea* was able to efficiently utilize aromatic, asp, glu, asn, pro, and basic amino acids as nitrogen sources. These results suggest that Unknown 4 may be negatively affecting nitrogen source utilization in *M. grisea.* A final tier of experiments was performed to address a potential nitrogen source utilization defect in the presence of Unknown 4.

Nutritional Profiling: Tier 4

Nitrogen source assimilation has been studied in several filamentous fungi. Typically, nitrate is converted to nitrite by nitrate reductase. Nitrite is converted to ammonia by nitrite reductase followed by assimilation into glutamine by glutamine synthetase. The amine group can then be used to generate glutamate from alpha-ketoglutarate. In *Aspergillus nidulans*, the regulation of nitrogen utilization has been studied extensively. When the preferred nitrogen sources, ammonia or glutamine, are present, nitrogen metabolite repression inhibits expression of genes required for utilization of other nitrogen sources such as nitrate, nitrite, and glutamate.

The effect of Unknown 4 on nitrogen source utilization was tested by providing various nitrogen sources. Growth of *M. grisea* with and without Unknown 4 in the presence of each of the nitrogen sources was tested.

Growth of *M. grisea* in the presence of Unknown 4 was recovered when ammonium or glutamine was used as a nitrogen source. Reduced growth was observed when nitrate or glutamate was used as a nitrogen source. Growth was inhibited completely in the presence of nitrite as the sole nitrogen source.

The fungal nutritional profiling results from Unknown 4 were compared to glyphosate at the same and higher concentrations (250 μg/ml and 1 mg/ml, respectively). The growth results with glyphosate at 250 μg/ml for Tiers 3 and 4 were nearly identical as compared to Unknown 4. The growth results with glyphosate at 1.0 mg/ml were consistent with the MOA of glyphosate, a block in aromatic amino acid biosynthesis. Growth inhibition by glyphosate at this concentration was remediated by inclusion of aromatic amino acids to the media. Based on these results, it was determined that the MOA of Unknown 4 was aromatic amino acid biosynthesis.

Validation Data for Isoxaflutole

The site-of-action of isoxaflutole is 4-hydroxyphenylpyruvate dioxygenase (HPPD, E.C. 1.13.11.27), which converts 4-hydroxyphenylpyruvate to homogentisate. Homogentisate is a precursor to α-tocopherols and plastoquinones. It is believed that carotenoid biosynthesis is indirectly inhibited by depletion of plastoquinones, a cofactor of phytoene desaturase, resulting in the bleaching phenotype observed with isoxaflutole. Tyrosine is an upstream precursor to homogentisate biosynthesis and, in some organisms including humans, phenylalanine can be converted to tyrosine via phenylalanine hydrolase.

Examination of the metabolite data for isoxaflutole revealed that both tyrosine and phenylalanine were up-regulated relative to the control. Homogentisate was undetectable in all samples including the controls. Alpha-tocopherol was detected, but the levels were not significantly changed relative to the control at the early time points. The identification of increases in tyrosine and phenylalanine in the isoxaflutole data support the use of metabolite data for analysis of herbicide site- or pathway-of-action. However, alterations in the expression of genes involved in the homogentisate biosynthetic pathway were not observed in these experiments. It is possible that the specific effects of isoxaflutole on this pathway do not perturb gene expression of this pathway specifically or at this early time point. Further analysis of gene expression at later time points is required.

Summary of the Analysis of Unknown 1

Phenotypic data from plants following Unknown 1 treatment suggests that the observed mode-of-action is similar to carotenoid biosynthesis inhibitors. Cluster analysis using the corresponding metabolite or gene expression data did not group this compound with the other bleaching herbicides (amitrole, isoxaflutole, and norflurazon), although the latter two clustered relatively close based on metabolite data at both the 20 minute and 1 hour time points. The fatty acid profile of *Arabidopsis* treated with Unknown 1 was altered. An increase in saturated and mono-unsaturated C18 fatty acids (Table 7) and linolenic acid was observed. An increase in linolenic acid was observed in several other treatments and may be related to a general stress response that results in the production of jasmonic acid. However, the increase in C18 fatty acids is unique to Unknown 1 and treatment of plants with any C18 fatty acid has been shown to induce cell death.

In the fungal nutritional profiling platform, Unknown 1 was able to completely inhibit growth of *M. grisea* in minimal and supplemented media. In addition, no growth defect was observed in minimal, supplemented, or minimal plus tyrosine as sole nitrogen source at a sub-inhibitory concentration. When treated with isoxaflutole at concentrations insufficient to inhibit growth, *M. grisea* growth was inhibited in minimal plus tyrosine media, while growth in minimal media was unaffected. Since the results differ from those obtained in Unknown 1, the target of isoxaflutole (HPPD) is not likely the same as the target of Unknown 1.

Summary of the Analysis of Unknown 4

The fungal nutritional profiling results obtained from Unknown 4 at the partially inhibitory concentration (250 μg/ml) were nearly identical to the growth characteristics of glyphosate at the same concentration (partially inhibitory) in the various media tested in Tiers 3 and 4. Based on these results, it was determined that the mode-of-action of Unknown 4 was aromatic amino acid biosynthesis. However, the results for both Unknown 4 and glyphosate suggest that they effect nitrogen utilization. Both inhibited growth of *M. grisea* when nitrate, nitrite, or glutamate was provided as the sole nitrogen source. Little growth defect was observed when ammonium or glutamine was provided. The results differ from glufosinate, whose site-of-action is glutamine synthetase. In the presence of glufosinate, *M. grisea* is only able to utilize glutamine and glutamate as nitrogen sources.

Thus, it is hypothesized that Unknown 4 may also effect nitrogen utilization and/or metabolism in *Arabidopsis*. In plants, nitrogen regulation is very complex and is closely associated with carbon utilization. However, studies of nitrate addition to N-starved *Arabidopsis* plants have identified several nitrate-regulated genes. If Unknown 4 inhibits nitrogen utilization, addition of this compound to *Arabidopsis* may have the opposite effect on these genes. Table 10 lists a subset of these genes and their relative expression levels following treatment with Unknown 4.

TABLE 10

Expression of Nitrate Regulated Genes Following Unknown 4 Treatment

| Gene | Unknown 4 | Nitrate Regulation |
|---|---|---|
| Phosphate transporter | ↓ | ↑ |
| Transaldolase | ↓ | ↑ |
| Transketolase | ↓ | ↑ |
| Malate Dehydrogenase | ↓ | ↑ |
| MYB transcription factor | ↓ | ↑ |
| Nitrate transporter | ↓ | ↑ |
| Glutamine synthetase(2) | ↓ | ↑ |
| Glutamate synthetase | ↓ | ↑ |
| MADs Box(2) | ↑ | ↓ |

Both fungal growth and gene expression data support the hypothesis that Unknown 4 alters nitrogen source metabolism in both organisms. Fungal growth data helped guide the analysis of both gene expression and metabolite data, although no specific conclusions were made from the metabolite data at the recorded time points. Since plants treated with Unknown 4 exhibited large perturbation in the total number of genes, an internal database was searched to identify whether any of the genes altered by Unknown 4 treatment were found to be essential for plant growth and development. The internal database search has revealed that a total of 86 genes that were altered by Unknown 4 treatment were found to be essential for plant growth and development (Table 11). A subset of these 86 genes includes five genes believed to participate in nitrogen metabolism, which further lends credibility to the conclusions derived from the fungal nutritional profiling platform discussed herein.

TABLE 11

Genes Altered by Various herbicides and Identified as Essential Genes

| Compound | No. of Lethal Genes Altered |
|---|---|
| Unknown 1 | 8 |
| Unknown 2 | 7 |
| Unknown 3 | 6 |
| Unknown 4 | 86 |
| Unknown 5 | 12 |
| Asulam | 5 |
| Chlorsulfuron | 8 |
| Glufosinate | 10 |
| Isoxaflutole | 15 |
| Naptalam | 3 |

Phenotypic, biochemical, and gene expression data were gathered to determine the effects of five unknown herbicide candidates and up to 18 commercial herbicides in *Arabidopsis* after brief treatments with a high dose of each compound. Fungal nutritional profiling was employed as a surrogate biological system to examine the effects of nutrient utilization in *M. grisea* in the presence of each compound.

From the data collected, an example was obtained in which metabolites upstream from the site-of-action were accumulating after 1 hour (isoxaflutole). It was also shown that by using results from fungal nutritional profiling, a hypothetical mode-of-action of Unknown 4 in *M. grisea* was posited and supported by gene expression data from *Arabidopsis.*

As described in Specific Example 2, site-of-action experimental data were collected from samples taken at relatively late time points as compared to the presently described study. Sample collections were calibrated to each herbicide based on 10%, 30%, and 70% of the time required for full symptom development. For example, the 10% and 70% sampling points for the fast acting herbicide, paraquat, were 5 and 48 hours, respectively, while the analogous time points for the slow acting herbicide, chlorsulfuron, were 24 and 168 hours, respectively. Although clustering of the herbicides based on gene expression and metabolite data was more accurate using these time points, the identification of site- or pathway-of-action was not achieved.

In the experiments performed in the present study, the time points for sampling were fixed at 20 minutes and 1 hour following treatment, without accounting for the kinetics of action. Gene expression and metabolite data from these early time points did not cluster as expected based on known modes of action (MOAs). It is well known that the time to response varies due to many factors, such as uptake and transport, even for compounds that target the same site. Thus, at fixed time points as used in the present study, the genes and metabolites specifically perturbed by each compound or MOA class may not be fully expressed or expressed to the same levels.

In spite of the fact that the experiments presented herein may not be the most ideal sampling time points, informative data were obtained. Metabolites upstream of the SOA of isoxaflutole (tyrosine and phenylalanine), began to accumulate relative to the control after one hour. In addition, the metabolites downstream from the SOA of glyphosate (tyrosine), decreased relative to the control after one hour. A group of stress related metabolites were observed to increase after one hour in 12 of 23 herbicides tested including Unknown 1, Unknown 2, and Unknown 4, suggesting that the kinetics of action of these herbicides were rapid. Three unknown metabolites (pLCcpnd9, 78, and 310) were also observed to increase in eight treatments after 20 minutes and thus, they may represent early stress markers.

Based on the results as described herein, it is hypothesized that experiments performed with intermediate time points which are calibrated to each herbicide may help more accurately identify the point at which clustering begins to occur (i.e. later or equal to the time points used in the present study, but earlier than the time points used in the previous study). With the addition of initial clustering data, the data sets may be enriched for specific metabolites and gene expression responses that can be used to identify the site- or pathway-of-action. This can be tested using commercial herbicides with known MOAs.

The following is an example of an approach to optimizing and implementing an experimental design to increase the value of the described MOA analysis platform.

Define the kinetics-of-action. Several herbicides had very little effect on metabolite regulation in either time point tested (Table 7). This suggests that the herbicide may not have reached its target within the timeframe of sampling. Cell leakage assays could be used to identify the point at which herbicidal action results in cell damage prior to the production of a visible phenotype. The onset of the visible phenotype can also be used as a landmark. Sampling times could be chosen to bracket these time points.

Add additional time points. Increasing the number of time points for each herbicide and bracketing relative to a kinetics-of-action would allow for trend analysis over time thereby enhancing the ability to interpret metabolite and gene expression data. Additional time points will not require much more of each test compound with the present treatment procedure. At a rate equivalent to 1.0 kg/ha, only 0.85 mg of herbicide was required per time point. Thus, 10 mg of a test compound can provide several more time points than was generated for this study.

Collect data for herbicides with known modes/sites-of-action. Data from herbicides with known modes/sites-of-action will help validate the experimental design, enhance comparative approaches for analysis of new herbicides, and assist in the identification of herbicides candidates with novel modes-of-action. In addition, these commercial herbicides can be used to determine the most appropriate sampling points for various site-of-action classes. Proper clustering of commercial herbicides with known sites-of-action will validate particular sampling regimes.

Reanalyze metabolite data as new standards are run for peak identification. An ongoing standards program for identifying metabolites seen in biochemical profiling data could result in previously unrevealed and/or unidentified metabolites. Resolution within and between pathways will be enhanced as new metabolites are accurately identified. Advantageously, data already generated can be reanalyzed as new peaks are identified, thereby eliminating the need to repeat experiments.

Perform gene expression analysis on the same samples generated for metabolite analysis. Biological samples or total RNA can be delivered for gene expression analysis. Gene expression analysis is a complement to metabolite analysis by providing a link between metabolite changes and gene expression changes. Previous reports have demonstrated that greater degrees of clarity can be achieved using multiple data streams for cluster analysis. With a proper sampling regime, gene expression analysis should also provide valuable data for identifying perturbed genes/pathways. Combined with the metabolite data, a higher resolution picture can emerge.

Continue using fungal nutritional profiling. Based on the analysis of commercial herbicides, a positive result can identify the target pathway and may even identify the site-of-action in some cases. Additionally, the compound requirements are very small. Only 1.0 mg of herbicide was required for the extended fungal nutritional profiling experiments described for Unknown 4.

The above-described specific example illustrates the value of combining different types of data to obtain a more complete representation of a biological system. In this specific example, the combination of gene expression data, metabolite data, and phenotypic data allowed experimental conclusions to be drawn from coherent data that was otherwise not likely have been drawn from a collective review of gene expression data, metabolite data, and phenotypic data analyzed separately. Adding a fourth data source, that is nutritional profiling, only serves to increase the information available for drawing biologically relevant conclusions, the results of which were used to guide the analysis of the gene expression and metabolite data. Additionally, populating the experimental data sets with data from "known" samples to use as controls gives valuable guidance when looking at the large, combined, complex data sets.

The methods of the present invention provide ways to achieve creation of coherent data sets from data such as that set forth in the above specific example. A coherent data set is not necessarily a closed system, and can accommodate the addition of new data as it becomes available. The above-described optimization process is an example of how the specific example could be modified to strengthen its value as a model for herbicide site- or pathway-of-action studies. The SOA1 (Specific Example 2) and MOA1 (Specific Example 3) studies outlined herein create the foundation for a comprehensive herbicide site-, mode-, and pathway-of-action coherent data set.

The results of the foregoing study, MOA1, show that it is possible to accurately predict the MOA of herbicides using a combination of technologies when the MOA is represented in an existing database. The strategy set forth herein, of standardizing and combining disparate data into coherent data sets for the analysis of biological samples, will increase the predictive power of the analysis. The strategy is applicable to any experimental system and any data or technology, including alternatives not explored herein, such as protein expression and activity profiling.

SPECIFIC EXAMPLE 4

Preparation of Cell Culture Samples for Analysis

Cell culture samples were either freeze-dried or fresh-frozen at −80° C. Cell culture samples were prepared for gene expression and LC-MS analysis as described in the above examples for plant samples. For GC-MS analysis, the lyophilized sample material was extracted and derivatized in 96-well plates. The procedure yielded trimethylsilyl (TMS) derivatives for a variety of compounds including organic acids, fatty acids, amino acids, sugars, alcohols, and sterols.

The basic derivatization procedure involved a two-step derivatization using MSTFA (methyl trimethylsilyl trifluoroacetamide) in acetonitrile, acidified with trifluoroacetic acid, followed by derivatization with a strongly basic silylating agent such as TMSDMA (trimethylsilyldimethylamine).

SPECIFIC EXAMPLE 5

Yeast Azole Drug Experiment

Ergosterol is an essential component of fungal plasma membranes. It affects membrane permeability and the activities of membrane-bound enzymes. This sterol is a major component of secretory vesicles and has an important role in mitochondrial respiration and oxidative phosphorylation. G. Daum et al., 14 YEAST 11471–1510 (1998). It can thus be expected that changes in ergosterol levels and sterol structure influence the activities of several metabolic pathways. Enzymes in the ergosterol biosynthetic pathway are the targets of a number of anti-fungal agents. Over the past 40 years, amphoteracin B synthesized by *Streptomyces nodosus* has been the mainstay of antifungal therapy for severe systemic mycotic infections. F. C. Odds, *Antifungal Therapy*, in PRINCIPLES AND PRACTICE OF CLINICAL MYCOLOGY 35–48 (C. C. Kibbler et al. eds., 1996); H. J. Vanden Bossche et al., *Discovery, Chemistry, Mode of Action, and Selectivity of Itraconazole*, in CUTANEOUS ANTIFUNGAL AGENTS 263–283 (J. W. Rippon & R. A. Fromtling eds., 1993).

Amphoteracin B is capable of binding irreversibly to ergosterol in the fungal cytoplasmic membrane, thus increasing membrane permeability with ultimate fungal cell death. Despite its proven efficacy, use of the conventional formulation of amphoteracin B (amphoteracin B deoxycholate) is limited by potentially severe adverse reactions, especially nephrotoxicity and infusion-related events. Over the past 20 years, azoles, primarily ketoconazole and fluconazole that are less toxic alternatives to amphoteracin B, have become attractive. The anti-fungal activities of azole derivatives arise from a complex multi-mechanistic process initiated by the inhibition of two cytochromes P450 involved in the biosynthesis of ergosterol, namely, the P450 that catalyzes the 14-demethylation of lanosterol or eburicol (encoded by erg11), and 22-desaturase (encoded by erg5). D. C. Lamb et al., 43 ANTIMICROB. AGENTS CHEMOTHER. 1725–1728 (1999).

However, there are problems with current azoles, namely, their relatively poor efficacy against invasive mold infections and concern about emerging clinical and microbiologic resistance to azoles. Due to the increasing prevalence of disseminated fungal infections associated with the acquired immune deficiency syndrome (AIDS) epidemic, increased utilization of organ transplantation and immunosuppression, and the increased number of invasive fungal nosocomial infections, antifungal agents are more widely used than ever before. Consequently, there is a need for alternative drugs that are both efficacious and well tolerated. Posaconazole is a triazole that is structurally related to Itraconazole. It is currently in Phase III trials by Schering-Plough Corporation. Compared to two early azole drugs, posaconazole is a significantly more potent inhibitor of sterol C14 demethylation, particularly in *Cryptococcus neoformans* and *Aspergillus* spp. K. L. Oakley et al., 41 ANTIMICROB. AGENTS CHEMOTHER. 1124–1126 (1997).

The rapid development of genomics in the past several years provided unique access to genes and regulatory elements of individual genes at the genome level. Successful application of the genomic techniques, such as DNA microarrays for exploring transcriptional profiles and genome differences for a variety of microorganisms, has greatly facilitated an understanding of mode of action of various anti-fungal drugs. M. D. De Backer, et al., 45 ANTIMICROB. AGENTS CHEMOTHER. 1660–1670 (2001); M. H. Jia et al., 3 PHYSIOL. GENOMICS. 83–92 (2000). However, microarrays might not provide direct information about how the mRNA change is coupled to the change in biological functions, because the rate of enzymatic reactions is a function of substrates and products (metabolomes). O. Fiehn, 48 PLANT MOL. BIOL. 155–171 (2002); B. H. Ter Kuile & H. V. Westerhoff, 500 FEBS LETT. 169–171 (2001).

Moreover, for most organisms, there is no direct relationship between metabolites and genes in the way that there is for mRNA and proteins. For example, *S. cerevisiae* has fewer than 600 low-molecular-weight metabolite intermediates and has approximately 6200 protein-encoding genes. Metabolomics, as a method to define the small molecule diversity in cell and to display the differences of small molecule abundance, exhibits many advantages in terms of metabolic analyses. As functional entities within cells, metabolite concentration levels are varied as a consequence of genetic and/or physiological changes. Profiling of up to 68 primary metabolites has been successfully demonstrated to be useful for clinical research by differentially comparing healthy human tissues with diseased ones. J. M. Halket et al., 13 RAPID COMMUN. MASS SPECTROM. 279–284 (1999). A similar approach has been taken in plant research, wherein mass spectrometry has been applied to profile a limited number of primary metabolites. M. A. Adams et al., 266 ANAL. BIOCHEM. 77–84 (1999).

Metabolomics study is an important part of an integrative approach for accessing cellular metabolism and understanding mode of action of drugs. In the present specific example, the methods of the invention are applied to an integrated genomic and metabolomic approach to reveal the mode of action of antifungal drugs. Using *S. cerevisiae* as a model system, the global metabolic consequences caused by the treatment of four antifungal drugs (amphoteracin B, ketoconazole, fluconazole, and posaconazole) were examined at both the transcriptome (RNA) and metabolome (small molecule) levels. The integrative analyses presented a global view of the metabolic changes associated with each drug treatment, thus allowing for a better interpretation of the mode of action of antifungal drugs.

Materials and Methods

Strains and Media

*Saccharomyces cerevisiae* wild type strain BY4743 was purchased from American Type Culture Center (ATCC, Manassas, Va.). The yeast strain was grown in YPD or SD media. H. Ito et al., 153 J. BACTERIOL. 163–168 (1983). The cultures started from fresh single colonies were grown in 1.0 ml YPD overnight at 30° C. (The $OD_{600}$ values of overnight cultures are normally around 2.0 to 3.0 after 16 hours of growth). The $OD_{600}$ was adjusted to 1.0 with YPD media, then 2.0 ml of each was inoculated into three 250 ml flasks, each containing 50 ml of SD media. When the $OD_{600}$ reached 2.0, an amount equivalent to 2×MIC (minimal inhibitory concentration) of each of the four tested antifungal drugs was dissolved into 0.5 ml dimethyl sulphoxide (DMSO) and added into the culture. The cells were kept growing for another two hours, then collected by centrifugation at 4000 rpm for 5 minutes at 4° C. Pellets were washed once with ice-cold water, then were lyophilized overnight at 4° C.

Determination of MIC

Antifungal drugs amphoteracin B, ketoconazole, and fluconazole were purchased from Sigma (Sigma Chemical Co., St. Louis, Mo.), and posaconazole was a gift from Duke Medical Center (Duke Univ. Medical Center, Durham, N.C.). Minimal inhibitory concentration was determined using 96-well plates. 100 µl of the overnight culture was added to fresh YPD media in a new sterile tube. The new tube was returned to the 37° C. shaker and incubated for 4 hours. The cells were spun down in the microcentrifuge and washed twice with sterile $dH_2O$. The cells were diluted into YPD media and loaded into 96-well plates. The tested antifungal drug was dissolved into DMSO and added into plates at the final DMSO concentration of 1.0%.

RNA Extraction and Microarray Preparation

Approx. 18±1 mg of lyophilized yeast cells in a 1.5 ml microcentrifuge tube were rehydrated in 75 µL RNA LATER (Ambion, Inc., Austin, Tex.) and incubated for 30 minutes. 875 µl TRIZOL Reagent (GibcoBRL, Rockville, Md.) were added to each tube. The tubes were vortexed for 15 seconds and allowed to rest for 45 seconds, repeated, and continued for a total of 5 minutes. 240 µL 100% Chloroform (RNAase-free) was added to each tube. Tubes were vortexed for 30 seconds, then incubated for 10 minutes at room temperature (RT). The tubes were then spun at 14,000 rpm in a refrigerated eppendorf centrifuge at 4° C. for 5 minutes. 570 µl of the aqueous phase was removed and placed in a new, RNAase-free 2.0 ml tube. 430 µl nuclease-free water (Ambion, Inc., Austin, Tex.), and 1.0 ml 100% isopropanol, were added to each tube and mixed thoroughly by inversion. Tubes were incubated for 10 minutes at RT. Samples were centrifuged for 20 minutes as before. Pellets were washed with 400 µl 70% ethanol and centrifuged for 10 minutes as before. The pellet was then dissolved in 100 µl nuclease-free water. RNA quality was determined using the Bioanalyzer 2100 and the RNA 6000 assay (Agilent Technologies, Palo Alto, Calif.) according to manufacturer's instructions. RNA concentrations were determined spectrophotometrically by measuring the absorption at 260 nm in an Ultrospec 2000 (Pharmacia Biotech, Piscataway, N.J.). Microarrays containing approximately 6200 S. cerevisiae genes, essentially covering the entire genome, were generated by Agilent Technologies using oligonucleotides 60 bases in length synthesized in situ by an ink-jet printing method (Agilent Technologies, Palo Alto, Calif.).

Microarray Hybridizations

RNA samples were labeled with either Cy3 or Cy5 using Agilent's Fluorescent Linear Amplification Kit according to the manufacturer's instructions (Agilent Technologies, Palo Alto, Calif.). Labeled cRNAs were evaluated using the RNA 6000 assay on the Agilent Bioanalyzer 2100. Labeled cRNA concentrations were determined spectrophotometrically by measuring the absorption at 260 nm in an Ultrospec 2000 (Pharmacia Biotech, Piscataway, N.J.). Probe solutions containing 125 ng of labeled cRNA for each mutant and its paired control were prepared using Agilent's in situ Hybridization Reagent Kit (Agilent Technologies, Palo Alto, Calif.). Each pair of samples to be hybridized were independently labeled and hybridized utilizing a fluor reversal for a total of two hybridizations per sample pair. The microarrays were scanned simultaneously in the Cy3 and Cy5 channels with Agilent's 48-slide, Dual Laser DNA Microarray Scanner (Agilent Technologies, Palo Alto, Calif.) at 10 µm resolution using default settings.

Microarray Data Processing and Analyses

Image Analysis Software (Version A.4.0.45, Agilent Technologies, Palo Alto, Calif.) was used for image analysis. Each feature was determined from an array's associated pattern file and a detection algorithm. Intensity values for each feature were determined after subtracting background derived from an average of negative control features. Features with unusual pixel intensity statistics (e.g., high non-uniformity, saturation in either channel, and the like) were excluded from downstream analyses. Data was loaded into the Rosetta RESOLVER database (Rosetta Inpharmatics Inc., Kirkland, Wash.) for storage and analysis. Data was evaluated after combining results from fluor reversal replicate hybridizations. The annotation of yeast ORFs was obtained from Proteome BIOKNOWLEDGE Library (Incyte Genomics, Palo Alto, Calif.).

GC-MS Derivatization and Analyses

Approximately 10 mg of dried ground cells were extracted in solvent, converted to trimethylsilyl derivatives in-situ, and analyzed by gas chromatography with time of flight mass spectrometry (GC/TOF-MS) as desribed previously. Separations were conducted using a 50% phenyl- 50% methyl stationary phase, helium carrier gas, and a programmed oven temperature that ramped from a starting temperature of 50° C. to a final temperature of over 300° C. Compounds detected by GC-MS with an electron impact (EI) ion source were cataloged based on Kovats retention indices and mass-to-charge ratio (m/z) of the ions characteristic of each peak. Commercially available reference compounds were obtained from Sigma-Aldrich (Sigma Chemical Co., St. Louis, Mo.) or VWR (VWR Scientific Products, Baltimore, Md.). Table 12 provides a list of detected compounds.

LC-MS Procedures

Approximately 10 mg of dried ground cells were extracted in 0.5 ml 10% aqueous methanol containing labeled internal standards. Tissue was disrupted by a 30 second pulse of high-level sonic energy (lithotripsy), at a maximum temperature of 30° C. The extract was centrifuged at 4000 rpm for 2 minutes. The supernatant, diluted with an equal volumn of 50% aqueous acetonitrile (V/V) was chromatographed on C18 HPLC in an acetonitrile/water gradient containing 5 mM ammonium acetate. Samples were passed through a splitter and the split flow was infused to the trubo-ionspray ionization sources of two Mariner LC TOF mass spectrometers (PerSeptive Biosystems Inc., Framingham, Mass.). Ion sources were optimized to generate and monitor positive (pLC) and negative (nLC) ions, respectively. The Total Ion Chromatogram (TIC) was analyzed for compounds with masses ranging from 80 to 900 Da. Individual ion traces were used for both calibration and quantification. Relative amounts of compounds were determined using intensity and peak areas of individual ion traces. Isotopically labeled internal standards were used for peak area ratios, response factor determination, and normalization of data throughout the experiment. Table 12 provides a list of detected compounds.

TABLE 12

Detected Metabolites

| Treatment | Compound | Platform | p-Value | Fold Change |
|---|---|---|---|---|
| Amphoteracin B | 2-ketobutyric acid | nLC | 0.225631474 | −0.999150382 |
| Amphoteracin B | 2-ketoglutaric | nLC | 0.622408732 | 8.790891018 |
| Amphoteracin B | 3-indolylacetonitri | nLC | 0.197015297 | −0.999782451 |
| Amphoteracin B | 4ambutyrate/dimglyc | pLC | 0.920009792 | 0.01278731 |
| Amphoteracin B | 4-aminobenzoic acid | pLC | 1 | 0 |
| Amphoteracin B | 4aminobutyrate/dimg | nLC | 0.820379809 | −0.198261949 |
| Amphoteracin B | 4-methylcatechol | nLC | 1 | 0 |
| Amphoteracin B | 4-methylcatechol | PLC | 1 | 0 |
| Amphoteracin B | 5hydroxyLtryptophan | nLC | 1 | 0 |
| Amphoteracin B | 5hydroxyLtryptophan | pLC | 1 | 0 |
| Amphoteracin B | 6benzylaminopurine | PLC | 1 | 0 |
| Amphoteracin B | 6-benzylaminopurine | nLC | 1 | 0 |
| Amphoteracin B | abscisic acid | nLC | 1 | 0 |
| Amphoteracin B | abscisic acid | LC | 1 | 0 |
| Amphoteracin B | aconitic acid | nLC | 0.891314692 | 0.542608239 |
| Amphoteracin B | adenine | nLC | 1 | 0 |
| Amphoteracin B | adenine | pLC | 0.892253251 | 0.115293431 |
| Amphoteracin B | adenosine | nLC | 1 | 0 |
| Amphoteracin B | adenosine | LC | 1 | 0 |
| Amphoteracin B | alanine | GC | 0.054639399 | −0.777259086 |
| Amphoteracin B | alanine | nLC | 0.62524207 | 0.159889332 |
| Amphoteracin B | alanine/sarcosine | pLC | 0.540255177 | 0.260223791 |
| Amphoteracin B | allantoic acid | nLC | 0.777964345 | −0.145621023 |
| Amphoteracin B | allantoic acid | pLC | 1 | 0 |
| Amphoteracin B | allantoin | nLC | 0.149169352 | 3.969743665 |
| Amphoteracin B | anthranilic acid | nLC | 1 | 0 |
| Amphoteracin B | anthranilic acid | pLC | 1 | 0 |
| Amphoteracin B | arginine | nLC | 0.315413423 | −0.48852387 |
| Amphoteracin B | arginine | pLC | 0.522893347 | 0.466194768 |
| Amphoteracin B | argininosuccinate | nLC | 1 | 0 |
| Amphoteracin B | argininosuccinate | LC | 1 | 0 |
| Amphoteracin B | asparagine | GC | 6.41E-06 | −0.999990003 |
| Amphoteracin B | asparagine | nLC | 0.758489047 | 0.151122053 |
| Amphoteracin B | asparagine | pLC | 0.526485859 | 0.634356489 |
| Amphoteracin B | aspartic | nLC | 0.703732114 | 0.240696517 |
| Amphoteracin B | aspartic acid | GC | 0.024172801 | −0.974333333 |
| Amphoteracin B | aspartic acid | pLC | 0.626001257 | 0.359387817 |
| Amphoteracin B | benzoic acid | nLC | 1 | 0 |
| Amphoteracin B | biotin | nLC | 0.363209057 | 1.077063265 |
| Amphoteracin B | biotin | pLC | 1 | 0 |
| Amphoteracin B | caffeic acid | nLC | 0.427037943 | −0.58815132 |
| Amphoteracin B | caffeine | LC | 1 | 0 |
| Amphoteracin B | campesterol | GC | 1 | 0 |
| Amphoteracin B | catechol | nLC | 1 | 0 |
| Amphoteracin B | cinnamic acid | nLC | 1 | 0 |
| Amphoteracin B | citric acid TME | pLC | 1 | 0 |
| Amphoteracin B | citricanoic/itaconi | nLC | 1 | 0 |
| Amphoteracin B | citrulline | nLC | 0.217809679 | 1659.333333 |
| Amphoteracin B | citrulline | pLC | 0.433366283 | 1.798113764 |
| Amphoteracin B | coumaric acid | nLC | 1 | 0 |
| Amphoteracin B | cytidine | nLC | 0.000680198 | −0.998602701 |
| Amphoteracin B | cytidine | pLC | 1 | 0 |
| Amphoteracin B | cytosine | nLC | 1 | 0 |
| Amphoteracin B | cytosine | pLC | 1 | 0 |
| Amphoteracin B | decanoic acid | nLC | 0.824169685 | −0.087161599 |
| Amphoteracin B | desmosterol | GC | 1 | 0 |
| Amphoteracin B | diaminopimelic acid | nLC | 1 | 0 |
| Amphoteracin B | diaminopimelic acid | pLC | 1 | 0 |
| Amphoteracin B | dihydrofolic acid | nLC | 1 | 0 |
| Amphoteracin B | dihydrofolic acid | pLC | 1 | 0 |
| Amphoteracin B | dipicolinic acid | pLC | 1 | 0 |
| Amphoteracin B | disaccharide1 | GC | 7.54E-06 | −0.99999 |
| Amphoteracin B | disaccharide2 | GC | 0.000388379 | −0.997666667 |
| Amphoteracin B | disaccharide3 | GC | 0.000700744 | −0.997666667 |
| Amphoteracin B | DLaminoadipic acid | nLC | 0.40985594 | 1.410752688 |
| Amphoteracin B | DL-aminoadipic acid | pLC | 0.229215472 | 0.470273881 |
| Amphoteracin B | ergosterol | GC | 0.114118055 | 2.303333333 |
| Amphoteracin B | estrone | nLC | 1 | 0 |
| Amphoteracin B | farnesol | nLC | 1 | 0 |
| Amphoteracin B | folic acid | nLC | 1 | 0 |
| Amphoteracin B | folic acid | pLC | 1 | 0 |
| Amphoteracin B | fucosterol | GC | 0.186711806 | −0.655333333 |
| Amphoteracin B | fumaric/3m2oxobutan | nLC | 0.238894937 | 0.442276246 |
| Amphoteracin B | gallic acid | nLC | 0.29960644 | 0.162157188 |
| Amphoteracin B | gibberellic | nLC | 1 | 0 |

TABLE 12-continued

Detected Metabolites

| Treatment | Compound | Platform | p-Value | Fold Change |
|---|---|---|---|---|
| Amphoteracin B | glucosamine | pLC | 1 | 0 |
| Amphoteracin B | glucosamine6PO4 | nLC | 0.273438701 | −0.995114007 |
| Amphoteracin B | glucosamine6PO4 | pLC | 1 | 0 |
| Amphoteracin B | glutamate | pLC | 0.563874982 | 0.43414851 |
| Amphoteracin B | glutamic/acetylseri | nLC | 0.733962176 | 0.141411563 |
| Amphoteracin B | glutamine | GC | 0.019324613 | −0.911637212 |
| Amphoteracin B | glutamine/lysine | nLC | 0.835677767 | 0.079191524 |
| Amphoteracin B | glutamine/lysine | LC | 0.618892728 | 0.398094054 |
| Amphoteracin B | glutathione | pLC | 0.951676383 | −0.033484535 |
| Amphoteracin B | glycanopyrose | GC | 0.041202857 | −0.957996667 |
| Amphoteracin B | glycerol | GC | 0.089234962 | −0.815 |
| Amphoteracin B | glycine | GC | 0.431923912 | 0.880666667 |
| Amphoteracin B | guanine | nLC | 1 | 0 |
| Amphoteracin B | guanosine | nLC | 0.425021511 | 1.131147541 |
| Amphoteracin B | guanosine | LC | 0.886514477 | 0.759776536 |
| Amphoteracin B | hexadecanoic acid | GC | 0.921125845 | −0.242666667 |
| Amphoteracin B | histidine | nLC | 1 | 0 |
| Amphoteracin B | histidine | pLC | 1 | 0 |
| Amphoteracin B | homogentisic/uric | nLC | 1 | 0 |
| Amphoteracin B | hydrocortisone | nLC | 1 | 0 |
| Amphoteracin B | hydrocortisone | pLC | 1 | 0 |
| Amphoteracin B | hypoxanthine | nLC | 0.372039959 | 0.165495208 |
| Amphoteracin B | hypoxanthine | pLC | 0.74082632 | 0.205678879 |
| Amphoteracin B | indole3pyruvic acid | nLC | 1 | 0 |
| Amphoteracin B | inostol/glucos/sorb | nLC | 0.41837757 | −0.590534418 |
| Amphoteracin B | iso citric acid | GC | 0.233348939 | −0.618333333 |
| Amphoteracin B | isocitric/citric/qu | nLC | 0.027544382 | 2.549468869 |
| Amphoteracin B | isoleucine | GC | 0.021030517 | −0.953333333 |
| Amphoteracin B | itaconic acid dimes | LC | 1 | 0 |
| Amphoteracin B | jasmonic acid | nLC | 1 | 0 |
| Amphoteracin B | kinetin | nLC | 1 | 0 |
| Amphoteracin B | kinetin | pLC | 1 | 0 |
| Amphoteracin B | lactic acid | nLC | 0.077524891 | −0.025833603 |
| Amphoteracin B | lanosterol | GC | 7.71E-06 | −0.99999 |
| Amphoteracin B | lauric acid | nLC | 0.972245476 | 0.122549629 |
| Amphoteracin B | leucine | GC | 0.015876175 | −0.944333333 |
| Amphoteracin B | leucine/isoleucine/ | nLC | 0.763305915 | 0.131916357 |
| Amphoteracin B | leucine/isoleucine/ | pLC | 0.723852356 | 0.274641204 |
| Amphoteracin B | luteolin | nLC | 1 | 0 |
| Amphoteracin B | luteolin | pLC | 1 | 0 |
| Amphoteracin B | lysine | GC | 0.488896519 | −0.392535821 |
| Amphoteracin B | malic acid | GC | 0.015444108 | −0.963005665 |
| Amphoteracin B | malic acid | nLC | 0.497517178 | 0.621171595 |
| Amphoteracin B | malonic acid | nLC | 1 | 0 |
| Amphoteracin B | mannitol | pLC | 0.575742486 | 0.45428497 |
| Amphoteracin B | menthol* | nLC | 0.852876357 | −0.07013498 |
| Amphoteracin B | methionine | nLC | 1 | 0 |
| Amphoteracin B | methionine | LC | 0.367502423 | 0.329889113 |
| Amphoteracin B | mevalonic acid lactone | GC | 0.690626296 | −0.127624125 |
| Amphoteracin B | mevalonic lactone | pLC | 0.251617022 | −0.460562414 |
| Amphoteracin B | NacetylDglucosamine | nLC | 1 | 0 |
| Amphoteracin B | NacetylDglucosamine | pLC | 1 | 0 |
| Amphoteracin B | NacetylLglutamate | nLC | 0.840704909 | −0.107788162 |
| Amphoteracin B | NacetylLglutamate | LC | 1 | 0 |
| Amphoteracin B | NacetylLornithine | nLC | 1 | 0 |
| Amphoteracin B | NacetylLornithine | pLC | 0.392871315 | 1.318875781 |
| Amphoteracin B | niacinamide | LC | 1 | 0 |
| Amphoteracin B | nicotinic acid | nLC | 0.972130606 | 0.31 3077939 |
| Amphoteracin B | nicotinic acid | pLC | 7.53474E-05 | −0.99893617 |
| Amphoteracin B | nopaline | nLC | 0.369522244 | 0.334229391 |
| Amphoteracin B | nopaline | pLC | 1 | 0 |
| Amphoteracin B | octadecanoic acid | GC | 0.660192025 | 0.21 |
| Amphoteracin B | oleic acid | GC | 0.325422554 | −0.459333333 |
| Amphoteracin B | oleic acid | nLC | 0.880270386 | 0.688969565 |
| Amphoteracin B | ornithine | nLC | 0.473753211 | 2.534415913 |
| Amphoteracin B | ornithine | pLC | 0.48461244 | 0.504866344 |
| Amphoteracin B | ornithine2 | GC | 1.48992E-05 | −0.99999 |
| Amphoteracin B | ornithine3 | GC | 0.011300115 | −0.985326667 |
| Amphoteracin B | orotic acid | nLC | 0.186179266 | 8380 |
| Amphoteracin B | palmiteliadic acid | GC | 0.503020409 | 0.515 |
| Amphoteracin B | palmitic acid | nLC | 0.90280612 | 0.397948025 |
| Amphoteracin B | phenylalanine | GC | 0.010760299 | −0.979659887 |
| Amphoteracin B | phenylalanine | nLC | 0.76165051 | −0.190559006 |
| Amphoteracin B | phenylalanine | LC | 0.573569375 | 0.403640768 |

TABLE 12-continued

Detected Metabolites

| Treatment | Compound | Platform | p-Value | Fold Change |
|---|---|---|---|---|
| Amphoteracin B | phenylpyruvic acid | nLC | 1 | 0 |
| Amphoteracin B | phosphate | GC | 0.983733869 | −0.007333333 |
| Amphoteracin B | phosphoenolpyruvate | nLC | 1 | 0 |
| Amphoteracin B | phosphoenolpyruvate | pLC | 1 | 0 |
| Amphoteracin B | pinitol | nLC | 1 | 0 |
| Amphoteracin B | pipecolic acid | nLC | 0.871015411 | 0.081118937 |
| Amphoteracin B | pipecolic acid | LC | 0.556385814 | 0.523741811 |
| Amphoteracin B | porphobilinogen | nLC | 1 | 0 |
| Amphoteracin B | progesterone | pLC | 1 | 0 |
| Amphoteracin B | proline | nLC | 0.518220081 | 0.460347915 |
| Amphoteracin B | proline | pLC | 0.474762121 | 0.670657914 |
| Amphoteracin B | pyridoxine | nLC | 0.708651225 | −0.129434556 |
| Amphoteracin B | pyridoxine | pLC | 0.776529987 | −0.168408149 |
| Amphoteracin B | pyrimidine | GC | 0.744108261 | −0.185 |
| Amphoteracin B | retinoic acid | nLC | 1 | 0 |
| Amphoteracin B | riboflavin | LC | 1 | 0 |
| Amphoteracin B | salicylic/HObenzoic | nLC | 1 | 0 |
| Amphoteracin B | selenoOLmethionine | nLC | 0.711447529 | 0.851513124 |
| Amphoteracin B | selenoDLmethionine | pLC | 0.888275646 | 1.177511152 |
| Amphoteracin B | serine | nLC | 0.766811518 | 0.10907441 |
| Amphoteracin B | serine | LC | 0.716422123 | 0.201058201 |
| Amphoteracin B | shikimic acid | nLC | 1 | 0 |
| Amphoteracin B | sinapinic acid | nLC | 1 | 0 |
| Amphoteracin B | sorbitol/mannitol | nLC | 0.68492695 | 0.216175129 |
| Amphoteracin B | squalene | GC | 0.254158772 | −0.574475175 |
| Amphoteracin B | succinic | nLC | 0.193450596 | 0.866316251 |
| Amphoteracin B | sucrose | nLC | 0.225682636 | 0.449275362 |
| Amphoteracin B | sugar? | GC | 0.019518223 | −0.932993333 |
| Amphoteracin B | sugar-phosphate | nLC | 0.878141701 | −0.106666667 |
| Amphoteracin B | sugar-phosphate | pLC | 1 | 0 |
| Amphoteracin B | tetradecanoic acid | GC | 0.793963653 | 0.079666667 |
| Amphoteracin B | tetradecanoic acid | nLC | 0.782765706 | −0.077232772 |
| Amphoteracin B | thiamine | pLC | 1 | 0 |
| Amphoteracin B | threonine/homoserin | nLC | 0.769444989 | 0.126655553 |
| Amphoteracin B | threonine/homoserin | pLC | 0.668114613 | 0.314511535 |
| Amphoteracin B | threonine2 | GC | 0.073159868 | −0.855333333 |
| Amphoteracin B | threonine3 | GC | 0.063199416 | −0.893333333 |
| Amphoteracin B | thymine | nLC | 1 | 0 |
| Amphoteracin B | thymine | pLC | 1 | 0 |
| Amphoteracin B | tms glutamine3 | GC | 0.003279434 | −0.893478913 |
| Amphoteracin B | tms lysine4 | GC | 0.032217789 | −0.97833 |
| Amphoteracin B | TMS mevalonic acid lactone | GC | 0.012983194 | −0.976652217 |
| Amphoteracin B | tms tyrosine2 | GC | 0.601581614 | −0.359333333 |
| Amphoteracin B | tms tyrosine3 | GC | 0.029953667 | −0.947315772 |
| Amphoteracin B | tryptophan | nLC | 0.380816515 | 1.141975309 |
| Amphoteracin B | tryptophan | pLC | 1 | 0 |
| Amphoteracin B | tyrosine | nLC | 0.807539229 | 0.098201061 |
| Amphoteracin B | tyrosine | LC | 0.735174542 | 0.234676626 |
| Amphoteracin B | uracil | nLC | 0.359441135 | 1.510500389 |
| Amphoteracin B | uric acid | pLC | 0.069269066 | 308 |
| Amphoteracin B | uridine | nLC | 0.293422211 | 0.112573965 |
| Amphoteracin B | urocanic acid | nLC | 1 | 0 |
| Amphoteracin B | urocanic acid | pLC | 1 | 0 |
| Amphoteracin B | valine | GC | 0.026729753 | −0.867333333 |
| Amphoteracin B | valine | nLC | 0.732516759 | 0.162425739 |
| Amphoteracin B | xanthosine(diH2O) | pLC | 1 | 0 |
| Amphoteracin B | xanthosineDiH2O | nLC | 1 | 0 |
| Amphoteracin B | zeatin | nLC | 1 | 0 |
| Amphoteracin B | zeatin | pLC | 1 | 0 |
| Fluconazole | 2-ketobutyric acid | nLC | 0.225631474 | −0.999150382 |
| Fluconazole | 2-ketoglutaric | nLC | 0.050037991 | −0.999457799 |
| Fluconazole | 3-indolylacetonitri | nLC | 0.197015297 | −0.999782451 |
| Fluconazole | 4ambutyrate/dimglyc | LC | 0.55610932 | −0.438329556 |
| Fluconazole | 4-aminobenzoic acid | pLC | 1 | 0 |
| Fluconazole | 4aminobutyrate/dimg | nLC | 0.796062459 | 0.13842334 |
| Fluconazole | 4-methylcatechol | nLC | 1 | 0 |
| Fluconazole | 4-methylcatechol | pLC | 1 | 0 |
| Fluconazole | 5hydroxyLtryptophan | nLC | 1 | 0 |
| Fluconazole | 5hydroxyLtryptophan | pLC | 1 | 0 |
| Fluconazole | 6benzylaminopurine | pLC | 1 | 0 |
| Fluconazole | 6-benzylaminopurine | nLC | 1 | 0 |
| Fluconazole | abscisic acid | nLC | 1 | 0 |
| Fluconazole | abscisic acid | LC | 1 | 0 |
| Fluconazole | aconitic acid | nLC | 0.785890509 | 0.648259692 |

TABLE 12-continued

Detected Metabolites

| Treatment | Compound | Platform | p-Value | Fold Change |
|---|---|---|---|---|
| Fluconazole | adenine | nLC | 1 | 0 |
| Fluconazole | adenine | pLC | 0.842498314 | −0.094389696 |
| Fluconazole | adenosine | nLC | 1 | 0 |
| Fluconazole | adenosine | LC | 1 | 0 |
| Fluconazole | alanine | GC | 0.672016949 | 0.308436145 |
| Fluconazole | alanine | nLC | 0.514232967 | 0.3989834 |
| Fluconazole | alanine/sarcosine | LC | 0.569965606 | 0.126948182 |
| Fluconazole | allantoic acid | nLC | 0.693763056 | 0.239201283 |
| Fluconazole | allantoic acid | pLC | 1 | 0 |
| Fluconazole | allantoin | nLC | 0.201180044 | 0.394248589 |
| Fluconazole | anthranilic acid | nLC | 1 | 0 |
| Fluconazole | anthranilic acid | LC | 1 | 0 |
| Fluconazole | arginine | nLC | 0.172474156 | 0.648362584 |
| Fluconazole | arginine | pLC | 0.591952135 | 0.1179275 |
| Fluconazole | argininosuccinate | nLC | 1 | 0 |
| Fluconazole | argininosuccinate | pLC | 1 | 0 |
| Fluconazole | asparagine | GC | 0.599221641 | 0.399866711 |
| Fluconazole | asparagine | nLC | 0.589600334 | 0.354464539 |
| Fluconazole | asparagine | pLC | 0.605531557 | 0.319224556 |
| Fluconazole | aspartic | nLC | 0.515133125 | 0.499266169 |
| Fluconazole | aspartic acid | GC | 0.621393579 | 0.433666667 |
| Fluconazole | aspartic acid | pLC | 0.67688527 | 0.214006141 |
| Fluconazole | benzoic acid | nLC | 1 | 0 |
| Fluconazole | biotin | nLC | 0.405953433 | 0.345482947 |
| Fluconazole | biotin | pLC | 1 | 0 |
| Fluconazole | caffeic acid | nLC | 0.584388595 | −0.471092077 |
| Fluconazole | caffeine | pLC | 1 | 0 |
| Fluconazole | campesterol | GC | 1 | 0 |
| Fluconazole | catechol | nLC | 1 | 0 |
| Fluconazole | cinnamic acid | nLC | 1 | 0 |
| Fluconazole | citric acid TME | pLC | 1 | 0 |
| Fluconazole | citricanoic/itaconi | nLC | 1 | 0 |
| Fluconazole | citrulline | nLC | 1 | 0 |
| Fluconazole | citrulline | pLC | 0.821686047 | 0.082522841 |
| Fluconazole | coumaric acid | nLC | 1 | 0 |
| Fluconazole | cytidine | nLC | 0.067383137 | −0.796925943 |
| Fluconazole | cytidine | pLC | 1 | 0 |
| Fluconazole | cytosine | nLC | 1 | 0 |
| Fluconazole | cytosine | pLC | 1 | 0 |
| Fluconazole | decanoic acid | nLC | 0.523474499 | 0.184634286 |
| Fluconazole | desmosterol | GC | 1 | 0 |
| Fluconazole | diaminopimelic acid | nLC | 1 | 0 |
| Fluconazole | diaminopimelic acid | pLC | 1 | 0 |
| Fluconazole | dihydrofolic acid | nLC | 1 | 0 |
| Fluconazole | dihydrofolic acid | pLC | 1 | 0 |
| Fluconazole | dipicolinic acid | pLC | 1 | 0 |
| Fluconazole | disaccaride1 | GC | 0.581808965 | 0.388333333 |
| Fluconazole | disaccaride2 | GC | 0.805350356 | 0.151666667 |
| Fluconazole | disaccaride3 | GC | 0.500838115 | 0.580333333 |
| Fluconazole | DLaminoadipic acid | nLC | 0.961148179 | 0.443010753 |
| Fluconazole | DL-aminoadipic acid | LC | 0.258675092 | 0.115480962 |
| Fluconazole | ergosterol | GC | 0.411376724 | 0.948 |
| Fluconazole | estrone | nLC | 1 | 0 |
| Fluconazole | farnesol | nLC | 1 | 0 |
| Fluconazole | folic acid | nLC | 1 | 0 |
| Fluconazole | folic acid | pLC | 1 | 0 |
| Fluconazole | fucosterol | GC | 0.015716048 | 6.665 |
| Fluconazole | fumaric/3m2oxobutan | nLC | 0.212701071 | 0.600893928 |
| Fluconazole | gallic acid | nLC | 0.235229644 | 0.507086324 |
| Fluconazole | gibberellic | nLC | 1 | 0 |
| Fluconazole | glucosamine | pLC | 1 | 0 |
| Fluconazole | glucosamine6PO4 | nLC | 0.273438701 | −0.995114007 |
| Fluconazole | glucosamine6PO4 | pLC | 1 | 0 |
| Fluconazole | glutamate | pLC | 0.883828911 | −0.061793299 |
| Fluconazole | glutamic/acetylseri | nLC | 0.56055075 | 0.384161186 |
| Fluconazole | glutamine | GC | 0.485843991 | 0.524174725 |
| Fluconazole | glutamine/lysinen | LC | 0.609631316 | 0.330898992 |
| Fluconazole | glutamine/lysinep | LC | 0.670624203 | 0.224216219 |
| Fluconazole | glutathione | pLC | 0.92752344 | −0.058315351 |
| Fluconazole | glycanopyrose | GC | 0.347157825 | 1.202333333 |
| Fluconazole | glycerol | GC | 0.668832185 | 0.218666667 |
| Fluconazole | glycine | GC | 0.802369966 | −0.103666667 |
| Fluconazole | guanine | nLC | 1 | 0 |
| Fluconazole | guanosine | nLC | 0.285463594 | −0.992974239 |
| Fluconazole | guanosine | LC | 0.060854626 | −0.998137803 |

TABLE 12-continued

Detected Metabolites

| Treatment | Compound | Platform | p-Value | Fold Change |
|---|---|---|---|---|
| Fluconazole | hexadecanoic acid | GC | 0.652442377 | 0.134333333 |
| Fluconazole | histidine | nLC | 1 | 0 |
| Fluconazole | histidine | pLC | 1 | 0 |
| Fluconazole | homogentisic/uric | nLC | 1 | 0 |
| Fluconazole | hydrocortisone | nLC | 1 | 0 |
| Fluconazole | hydrocortisone | LC | 1 | 0 |
| Fluconazole | hypoxanthine | nLC | 0.259732062 | 0.77571885 |
| Fluconazole | hypoxanthine | pLC | 0.736842203 | 0.129759971 |
| Fluconazole | indole3pyruvic acid | nLC | 1 | 0 |
| Fluconazole | inostol/glucos/sorb | nLC | 0.57332042 | −0.47442546 |
| Fluconazole | iso citric acid | GC | 0.588523447 | 0.392333333 |
| Fluconazole | isocitric/citric/qu | nLC | 0.288980226 | 1.457227098 |
| Fluconazole | isoleucine | GC | 0.634637433 | 0.391 |
| Fluconazole | itaconic acid dimes | pLC | 1 | 0 |
| Fluconazole | jasmonic acid | nLC | 1 | 0 |
| Fluconazole | kinetin | nLC | 1 | 0 |
| Fluconazole | kinetin | pLC | 1 | 0 |
| Fluconazole | lactic acid | nLC | 0.90233218 | −0.043897702 |
| Fluconazole | lanosterol | GC | 0.021305043 | 8.462333333 |
| Fluconazole | lauric acid | nLC | 0.405736617 | 0.390567367 |
| Fluconazole | leucine | GC | 0.655160145 | 0.338666667 |
| Fluconazole | leucine/isoleucine/ | nLC | 0.610189969 | 0.330601522 |
| Fluconazole | leucine/isoleucine/ | pLC | 0.684383809 | 0.163833602 |
| Fluconazole | luteolin | nLC | 1 | 0 |
| Fluconazole | luteolin | pLC | 1 | 0 |
| Fluconazole | lysine | GC | 0.59676416 | 0.341219594 |
| Fluconazole | malic acid | GC | 0.629662238 | 0.397534155 |
| Fluconazole | malic acid | nLC | 0.575009587 | 0.43661293 |
| Fluconazole | malonic acid | nLC | 1 | 0 |
| Fluconazole | mannitol | pLC | 0.743695348 | 0.151992706 |
| Fluconazole | menthol* | nLC | 0.860810154 | 0.047582203 |
| Fluconazole | methionine | nLC | 1 | 0 |
| Fluconazole | methionine | pLC | 0.279599722 | −0.290574597 |
| Fluconazole | mevalonic acid lactone | GC | 0.704278777 | 0.233255582 |
| Fluconazole | mevalonic lactone | pLC | 0.241778766 | −0.517489712 |
| Fluconazole | NacetylDglucosamine | nLC | 1 | 0 |
| Fluconazole | NacetylDglucosamine | pLC | 1 | 0 |
| Fluconazole | NacetylLglutamate | nLC | 0.839927069 | 0.136915888 |
| Fluconazole | NacetylLglutamate | pLC | 1 | 0 |
| Fluconazole | NacetylLornithine | nLC | 1 | 0 |
| Fluconazole | NacetylLornithine | pLC | 0.718034342 | 0.158396947 |
| Fluconazole | niacinamide | pLC | 1 | 0 |
| Fluconazole | nicotinic acid | nLC | 0.061536585 | 2.442536328 |
| Fluconazole | nicotinic acid | pLC | 0.052262619 | −0.79822695 |
| Fluconazole | nopaline | nLC | 0.350953395 | 0.343189964 |
| Fluconazole | nopaline | pLC | 1 | 0 |
| Fluconazole | octadecanoic acid | CC | 0.889163721 | 0.082 |
| Fluconazole | oleic acid | GC | 0.364873247 | −0.307333333 |
| Fluconazole | oleic acid | nLC | 0.966227899 | −0.016835748 |
| Fluconazole | ornithine | nLC | 0.603376392 | 0.350845648 |
| Fluconazole | ornithine | pLC | 0.464434284 | 0.477540988 |
| Fluconazole | ornithine2 | CC | 0.607787058 | 0.447333333 |
| Fluconazole | ornithine3 | GC | 0.69362274 | 0.264666667 |
| Fluconazole | orotic acid | nLC | 1 | 0 |
| Fluconazole | palmiteliadic acid | CC | 0.813004804 | −0.088666667 |
| Fluconazole | palmitic acid | nLC | 0.914973348 | −0.023301814 |
| Fluconazole | phenylalanine | CC | 0.711787949 | 0.277425809 |
| Fluconazole | phenylalanine | nLC | 0.763353558 | 0.152670808 |
| Fluconazole | phenylalanine | pLC | 0.843620891 | −0.180920325 |
| Fluconazole | phenylpyruvic acid | nLC | 1 | 0 |
| Fluconazole | phosphate | CC | 0.147008309 | −0.507996667 |
| Fluconazole | phosphoenolpyruvate | nLC | 1 | 0 |
| Fluconazole | phosphoenolpyruvate | pLC | 1 | 0 |
| Fluconazole | pinitol | nLC | 1 | 0 |
| Fluconazole | pipecolic acid | nLC | 0.651219102 | 0.290059228 |
| Fluconazole | pipecolic acid | pLC | 0.666832577 | 0.25832748 |
| Fluconazole | porphobilinogen | nLC | 1 | 0 |
| Fluconazole | progesterone | pLC | 1 | 0 |
| Fluconazole | proline | nLC | 0.546594543 | 0.416410847 |
| Fluconazole | proline | pLC | 0.606102286 | 0.207549593 |
| Fluconazole | pyridoxine | nLC | 0.922916545 | −0.042014772 |
| Fluconazole | pyridoxine | pLC | 0.441455035 | −0.383106649 |
| Fluconazole | pyrimidine | CC | 0.73632437 | 0.245666667 |
| Fluconazole | retinoic acid | nLC | 1 | 0 |

TABLE 12-continued

Detected Metabolites

| Treatment | Compound | Platform | p-Value | Fold Change |
|---|---|---|---|---|
| Fluconazole | riboflavin | pLC | 1 | 0 |
| Fluconazole | salicylic/HObenzoic | nLC | 1 | 0 |
| Fluconazole | selenoDLmethionine | nLC | 0.319500806 | −0.574763923 |
| Fluconazole | selenoDLmethionine | pLC | 0.232642988 | −0.686509768 |
| Fluconazole | serine | nLC | 0.582348829 | 0.393647913 |
| Fluconazole | serine | LC | 0.76807688 | 0.109960893 |
| Fluconazole | shikimic acid | nLC | 1 | 0 |
| Fluconazole | sinapinic acid | nLC | 1 | 0 |
| Fluconazole | sorbitol/mannitol | nLC | 0.591808093 | 0.364953887 |
| Fluconazole | squalene | GC | 0.602775269 | 0.199933356 |
| Fluconazole | succinic | nLC | 0.2522213 | 0.309417433 |
| Fluconazole | sucrose | nLC | 0.241405138 | 0.310410154 |
| Fluconazole | sugar? | GC | 0.580258174 | 0.481666667 |
| Fluconazole | sugar-phosphate | nLC | 0.956717825 | −0.053057471 |
| Fluconazole | sugar-phosphate | pLC | 1 | 0 |
| Fluconazole | tetradecanoic acid | GC | 0.856705431 | 0.079666667 |
| Fluconazole | tetradecanoic acid | nLC | 0.46350082 | 0.54945313 |
| Fluconazole | thiamine | pLC | 1 | 0 |
| Fluconazole | threonine/homoserin | nLC | 0.608964827 | 0.325738631 |
| Fluconazole | threonine/homoserin | pLC | 0.718235353 | 0.160353176 |
| Fluconazole | threonine2 | GC | 0.525080919 | 0.505333333 |
| Fluconazole | threonine3 | GC | 0.75349746 | 0.251333333 |
| Fluconazole | thymine | nLC | 1 | 0 |
| Fluconazole | thymine | pLC | 1 | 0 |
| Fluconazole | tms glutamine3 | GC | 0.254931664 | 0.727121187 |
| Fluconazole | tms lysine4 | GC | 0.627281408 | 0.365666667 |
| Fluconazole | TMS mevalonic acid lactone | GC | 0.822784777 | 0.143381127 |
| Fluconazole | tms tyrosine2 | GC | 0.407503096 | 0.864333333 |
| Fluconazole | tms tyrosine3 | GC | 0.646523562 | 0.332110704 |
| Fluconazole | tryptophan | nLC | 0.360511436 | 1.648709315 |
| Fluconazole | tryptophan | pLC | 1 | 0 |
| Fluconazole | tyrosine | nLC | 0.701987245 | 0.230338937 |
| Fluconazole | tyrosine | pLC | 0.761710986 | 0.109881652 |
| Fluconazole | uracil | nLC | 0.357108991 | 1.256157636 |
| Fluconazole | uric acid | pLC | 1 | 0 |
| Fluconazole | uridine | nLC | 0.242998296 | 0.346301775 |
| Fluconazole | urocanic acid | nLC | 1 | 0 |
| Fluconazole | urocanic acid | pLC | 1 | 0 |
| Fluconazole | valine | GC | 0.711843212 | 0.272666667 |
| Fluconazole | valine | nLC | 0.6138852 | 0.323524419 |
| Fluconazole | xanthosine(diH2O) | pLC | 1 | 0 |
| Fluconazole | xanthosineDiH2O | nLC | 1 | 0 |
| Fluconazole | zeatin | nLC | 1 | 0 |
| Fluconazole | zeatin | pLC | 1 | 0 |
| Ketoconazole | 2-ketobutyric acid | nLC | 0.9639671 | 0.480600397 |
| Ketoconazole | 2-ketoglutaric | nLC | 0.050037991 | −0.999457799 |
| Ketoconazole | 3-indolylacetonitri | nLC | 0.95501953 | 0.699782451 |
| Ketoconazole | 4ambutyrate/dimglyc | pLC | 0.524137071 | 0.584817093 |
| Ketoconazole | 4-aminobenzoic acid | pLC | 1 | 0 |
| Ketoconazole | 4aminobutyrate/dimg | nLC | 0.461393936 | −0.485785227 |
| Ketoconazole | 4-methylcatechol | nLC | 1 | 0 |
| Ketoconazole | 4-methylcatechol | pLC | 1 | 0 |
| Ketoconazole | 5hydroxyLtryptophan | nLC | 1 | 0 |
| Ketoconazole | 5hydroxyLtryptophan | pLC | 1 | 0 |
| Ketoconazole | 6benzylaminopurine | pLC | 1 | 0 |
| Ketoconazole | 6-benzylaminopurine | nLC | 1 | 0 |
| Ketoconazole | abscisic acid | nLC | 1 | 0 |
| Ketoconazole | abscisic acid | pLC | 1 | 0 |
| Ketoconazole | aconitic acid | nLC | 0.67459115 | 0.635606581 |
| Ketoconazole | adenine | nLC | 1 | 0 |
| Ketoconazole | adenine | pLC | 0.996845972 | 0.018126006 |
| Ketoconazole | adenosine | nLC | 1 | 0 |
| Ketoconazole | adenosine | pLC | 0.061512704 | 549.3333333 |
| Ketoconazole | alanine | GC | 0.742203249 | 0.23141047 |
| Ketoconazole | alanine | nLC | 0.560597277 | −0.528917036 |
| Ketoconazole | alanine/sarcosine | pLC | 0.571450791 | −0.504395897 |
| Ketoconazole | allantoic acid | nLC | 0.151749563 | −0.686669081 |
| Ketoconazole | allantoic acid | pLC | 1 | 0 |
| Ketoconazole | allantoin | nLC | 0.888672729 | −0.340295275 |
| Ketoconazole | anthranilic acid | nLC | 1 | 0 |
| Ketoconazole | anthranilic acid | pLC | 1 | 0 |
| Ketoconazole | arginine | nLC | 0.031257842 | −0.999961229 |
| Ketoconazole | arginine | pLC | 0.028481658 | −0.996209523 |
| Ketoconazole | argininosuccinate | nLC | 1 | 0 |

TABLE 12-continued

Detected Metabolites

| Treatment | Compound | Platform | p-Value | Fold Change |
|---|---|---|---|---|
| Ketoconazole | argininosuccinate | pLC | 1 | 0 |
| Ketoconazole | asparagine | GC | 0.381635461 | 0.583138954 |
| Ketoconazole | asparagine | nLC | 0.594223659 | −0.405454029 |
| Ketoconazole | asparagine | pLC | 0.807721418 | −0.106515886 |
| Ketoconazole | aspartic | nLC | 0.620101115 | −0.403930348 |
| Ketoconazole | aspartic acid | GC | 0.664887605 | 0.299666667 |
| Ketoconazole | aspartic acid | pLC | 0.794913561 | −0.208404622 |
| Ketoconazole | benzoic acid | nLC | 0.217027236 | 1719.333333 |
| Ketoconazole | biotin | nLC | 0.981428203 | −0.180942463 |
| Ketoconazole | biotin | LC | 1 | 0 |
| Ketoconazole | caffeic acid | nLC | 0.22121578 | −0.429418547 |
| Ketoconazole | caffeine | pLC | 1 | 0 |
| Ketoconazole | campesterol | GC | 1 | 0 |
| Ketoconazole | catechol | nLC | 1 | 0 |
| Ketoconazole | cinnamic acid | nLC | 1 | 0 |
| Ketoconazole | citric acid TME | pLC | 1 | 0 |
| Ketoconazole | citricanoic/itaconi | nLC | 0.219726535 | 1522.333333 |
| Ketoconazole | citrulline | nLC | 1 | 0 |
| Ketoconazole | citrulline | pLC | 0.889543516 | 0.651144513 |
| Ketoconazole | coumaric acid | nLC | 1 | 0 |
| Ketoconazole | cytidine | nLC | 0.102328077 | −0.36143456 |
| Ketoconazole | cytidine | pLC | 0.068336435 | 393.6666667 |
| Ketoconazole | cytosine | nLC | 1 | 0 |
| Ketoconazole | cytosine | pLC | 1 | 0 |
| Ketoconazole | decanoic acid | nLC | 0.18889589 | −0.387872406 |
| Ketoconazole | desmosterol | GC | 1 | 0 |
| Ketoconazole | diaminopimelic acid | nLC | 0.208740638 | 2537 |
| Ketoconazole | diaminopimelic acid | PLC | 1 | 0 |
| Ketoconazole | dihydrofolic acid | nLC | 1 | 0 |
| ketoconazole | dihydrofolic acid | pLC | 1 | 0 |
| Ketoconazole | dipicolinic acid | pLC | 1 | 0 |
| Ketoconazole | disaccaride1 | GC | 0.247275227 | 1.231666667 |
| Ketoconazole | disaccaride2 | GC | 0.57432915 | 0.405 |
| Ketoconazole | disaccaride3 | GC | 0.273927592 | 1.143666667 |
| Ketoconazole | DLaminoadipic acid | nLC | 0.282562804 | −0.993548387 |
| Ketoconazole | DL-aminoadipic acid | pLC | 0.041949247 | −0.999749499 |
| Ketoconazole | ergosterol | GC | 0.457850979 | 0.792666667 |
| Ketoconazole | estrone | nLC | 1 | 0 |
| Ketoconazole | farnesol | nLC | 1 | 0 |
| Ketoconazole | folic acid | nLC | 1 | 0 |
| Ketoconazole | folic acid | LC | 1 | 0 |
| Ketoconazole | fucosterol | GC | 0.007283106 | 7.146333333 |
| Ketoconazole | fumaric/3m2oxobutan | nLC | 0.879463953 | −0.442058214 |
| Ketoconazole | gallic acid | nLC | 0.341926441 | −0.699797534 |
| Ketoconazole | gibberellic | nLC | 1 | 0 |
| Ketoconazole | glucosamine | LC | 1 | 0 |
| Ketoconazole | glucosamine6PO4 | nLC | 0.993629524 | −0.058631922 |
| Ketoconazole | glucosamine6PO4 | pLC | 0.07458733 | 260.6666667 |
| Ketoconazole | glutamate | LC | 0.713626372 | −0.245514762 |
| Ketoconazole | glutamic/acetylseri | nLC | 0.537323804 | −0.522523365 |
| Ketoconazole | glutamine | GC | 0.335902006 | 0.709569857 |
| Ketoconazole | glutamine/lysine | nLC | 0.673999294 | −0.320397038 |
| Ketoconazole | glutamine/lysine | LC | 0.788208454 | −0.193172287 |
| Ketoconazole | glutathione | LC | 0.911022134 | −0.057412545 |
| Ketoconazole | glycanopyrose | GC | 0.225636823 | 1.592 |
| Ketoconazole | glycerol | GC | 0.126154516 | 0.915 |
| Ketoconazole | glycine | GC | 0.896523858 | −0.059666667 |
| Ketoconazole | guanine | nLC | 1 | 0 |
| Ketoconazole | guanosine | nLC | 0.285463594 | −0.992974239 |
| Ketoconazole | guanosine | LC | 0.232818183 | 0.862197393 |
| Ketoconazole | hexadecanoic acid | GC | 0.554936207 | 0.373 |
| Ketoconazole | histidine | nLC | 1 | 0 |
| Ketoconazole | histidine | LC | 1 | 0 |
| Ketoconazole | homogentisic/uric | nLC | 1 | 0 |
| Ketoconazole | hydrocortisone | nLC | 1 | 0 |
| Ketoconazole | hydrocortisone | pLC | 1 | 0 |
| Ketoconazole | hypoxanthine | nLC | 0.417257665 | −0.476677316 |
| Ketoconazole | hypoxanthine | pLC | 0.721865016 | −0.280334476 |
| Ketoconazole | indole3pyruvic acid | nLC | 1 | 0 |
| Ketoconazole | inostol/glucos/sorb | nLC | 0.887855007 | 0.315683171 |
| Ketoconazole | iso citric acid | GC | 0.26048524 | 0.964333333 |
| Ketoconazole | isocitric/citric/qu | nLC | 0.977182788 | −0.248481007 |
| Ketoconazole | isoleucine | GC | 0.593930199 | 0.453666667 |
| Ketoconazole | itaconic acid dimes | pLC | 1 | 0 |
| Ketoconazole | jasmonic acid | nLC | 1 | 0 |

TABLE 12-continued

Detected Metabolites

| Treatment | Compound | Platform | p-Value | Fold Change |
|---|---|---|---|---|
| Ketoconazole | kinetin | nLC | 1 | 0 |
| Ketoconazole | kinetin | pLC | 1 | 0 |
| Ketoconazole | lactic acid | nLC | 0.355289051 | 0.475040466 |
| Ketoconazole | lanosterol | GC | 0.013296827 | 8.435666667 |
| Ketoconazole | lauric acid | nLC | 0.921247829 | −0.042003398 |
| Ketoconazole | leucine | GC | 0.510722073 | 0.628333333 |
| Ketoconazole | leucine/isoleucine/ | nLC | 0.69030324 | −0.339497239 |
| Ketoconazole | leucine/isoleucine/ | pLC | 0.694390781 | −0.279509064 |
| Ketoconazole | luteolin | nLC | 1 | 0 |
| Ketoconazole | luteolin | LC | 1 | 0 |
| Ketoconazole | lysine | GC | 0.312893118 | 0.702765745 |
| Ketoconazole | malic acid | GC | 0.230440196 | 0.374878374 |
| Ketoconazole | malic acid | nLC | 0.741534381 | −0.202679583 |
| Ketoconazole | malonic acid | nLC | 0.229622684 | 993.6666667 |
| Ketoconazole | mannitol | LC | 0.075185984 | −0.482808023 |
| Ketoconazole | menthol* | nLC | 0.894522787 | 0.0558346 |
| Ketoconazole | methionine | nLC | 1 | 0 |
| Ketoconazole | methionine | LC | 0.000132547 | −0.999243952 |
| Ketoconazole | mevalonic acid lactone | GC | 0.299567095 | 0.345884705 |
| Ketoconazole | mevalonic lactone | pLC | 0.000458094 | −0.999742798 |
| Ketoconazole | NacetylDglucosamine | nLC | 1 | 0 |
| Ketoconazole | NacetylDglucosamine | pLC | 1 | 0 |
| Ketoconazole | NacetylLglutamate | nLC | 0.766840163 | −0.16152648 |
| Ketoconazole | NacetylLglutamate | LC | 0.000379693 | 1232.333333 |
| Ketoconazole | NacetylLornithine | nLC | 1 | 0 |
| Ketoconazole | NacetylLornithine | pLC | 0.904993806 | −0.081367106 |
| Ketoconazole | niacinamide | LC | 1 | 0 |
| Ketoconazole | nicotinic acid | nLC | 0.995525033 | −0.042272127 |
| Ketoconazole | nicotinic acid | pLC | 7.53474E-05 | −0.99893617 |
| Ketoconazole | nopaline | nLC | 0.065964767 | −0.997311828 |
| Ketoconazole | nopaline | LC | 1 | 0 |
| Ketoconazole | octadecanoic acid | GC | 0.241136181 | 0.512333333 |
| Ketoconazole | oleic acid | GC | 0.457404638 | −0.388333333 |
| Ketoconazole | oleic acid | nLC | 0.15269473 | −0.526000068 |
| Ketoconazole | ornithine | nLC | 0.240401148 | −0.414620442 |
| Ketoconazole | ornithine | pLC | 0.216567154 | −0.871917457 |
| Ketoconazole | ornithine2 | GC | 0.08811091 | −0.782333333 |
| Ketoconazole | ornithine3 | GC | 0.511712533 | 0.486333333 |
| Ketoconazole | orotic acid | nLC | 0.218957363 | 1575.666667 |
| Ketoconazole | palmiteliadic acid | GC | 0.690588295 | −0.187 |
| Ketoconazole | palmitic acid | nLC | 0.55407711 | −0.44537984 |
| Ketoconazole | phenylalanine | GC | 0.570127457 | 0.364454818 |
| Ketoconazole | phenylalanine | nLC | 0.190982317 | −0.591801 242 |
| Ketoconazole | phenylalanine | pLC | 0.202078489 | −0.36668569 |
| Ketoconazole | phenylpyruvic acid | nLC | 1 | 0 |
| Ketoconazole | phosphate | GC | 0.602201543 | −0.268333333 |
| Ketoconazole | phosphoenolpyruvate | nLC | 1 | 0 |
| Ketoconazole | phosphoenolpyruvate | pLC | 1 | 0 |
| Ketoconazole | pinitol . | nLC | 0.244808608 | 545 |
| Ketoconazole | pipecolic acid | nLC | 0.223402828 | −0.41143749 |
| Ketoconazole | pipecolic acid | pLC | 0.804903885 | −0.15667062 |
| Ketoconazole | porphobilinogen | nLC | 1 | 0 |
| Ketoconazole | progesterone | pLC | 1 | 0 |
| Ketoconazole | proline | nLC | 0.637191689 | −0.353351241 |
| Ketoconazole | proline | pLC | 0.793251122 | −0.161195947 |
| Ketoconazole | pyridoxine | nLC | 0.839423897 | −0.092505146 |
| Ketoconazole | pyridoxine | pLC | 0.894790663 | −0.075068589 |
| Ketoconazole | pyrimidine | GC | 0.296853911 | 0.740333333 |
| Ketoconazole | retinoic acid | nLC | 1 | 0 |
| Ketoconazole | riboflavin | pLC | 1 | 0 |
| Ketoconazole | salicylic/HObenzoic | nLC | 1 | 0 |
| Ketoconazole | selenoDLmethionine | nLC | 0.617802219 | 0.965499294 |
| Ketoconazole | selenoDLmethionine | pLC | 0.501432519 | 1.149746193 |
| Ketoconazofe | serine | nLC | 0.602918586 | −0.469419238 |
| Ketoconazole | serine | pLC | 0.705817734 | −0.313779618 |
| Ketoconazole | shikimic acid | nLC | 0.159073415 | 49446.33333 |
| Ketoconazole | sinapinic acid | nLC | 1 | 0 |
| Ketoconazole | sorbitol/mannitol | nLC | 0.326913111 | 0.469342252 |
| Ketoconazole | squalene | GC | 0.646962325 | 0.437187604 |
| Ketoconazole | succinic | nLC | 0.934705564 | −0.266228647 |
| Ketoconazole | sucrose | nLC | 0.356348305 | −0.516908213 |
| Ketoconazole | sugar? | GC | 0.518028398 | 0.534666667 |
| Ketoconazole | sugar-phosphate | nLC | 0.607811705 | −0.290298851 |
| Ketoconazole | sugar-phosphate | pLC | 0.065129247 | 385 |

TABLE 12-continued

Detected Metabolites

| Treatment | Compound | Platform | p-Value | Fold Change |
|---|---|---|---|---|
| Ketoconazole | tetradecanoic acid | GC | 0.542673889 | 0.259333333 |
| Ketoconazole | tetradecanoic acid | nLC | 0.826830708 | −0.141716433 |
| Ketoconazole | thiamine | pLC | 1 | 0 |
| Ketoconazole | threonine/homoserin | nLC | 0.720684532 | −0.320459387 |
| Ketoconazole | threonine/homoserin | pLC | 0.729834457 | −0.252954999 |
| Ketoconazole | threonine2 | GC | 0.369980722 | 0.630333333 |
| Ketoconazole | threonine3 | GC | 0.771315792 | 0.184666667 |
| Ketoconazole | thymine | nLC | 1 | 0 |
| Ketoconazole | thymine | pLC | 1 | 0 |
| Ketoconazole | tms glutamine3 | GC | 0.225243815 | 0.826971162 |
| Ketoconazole | tms lysine4 | GC | 0.548698451 | 0.452 |
| Ketoconazole | TMS mevalonic acid lactone | GC | 0.083516634 | −0.859283094 |
| Ketoconazole | tms tyrosine2 | GC | 0.215698651 | 1.561666667 |
| Ketoconazole | tms tyrosine3 | GC | 0.505545511 | 0.437812604 |
| Ketoconazole | tryptophan | nLC | 0.997101896 | 0.03030303 |
| Ketoconazole | tryptophan | LC | 1 | 0 |
| Ketoconazole | tyrosine | nLC | 0.682093146 | −0.323276916 |
| Ketoconazole | tyrosine | pLC | 0.774022599 | −0.222804007 |
| Ketoconazole | uracil | nLC | 0.223581594 | −0.999222193 |
| Ketoconazole | uric acid | pLC | 1 | 0 |
| Ketoconazole | uridine | nLC | 0.327767929 | −0.740828402 |
| Ketoconazole | urocanic acid | nLC | 0.253172611 | 401.3333333 |
| Ketoconazole | urocanic acid | pLC | 1 | 0 |
| Ketoconazole | valine | GC | 0.634337015 | 0.357 |
| Ketoconazole | valine | nLC | 0.630670374 | −0.382933416 |
| Ketoconazole | xanthosine(diH2O) | LC | 1 | 0 |
| Ketoconazole | xanthosineDiH2O | nLC | 1 | 0 |
| Ketoconazole | zeatin | nLC | 1 | 0 |
| Ketoconazole | zeatin | pLC | 1 | 0 |
| Posaconazole | 2-ketobutyric acid | nLC | 0.225631474 | −0.999150382 |
| Posaconazole | 2-ketoglutaric | nLC | 0.578339703 | 11.32767034 |
| Posaconazole | 3-indolylacetonitri | nLC | 0.197015297 | −0.999782451 |
| Posaconazole | 4ambutyrate/dimglyc | pLC | 0.963777302 | 31.37374555 |
| Posaconazole | 4-aminobenzoic acid | pLC | 1 | 0 |
| Posaconazole | 4aminobutyrate/dimg | nLC | 0.934446326 | −0.008938547 |
| Posaconazole | 4-methylcatechol | nLC | 1 | 0 |
| Posaconazole | 4-methylcatechol | nLC | 1 | 0 |
| Posaconazole | 5hydroxyLtryptophan | nLC | 1 | 0 |
| Posaconazole | 5hydroxyLtryptophan | LC | 1 | 0 |
| Posaconazole | 6benzylaminopurine | pLC | 1 | 0 |
| Posaconazole | 6-benzylaminopurine | nLC | 1 | 0 |
| Posaconazole | abscisic acid | nLC | 1 | 0 |
| Posaconazole | abscisic acid | LC | 1 | 0 |
| Posaconazole | aconitic acid | nLC | 0.14418007 | 1.874075272 |
| Posaconazole | adenine | nLC | 1 | 0 |
| Posaconazole | adenine | LC | 0.97905854 | −0.014499036 |
| Posaconazole | adenosine | nLC | 0.288782643 | 128.3333333 |
| Posaconazole | adenosine | pLC | 1 | 0 |
| Posaconazole | alanine | GC | 0.443509194 | 1.035345115 |
| Posaconazole | alanine | nLC | 0.665454482 | 0.109114473 |
| Posaconazole | alanine/sarcosine | pLC | 0.572428945 | 0.101305448 |
| Posaconazole | allantoic acid | nLC | 0.591698395 | 0.332057317 |
| Posaconazole | allantoic acid | pLC | 1 | 0 |
| Posaconazole | allantoin | nLC | 0.125054459 | 5.970180955 |
| Posaconazole | anthranilic acid | nLC | 1 | 0 |
| Posaconazole | anthranilic acid | pLC | 1 | 0 |
| Posaconazole | arginine | nLC | 0.209275262 | 0.17072036 |
| Posaconazole | arginine | pLC | 0.655241349 | 0.033825172 |
| Posaconazole | argininosuccinate | nLC | 0.259815185 | 318.3333333 |
| Posaconazole | argininosuccinate | pLC | 1 | 0 |
| Posaconazole | asparagine | GC | 0.915263335 | 0.144951683 |
| Posaconazole | asparagine | nLC | 0.898337684 | 0.00686488 |
| Posaconazole | asparagine | pLC | 0.571388297 | 0.430210016 |
| Posaconazole | aspartic | nLC | 0.639830963 | 0.304975124 |
| Posaconazole | aspartic acid | GC | 0.860113055 | −0.071 |
| Posaconazole | aspartic acid | LC | 0.605000404 | 0.362551855 |
| Posaconazole | benzoic acid | nLC | 1 | 0 |
| Posaconazole | biotin | nLC | 0.22367742 | −0.999218953 |
| Posaconazole | biotin | LC | 1 | 0 |
| Posaconazole | caffeic acid | nLC | 0.580263509 | −0.490034591 |
| Posaconazole | caffeine | pLC | 1 | 0 |
| Posaconazole | campesterol | GC | 1 | 0 |
| Posaconazole | catechol | nLC | 1 | 0 |
| Posaconazole | cinnamic acid | nLC | 1 | 0 |

TABLE 12-continued

Detected Metabolites

| Treatment | Compound | Platform | p-Value | Fold Change |
|---|---|---|---|---|
| Posaconazole | citric acid TME | pLC | 1 | 0 |
| Posaconazole | citricanoic/itaconi | nLC | 1 | 0 |
| Posaconazole | citrulline | nLC | 0.225951875 | 1160 |
| Posaconazole | citrulline | pLC | 0.777333431 | 0.10109048 |
| Posaconazole | coumaric acid | nLC | 1 | 0 |
| Posaconazole | cytidine | nLC | 0.000680198 | −0.998602701 |
| Posaconazole | cytidine | pLC | 1 | 0 |
| Posaconazole | cytosine | nLC | 1 | 0 |
| Posaconazole | cytosine | pLC | 0.226462948 | 1135 |
| Posaconazole | decanoic acid | nLC | 0.787160954 | 0.126277917 |
| Posaconazole | desmosterol | GC | 1 | 0 |
| Posaconazole | diaminopimelic acid | nLC | 1 | 0 |
| Posaconazole | diaminopimelic acid | pLC | 1 | 0 |
| Posaconazole | dihydrofolic acid | nLC | 1 | 0 |
| Posaconazole | dihydrofolic acid | pLC | 1 | 0 |
| Posaconazole | dipicolinic acid | LC | 1 | 0 |
| Posaconazole | disaccharide1 | GC | 0.958378084 | 0.047333333 |
| Posaconazole | disaccharide2 | GC | 0.718230465 | 0.313 |
| Posaconazole | disaccharide3 | GC | 0.830961848 | 0.340666667 |
| Posaconazole | DLaminoadipic acid | nLC | 0.282562804 | −0.993548387 |
| Posaconazole | DL-aminoadipic acid | pLC | 0.17973736 | 1.684786239 |
| Posaconazole | ergosterol | GC | 0.485731041 | 0.808 |
| Posaconazole | estrone | nLC | 1 | 0 |
| Posaconazole | farnesol | nLC | 1 | 0 |
| Posaconazole | folic acid | nLC | 1 | 0 |
| Posaconazole | folic acid | PLC | 1 | 0 |
| Posaconazole | fucosterol | GC | 0.006770761 | 6.722333333 |
| Posaconazole | fumaric/3m2oxobutan | nLC | 0.043783124 | −0.999672953 |
| Posaconazole | gallic acid | nLC | 0.246548839 | 0.441376772 |
| Posaconazole | gibberellic | nLC | 1 | 0 |
| Posaconazole | glucosamine | pLC | 1 | 0 |
| Posaconazole | glucosamine6PO4 | nLC | 0.273438701 | −0.995114007 |
| Posaconazole | glucosamine6PO4 | pLC | 1 | 0 |
| Posaconazole | glutamate | pLC | 0.553271067 | 0.376935809 |
| Posaconazole | glutamic/acetylseri | nLC | 0.593398809 | 0.322249352 |
| Posaconazole | glutamine | GC | 0.460619522 | 0.643881294 |
| Posaconazole | glutamine/lysine | nLC | 0.821564835 | 0.098138243 |
| Posaconazole | glutamine/lysine | pLC | 0.621404602 | 0.303010036 |
| Posaconazole | glutathione | pLC | 0.960269566 | 0.010099676 |
| Posaconazole | glycanopyrose | GC | 0.288716505 | 1.593666667 |
| Posaconazole | glycerol | GC | 0.615962586 | 0.187333333 |
| Posaconazole | glycine | GC | 0.96573947 | 0.082666667 |
| Posaconazole | guanine | nLC | 1 | 0 |
| Posaconazole | guanosine | nLC | 0.285463594 | −0.992974239 |
| Posaconazole | guanosine | pLC | 0.988504987 | 0.046554935 |
| Posaconazole | hexadecanoic acid | GC | 0.773386672 | −0.018666667 |
| Posaconazole | histidine | nLC | 1 | 0 |
| Posaconazole | histidine | pLC | 1 | 0 |
| Posaconazole | homogentisic/uric | nLC | 1 | 0 |
| Posaconazole | hydrocortisone | nLC | 1 | 0 |
| Posaconazole | hydrocortisone | pLC | 1 | 0 |
| Posaconazole | hypoxanthine | nLC | 0.966438425 | 0.175079872 |
| Posaconazole | hypoxanthine | pLC | 0.724112426 | 0.134993684 |
| Posaconazole | indole3pyruvic acid | nLC | 1 | 0 |
| Posaconazole | nostol/glucos/sorb | nLC | 0.570836266 | −0.492985425 |
| Posaconazole | iso citric acid | GC | 0.584793588 | 0.4 |
| Posaconazole | isocitric/citric/qu | nLC | 0.282679268 | 1.710695637 |
| Posaconazole | isoleucine | GC | 0.815398307 | 0.102333333 |
| Posaconazole | laconic acid dimes | pLC | 1 | 0 |
| Posaconazole | jasmonic acid | nLC | 1 | 0 |
| Posaconazole | kinetin | nLC | 1 | 0 |
| Posaconazole | kinetin | pLC | 1 | 0 |
| Posaconazole | lactic acid | nLC | 0.671735246 | 0.598705083 |
| Posaconazole | lanosterol | GC | 0.025813439 | 7.463666667 |
| Posaconazole | lauric acid | nLC | 0.184704286 | 0.983298106 |
| Posaconazole | leucine | GC | 0.605917046 | 0.334 |
| Posaconazole | leucine/isoleucine/ | nLC | 0.852184303 | 0.031580645 |
| Posaconazole | leucine/isoleucine/ | pLC | 0.772087466 | 0.049372553 |
| Posaconazole | luteolin | nLC | 1 | 0 |
| Posaconazole | luteolin | LC | 1 | 0 |
| Posaconazole | lysine | GC | 0.738361003 | 0.158613795 |
| Posaconazole | malic acid | GC | 0.620850674 | 0.294235255 |
| Posaconazole | malic acid | nLC | 0.671650538 | 0.310055664 |
| Posaconazole | malonic acid | nLC | 1 | 0 |
| Posaconazole | mannitol | pLC | 0.562416384 | 0.391898932 |

TABLE 12-continued

Detected Metabolites

| Treatment | Compound | Platform | p-Value | Fold Change |
|---|---|---|---|---|
| Posaconazole | menthol* | nLC | 0.804746729 | 0.08120719 |
| Posaconazole | methionine | nLC | 1 | 0 |
| Posaconazole | methionine | pLC | 0.250499977 | −0.399697581 |
| Posaconazole | mevalonic acid lactone | GC | 0.299851368 | 0.555481506 |
| Posaconazole | mevalonic lactone | pLC | 0.315594728 | −0.083676269 |
| Posaconazole | NacetylDglucosamine | nLC | 1 | 0 |
| Posaconazole | NacetylLglucosamine | pLC | 1 | 0 |
| Posaconazole | NacetylLglutamate | nLC | 0.892160969 | −0.07165109 |
| Posaconazole | NacetylLglutamate | pLC | 1 | 0 |
| Posaconazole | NacetylLornithine | nLC | 1 | 0 |
| Posaconazole | NacetylLornithine | pLC | 0.729225825 | 0.133761277 |
| Posaconazole | niacinamide | pLC | 1 | 0 |
| Posaconazole | nicotinic acid | nLC | 0.405290885 | 1.421400264 |
| Posaconazole | nicotinic acid | pLC | 0.050517148 | −0.814184397 |
| Posaconazole | nopaline | nLC | 0.251582538 | 0.755376344 |
| Posaconazole | nopaline | pLC | 1 | 0 |
| Posaconazole | octadecanoic acid | GC | 0.456065185 | 0.321 |
| Posaconazole | oleic acid | GC | 0.32058481 | −0.505666667 |
| Posaconazole | oleic acid | nLC | 0.422001256 | 0.5606148 |
| Posaconazole | ornithine | nLC | 0.434565877 | 2.313985503 |
| Posaconazole | ornithine | pLC | 0.497418018 | 0.43013985 |
| Posaconazole | ornithine2 | GC | 0.692849376 | −0.138333333 |
| Posaconazole | ornithine3 | GC | 0.965157424 | 0.041 |
| Posaconazole | orotic acid | nLC | 1 | 0 |
| Posaconazole | palmiteliadic acid | GC | 0.59834357 | −0.245333333 |
| Posaconazole | palmitic acid | nLC | 0.754817355 | 0.151759295 |
| Posaconazole | phenylalanine | GC | 0.931065787 | 0.060686896 |
| Posaconazole | phenylalanine | nLC | 0.879237271 | −0.037018634 |
| Posaconazole | phenylalanine | pLC | 0.851071927 | −0.15852366 |
| Posaconazole | phenylpyruvic acid | nLC | 1 | 0 |
| Posaconazole | phosphate | GC | 0.697409194 | −0.183333333 |
| Posaconazole | phosphoenolpyruvate | nLC | 1 | 0 |
| Posaconazole | phosphoenolpyruvate | LC | 1 | 0 |
| Posaconazole | pinitol | nLC | 1 | 0 |
| Posaconazole | pipecolic acid | nLC | 0.742425122 | 0.180566672 |
| Posaconazole | pipecolic acid | pLC | 0.631202801 | 0.344440479 |
| Posaconazote | porphobilinogen | nLC | 1 | 0 |
| Posaconazole | progesterone | pLC | 1 | 0 |
| Posaconazole | proline | nLC | 0.610694274 | 0.31465848 |
| Posaconazole | proline | LC | 0.536721684 | 0.315655773 |
| Posaconazole | pyridoxine | nLC | 0.826237958 | −0.101465068 |
| Posaconazole | pyridoxine | pLC | 0.680775731 | −0.238981963 |
| Posaconazole | pyrimidine | GC | 0.727269762 | 0.159 |
| Posaconazole | retinoic acid | nLC | 1 | 0 |
| Posaconazole | riboflavin | pLC | 1 | 0 |
| Posaconazole | salicylic/HObenzoic | nLC | 1 | 0 |
| Posaconazole | selenoDLmethionine | nLC | 0.205679572 | −0.672168934 |
| Posaconazole | selenoDLmethionine | pLC | 0.20869348 | −0.70827565 |
| Posaconazole | serine | nLC | 0.731434141 | 0.15199637 |
| Posaconazole | serine | pLC | 0.687746939 | 0.241660916 |
| Posaconazole | shikimic acid | nLC | 1 | 0 |
| Posaconazole | sinapinic acid | nLC | 1 | 0 |
| Posaconazole | sorbitol/mannitol | nLC | 0.98832955 | 0.009121314 |
| Posaconazole | squalene | GC | 0.914326664 | 0.074308564 |
| Posaconazole | succinic | nLC | 0.310191321 | −0.061410425 |
| Posaconazole | sucrose | nLC | 0.251150065 | 0.184711566 |
| Posaconazole | sugar? | GC | 0.554618941 | 0.692333333 |
| Posaconazole | sugar-phosphate | nLC | 0.96801556 | −0.045425287 |
| Posaconazole | sugar-phosphate | pLC | 1 | 0 |
| Posaconazole | tetradecanoic acid | GC | 0.177413951 | −0.213996667 |
| Posaconazole | tetradecanoic acid | nLC | 0.321679695 | 1.028651949 |
| Posaconazole | thiamine | pLC | 1 | 0 |
| Posaconazole | threonine/homoserin | nLC | 0.857401539 | 0.040335278 |
| Posaconazole | threonine/homoserin | pLC | 0.729627613 | 0.143726858 |
| Posaconazole | threonine2 | GC | 0.57620146 | 0.457 |
| Posaconazole | threonine3 | GC | 0.770574923 | 0.225 |
| Posaconazole | thymine | nLC | 1 | 0 |
| Posaconazole | thymine | pLC | 1 | 0 |
| Posaconazole | tms glutamine3 | GC | 0.344885321 | 0.670945158 |
| Posaconazole | tms lysine4 | GC | 0.950359185 | 0.056666667 |
| Posaconazole | TMS mevalonic acid lactone | GC | 0.544918115 | −0.31177059 |
| Posaconazole | tms tyrosine2 | GC | 0.380871273 | 1.228333333 |
| Posaconazole | tms tyrosine3 | GC | 0.744372821 | 0.191063688 |

TABLE 12-continued

Detected Metabolites

| Treatment | Compound | Platform | p-Value | Fold Change |
|---|---|---|---|---|
| Posaconazole | tryptophan | nLC | 0.300215958 | 4.67620651 |
| Posaconazole | tryptophan | pLC | 1 | 0 |
| Posaconazole | tyrosine | nLC | 0.892502344 | 0.028199192 |
| Posaconazole | tyrosine | pLC | 0.766496027 | 0.100772162 |
| Posaconazole | uracil | nLC | 0.969596144 | −0.27793622 |
| Posaconazole | uric acid | pLC | 1 | 0 |
| Posaconazole | uridine | nLC | 0.29522738 | 0.028550296 |
| Posaconazole | urocanic acid | nLC | 1 | 0 |
| Posaconazole | urocanic acid | pLC | 1 | 0 |
| Posaconazole | valine | GC | 0.599781403 | 0.345 |
| Posaconazole | valine | nLC | 0.868983593 | 0.019504668 |
| Posaconazole | xanthosine(diH2O) | pLC | 1 | 0 |
| Posaconazole | xanthosineDiH2O | nLC | 1 | 0 |
| Posaconazole | zeatin | nLC | 1 | 0 |
| Posaconazole | zeatin | pLC | 1 | 0 |

The four antifungal drugs examined in the present study, Amphoteracin B, Ketoconazole, Fluconazole, and Posaconazole, are known to have different effects when applied therapeutically. They are also quite different structurally, as is shown in FIG. 18, so it is not clear which characteristics are responsible for their differences. Therefore, it is desirable to determine how the compounds differentially interact within living cells, including the cells of pathogens and the cells of patients. The present experiment is designed to address these questions by examining which pathways in yeast cells (a pathogen) are affected by the four antifungal compounds. Current state of the art limitations dictate that experiments examining different biological entities (DNA, RNA, protein, metabolites, phenotype) be designed and performed in individual technologies, or be designed and performed simultaneously or sequentially using different technologies, with disparate results then compared indirectly and analyzed. The present invention provides methods for obtaining integrated data from different technologies so that direct comparison and analysis are possible, enabling use of the most informative of data from as many different biological sources or technologies as a biologist elects to integrate. The methods set forth in the present invention lead to complex data sets, which hold vast amounts of data. Various specific examples of the present invention are provided. The herbicide site of action study presented in Specific Example 2 (SOA1) provides a coherent data set obtained from three different biological sources via integrated technologies, with the data combined for greatest gain of biological information. The herbicide mode of action study presented in Specific Example 3 (MOA1) provides a coherent data set obtained from three different biological sources via integrated technologies, with the data combined for greatest gain of biological information. MOA1 additionally provides for the use of a fourth technology, nutritional profiling, for use in guiding the analyses of the results from gene expression, metabolite, and phenotypic technologies. The antifungal study addressed in Specific Example 5, hereinafter AF1, presents an integrated data set for the identification of biochemical pathways associated with the effects of the drugs in question. A full analysis of the AF1 data set requires linkage of data to the affected biochemical pathways, so that the observed effects of each on both pathogen and patient are understood.

Figure 19:
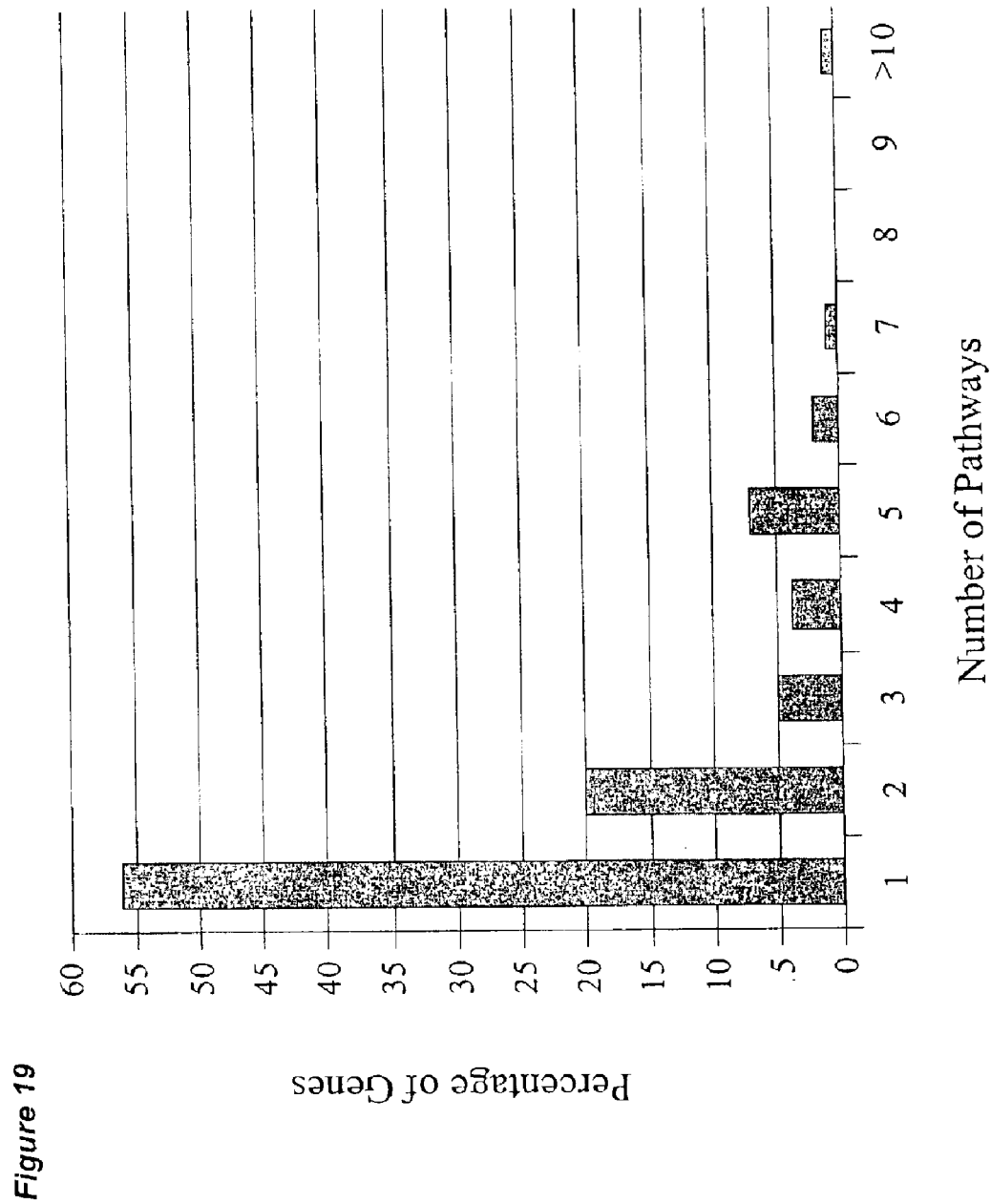
FIG. 19 illustrates the mapping of genes to pathways based on data obtained from experiment AF1, which examined the effects of the antifungal drugs Amphoteracin B, Ketoconazole, Fluconazole, and Posaconazole on yeast cells. Yeast gene accession numbers were parsed from KEGG pathway files resulting in the mapping of 1145 genes to 103 pathways. The percentage of genes (y-axis) is plotted versus the number of pathways (x-axis).

In AF1, two different technologies were utilized: gene expression analysis (for examination of mRNA expression) and metabolite analysis. More than 6300 genes were measured by gene expression and more than 600 chemical components were measured by LC-MS and GC-MS. As noted previously, existing metabolic databases may be helpful in practicing the methods and systems of the present invention, but many databases include limitations that make their use in data analysis and pathway mapping less than straightforward. In the case of AF1, use of the KEGG database to map gene information to pathways resulted in the mapping of 1145 significantly changed genes to a total of 103 pathways. A caveat limiting the reliance on the mapping data is that KEGG mapping is not unique (one gene does not map to a single pathway), and 45% of the genes mapped to more than one pathway, as shown in FIG. 19. This caveat to KEGG makes it difficult to pinpoint the correct pathway when attempting to link a gene to a specific pathway.

Since KEGG provides multiple pathway linkages for some genes (FIG. 19) and some compounds (FIG. 20), with seven compounds mapping to more than 10 pathways (Table 13), the invention provides a method for assigning pathway scores when mapping genes and compounds to pathways.

TABLE 13

Compounds Linked to More than 10 Pathways

| Kegg ID | Compound | # Pathways |
|---|---|---|
| C00009 | phosphate | 40 |
| C00025 | L-glutamate | 30 |
| C00026 | 2-ketoglutaric acid | 27 |
| C00049 | L-aspartic acid | 20 |
| C00065 | L-serine | 12 |
| C00078 | L-tryptophan | 11 |
| C00109 | 2-ketobutyric acid | 12 |

The pathway score indicates how meaningful the mapping is, or how likely it is to be correctly indicative of the pathway involved in the perturbation under examination. The method provides a pathway score based on perturbation levels of genes and/or compounds and the information content of each gene and/or compound in the pathway, i.e., a pathway score indicates the extent to which other pathways are mapped to a gene/compound. For example, imagine that two genes are perturbed in a particular experiment. One gene maps to only one pathway, giving a high degree of probability that the perturbed pathway is the one identified in the mapping. The second gene maps to three pathways. In the later example, there is only one-third the probability that the pathway identified in the mapping is the one perturbed. The present invention provides a method for calculating the pathway scores, so that more weight is given to a score of a gene or compound that maps to only one pathway than to a score of a gene or compound that maps to multiple pathways. Equation 1, a simplified example of this sort of calculation that does not take into account the degree of perturbation, follows:

$$\text{path\_score} = \frac{\sum_{i=1}^{j} \frac{1}{i_{\text{path\_count}}}}{n}$$

Where n=the total number of genes in the pathway; $i_{\text{path\_count}}$=the number of pathways containing a gene; and j=the number of genes in the pathway that are perturbed. Another factor to be considered when weighting a pathway score is the degree of perturbation. Degree of perturbation can be calculated, for example, based on a number of standard deviations from a norm, and included in an equation such as the one shown above, so that not only the number of pathways is taken into account, but also accounts for the amount of gene transcript or compound present as compared to a control.

Figure 20:
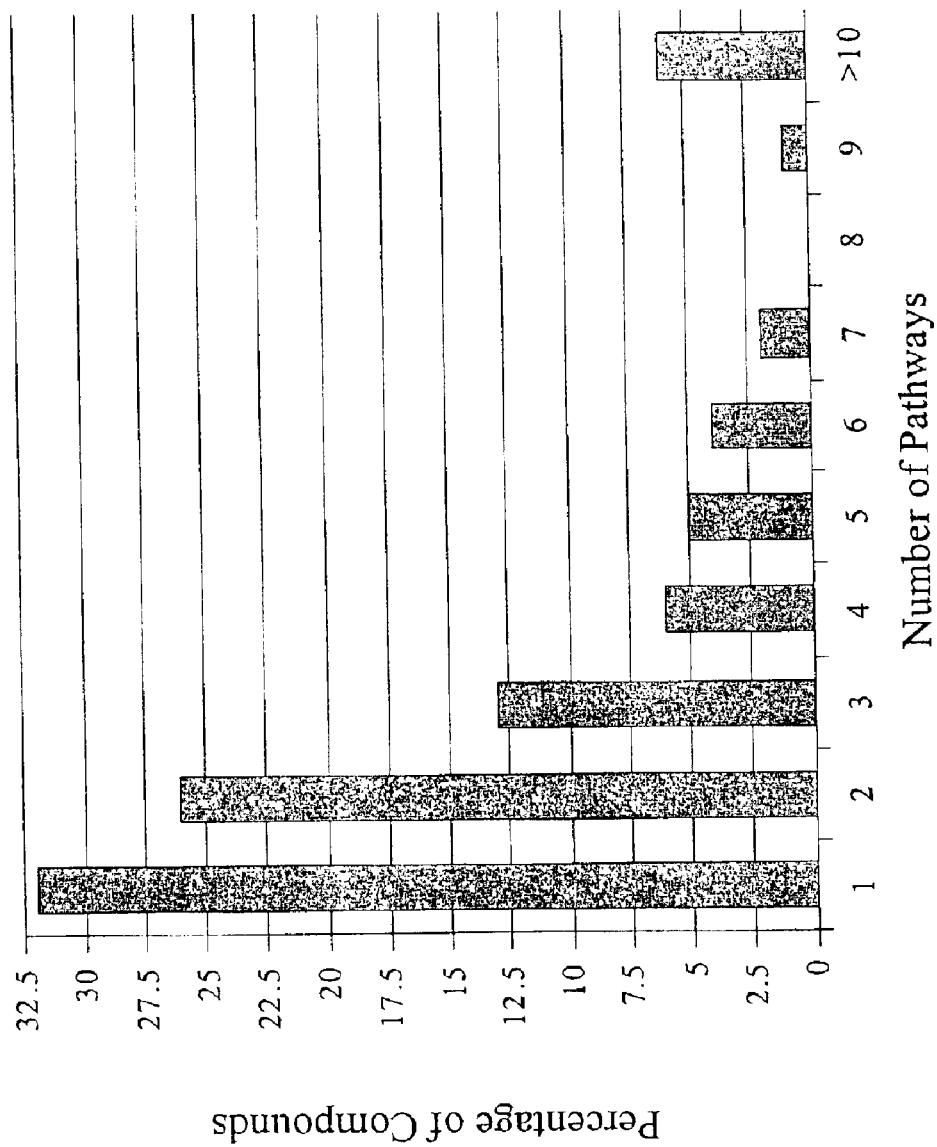
FIG. 20 illustrates the mapping of compounds to pathways based on data obtained from experiment AF1, which examined the effects of the antifungal drugs Amphoteracin B, Ketoconazole, Fluconazole, and Posaconazole on yeast cells. The percentage of compounds (y-axis) is plotted versus the number of pathways (x-axis). By linking through enzymes, 676 compounds were linked to 92 separate pathways. The 77 compounds detected in the experiment were mapped to 69 separate pathways.
Figure 21A:
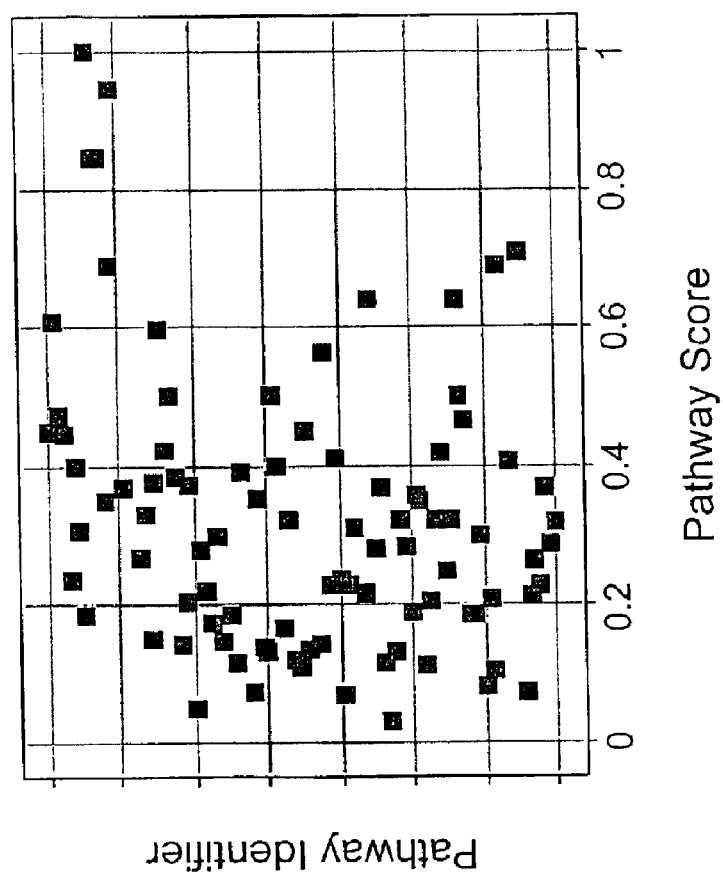
FIGS. 21A–21D depicts the pathway score attributed to gene expression data derived from yeast cells treated with antifungal compounds, Amphoteracin B, Ketoconazole, Fluconazole, and Posaconazole, in the AF1 study. The yeast genes most perturbed in the treated cells were linked to KEGG pathways (y-axis) and assigned a pathway score (x-axis) according to Equation 1.
Figure 21B:
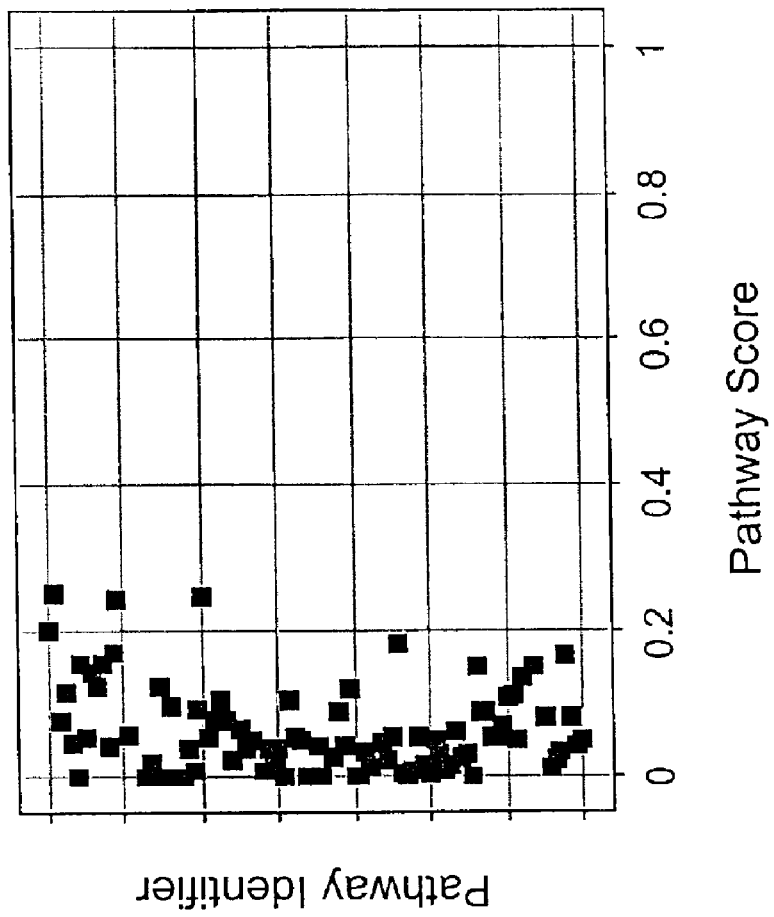
Figure 21C:
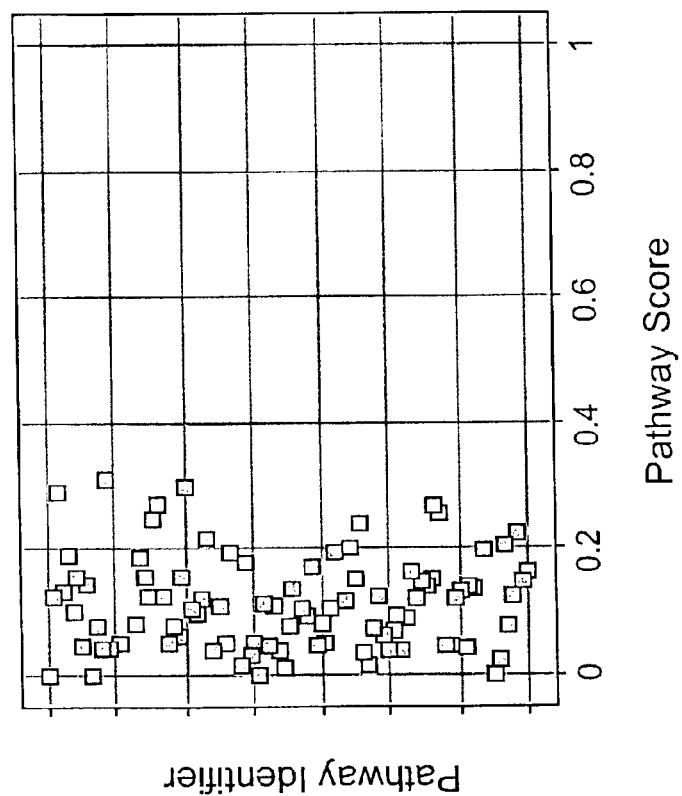
Figure 21D:
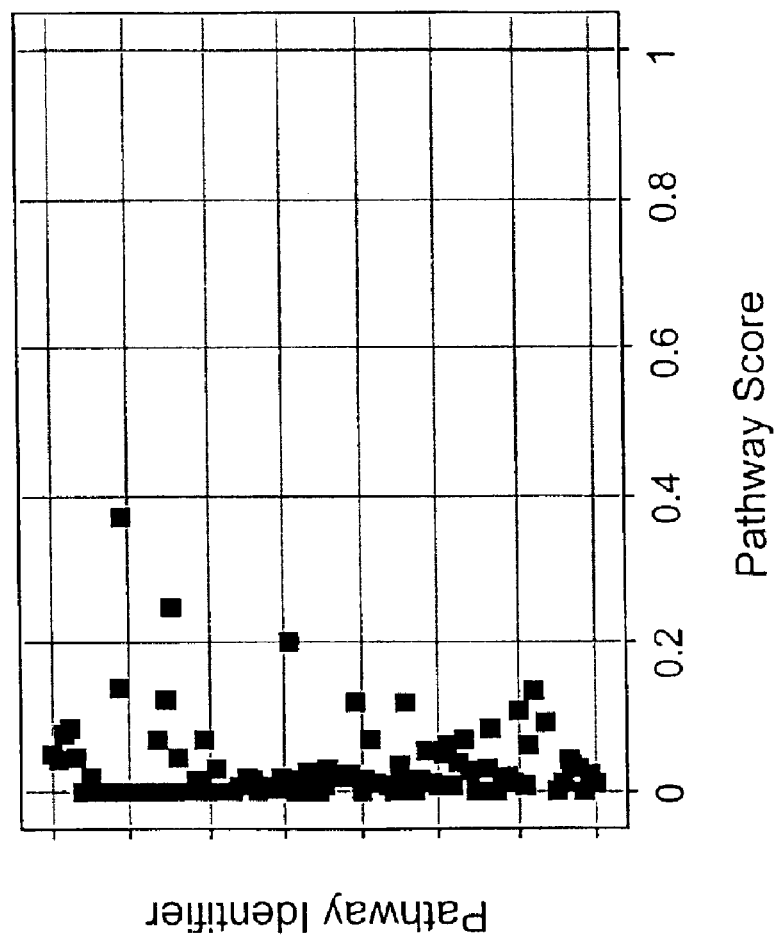

Compounds were also linked to pathways using the KEGG database. KEGG links 676 compounds measured in AF1 to a total of 92 pathways. Of the 676 compounds under consideration, 77 were detected in the AF1 samples. The 77 compounds map to 69 pathways, with approximately 68% of the compounds mapping to more than one pathway, as illustrated in FIG. 20. The multiple mapping feature of KEGG makes it difficult to pinpoint the correct pathway when trying to link a compound to a specific pathway. At least seven of the compounds mapped to more than 10 pathways, rendering the maps difficult to interpret (Table 13). A pathway score calculation is applied to the compounds to account for both information content (number of pathways a compound maps to) and perturbation level.

The above describes a mapping approach to link the total data set from the four antifungal drugs to a biochemical pathway or pathways which were perturbed under the experimental conditions applied. Due to inherent limitations of the KEGG database, the approach does not provide enough information for a complete analysis of the AF1 data. Therefore, the data from the four individual drug compounds was examined. As shown in Table 14, Amphoteracin B affects a much larger number of transcripts and compounds in the yeast cells than do any of the other 3 compounds.

TABLE 14

Number of Transcripts and Compounds Perturbed by Treatment

| Chemical Treatment | # Transcripts | | # Compounds | |
| --- | --- | --- | --- | --- |
|  | P < 0.1 | P < 0.05 | P < 0.1 | P < 0.05 |
| Amphoteracin B | 4652 | 4363 | 21 | 16 |
| Ketoconazole | 2026 | 1551 | 15 | 8 |
| Fluconazole | 1719 | 1411 | 6 | 2 |
| Posaconazole | 925 | 690 | 4 | 3 |

This observation suggests that the site(s) of action associated with Amphoteracin B are likely to be more widespread throughout the yeast cells, rather than focussed specifically on one or a few (possibly related) pathways. The other three drugs appear to have significantly fewer effects, indicating that their modes of action are probably less far-reaching throughout the cellular processes of the yeast (and possibly also less far-reaching for a patient receiving the compound as a drug therapy). Examination of both the transcript data and the compound data presented in Table 14 leads to the conclusion that Amphoteracin B affects many more yeast cellular pathways than do Ketoconazole, Fluconazole, and Posaconazole, and that therefore, the effects of Ketoconazole, Fluconazole, and Posaconazole are far more pathway-specific than that of Amphoteracin B.

The methods of the current invention require that data from different biological sources/technologies be considered together as one data set in order to get the most biologically accurate and representative information. An examination of the AF1 gene expression data alone gives a different impression than that obtained above when both the gene expression and the metabolite data were considered. As shown in FIG. 21, gene expression analysis indicates that Posaconazole has the most specific effect on the cell, and therefore might be the compound least likely to have toxic side effects. Although the present experiment only examined yeast cells, and not human cells, it can be interpolated that a compound affecting more biochemical pathways in a yeast cell might also be likely to affect more pathways in a human cell. Moreover, an experiment including human cells is straightforward to conduct, and is a logical follow-up to the AF1 study described herein. Examination of the AF1 gene expression data alone, as shown in FIG. 21, indicates that Posaconazole might be the compound of choice for safely treating patients. When the gene expression data was classified into pathway mappings, as shown in Table 15, Posaconazole appears to have the most specific effect, although this data indicates that Ketoconazole and Fluconazole also have much more specific effects than Amphoteracin B.

TABLE 15

Number of Pathways Affected by at Least One Gene

| Chemical Treatment | # Pathways (p < 0.05) |
| --- | --- |
| Amphoteracin B | 97 |
| Ketoconazole | 90 |
| Fluconazole | 79 |
| Posaconazole | 69 |

However, pathway analysis of the gene expression data shows that in all of the treatments, including the three azoles and Amphoteracin B, pathways related to cell proliferation are up-regulated (data taken from FIG. 21, in which the genes most perturbed were identified and linked to pathways).

Inclusion of the metabolite data provides an improved analysis and supports the usefulness of the methods of the present invention. Based on the results shown in Table 14, Posaconazole is less specific in its effect than is Fluconazole. Analysis of this data alone leads to the conclusion that Fluconazole is the most specific acting of the four antifungal drugs studied in AF1, and is therefore probably the drug of choice for safely treating patients.

The data were then combined to determine the number of reactions showing an enzyme and at least one compound perturbed, and to determine the number of pathways having at least one enzyme and one perturbed compound perturbed. The results of the analysis are represented in Tables 16 and 17, and were difficult to interpret, illustrating that the ability to draw conclusions from compound mapping to pathways is limited when absent additional data. Analysis of this data does not lead to the conclusion that Fluconazole is the most specific acting of the four antifungal drugs studied in AF1, but rather, indicates that Posaconazole is the drug with the most specific effect.

TABLE 16

Number of Reactions Having an Enzyme and at Least One Compound Perturbed

| Chemical Treatment | # Reactions |
|---|---|
| Amphoteracin B | 54 |
| Ketoconazole | 21 |
| Fluconazole | 2 |
| Posaconazole | 0 |

TABLE 17

Number Of Pathways Having at Least One Enzyme and One Compound Perturbed

| Chemical Treatment | # Reactions |
|---|---|
| Amphoteracin B | 37 |
| Ketoconazole | 24 |
| Fluconazole | 15 |
| Posaconazole | 3 |

Figure 22:
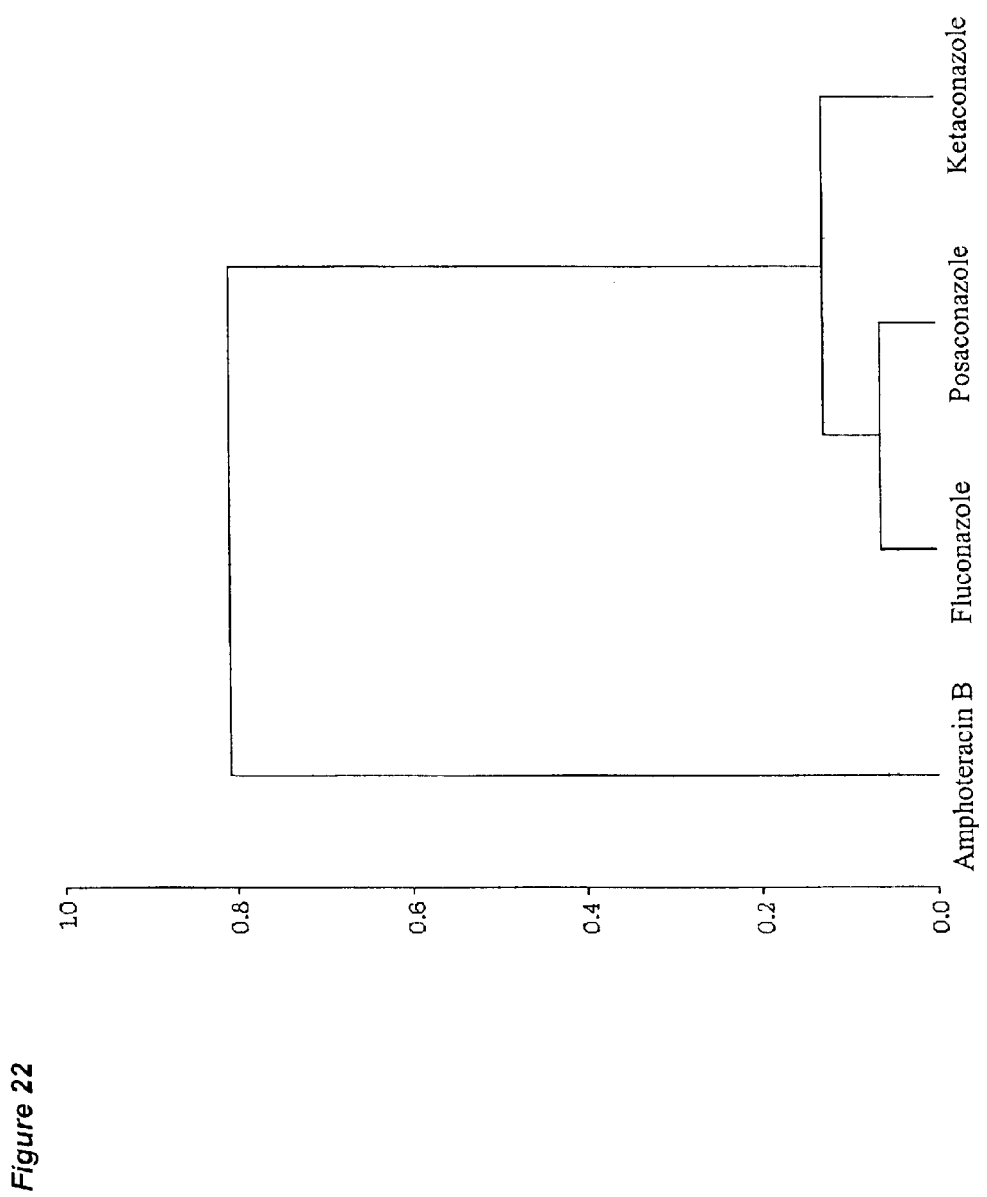
FIG. 22 is an illustration of the result obtained when the principal components (gene expression analysis and metabolite analysis) of the AF1 study are subjected to clustering analysis. The name of the treatment (x-axis) is plotted versus the semi partial r squared value (y-axis).

A coherent data set was created from data obtained from the four above-described drug compounds. The data were reduced by using principle components analysis and cluster analysis. As shown in FIG. 22, the three azole drugs cluster quite tightly together, indicating that their modes of action are more similar to each other than to the mode of action of Amphoteracin B. The observed clustering is in direct contrast to the gene expression data, which showed by pathway analysis that in all of the treatments, including the three azoles and Amphoteracin B, pathways related to cell proliferation are up-regulated (data taken from FIG. 21, in which the genes most perturbed were identified and linked to pathways).

Figure 23:
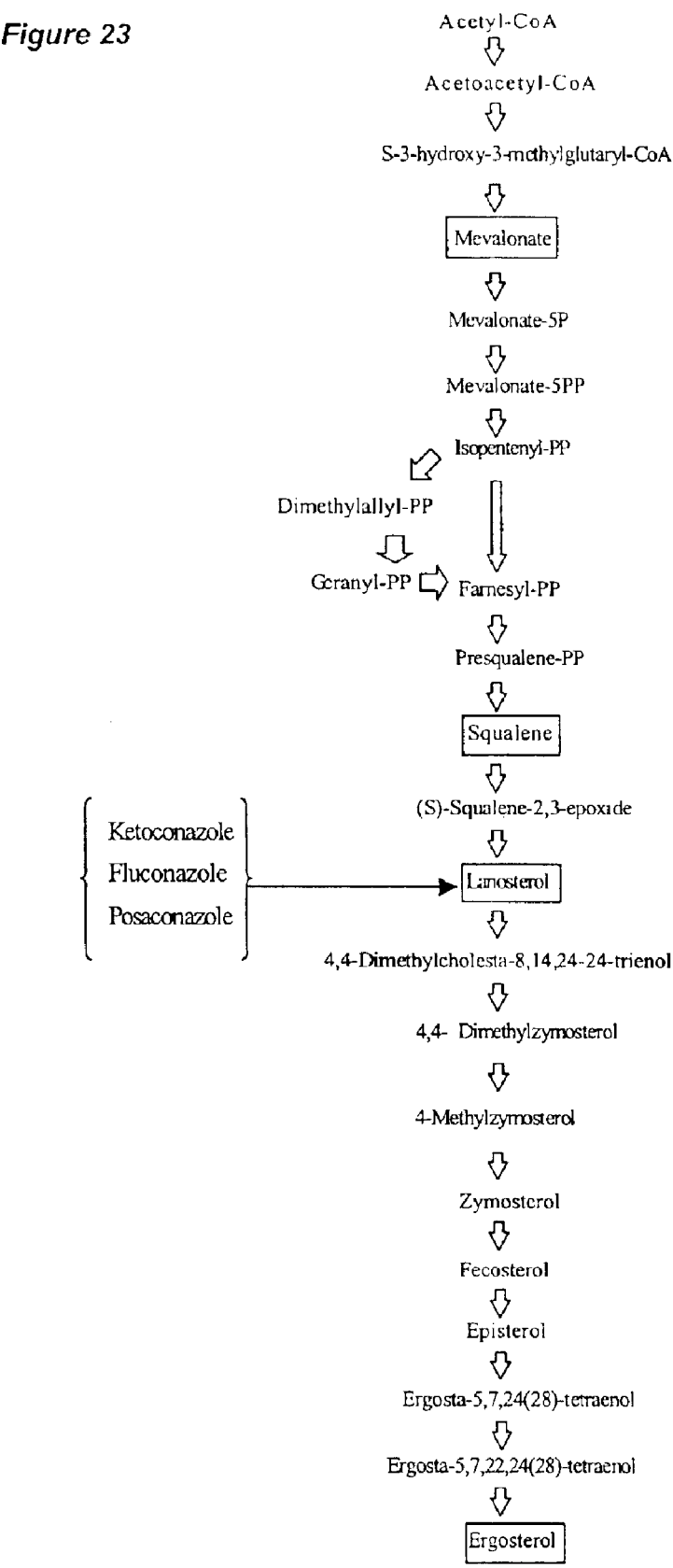
FIG. 23 is an illustration of the ergosterol biochemical pathway, showing where the azole drugs examined in the AF1 study have their effect.

A different analysis identified compounds perturbed in all four of the treatments. Specifically, the analysis showed that squalene and lanosterol (plus a few unknown peaks) increased in the azole compound-treated cells, but not in the Amphoteracin B-treated cells (see FIG. 23 for information directed to the pathway). This observation leads to the conclusion that the azole compounds are affecting the ergosterol pathway, a conclusion unsupported by gene expression data alone, which instead implicated cell proliferation pathways.

The AF1 example serves to support the methods and systems of the present invention by illustrating how the use of data from a single technology source provides, at best, a skewed image of biological reality. Reliance on a skewed conclusion may lead to deleterious effects, such as the administration of potentially dangerous and harmful compounds to patients. The AF1 example also serves to illustrate the problems present in the current state of the art when linking gene and metabolite data to specific biochemical pathways. It is invaluable to link metabolite data, gene expression data, annotation, phenotype data, or any other type of information to a specific pathway, and ultimately, to a disease state. As illustrated in FIG. 1, one way to obtain a data set that is meaningful and relevent to a biological system is to examine DNA, RNA, protein, metabolites, and phenotype, so that a comprehensive picture of the biological status of an organism is obtained. The present invention provides methods and systems for creating coherent data sets, which are biologically relevent and meaningful, and which can serve as models of biological systems.

SPECIFIC EXAMPLE 6

Mouse Fibroblast Azole Drug Experiment

As noted above in Specific Example 5, ergosterol is an essential component of fungal plasma membranes; it affects membrane permeability and the activities of membrane-bound enzymes. In the present example, the methods of the invention are applied to an integrated genomic and metabolomic approach to reveal the mode of action of anti-fungal drugs. Using cultured mouse fibroblasts (L929 cells) as a model system, the global metabolic consequences caused by the treatment of four antifungal drugs (amphoteracin B, ketoconazole, fluconazole, and posaconazole) are examined at both the transcriptome (RNA) and metabolome (small molecule) levels. The integrative analyses presents a global view of the metabolic changes associated with each drug treatment, thus allowing for a better interpretation of the mode of action of antifungal drugs.

Materials and Methods

Strains and Media

L929 murine fibroblast cells were purchased from ATCC Catalog No. CCL-1. The L929 cell line is grown under standard conditions suggested by ATCC guidelines (ATCC, Manassas, Va.). Cells are seeded in 75 $cm^2$ tissue culture flasks at a concentration that would yield 2.5–3.0×$10^6$ cells at treatment time. The cells are grown in DMEM:F12 (Sigma Chemical Co., St. Louis, Mo.) supplemented with 1% L-Glutamine and 10% fetal bovine serum at 37° C., 4.9% $CO_2$ and 95% humidity for at least 36 hours before treatment. The media is removed from the flasks and media with the chosen concentration of drug chemical is added to the flasks. At the designated time point, the cells are harvested by centrifugation following treatment with trypsin to release the cells. The pellet is washed three times in Hanks' Balanced Salts Solution (HBSS, Sigma Chemical Co., St. Louis, Mo.). Finally, the cells are resuspended in a small volume of HBSS and transferred into 2 ml tubes. The samples are centrifuged and the wash removed. Cell pellets are flash frozen in liquid nitrogen and stored at −80° C.

Determination of MIC

Antifungal drugs Amphotericin B, ketoconazole, and fluconazole were purchased from Sigma (Sigma Chemical Co., St. Louis, Mo.), and posaconazole was a gift from Duke Medical Center (Duke University, Durham, N.C.). The minimal inhibitory concentration (MIC) is determined using 96-well plates seeded at a concentration of 20,0000 cells/well and grown in DMEM:F12 (D6559, Sigma Chemical Co., St. Louis, Mo.) supplemented with 1% L-Glutamine and 10% FBS for 25 hours at 37° C., 4.9% $CO_2$ and 95% humidity. The cells are treated with each fungicide in a two fold dilution series with maximum concentration of 200 µg/ml. Each plate contains L929 cells treated with 25 ng and 50 ng TNFα and cells grown in media only, 0.5% and 1% DMSO. Cell viability is determined by quantifying the amount of ATP in metabolically active cells using CELLTITER-GLO Luminescent Cell Viability Assay (Promega Corp., Madison, Wis.). At the 24 hour time point, the media is removed from the wells, the cells are washed with PBS, and PBS is added to the wells. Promega's protocol for using the CELLTITER-GLO reagent is followed and the luminescence is measured on the Tecan Ultra luminometer (Tecan Systems, Inc., San Jose, Calif.).

RNA Extraction and Microarray Preparation

RNA is obtained from 2–10 million fresh frozen cells using methods that are well known in the art, such as a TRIZOL (GibcoBRL, Rockville, Md.) extraction method. Microarrays containing human genes, such as Agilent's (Agilent Technologies, Palo Alto, Calif.) cDNA Microarray Kit (containing over 12,000 of Incyte's Human Drug Target clones), are used for the hybridizations, according to the manufacturer's instructions.

Microarray Data Processing and Analyses

Data are analyzed using software such as Image Analysis Software (Version A.4.0.45, Agilent Technologies, Palo Alto, Calif.) and then loaded into a database appropriate for storage and further analysis, such as the Rosetta RESOLVER database (Rosetta Inpharmatics Inc., Kirkland, Wash.).

GC-MS Derivatization and Analyses

Approximately 500,000 cells are extracted in a solvent, converted to trimethylsilyl derivatives in-situ, and analyzed by gas chromatography with time of flight mass spectrometry (GC/TOF-MS). Separations are conducted using a 50% phenyl- 50% methyl stationary phase, helium carrier gas, and a programmed oven temperature that ramps from a starting temperature of 50° C. to a final temperature of over 300° C. Compounds detected by GC-MS with an electron impact (EI) ion source are cataloged based on Kovats retention indices and mass-to-charge ratio (m/z) of the ions characteristic of each peak. Commercially available reference compounds were obtained from Sigma-Aldrich (Sigma Chemical Co., St. Louis, Mo.) or VWR (VWR Scientific Products, Baltimore, Md.).

LC-MS Procedures

Approximately 500,000 cells are extracted in 0.5 ml 10% aqueous methanol containing labeled internal standards. Tissue is disrupted by a 30 second pulse of high level sonic energy (lithotripsy), at a maximum temperature of 30° C. The extract is centrifuged at 4000 rpm for 2 minutes. The supernatant, diluted with an equal volume of 50% aqueous acetonitrile (V/V) is chromatographed on C18 HPLC in an acetonitrile/water gradient containing 5 mM ammonium acetate. Samples are passed through a splitter and the split flow is infused to the turbo-ionspray ionization sources of two Mariner LC TOF mass spectrometers (PerSeptive Biosystems Inc., Framingham, Mass.). The sources are optimized to generate and monitor positive and negative ions, respectively. The Total Ion Chromatogram (TIC) is analyzed for compounds with masses ranging from 80 to 900 Da. Individual ion traces are used for both calibration and quantification. Relative amounts of the compounds are determined using the intensity and peak areas of individual ion traces. Isotopically labeled internal standards are used for peak area ratios, response factor determination, and normalization of data throughout the experiment.

Data Analysis

The data are analyzed according to the methods and systems of the current invention. The data from each sample are assigned a unique identifier, and are collected and stored in a computer tracking system, wherein the data are linked to the appropriate unique identifier. All linked data are converted to a numeric format, and the numeric data are converted to a common unit system, wherein the common unit system data are a coherent data set and can serve as a model for a biological system. Additionally, the coherent data set can be compared to a reference population to determine the most informative results from the experiment, so that a signature profile is established with the most informative results.

SPECIFIC EXAMPLE 7

Human Cell Azole Drug Experiment

Strains and Media

HepG2, a human hepatocyte line, is purchased from American Type Culture Center (ATCC, Manassas, Va.). The hepatocyte strain is grown under standard conditions as suggested by the ATCC guidelines (ATCC, Manassas, Va.). The media is removed from the flasks and media with the chosen concentration of drug chemical is added to the flasks. At the designated time point, the cells are harvested by centrifugation following treatment with trypsin to release the cells. The pellet is washed three times in Hanks' Balanced Salts Solution (HBSS, Sigma Chemical Co., St. Louis, Mo.). Finally, the cells are resuspended in a small volume of HBSS and transferred into 2 ml tubes. The samples are centrifuged and the wash removed. Cell pellets are flash frozen in liquid nitrogen and stored at −80° C.

Determination of MIC

Antifungal drugs Amphotericin B, ketoconazole, and fluconazole were purchased from Sigma (Sigma Chemical Co., St. Louis, Mo.), and posaconazole was a gift from Duke Medical Center (Duke University, Durham, N.C.). The minimal inhibitory concentration (MIC) is determined using 96-well plates seeded at a concentration of 20,0000 cells/well and grown in DMEM:F12 (D6559, Sigma Chemical Co., St. Louis, Mo.) supplemented with 1% L-Glutamine and 10% FBS for 25 hours at 37° C., 4.9% $CO_2$ and 95% humidity. The cells are treated with each fungicide in a two fold dilution series with maximum concentration of 200 µg/ml. Each plate contains HepG2 cells treated with 25 ng and 50 ng TNFα and cells grown in media only, 0.5% and 1% DMSO. Cell viability is determined by quantifying the amount of ATP in metabolically active cells using CELLTITER-GLO Luminescent Cell Viability Assay (Promega Corp., Madison, Wis.). At the 24 hour time point, the media is removed from the wells, the cells are washed with PBS, and PBS is added to the wells. Promega's protocol for using the CELLTITER-GLO reagent is followed and the luminescence is measured on the Tecan Ultra luminometer (Tecan Systems, Inc., San Jose, Calif.).

RNA Extraction and Microarray Preparation

RNA is obtained from 2–10 million fresh frozen cells using methods that are well known in the art, such as a TRIZOL (GibcoBRL, Rockville, Md.) extraction method. Microarrays containing human genes, such as Agilent's (Agilent Technologies, Palo Alto, Calif.) cDNA Microarray Kit (containing over 12,000 of Incyte's Human Drug Target clones), are used for the hybridizations, according to the manufacturer's instructions.

Microarray Data Processing and Analyses

Data are analyzed using software such as Image Analysis Software (Version A.4.0.45, Agilent Technologies, Palo Alto, Calif.) and then loaded into a database appropriate for storage and further analysis, such as the Rosetta RESOLVER database (Rosetta Inpharmatics Inc., Kirkland, Wash.).

GC-MS Derivatization and Analyses

Approximately 500,000 cells are extracted in a solvent, converted to trimethylsilyl derivatives in-situ, and analyzed by gas chromatography with time of flight mass spectrometry (GC/TOF-MS). Separations are conducted using a 50% phenyl–50% methyl stationary phase, helium carrier gas, and a programmed oven temperature that ramps from a starting temperature of 50° C. to a final temperature of over 300° C. Compounds detected by GC-MS with an electron impact (EI) ion source are cataloged based on Kovats retention indices and mass-to-charge ratio (m/z) of the ions characteristic of each peak. Commercially available reference compounds were obtained from Sigma-Aldrich (Sigma Chemical Co., St. Louis, Mo.) or VWR (VWR Scientific Products, Baltimore, Md.).

LC-MS Procedures

Approximately 500,000 cells are extracted in 0.5 ml 10% aqueous methanol containing labeled internal standards. Tissue is disrupted by a 30 second pulse of high level sonic energy (lithotripsy), at a maximum temperature of 30° C. The extract is centrifuged at 4000 rpm for 2 minutes. The supernatant, diluted with an equal volume of 50% aqueous acetonitrile (V/V) is chromatographed on C18 HPLC in an acetonitrile/water gradient containing 5 mM ammonium acetate. Samples are passed through a splitter and the split flow is infused to the turbo-ionspray ionization sources of two Mariner LC TOF mass spectrometers (PerSeptive Biosystems Inc., Framingham, Mass.). The sources are optimized to generate and monitor positive and negative ions, respectively. The Total Ion Chromatogram (TIC) is analyzed for compounds with masses ranging from 80 to 900 Da. Individual ion traces are used for both calibration and quantification. Relative amounts of the compounds are determined using the intensity and peak areas of individual ion traces. Isotopically labeled internal standards are used for peak area ratios, response factor determination, and normalization of data throughout the experiment.

Data Analysis

The data are analyzed according to the methods and systems of the current invention. The data from each sample are assigned a unique identifier, and are collected and stored in a computer tracking system, wherein the data are linked to the appropriate unique identifier. All linked data are converted to a numeric format, and the numeric data are converted to a common unit system, wherein the common unit system data are a coherent data set and can serve as a model for a biological system. Additionally, the coherent data set can be compared to a reference population to determine the most informative results from the experiment, so that a signature profile is established with the most informative results.

Further, the data from this experiment, Specific Example 7, are combined with the data from Specific Example 5, for an analysis and comparison of the effects of the four azole drugs on both the pathogen (the yeast cells in Specific Example 5) and the host (the human cells in Specific Example 7). These types of analyses promise great utility in the pharmaceutical arena, by streamlining the search for drug compounds most harmful to the pathogen and most efficacious to the patient/host.

Although the invention has been described with respect to a preferred embodiment thereof, it is to be also understood that it is not to be so limited since changes and modifications can be made therein which are within the full intended scope of this invention as defined by the appended claims.

We claim:

1. A system for examining metabolites in a biological sample, comprising:
    a) means for entering a unique identifier of at least one biological sample into a computer tracking system;
    b) means for simultaneously collecting data from said sample, for a plurality of peaks, each peak comprising at least one chemical component, wherein said data comprise data from at least LC-MS, GC-MS, and NMR;
    c) means for storing in said computer tracking system said chemical component data, wherein said data are linked to said unique identifier;
    d) means for characterizing and/or identifying said chemical components; and
    e) means for linking said characerized and/or identified chemical components to metabolites in biochemical pathways.

2. A system for examining metabolites in a biological sample, comprising:
    a) means for entering a unique identifier of at least one biological sample into a computer tracking system;
    b) means for simultaneously collecting data from said sample, for a plurality of peaks, each peak comprising at least one chemical component, wherein said data comprise data from at least LC-MS, GC-MS, and ICP-MS;
    c) means for storing in said computer tracking system said chemical component data, wherein said data are linked to said unique identifier;
    d) means for characterizing and/or identifying said chemical components; and
    e) means for linking said characerized and/or identified chemical components to metabolites in biochemical pathways.

* * * * *